(12) United States Patent
Yamamoto et al.

(10) Patent No.: US 9,738,831 B2
(45) Date of Patent: *Aug. 22, 2017

(54) OPTICALLY ISOTROPIC LIQUID CRYSTAL COMPOSITION AND OPTICAL DEVICE

(71) Applicants: JNC CORPORATION, Tokyo (JP); JNC PETROCHEMICAL CORPORATION, Tokyo (JP)

(72) Inventors: Shin-Ichi Yamamoto, Chiba (JP); Koki Sago, Chiba (JP); Yasuhiro Haseba, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/409,468

(22) PCT Filed: Jun. 18, 2013

(86) PCT No.: PCT/JP2013/066653
§ 371 (c)(1),
(2) Date: Dec. 18, 2014

(87) PCT Pub. No.: WO2013/191153
PCT Pub. Date: Dec. 27, 2013

(65) Prior Publication Data
US 2015/0240159 A1   Aug. 27, 2015

(30) Foreign Application Priority Data

Jun. 19, 2012   (JP) ................................ 2012-137736

(51) Int. Cl.

| | | |
|---|---|---|
| *G02F 1/1333* | (2006.01) | |
| *C09K 19/34* | (2006.01) | |
| *C09K 19/20* | (2006.01) | |
| *C09K 19/58* | (2006.01) | |
| *C07D 319/06* | (2006.01) | |
| *C09K 19/54* | (2006.01) | |
| *C09K 19/56* | (2006.01) | |
| *G02F 1/1334* | (2006.01) | |
| *G02F 1/1335* | (2006.01) | |
| *G02F 1/1343* | (2006.01) | |
| *C09K 19/02* | (2006.01) | |
| *C09K 19/04* | (2006.01) | |

(52) U.S. Cl.
CPC ........ *C09K 19/3402* (2013.01); *C07D 319/06* (2013.01); *C09K 19/0275* (2013.01); *C09K 19/20* (2013.01); *C09K 19/544* (2013.01); *C09K 19/56* (2013.01); *C09K 19/586* (2013.01); *C09K 19/588* (2013.01); *G02F 1/1334* (2013.01); *G02F 1/133528* (2013.01); *G02F 1/134309* (2013.01); *G02F 1/134363* (2013.01); *C09K 2019/0466* (2013.01); *C09K 2019/3422* (2013.01)

(58) Field of Classification Search
CPC .. C09K 19/3402; C09K 19/20; C09K 19/586; C09K 19/588; C09K 19/56; C09K 19/0275; C09K 2019/0466; C09K 2019/3422; G02F 1/1333; G02F 1/1334; G02F 1/133528; G02F 1/134309; G02F 1/134363; C07D 319/06
USPC .............. 252/299.01, 299.6, 299.61; 428/1.1
See application file for complete search history.

(56) References Cited

U.S. PATENT DOCUMENTS

| | | | |
|---|---|---|---|
| 6,329,027 B1 | 12/2001 | Kondo et al. | |
| 8,858,830 B2 * | 10/2014 | Yamamoto | C09K 19/3402 252/299.01 |
| 8,911,644 B2 * | 12/2014 | Yamamoto | C09K 19/3402 252/299.61 |
| 2006/0006363 A1 | 1/2006 | Heckmeier et al. | |
| 2006/0050354 A1 | 3/2006 | Heckmeier et al. | |
| 2006/0227283 A1 | 10/2006 | Ooi et al. | |
| 2008/0132716 A1 | 6/2008 | Lietzau et al. | |
| 2008/0259254 A1 | 10/2008 | Kikuchi et al. | |
| 2009/0262295 A1 | 10/2009 | Hong et al. | |
| 2009/0267025 A1 | 10/2009 | Schott et al. | |
| 2010/0258763 A1 | 10/2010 | Schott et al. | |
| 2011/0180756 A1 | 7/2011 | Goto et al. | |
| 2011/0242473 A1 | 10/2011 | Haseba et al. | |
| 2012/0012785 A1 | 1/2012 | Schott et al. | |
| 2012/0099039 A1 | 4/2012 | Haseba et al. | |
| 2013/0114009 A1 | 5/2013 | Yamamoto et al. | |
| 2013/0193376 A1 | 8/2013 | Schott et al. | |
| 2013/0278849 A1 | 10/2013 | Yamamoto et al. | |

(Continued)

FOREIGN PATENT DOCUMENTS

| | | |
|---|---|---|
| CN | 101143808 | 3/2008 |
| CN | 101526681 | 9/2009 |

(Continued)

OTHER PUBLICATIONS

"International Search Report (Form PCT/ISA/210)", mailed on Sep. 24, 2013, pp. 1-4.
Kikuchi et al., "Polymer-stabilized liquid crystal blue phases," Nature Materials, Sep. 2, 2002, pp. 64-68, vol. 1.
Hisakado et al., "Large Electro-optic Kerr Effect in Polymer-stabilized Liquid-Crystalline Blue Phases," Advanced Materials, Jan. 6, 2005, pp. 96-98, vol. 17, No. 1.

(Continued)

*Primary Examiner* — Geraldina Visconti
(74) *Attorney, Agent, or Firm* — Jianq Chyun IP Office

(57) ABSTRACT

A liquid crystal composition is described, containing a chiral agent and achiral component T containing at least one compound 1 having an unsubstituted or methyl group-substituted dioxane ring and having at least one —COO— or —CF$_2$O— as a connecting group, and exhibiting an optically isotropic liquid crystal phase.

29 Claims, 1 Drawing Sheet

(56) References Cited

U.S. PATENT DOCUMENTS

| | | | |
|---|---|---|---|
| 2013/0289316 A1 | 10/2013 | Haseba et al. | |
| 2014/0132868 A1* | 5/2014 | Sago | C09K 19/3402 349/42 |
| 2016/0002536 A1* | 1/2016 | Haseba | C09K 19/586 349/139 |

FOREIGN PATENT DOCUMENTS

| | | |
|---|---|---|
| EP | 1690917 | 8/2006 |
| JP | 56-164179 | 12/1981 |
| JP | 57-102981 | 6/1982 |
| JP | 64-079171 | 3/1989 |
| JP | 64-079172 | 3/1989 |
| JP | 2003-327966 | 11/2003 |
| JP | 2005-157109 | 6/2005 |
| JP | 2005-336477 | 12/2005 |
| JP | 2006-506477 | 2/2006 |
| JP | 2006-506515 | 2/2006 |
| JP | 2006-089622 | 4/2006 |
| JP | 2006-127707 | 5/2006 |
| JP | 2006-225655 | 8/2006 |
| JP | 2006-299084 | 11/2006 |
| JP | 2008-069153 | 3/2008 |
| JP | 2009-211074 | 9/2009 |
| JP | 2011-153202 | 8/2011 |
| WO | 98/23561 | 6/1998 |
| WO | 2005/080529 | 9/2005 |
| WO | 2005/090520 | 9/2005 |
| WO | 2006/063662 | 6/2006 |
| WO | 2010/058681 | 5/2010 |
| WO | 2010/134430 | 11/2010 |
| WO | 2012/043145 | 4/2012 |
| WO | 2013/065622 | 5/2013 |

OTHER PUBLICATIONS

Haseba et al., "Electro-optic effects of the optically isotropic state induced by the incorporative effects of a polymer network and the chirality of liquid crystal," Journal of the SID, Jun. 2006, pp. 551-556, vol. 14/6.

"Office Action of China Counterpart Application", issued on Dec. 2, 2015, pp. 1-21, with English translation thereof.

"2nd Office Action of China Counterpart Application", issued on Jul. 8, 2016, p. 1-p. 9, with English translation thereof.

"Office Action of Taiwan Counterpart Application" with English translation thereof, dated Dec. 5, 2016, p. 1-p. 11.

"Final Office Action of China Counterpart Application" with English translation thereof, dated Apr. 6, 2017, p. 1-p. 20.

"Notice of Allowance of Taiwan Counterpart Application" with English translation thereof, dated Apr. 25, 2017, p. 1-p. 4.

"Office Action of Japan Counterpart Application" with English translation thereof, dated Jun. 20, 2017, p. 1-p. 6.

\* cited by examiner

Measuring Optical System
(Use of comb-shaped electrode cell)

OPTICALLY ISOTROPIC LIQUID CRYSTAL COMPOSITION AND OPTICAL DEVICE

CROSS-REFERENCE TO RELATED APPLICATION

This application is a 371 application of an international PCT application serial no. PCT/JP2013/066653, filed on Jun. 18, 2013, which claims the priority benefits of Japan application no. 2012-137736, filed on Jun. 19, 2012. The entirety of each of the above-mentioned patent applications is hereby incorporated by reference herein and made a part of this specification.

TECHNICAL FIELD

The present invention relates to a liquid crystal composition useful, for example, as an optical device use material, an optical device using the liquid crystal composition, and so forth.

BACKGROUND ART

A liquid crystal display device using a liquid crystal composition is widely utilized for a display of a watch, a calculator, a word processor or the like. The liquid crystal display devices utilize refractive index anisotropy, dielectric anisotropy or the like of a liquid crystal compound. As an operating mode in the liquid crystal display device, a mode mainly using at least one polarizing plate to display an image is known, such as a phase change (PC), twisted nematic (TN), super twisted nematic (STN), bistable twisted nematic (BTN), electrically controlled birefringence (ECB), optically compensated bend (OCB), in-plane switching (IPS), or vertical alignment (VA) mode. Furthermore, a research has been recently conducted actively into a mode for developing electric birefringence by applying an electric field in an optically isotropic liquid crystal phase (Patent literature Nos. 1 to 16, Non-patent literature Nos. 1 to 3).

Furthermore, a proposal has been made for a wavelength variable filter, a wavefront control device, a liquid crystal lens, an aberration correction device, an aperture control device, an optical head device, or the like utilizing electric birefringence in a blue phase as one of the optically isotropic liquid crystal phases (Patent literature Nos. 10 to 12).

A classification based on a driving mode in the device includes a passive matrix (PM) and an active matrix (AM). The passive matrix (PM) is further classified into static, multiplex and so forth, and the AM is further classified into a thin film transistor (TFT), a metal insulator metal (MIM) and so forth.

CITATION LIST

Patent Literature

Patent literature No. 1: JP 2003-327966 A.
Patent literature No. 2: WO 2005/90520 A.
Patent literature No. 3: JP 2005-336477 A.
Patent literature No. 4: JP 2006-89622 A.
Patent literature No. 5: JP 2006-299084 A.
Patent literature No. 6: JP 2006-506477 A.
Patent literature No. 7: JP 2006-506515 A.
Patent literature No. 8: WO 2006/063662 A.
Patent literature No. 9: JP 2006-225655 A.
Patent literature No. 10: JP 2005-157109 A.
Patent literature No. 11: WO 2005/80529 A.
Patent literature No. 12: JP 2006-127707 A.
Patent literature No. 13: WO 1998/023561 A.
Patent literature No. 14: WO 2010/058681 A.
Patent literature No. 15: JP 2008-69153 A.
Patent literature No. 16: JP 2009-211074 A.

Non-Patent Literature

Non-patent literature No. 1: Nature Materials, 1, 64 (2002).
Non-patent literature No. 2: Adv. Mater., 17, 96 (2005).
Non-patent literature No. 3: Journal of the SID, 14, 551 (2006).

SUMMARY OF INVENTION

Technical Problem

Under circumstances described above, for example, desire has been expressed for a liquid crystal medium having stability to heat, light and so forth, a wide liquid crystal phase temperature range and very large dielectric anisotropy, and having an optically isotropic liquid crystal phase. Moreover, for example, desire has been expressed for various kinds of optical devices that can be used in a wide temperature range and have a short response time, a large contrast ratio and a low driving voltage.

Solution to the Problem

The invention provides, for example, a liquid crystal medium (a liquid crystal composition and a polymer/liquid crystal composite material), as described below, a mixture of a polymerizable monomer and the liquid crystal composition, an optical device including the liquid crystal medium, and a liquid crystal compound.

Item 1 is a liquid crystal composition that exhibits an optically isotropic liquid crystal phase and contains achiral component T containing a chiral agent and at least one compound 1 represented by formula (1):

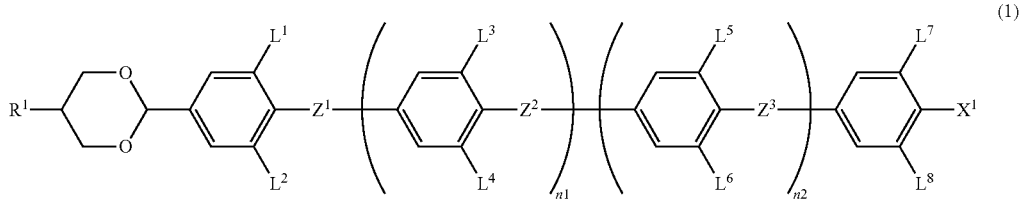

wherein, in the formula, $R^1$ is hydrogen or methyl;
$L^1, L^2, L^3, L^4, L^5, L^6, L^7$ and $L^8$ are each independently hydrogen or fluorine;
$Z^1, Z^2$ and $Z^3$ are each independently a single bond, —COO— or —CF$_2$O—, and at least one of $Z^1, Z^2$ and $Z^3$ is —COO— or —CF$_2$O—;
n1 and n2 are each independently 0 or 1;
$X^1$ is hydrogen, halogen, —SF$_5$ or alkyl having 1 to 10 carbons, and at least one of —CH$_2$— in the alkyl may be replaced by —O—, —S—, —COO— or —OCO—, at least one of —CH$_2$—CH$_2$— in the alkyl may be replaced by —CH=CH—, —CF=CF— or —C≡C—, and at least one of hydrogen in the alkyl may be replaced by fluorine or chlorine, however, a case where —O— and —CH=CH—, and —CO— and —CH=CH— are adjacent in X$^1$ is excluded.

Item 2 is the liquid crystal composition of item 1 in which compound 1 is represented by formulas (1-1-1), (1-1-2), (1-2-1) to (1-2-5), (1-3-1), (1-3-2), (1-4-1), (1-5-1) or (1-5-2) below:

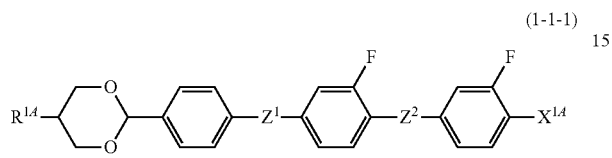
(1-1-1)

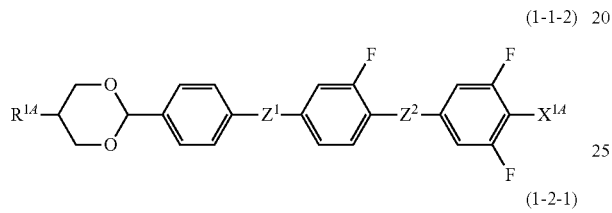
(1-1-2)

(1-2-1)

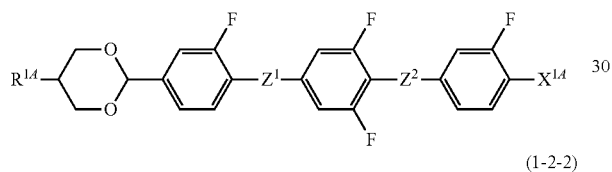
(1-2-2)

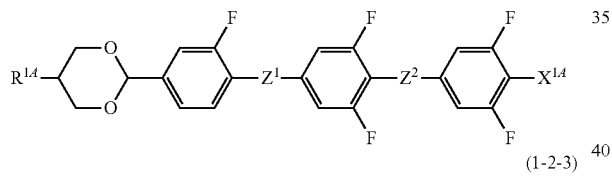
(1-2-3)

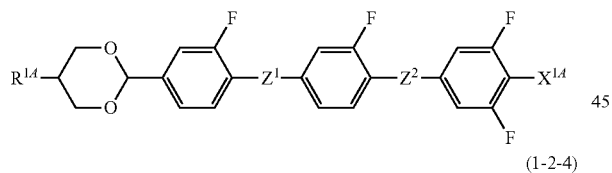
(1-2-4)

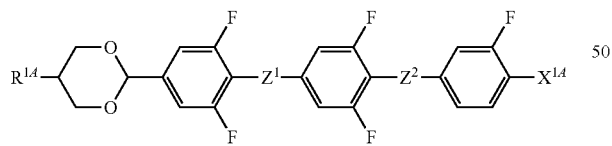
(1-2-5)

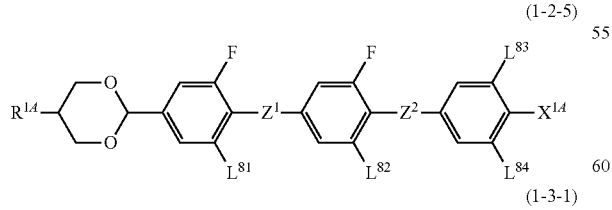
(1-3-1)

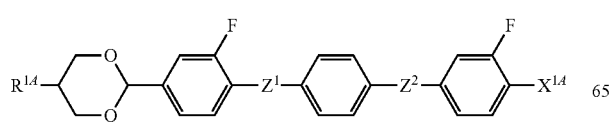

-continued

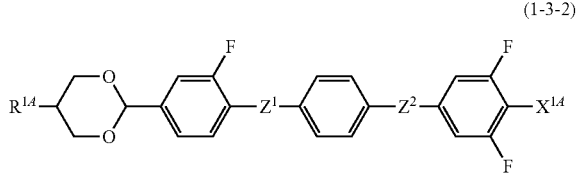
(1-3-2)

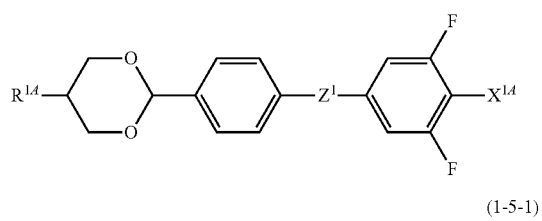
(1-4-1)

(1-5-1)

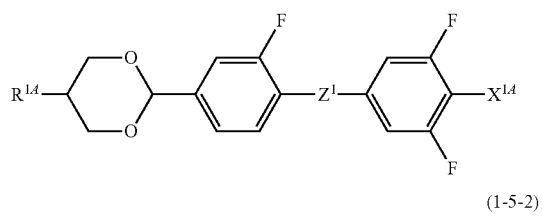
(1-5-2)

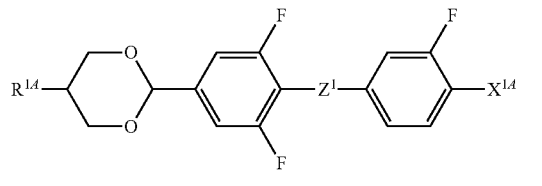

wherein, in the formula, R$^{1A}$ is hydrogen or methyl;

in formulas (1-1-1), (1-1-2), (1-2-1) to (1-2-5), (1-3-1) and (1-3-2), Z$^1$ and Z$^2$ are each independently a single bond, —COO— or —CF$_2$O—, however, at least one of Z$^1$ and Z$^2$ is —COO— or —CF$_2$O—;

in formulas (1-4-1), (1-5-1) and (1-5-2), Z$^1$ is —COO— or —CF$_2$O—, and L$^{81}$, L$^{82}$, L$^{83}$ and L$^{84}$ are each independently hydrogen or fluorine; and in the formula, X$^{1A}$ is fluorine, chlorine, —CF$_3$ or —OCF$_3$.

Item 3 is the liquid crystal composition of item 1 in which compound 1 is represented by formula (1-2-2-E), (1-2-5-E), (1-2-2-F) or (1-2-5-F):

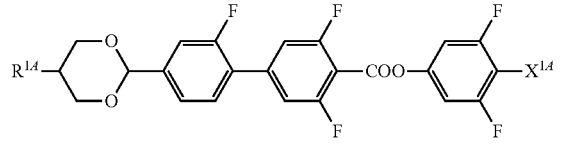
(1-2-2-E)

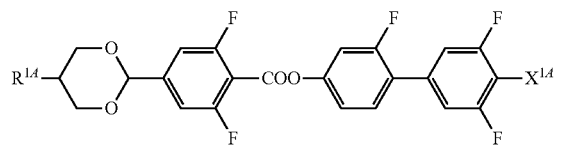
(1-2-5-E)

-continued

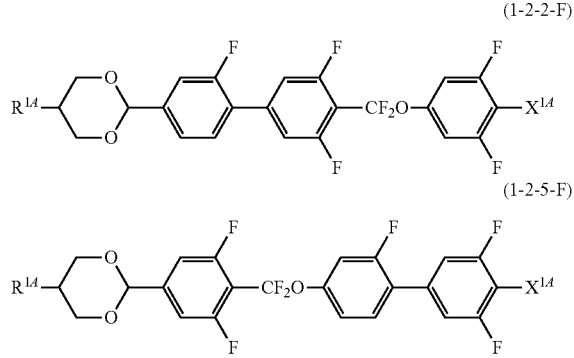

wherein, in the formula, $R^{1A}$ is hydrogen or methyl; and $X^{1A}$ is fluorine, chlorine, —$CF_3$ or —$OCF_3$.

Item 4 is the liquid crystal composition of item 2 or 3 in which $R^{1A}$ is methyl.

Item 5 is the liquid crystal composition of any one of items 1 to 4 which contains compound 1 in an amount of 1 wt % to 90 wt % based on the total weight of achiral component T.

Item 6 is the liquid crystal composition of any one of items 1 to 5 in which achiral component T contains at least one kind of compound 2 represented by formula 2:

one of —$CH_2$—$CH_2$— in the alkyl may be replaced by —CH=CH—, —CF=CF— or —C≡C—, and at least one of hydrogen in the alkyl may be replaced by fluorine or chlorine, however, a case where —O— and —CH=CH—, and —CO— and —CH=CH— are adjacent in $R^2$ is excluded;

ring $A^{21}$, ring $A^{22}$, ring $A^{23}$, ring $A^{24}$ and ring $A^{25}$ are each independently 1,4-cyclohexylene, 1,3-dioxane-2,5-diyl, 1,4-phenylene, 1,4-phenylene in which one or two of hydrogen are replaced by fluorine, or 1,4-phenylene in which two of hydrogen are each replaced by fluorine and chlorine, pyridine-2,5-diyl or pyrimidine-2,5-diyl;

$Z^{21}$, $Z^{22}$, $Z^{23}$, $Z^{24}$, $Z^{25}$ and $Z^{26}$ are each independently a single bond or alkylene having 1 to 4 carbons, and at least one of —$CH_2$— in the alkylene may be replaced by —O—, —COO— or —$CF_2$O—;

$L^{21}$, $L^{22}$ and $L^{23}$ are each independently hydrogen or fluorine;

$X^2$ is fluorine, chlorine, —$CF_3$ or —$OCF_3$; and n21, n22, n23, n24 and n25 are each independently 0 or 1, and satisfy an expression: $2 \leq n21+n22+n23+n24+n25 \leq 3$.

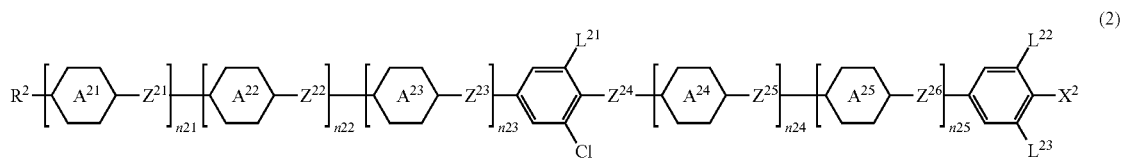

wherein, in the formula, $R^2$ is hydrogen or alkyl having 1 to 20 carbons, and at least one of —$CH_2$— in the alkyl may be replaced by —O—, —S—, —COO— or —OCO—, at least Item 7 is the liquid crystal composition of item 6 in which compound 2 is represented by formula (2-1-1-2) (2-1-2-1), (2-1-3-1) (2-1-3-2) (2-1-4-2) or (2-1-4-3):

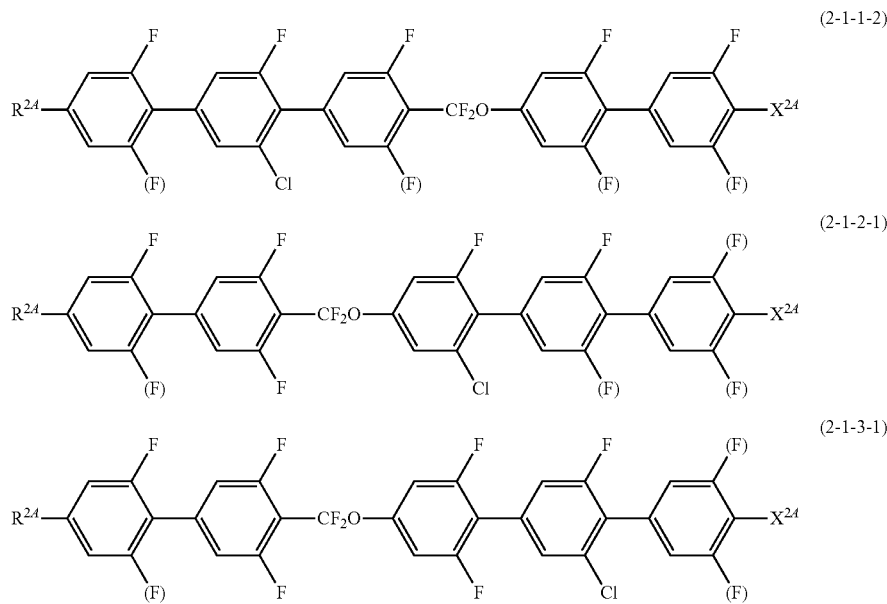

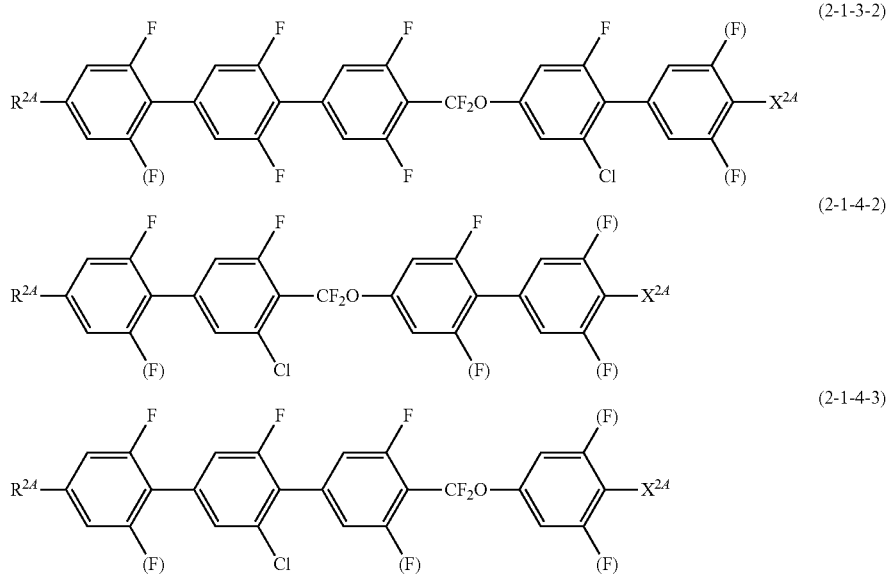

wherein, in the formula, $R^{2A}$ is alkyl having 1 to 12 carbons, alkoxy having 1 to 12 carbons, alkenyl having 2 to 12 carbons, or alkenyl having 2 to 12 carbons in which at least one of hydrogen is replaced by fluorine;

(F) is each independently hydrogen or fluorine; and $X^{2A}$ is fluorine, chlorine, —$CF_3$ or —$OCF_3$.

Item 8 is the liquid crystal composition of item 7 in which compound 2 is represented by the formula (2-1-1-2).

Item 9 is the liquid crystal composition of item 7 in which compound 2 is represented by the formula (2-1-4-3).

Item 10 is the liquid crystal composition of item 7 which contains a compound represented by the formula (2-1-1-2) and a compound represented by the formula (2-1-4-3) as compound 2.

Item 11 is the liquid crystal composition of any one of items 6 to 10 which contains compound 2 in a total amount of 0.5 wt % to 70 wt % based on the total weight of achiral component T.

Item 12 is the liquid crystal composition of any one of items 1 to 11 in which achiral component T further contains at least one kind of compound 3 represented by formula (3):

$$(3)$$

![](formula 3)

wherein, in the formula, $R^3$ is hydrogen or alkyl having 1 to 20 carbons, and at least one of —$CH_2$— in the alkyl may be replaced by —O—, —S—, —COO— or —OCO—, at least one of —$CH_2$—$CH_2$— in the alkyl may be replaced by —CH═CH—, —CF═CF— or —C≡C—, and at least one of hydrogen in the alkyl may be replaced by fluorine or chlorine, however, a case where —O— and —CH═CH—, and —CO— and —CH═CH— are adjacent in $R^3$ is excluded;

$Z^{31}$, $Z^{32}$ and $Z^{33}$ are each independently a single bond or alkylene having 1 to 4 carbons, and at least one of —$CH_2$— in the alkylene may be replaced by —O—, —COO— or —$CF_2O$—;

$L^{31}$, $L^{32}$, $L^{33}$, $L^{34}$ and $L^{35}$ are each independently hydrogen or fluorine;

$X^3$ is hydrogen, halogen, —$SF_5$ or alkyl having 1 to 10 carbons, and at least one of —$CH_2$— in the alkyl may be replaced by —O—, —S—, —COO— or —OCO—, at least one of —$CH_2$—$CH_2$— in the alkyl may be replaced by —CH═CH—, —CF═CF— or —C≡C—, and in the alkyl, at least one of hydrogen in a group in which at least one of —$CH_2$— in the alkyl is replaced by —O—, —S—, —COO— or —OCO— or in a group in which at least one of —$CH_2$—$CH_2$— in the alkyl is replaced by —CH═CH—, —CF═CF— or —C≡C— may be replaced by fluorine or chlorine, however, a case where —O— and —CH═CH—, and —CO— and —CH═CH— are adjacent in $X^3$ is excluded.

Item 13 is the liquid crystal composition of item 12 in which compound 3 is represented by formula (3-2) or (3-3):

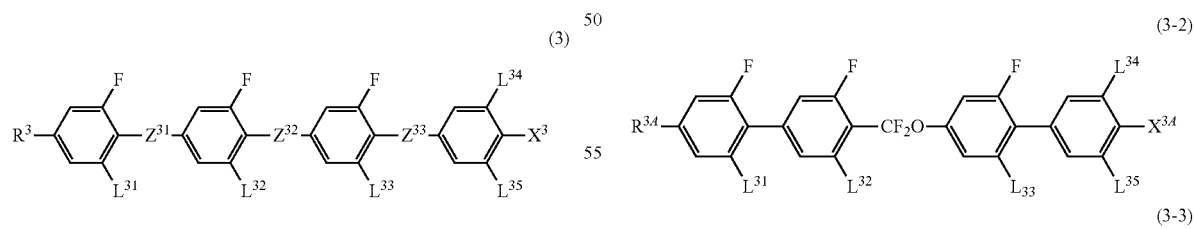

wherein, in the formula, $R^{3A}$ is each independently alkyl having 1 to 12 carbons, alkoxy having 1 to 12 carbons, alkenyl having 2 to 12 carbons, or alkenyl having 2 to 12 carbons in which at least one of hydrogen may be replaced by fluorine;

$L^{31}$ to $L^{35}$ are each independently hydrogen or fluorine; and $X^{3A}$ is fluorine, chlorine, —$CF_3$ or —$OCF_3$.

Item 14 is the liquid crystal composition of item 12 or 13 in which $R^3$ in formula (3) has a straight chain, and $R^{3A}$ in formulas (3-2) and (3-3) has a straight chain.

Item 15 is the liquid crystal composition of item 13 or 14 in which compound 3 is represented by formula (3-2).

Item 16 is the liquid crystal composition of item 13 or 14 in which compound 3 is represented by formula (3-3).

Item 17 is the liquid crystal composition of any one of items 12 to 16 which contains compound 3 in a total amount of 0.5 wt % to 70 wt % based on the total weight of achiral component T.

Item 18 is the liquid crystal composition of any one of items 12 to 17 which contains compound 1 in a total amount of 30 wt % to 70 wt %, compound 2 in a total amount of 10 wt % to 50 wt %, and compound 3 in a total amount of 10 wt % to 50 wt %, based on the total weight of achiral component T.

Item 19 is the liquid crystal composition of any one of items 1 to 18 in which achiral component T further contains at least one kind of compound 4 represented by formula (4):

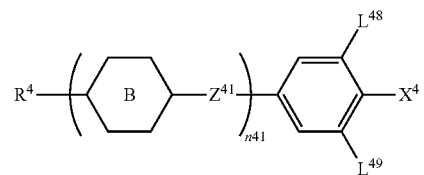
(4)

wherein, in the formula, $R^4$ is alkyl having 1 to 12 carbons, alkoxy having 1 to 12 carbons, alkenyl having 2 to 12 carbons, or alkenyl having 2 to 12 carbons in which at least one of hydrogen is replaced by fluorine;

ring B is each independently 1,4-cyclohexylene, 1,4-phenylene, 2-fluoro-1,4-phenylene, 3-fluoro-1,4-phenylene, 3,5-difluoro-1,4-phenylene, 3,5-dichloro-1,4-phenylene or pyrimidine-2,5-diyl;

$Z^{41}$ is each independently a single bond, ethylene, —COO—, —OCO—, —$CF_2O$— or —$OCF_2$—;

$L^{48}$ and $L^{49}$ are each independently hydrogen or fluorine;

$X^4$ is fluorine, chlorine, —$CF_3$ or —$OCF_3$;

n41 is 1, 2, 3 or 4, however, when n41 is 3 or 4, one of $Z^{41}$ is —$CF_2O$— or —$OCF_2$—, and when n41 is 3, a case where all of ring B are 1,4-phenylene replaced by fluorine is excluded.

Item 20 is the liquid crystal composition of item 19 in which compound 4 is at least one compound selected from the group consisting of compounds represented by formulas (4-1) to (4-9):

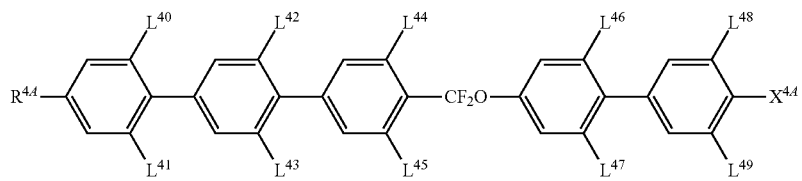
(4-1)

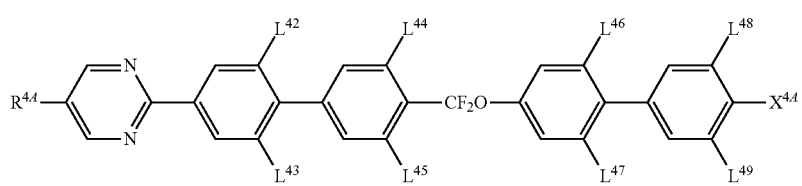
(4-2)

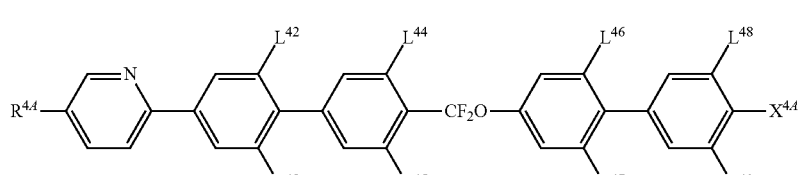
(4-3)

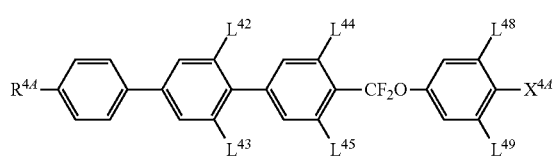
(4-4)

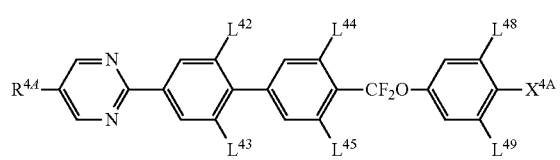
(4-5)

(4-6)

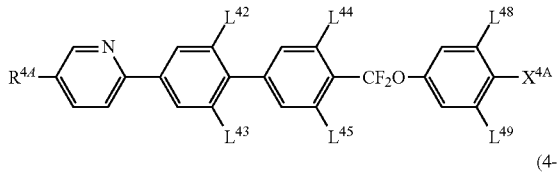

(4-7)

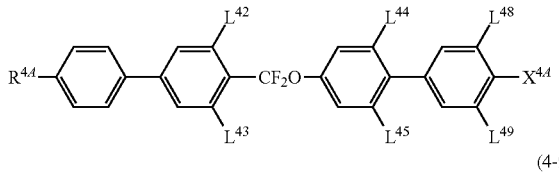

(4-8)

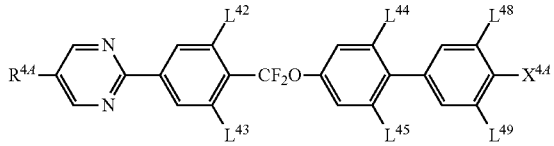

(4-9)

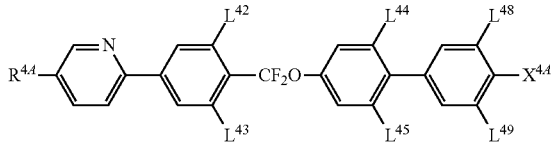

wherein, in the formula, $R^{4A}$ is each independently alkyl having 1 to 12 carbons, alkoxy having 1 to 12 carbons, alkenyl having 2 to 12 carbons, or alkenyl having 2 to 12 carbons in which at least one of hydrogen is replaced by fluorine;

$X^{4A}$ is fluorine, chlorine, —$CF_3$ or —$OCF_3$; and $L^{40}$ to $L^{49}$ are each independently hydrogen or fluorine.

Item 21 is the liquid crystal composition of any one of items 1 to 20 in which achiral component T further contains at least one kind of compound 5 represented by formula (5):

(5)

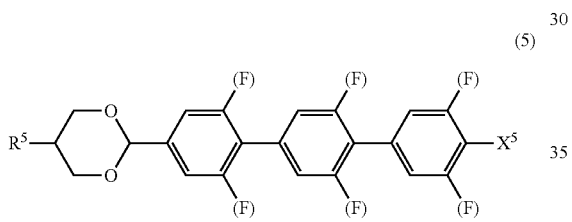

wherein, in the formula, $R^5$ is hydrogen or alkyl having 1 to 20 carbons, and at least one of —$CH_2$— in the alkyl may be replaced by —O—, —S—, —COO— or —OCO—, at least one of —$CH_2$—$CH_2$— in the alkyl may be replaced by —CH=CH—, —CF=CF— or —C≡C—, and at least one of hydrogen in the alkyl may be replaced by fluorine or chlorine, however, a case where —O— and —CH=CH—, and —CO— and —CH=CH— are adjacent in $R^5$ is excluded;

(F) is each independently hydrogen or fluorine;

$X^5$ is hydrogen, halogen, —$SF_5$ or alkyl having 1 to 10 carbons, and at least one of —$CH_2$— in the alkyl may be replaced by —O—, —S—, —COO— or —OCO, at least one of —$CH_2$—$CH_2$— in the alkyl may be replaced by —CH=CH—, —CF=CF— or —C≡C—, and in the alkyl, at least one of hydrogen in a group in which at least one of —$CH_2$— in the alkyl is replaced by —O—, —S—, —COO— or —OCO—, or in a group in which at least one of —$CH_2$—$CH_2$— in the alkyl is replaced by —CH=CH—, —CF=CF— or —C≡C— may be replaced by fluorine or chlorine, however, a case where —O— and —CH=CH—, and —CO— and —CH=CH— are adjacent in $X^5$ is excluded.

Item 22 is the liquid crystal composition of item 21 in which compound 5 is at least one compound selected from the group consisting of compounds represented by formulas (5-1) to (5-3):

(5-1)

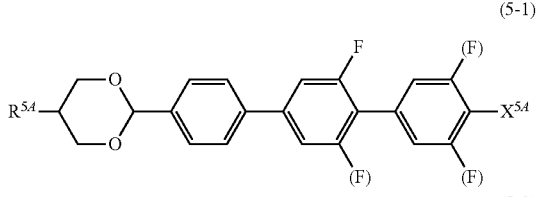

(5-2)

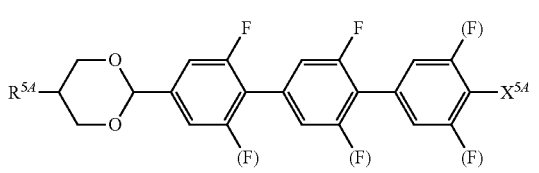

(5-3)

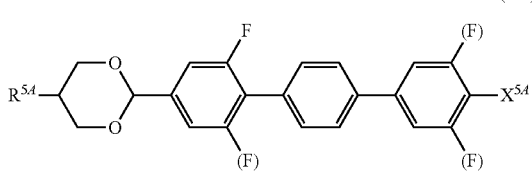

wherein, in the formula, $R^{5A}$ is alkyl having 1 to 12 carbons, alkoxy having 1 to 12 carbons, alkenyl having 2 to 12 carbons, or alkenyl having 2 to 12 carbons in which at least one of hydrogen is replaced by fluorine;

(F) is each independently hydrogen or fluorine; and $X^{5A}$ is fluorine, chlorine, —$CF_3$ or —$OCF_3$.

Item 23 is the liquid crystal composition of item 21 or 22 which contains compound 5 in a total amount of 1 wt % to 50 wt % based on the total weight of achiral component T.

Item 24 is the liquid crystal composition of any one of items 1 to 23 in which achiral component T further contains at least one kind of compound 6 represented by formula (6):

(6)

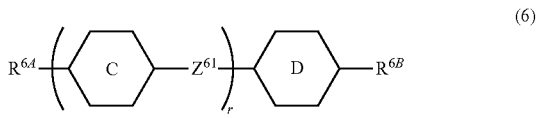

wherein, in the formula, $R^{6A}$ and $R^{6B}$ are each independently alkyl having 1 to 12 carbons, alkoxy having 1 to 12 carbons, alkenyl having 2 to 12 carbons, or alkenyl having 2 to 12 carbons in which at least one of hydrogen is replaced by fluorine;

ring C and ring D are each independently 1,4-cyclohexylene, 1,4-phenylene, 2-fluoro-1,4-phenylene, 3-fluoro-1,4-phenylene or 2,5-difluoro-1,4-phenylene;

$Z^{61}$ is each independently a single bond, ethylene, —COO— or —OCO—; and r is 1, 2 or 3.

Item 25 is the liquid crystal composition of item 24 in which compound 6 is at least one compound selected from the group consisting of compounds represented by formulas (6-1) to (6-13):

(6-1)
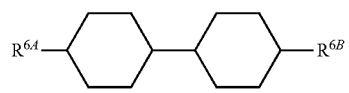

(6-2)
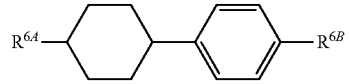

(6-3)
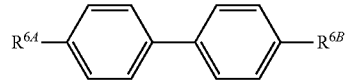

(6-4)
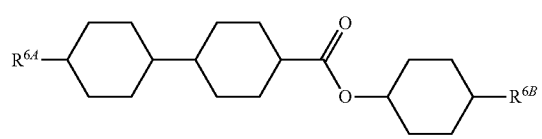

(6-5)
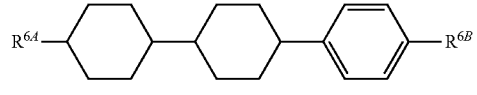

(6-6)
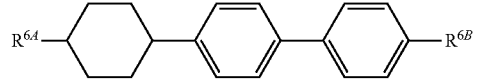

-continued (6-7)
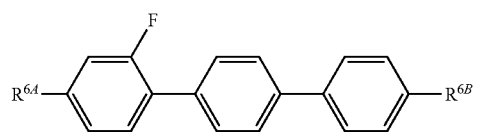

(6-8)
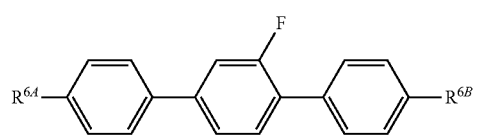

(6-9)
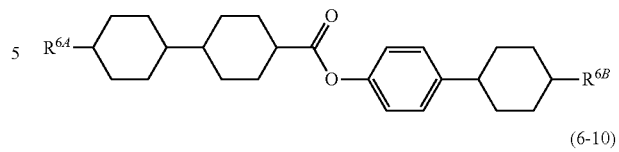

(6-10)
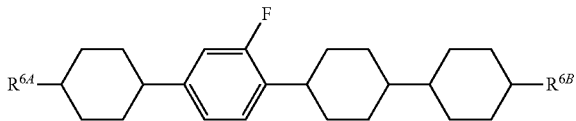

(6-11)
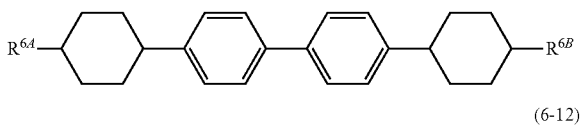

(6-12)
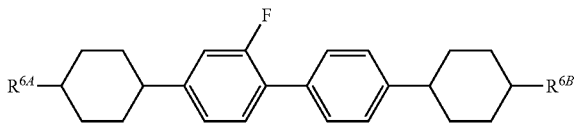

(6-13)
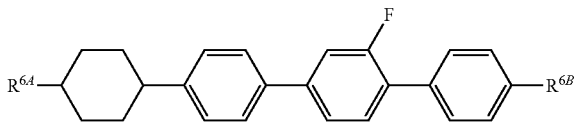

wherein, $R^{6A}$ and $R^{6B}$ are each independently alkyl having 1 to 12 carbons, alkoxy having 1 to 12 carbons, alkenyl having 2 to 12 carbons, or alkenyl having 2 to 12 carbons in which at least one of hydrogen is replaced by fluorine.

Item 26 is the liquid crystal composition of any one of items 1 to 25 in which achiral component T further contains at least one kind of compound 7 represented by formula (7):

(7)
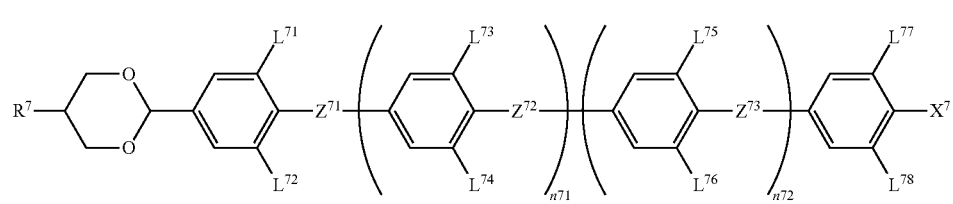

wherein, in the formula, $R^7$ is alkyl having 2 to 20 carbons, and at least one of —$CH_2$— in the alkyl may be replaced by —O—, —S—, —COO— or —OCO—, at least one of —$CH_2$—$CH_2$— in the alkyl may be replaced by —CH═CH—, —CF═CF— or —C≡C—, and at least one of hydrogen in the alkyl may be replaced by fluorine or chlorine, however, a case where —O— and —CH═CH—, and —CO— and —CH═CH— are adjacent in $R^7$ is excluded;

$L^{71}$, $L^{72}$, $L^{73}$, $L^{74}$, $L^{75}$, $L^{76}$, $L^{77}$ and $L^{78}$ are each independently hydrogen or fluorine;

$Z^{71}$, $Z^{72}$ and $Z^{73}$ are each independently a single bond or —COO—, —$CF_2O$—, and at least one thereof is —COO— or —$CF_2O$—;

n71 and n72 are each independently 0 or 1;

$X^7$ is hydrogen, halogen, —SF$_5$ or alkyl having 1 to 10 carbons, and at least one of —CH$_2$— in the alkyl may be replaced by —O—, —S—, —COO— or —OCO—, at least one of —CH$_2$—CH$_2$— in the alkyl may be replaced by —CH=CH—, —CF=CF— or —C≡C—, and in the alkyl, at least one of hydrogen in a group in which at least one of —CH$_2$— in the alkyl is replaced by —O—, —S—, —COO— or —OCO—, or in a group in which at least one of —CH$_2$—CH$_2$— in the alkyl is replaced by —CH=CH—, —CF=CF— or —C≡C— may be replaced by fluorine or chlorine, however, a case where —O— and —CH=CH—, and —CO— and —CH=CH— are adjacent in $X^7$ is excluded.

Item 27 is the liquid crystal composition of item 26 in which compound 7 is at least one compound selected from the group consisting of compounds represented by formulas (7-1) to (7-8):

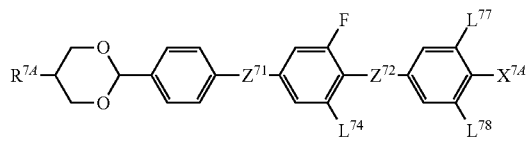
(7-1)

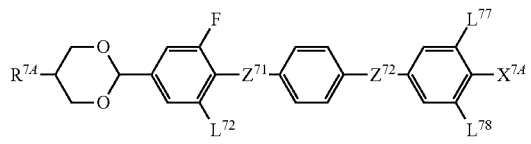
(7-2)

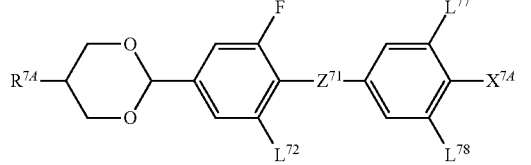
(7-3)

(7-4)

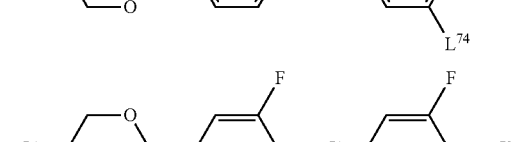
(7-5)

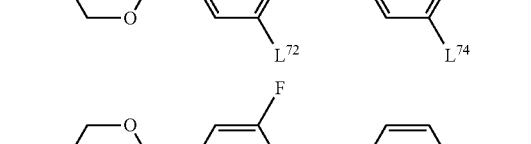
(7-6)

(7-7)

(7-8)

wherein, in the formula, $R^{7A}$ is hydrogen and methyl;

$L^{72}$, $L^{74}$, $L^{75}$, $L^{76}$, $L^{77}$ and $L^{78}$ are each independently hydrogen or fluorine;

in formulas (7-1) to (7-3) and (7-6) to (7-8), $Z^{71}$ and $Z^{72}$ are each independently a single bond, —COO— or —CF$_2$O—, however, at least one of $Z^{71}$ and $Z^{72}$ is —COO— or —CF$_2$O—, and in formulas (7-4) and (7-5), $Z^{71}$ is each independently —COO— or —CF$_2$O—, and $X^{7A}$ is fluorine, chlorine, —CF$_3$ or —OCF$_3$.

Item 28 is the liquid crystal composition of item 26 in which compound 7 is at least one compound selected from the group consisting of compounds represented by formulas (7-1-1), (7-1-2), (7-2-1) to (7-2-5), (7-3-1), (7-3-2), (7-4-1), (7-5-1) and (7-5-2):

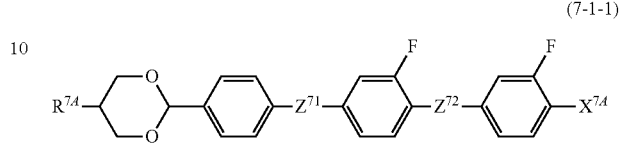
(7-1-1)

-continued

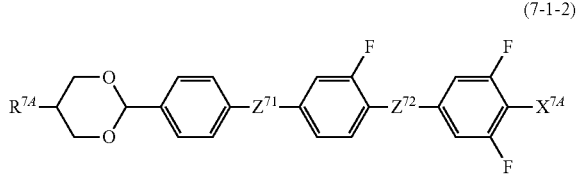
(7-1-2)

(7-2-1)
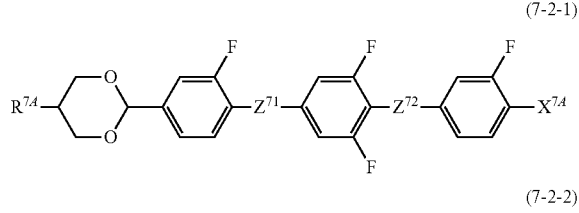

(7-2-2)
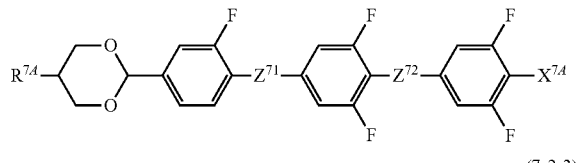

(7-2-3)
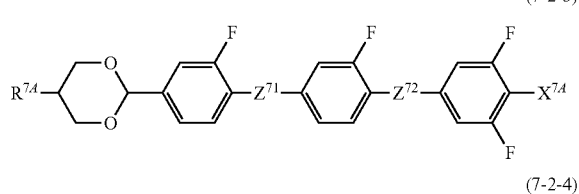

(7-2-4)
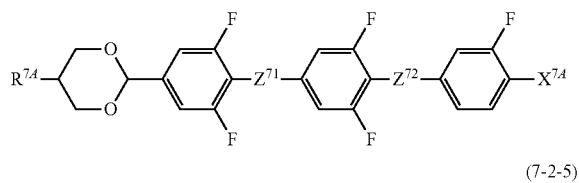

(7-2-5)
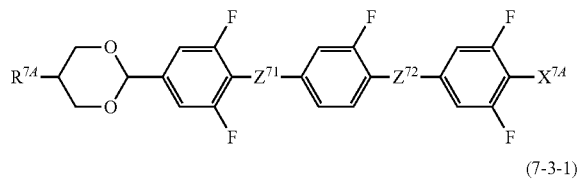

(7-3-1)
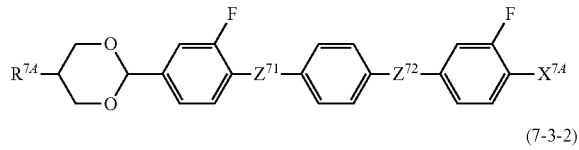

(7-3-2)
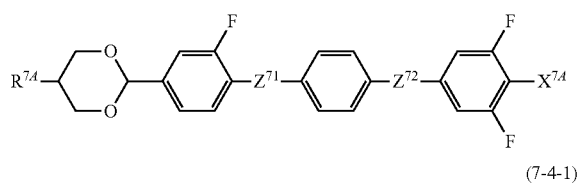

(7-4-1)
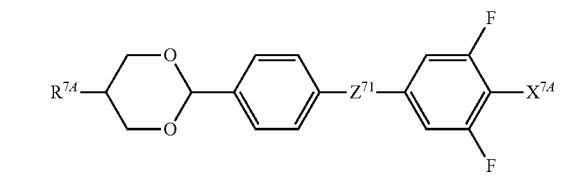

(7-5-1)
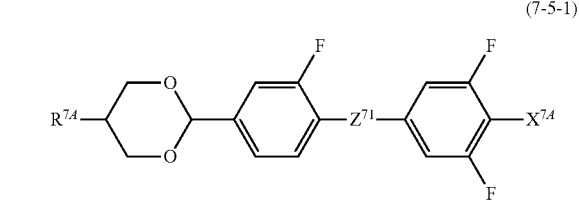

(7-5-2)
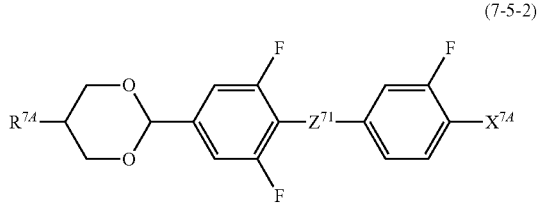

wherein, in the formula, $R^{7A}$ is alkyl having 2 to 12 carbons, alkoxy having 1 to 11 carbons, alkenyl having 2 to 12 carbons, or alkenyl having 2 to 12 carbons in which at least one of hydrogen is replaced by fluorine;

in formulas (7-1-1), (7-1-2), (7-2-1) to (7-2-5), (7-3-1) and (7-3-2), $Z^{71}$ and $Z^{72}$ are each independently a single bond, —COO— or —CF$_2$O—, however, at least one of $Z^{71}$ and $Z^{72}$ is —COO— or —CF$_2$O—, and in formulas (7-4-1), (7-5-1) and (7-5-2), $Z^{71}$ is —COO— or —CF$_2$O—; and $X^{7A}$ is fluorine, chlorine, —CF$_3$ or —OCF$_3$.

Item 29 is the liquid crystal composition of item 26 in which compound 7 is at least one compound selected from the group consisting of compounds represented by formulas (7-2-2-E), (7-2-5-E), (7-2-2-F) and (7-2-5-F):

(7-2-2-E)
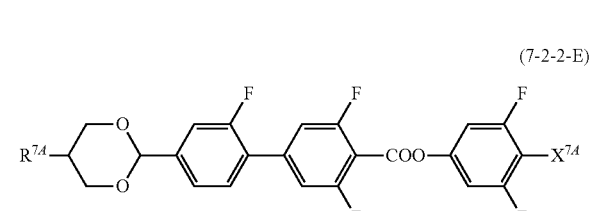

(7-2-5-E)

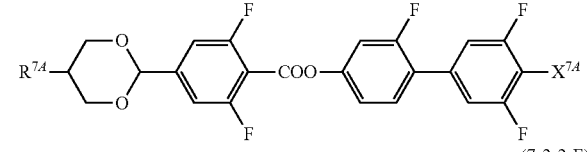

(7-2-2-F)
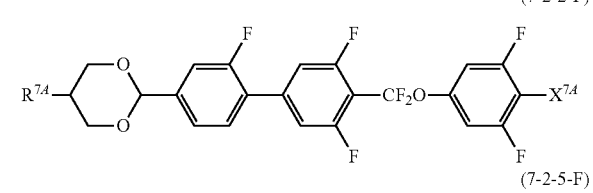

(7-2-5-F)
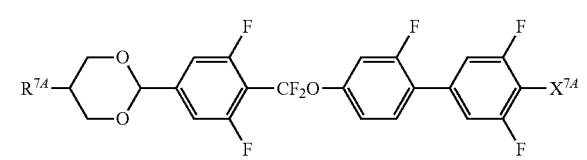

wherein, in the formula, $R^{7A}$ is alkyl having 2 to 12 carbons, alkoxy having 1 to 11 carbons, alkenyl having 2 to 12 carbons, or alkenyl having 2 to 12 carbons in which at least one of hydrogen is replaced by fluorine; and $X^{7A}$ is fluorine, chlorine, —CF$_3$ or —OCF$_3$.

Item 30 is the liquid crystal composition of any one of items 26 to 29 which contains compound 1 in a total amount of 5 wt % to 30 wt %, and containing compound 7 in a total amount of 30 wt % to 70 wt %, based on the total weight of achiral component T.

Item 31 is the liquid crystal composition of any one of items 1 to 30 in which a chiral agent is at least one compound selected from the group consisting of compounds represented by formulas (K1) to (K5):

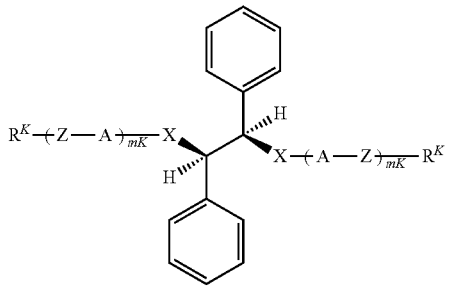
(K1)

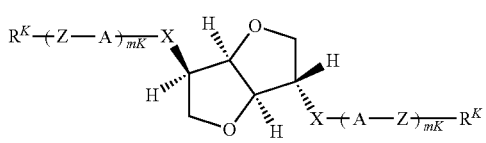
(K2)

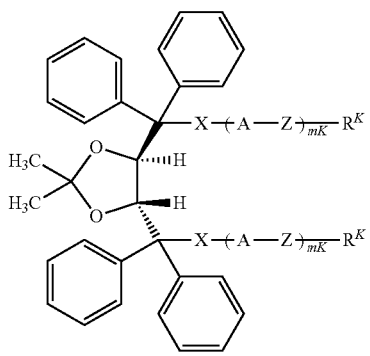
(K3)

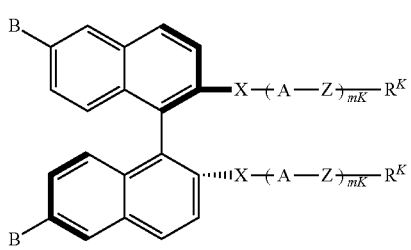
(K4)

(K5)

wherein, in the formula, $R^K$ is each independently hydrogen, halogen, —C≡N, —N=C=O, —N=C=S or alkyl having 1 to 20 carbons, and arbitrary —CH$_2$— in the alkyl may be replaced by —O—, —S—, —COO— or —OCO—, at least one of —CH$_2$— in the alkyl may be replaced by —O—, —S—, —COO— or —OCO—, at least one of —CH$_2$—CH$_2$— in the alkyl may be replaced by —CH=CH—, —CF=CF— or —C≡C—, and in the alkyl, at least one of hydrogen in a group in which at least one of —CH$_2$— in the alkyl is replaced by —O—, —S—, —COO— or —OCO—, or in a group in which at least one of —CH$_2$—CH$_2$— in the alkyl is replaced by —CH=CH—, —CF=CF— or —C≡C— may be replaced by fluorine or chlorine;

A is each independently an aromatic 6-membered to 8-membered ring, a non-aromatic 3-membered to 8-membered ring, or a condensed ring having 9 or more carbons, and at least one of hydrogen on the rings may be replaced by halogen, alkyl or haloalkyl having 1 to 3 carbons, —CH$_2$— of the ring may be replaced by —O—, —S— or —NH—, and —CH= may be replaced by —N=;

B is each independently hydrogen, halogen, alkyl having 1 to 3 carbons, haloalkyl having 1 to 3 carbons, an aromatic 6-membered to 8-membered ring, a non-aromatic 3-membered to 8-membered ring, or a condensed ring having 9 or more carbons, arbitrary hydrogen on the rings may be replaced by halogen, alkyl or haloalkyl having 1 to 3 carbons, —CH$_2$— may be replaced by —O—, —S— or —NH—, and —CH= may be replaced by —N=;

Z is each independently a single bond or alkylene having 1 to 8 carbons, and arbitrary —CH$_2$— in the alkylene may be replaced by —O—, —S—, —COO—, —OCO—, —CSO—, —OCS—, —N=N—, —CH=N— or —N=CH—, at least one of —CH$_2$—CH$_2$— in the alkylene may be replaced by —CH=CH—, —CF=CF— or —C≡C—, and in the alkylene, at least one of hydrogen in a group in which at least one of —CH$_2$— in the alkylene is replaced by —O—, —S—, —COO— or —OCO—, or in a group in which at least one of —CH$_2$—CH$_2$— in the alkylene is replaced by —CH=CH—, —CF=CF— or —C≡C— may be replaced by halogen;

X is each independently a single bond, —COO—, —OCO—, —CH$_2$O—, —OCH$_2$—, —CF$_2$O—, —OCF$_2$— or —CH$_2$CH$_2$—; and mK is each independently an integer from 1 to 4.

Item 32 is the liquid crystal composition of any one of items 1 to 30 in which the chiral agent is at least one compound selected from the group consisting of compounds represented by formulas (K4-1) to (K4-6) and (K5-1) to (K5-3):

(K4-1)

(K4-2)

-continued

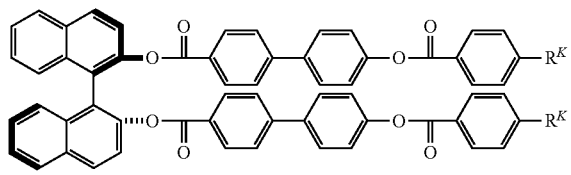
(K4-3)

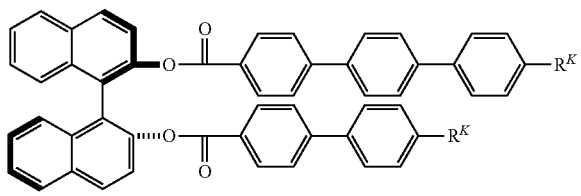
(K4-4)

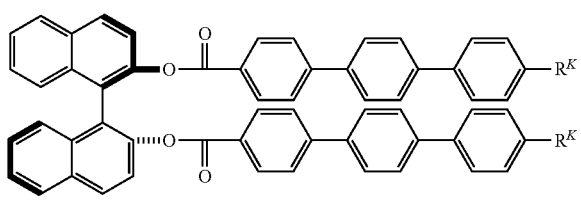
(K4-5)

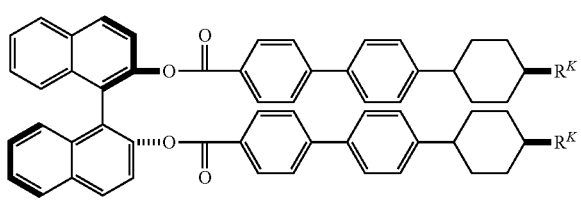
(K4-6)

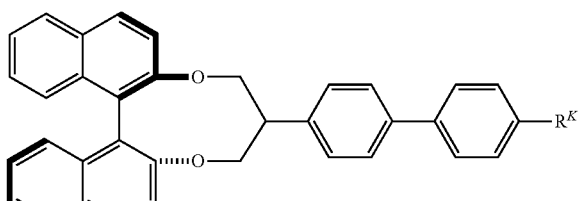
(K5-1)

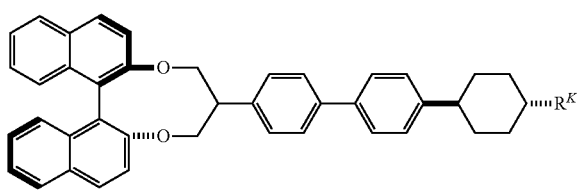
(K5-2)

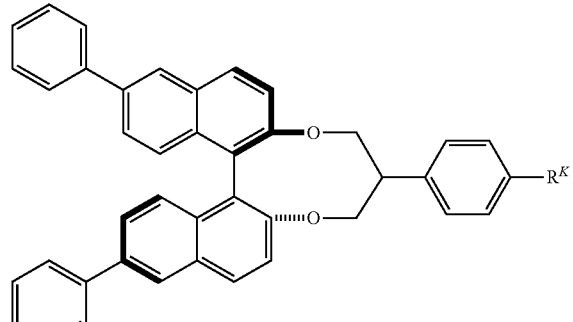
(K5-3)

wherein, in the formula, $R^K$ is each independently alkyl having 3 to 10 carbons or alkoxy having 3 to 10 carbons, and at least one of —$CH_2$— in the alkyl or the alkoxy may be replaced by —CH=CH—, however, a case where —O— and —C≡C— are adjacent is excluded.

Item 33 is the liquid crystal composition of any one of items 1 to 32 in which a chiral nematic phase is exhibited at any one in a temperature range from −20° C. to 70° C., and a helical pitch is 700 nm or less at least in part of the temperature range.

Item 34 is the liquid crystal composition of any one of items 1 to 33 which contains at least one selected from the group consisting of an antioxidant and an ultraviolet light absorbent.

Item 35 is a mixture containing the liquid crystal composition of any one of items 1 to 34 and a polymerizable monomer.

Item 36 is a polymer/liquid crystal composite material that is obtained by polymerizing the mixture of item 35 and is used in a device to be driven in an optically isotropic liquid crystal phase.

Item 37 is the polymer/liquid crystal composite material of item 36 which is obtained by polymerizing the mixture of item 35 in a non-liquid crystal isotropic phase or an optically isotropic liquid crystal phase.

Item 38 is an optical device having a liquid crystal medium arranged between substrates in which an electrode is arranged on one face or on both faces of the substrates, and an electric field applying means for applying an electric field to the liquid crystal medium through the electrode, wherein the liquid crystal medium is the liquid crystal composition of any one of items 1 to 34 or the polymer/liquid crystal composite material of item 36 or 37.

Item 39 is an optical device having one set of substrates in which an electrode is arranged on one face or on both faces thereof, and at least one thereof is transparent, a liquid crystal medium arranged between the substrates, a polarizing plate arranged outside the substrate, and an electric field applying means for applying an electric field to the liquid crystal medium through the electrode, wherein the liquid crystal medium is the liquid crystal composition of any one of items 1 to 34 or the polymer/liquid crystal composite material of item 36 or 37.

Item 40 is the optical device of item 38 or 39 in which the electrodes are composed so as to allow application of an electric field at least in two directions on at least one substrate of one set of substrates.

Item 41 is the optical device of item 38 or 39 in which the electrodes are composed so as to allow application of an electric field at least in two directions on one substrate or both substrates of one set of substrates arranged in parallel to each other.

Item 42 is the optical device of item 38 or 39 in which the electrodes are arranged in a matrix to compose pixel electrodes, each pixel has an active device, and the active device is a thin film transistor (TFT).

Item 43 is use of the liquid crystal composition of any one of items 1 to 34 in an optical device.

Item 44 is a compound represented by formula (1-2-5):

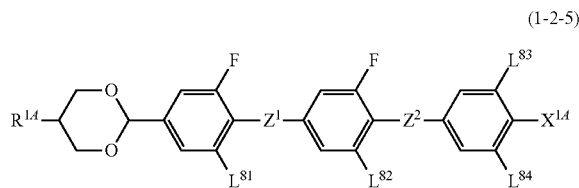

(1-2-5)

wherein, in the formula, $R^{1A}$ is hydrogen or methyl;

$L^{81}$, $L^{82}$, $L^{83}$ and $L^{84}$ are each independently hydrogen or fluorine;

$Z^1$ and $Z^2$ are each independently a single bond, —COO— or —CF$_2$O—, however, at least one of $Z^1$ and $Z^2$ is —COO— or —CF$_2$O—; and $X^{1A}$ is fluorine, chlorine, —CF$_3$ or —OCF$_3$.

Item 45 is the compound of item 44 in which in formula (1-2-5), $Z^1$ is —COO— or —CF$_2$O—; and $Z^2$ is a single bond.

Item 46 is the compound of item 44 in which in formula (1-2-5), $R^{1A}$ is hydrogen;

$Z^1$ is —COO— or —CF$_2$O—; and $Z^2$ is a single bond.

"Liquid crystal compound" herein represents a compound having a mesogen, and is not limited to a compound having a liquid crystal phase. Specifically, the liquid crystal compound is a generic term for a compound having the liquid crystal phase such as a nematic phase and a smectic phase, and a compound having no liquid crystal phase but being useful as a component of the liquid crystal composition.

"Liquid crystal medium" is a generic term for the liquid crystal composition and the polymer/liquid crystal composite.

"Achiral component" is an achiral mesogen compound, and a component containing neither an optically active compound nor a compound having a polymerizable functional group. Therefore, "achiral component" includes no chiral agent, no monomer, no polymerization initiator, no curing agent and no stabilizer.

"Chiral agent" is the optically active compound, and a component to be added with desired twisted alignment of molecules.

"Liquid crystal display device" is a generic term for a liquid crystal display panel and a liquid crystal display module.

Moreover, "optical device" means various kinds of devices that perform a function of optical modulation, optical switching or the like by utilizing an electro-optic effect. Specific examples include an optical modulator used for a display device (liquid crystal display device), an optical communication system, optical information processing and various kinds of sensor systems. With regard to optical modulation that utilizes a change of a refractive index by applying voltage to an optically isotropic liquid crystal medium, a Kerr effect is known. The Kerr effect means a phenomenon in which a value of electric birefringence $\Delta n(E)$ is proportional to a square of electric field E, and an equation: $\Delta n(E) = K\lambda E^2$ is satisfied in a material showing the Kerr effect (K: Kerr coefficient (Kerr constant), $\lambda$: wavelength). Here, the value of electric birefringence means a value of refractive index anisotropy induced when the electric field is applied to an isotropic medium.

"Liquid crystal compound," "liquid crystal composition" and "liquid crystal display device" may be occasionally abbreviated as "compound," "composition" and "device," respectively.

Moreover, a higher limit of a temperature range of the liquid crystal phase refers to a phase transition temperature between the liquid crystal phase and an isotropic phase, and may be occasionally abbreviated simply as "clearing point" or "maximum temperature." A lower limit of the temperature range of the liquid crystal phase may be occasionally abbreviated as "minimum temperature." A compound represented by formula (1) may be occasionally abbreviated as "compound (1)." The abbreviation may occasionally apply to a compound represented by formula (2) or the like. In formulas (2) to (5), a symbol such as $A^1$, B or C surrounded by a hexagonal shape corresponds to ring $A^1$, ring B or ring C, respectively. An amount of compound expressed in terms of percentage is expressed in terms of weight percentage (wt %) based on the total weight of the composition. A plurality of identical symbols such as ring $A^1$, $Y^1$ and B are described in identical formulas or different formulas, but the symbols may be identical or different.

Specific examples of "alkyl" herein include —CH$_3$, —C$_2$H$_5$, —C$_3$H$_7$, —C$_4$H$_9$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, —C$_{12}$H$_{25}$, —C$_{13}$H$_{27}$, —C$_{14}$H$_{29}$ and —C$_{15}$H$_{31}$.

Specific examples of "alkoxy" herein include —OCH$_3$, —OC$_2$H$_5$, —OC$_3$H$_7$, —OC$_4$H$_9$, —OC$_5$H$_{11}$, —OC$_6$H$_{13}$, —OC$_7$H$_{15}$, —OC$_8$H$_{17}$, —OC$_9$H$_{19}$, —OC$_{10}$H$_{21}$, —OC$_{11}$H$_{23}$, —OC$_{12}$H$_{25}$, —OC$_{13}$H$_{27}$ and —OC$_{14}$H$_{29}$.

Specific examples of "alkoxyalkyl" herein include —CH$_2$OCH$_3$, —CH$_2$OC$_2$H$_5$, —CH$_2$OC$_3$H$_7$, —(CH$_2$)$_2$OCH$_3$, —(CH$_2$)$_2$—OC$_2$H$_5$, —(CH$_2$)$_2$—OC$_3$H$_7$, —(CH$_2$)$_3$—OCH$_3$, —(CH$_2$)$_4$—OCH$_3$ and —(CH$_2$)$_5$—OCH$_3$.

Specific examples of "alkenyl" herein include —CH=CH$_2$, —CH=CHCH$_3$, —CH$_2$CH=CH$_2$, —CH=CHC$_2$H$_5$, —CH$_2$CH=CHCH$_3$, (CH$_2$)$_3$—CH=CH$_2$, —CH=CHC$_3$H$_7$, —CH$_2$CH=CHC$_2$H$_5$, —(CH$_2$)$_2$—CH=CHCH$_3$ and —(CH$_2$)$_3$—CH=CH$_2$.

Specific examples of "alkenyloxy" herein include —OCH$_2$CH=CH$_2$, —OCH$_2$CH=CHCH$_3$ and —OCH$_2$CH=CHC$_2$H$_5$.

Specific examples of "alkynyl" herein include —C≡CH, —C≡CCH$_3$, —CH$_2$C≡CH, —C≡CC$_2$H$_5$, CH$_2$C≡CCH$_3$, —$(CH_2)_2$—C≡CH, —C≡$CC_3H_7$, —$CH_2$C≡$CC_2H_5$, —$(CH_2)_2$—C≡$CCH_3$ and —C≡$C(CH_2)_5$.

Advantageous Effects of Invention

A preferred liquid crystal composition, polymer/liquid crystal composite material and so forth of the invention contain a comparatively large amount of compound represented by formula (1) to show stability to heat, light and so forth and a high maximum temperature and a low minimum temperature of an optically isotropic liquid crystal phase, and to have a large dielectric anisotropy and refractive index anisotropy.

The polymer/liquid crystal composite material in a preferred embodiment of the invention shows a high maximum temperature and a low minimum temperature of the optically isotropic liquid crystal phase, and has a low driving voltage in an optical device to be driven in the optically isotropic liquid crystal phase.

Moreover, the optical device to be driven in the optically isotropic liquid crystal phase according to the preferred embodiment of the invention can be used in a wide temperature range and can be driven at a low voltage to allow a high-speed electro-optic response, and has a large contrast ratio.

DESCRIPTION OF EMBODIMENTS

Figure 1:
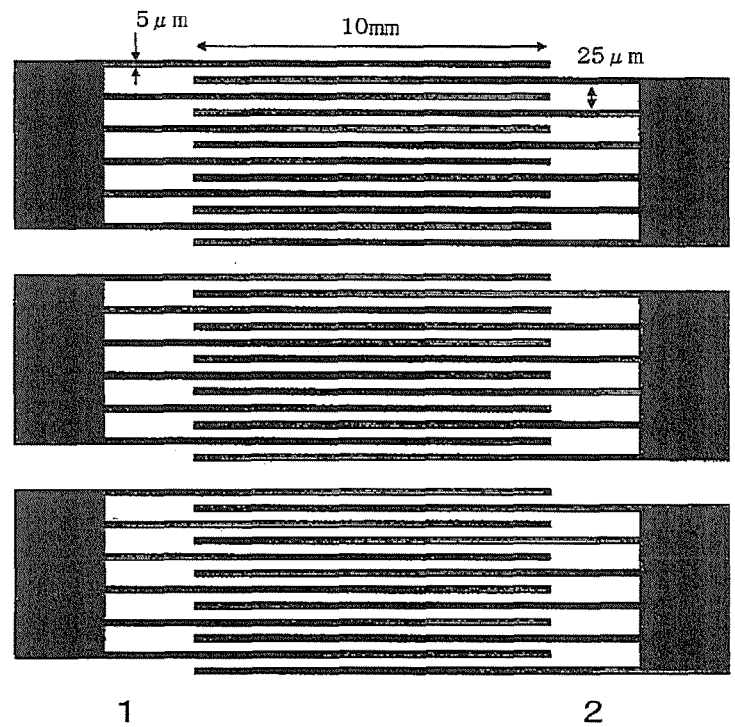
FIG. 1 shows a comb-shaped electrode substrate used in Examples.

A liquid crystal composition of the invention contains achiral component T and a chiral agent to develop an optically isotropic liquid crystal phase. The liquid crystal composition of the invention may further contain a solvent, a monomer, an initiator, a curing agent and a stabilizer (an antioxidant or an ultraviolet light absorbent) in addition to achiral component T and the chiral agent.

1. Achiral Component T

The liquid crystal composition of the invention contains achiral component T and the chiral agent to develop the optically isotropic liquid crystal phase.

Achiral component T contains compound 1, and as required, at least one compound selected from the group consisting of compounds 2 to 7. Achiral component T preferably contains compounds 2, 3, 5 and 7 in addition to compound 1, and can further contain compounds 4 and 6 according to properties required. Compounds 1 to 7 are a liquid crystal compound.

Achiral component T of the invention includes a case where one kind of compound is contained or a case where two or more kinds of compounds are contained, as compounds 1 to 7. More specifically, a liquid crystal composition of the invention may contain, as compound 1, a plurality of kinds of compound 1 represented by formula (1) and having structures different from each other. The same applies also to compounds 2 to 7.

1-1. Compound 1

The liquid crystal composition having the optically isotropic liquid crystal phase according to the invention contains achiral component T and the chiral agent, and achiral component T contains compound (1) represented by formula (1).

A first embodiment of the liquid crystal composition of the invention is a composition containing a first component and any other component whose component name is not particularly shown herein.

In $X^1$ in formula (1), specific examples of alkyl in which hydrogen is replaced by fluorine include —$CHF_2$, —$CF_3$, —$CF_2CH_2F$, —$CF_2CHF_2$, —$CH_2CF_3$, —$CF_2CF_3$, —$(CH_2)_3$—F, —$(CF_2)_3$—F, —$CF_2CHFCF_3$ and —$CHFCF_2CF_3$. Specific examples of alkoxy in which hydrogen is replaced by fluorine include —$OCHF_2$, —$OCF_3$, —$OCF_2CH_2F$, —$OCF_2CHF_2$, —$OCH_2CF_3$, —O—$(CF_2)_3$—F, —$OCF_2CHFCF_3$ and —$OCHFCF_2CF_3$. Specific examples of alkenyl in which hydrogen is replaced by fluorine include —CH=$CF_2$, —CF=CHF, —CH=$CHCH_2F$, —CH=$CHCF_3$, —$(CH_2)_2$—CH=$CF_2$, —$CH_2$CH=$CHCF_3$ and —CH=$CHCF_2CF_3$.

$R^1$ in formula (1) is hydrogen or methyl. Such $R^1$ further significantly contributes to reduction of the driving voltage in comparison with a compound in which $R^1$ is alkyl having two or more carbons.

Moreover, a compound in which $R^1$ is methyl has a higher clearing point in comparison with a compound in which $R^1$ is hydrogen.

When $X^1$ in formula (1) is fluorine, chlorine, —$SF_5$, —$CF_3$, —$OCF_3$ or —CH=CH—$CF_3$, compound (1) has a large dielectric anisotropy. When $X^1$ is fluorine, —$CF_3$ or —$OCF_3$, compound (1) is chemically stable.

Specific examples of preferred $X^1$ include fluorine, chlorine, —$CF_3$, —$CHF_2$, —$OCF_3$ and —$OCHF_2$. Specific examples of further preferred $X^1$ include fluorine, chlorine, —$CF_3$ and —$OCF_3$. When $X^1$ is chlorine or fluorine, a melting point is low, and compatibility with other liquid crystal compounds is particularly excellent. When $X^1$ is —$CF_3$, —$CHF_2$, —$OCF_3$ and —$OCHF_2$, a particularly large dielectric anisotropy is exhibited.

As compound 1, compounds represented by formulas (1-1-1), (1-1-2), (1-2-1) to (1-2-5), (1-3-1), (1-3-2), (1-4-1), (1-5-1) and (1-5-2) are preferred, and compounds represented by formulas (1-2-1) to (1-2-5) are further preferred.

The invention includes, in aralkyl component T, a case where a component is composed of one kind of compound as compound 1, and also a case where a component contains two or more kinds of compounds represented by formula (1) as compound 1.

As the case where the component is composed of two or more kinds of compounds represented by formula (1) as compound 1, compounds represented by formula (1-2-2) or formula (1-2-5) are preferred as compound 1. In the compound represented by formula (1-2-2), a compound represented by formula (1-2-2-E) or a compound represented by formula (1-2-5-F) is preferably used as compound 1. In the compound represented by formula (1-2-5), $L^{81}$, $L^{83}$ and $L^{84}$ are preferably fluorine, and $L^{82}$ is preferably hydrogen, and a compound represented by formula (1-2-5-E) or a compound represented by formula (1-2-5-F) is preferably used as compound 1.

Compound 1 is contained in an amount of, preferably, 1 to 90 wt %, further preferably, 3 to 80 wt %, particularly preferably, 5 to 50 wt %, and still further preferably, 5 to 40 wt %, based on the total weight of achiral component T.

Moreover, a total amount of compounds represented by formula (1-2-5) is preferably 5 to 30 wt %, and further preferably, 10 to 25 wt %, based on the total weight of achiral component T.

1-2. Properties of Compound 1

Compound 1 is represented by formula (1), has an unsubstituted or methyl group-substituted dioxane ring, and has at least one —COO— or —CF$_2$O— connecting group.

Under conditions in which a device is ordinarily used, compound 1 is significantly physically and chemically stable, and has a comparatively good compatibility with other compounds. A composition containing the compound is stable under the conditions in which the device is ordinarily used. Accordingly, when compound 1 is used in the liquid crystal composition, a temperature range of the optically isotropic liquid crystal phase can be extended, and the composition can be used in the form of a display device in a wide temperature range.

Moreover, compound 1 has a large dielectric anisotropy and a comparatively large refractive index anisotropy, and therefore compound 1 is useful as a component for decreasing a driving voltage of the liquid crystal composition to be driven in the optically isotropic liquid crystal phase.

Thus, compound 1 has an excellent feature of decreasing the driving voltage by using only a small amount of the compound. Moreover, compound 1 exhibits a significantly large dielectric anisotropy.

1-3. Synthesis of Compound 1

Compound 1 can be prepared by suitably combining techniques in synthetic organic chemistry. Methods for introducing an objective terminal group, ring and bonding group into a starting material are described in Organic Syntheses (John Wiley & Sons, Inc.), Organic Reactions (John Wiley & Sons, Inc.), Comprehensive Organic Synthesis (Pergamon Press), New Experimental Chemistry Course (Shin Jikken Kagaku Koza in Japanese) (Maruzen Co., Ltd.), or the like.

For example, compound 1 can be prepared by correspondingly applying the method described in JP 2959526 B.

2-1. Compound 2

The liquid crystal composition or the like of the invention may also contain at least one kind of compound 2 represented by formula (2) in addition compound 1.

R$^2$ in formula (2) is preferably alkyl having 1 to 12 carbons, alkoxy having 1 to 12 carbons, alkenyl having 2 to 12 carbons, or alkenyl having 2 to 12 carbons in which at least one of hydrogen is replaced by fluorine.

In view of stability or dielectric anisotropy of the compound, ring A$^{21}$, ring A$^{22}$, ring A$^{23}$, ring A$^{24}$ and ring A$^{25}$ in formula (2) is preferably 1,4-phenylene, or 1,4-phenylene in which one or two of hydrogen are replaced by fluorine.

Z$^{21}$, Z$^{22}$, Z$^{23}$, Z$^{24}$, Z$^{25}$ and Z$^{26}$ in formula (2) are independently a single bond or alkylene having 1 to 4 carbons, and at least one of —CH$_2$— in the alkylene may be replaced by —O—, —COO— or —CF$_2$O—. All of Z$^{21}$, Z$^{22}$, Z$^{23}$, Z$^{24}$, Z$^{25}$ and Z$^{26}$ in formula (2) are preferably a single bond or at least one of Z$^{21}$, Z$^{22}$, Z$^{23}$, Z$^{24}$, Z$^{25}$ and Z$^{26}$ is preferably —COO— or —CF$_2$O—. When compatibility with other liquid crystal compounds is emphasized, at least one of Z$^{21}$, Z$^{22}$, Z$^{23}$, Z$^{24}$, Z$^{25}$ and Z$^{26}$ is preferably —CF$_2$O—.

In formula (2), n24 is, particularly preferably, 1 and Z$^{25}$ is —CF$_2$O—.

X$^2$ in formula (2) is fluorine, chlorine, —CF$_3$, —CHF$_2$, —CH$_2$F, —OCF$_3$, —OCHF$_2$, —OCH$_2$F, —OCF$_2$CFHCF$_3$ or —CH=CHCF$_3$, and is preferably fluorine, chlorine, —CF$_3$ and —OCF$_3$.

In compound 2, a compound represented by formula (2-1) is preferably used.

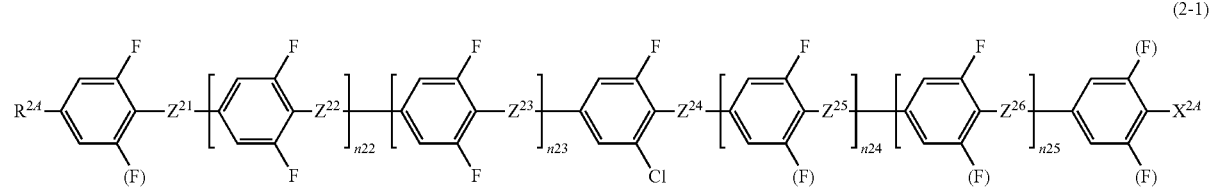

(2-1)

wherein, in the formula, R$^{24}$ is alkyl having 1 to 12 carbons, alkoxy having 1 to 12 carbons, alkenyl having 2 to 12 carbons, or alkenyl having 2 to 12 carbons in which at least one of hydrogen is replaced by fluorine;

Z$^{21}$, Z$^{22}$, Z$^{23}$, Z$^{24}$, Z$^{25}$ and Z$^{26}$ are each independently a single bond or alkylene having 1 to 4 carbons, and at least one of —CH$_2$— in the alkylene may be replaced by —O—, —OCO— or —CF$_2$O—;

X$^{24}$ is fluorine, chlorine, —CF$_3$ or —OCF$_3$; and (F) each independently represents hydrogen or fluorine.

In R$^{24}$ in formula (2) and formula (2-1), and in alkenyl in Z$^{21}$ to Z$^{26}$, a preferred configuration of —CH=CH— depends on a position of a double bond. A trans configuration is preferred in alkenyl having the double bond in an odd-numbered position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$ and —C$_2$H$_4$CH=CHC$_2$H$_5$. A cis configuration is preferred in alkenyl having the double bond in an even-numbered position, such as —CH$_2$CH=CHCH$_3$, —CH$_2$CH=CHC$_2$H$_5$ and —CH$_2$CH=CHC$_3$H$_7$. An alkenyl compound having the preferred configuration has a high maximum temperature or a wide temperature range of the liquid crystal phase. A detailed description is found in Mol. Cryst. Liq. Cryst., 1985, 131, 109 and Mol. Cryst. Liq. Cryst., 1985, 131, 327.

Z$^{21}$, Z$^{22}$, Z$^{23}$, Z$^{24}$, Z$^{25}$ and Z$^{26}$ are each independently a single bond or —CF$_2$O—, and when compatibility with other liquid crystal compounds is emphasized, at least one of Z$^{21}$, Z$^{22}$, Z$^{23}$, Z$^{24}$, Z$^{25}$ and Z$^{26}$ is preferably —CF$_2$O—.

In formula (2-1), n 24 is, particularly preferably, 1 and Z$^{25}$ is —CF$_2$O—.

In compound 2, compounds represented by formulas (2-1-1) to (2-1-5) are further preferably used.

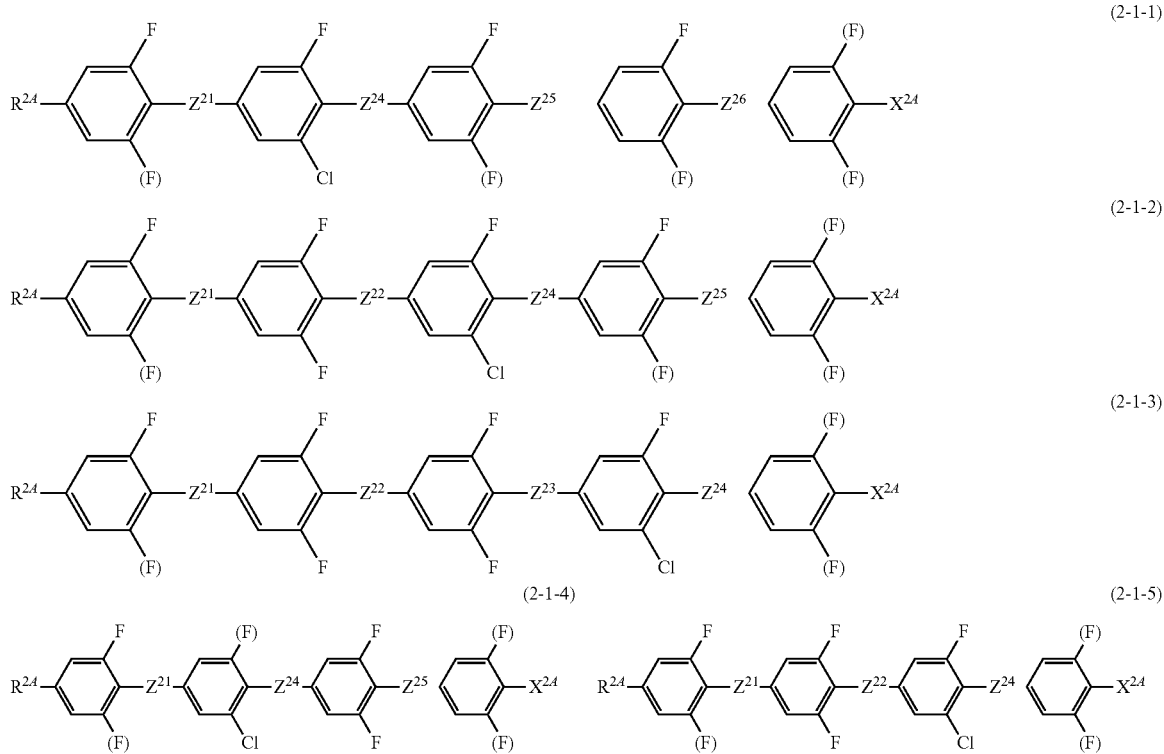
wherein, in the formula, $R^{2A}$, $Z^{21}$ to $Z^{26}$, $X^{2A}$ and (F) are defined in a manner identical with the definitions in formula (2-1).
In the case where compounds represented by formulas (2-1-1) to (2-1-5) are used as compound 2, compounds represented by formulas (2-1-1-1) to (2-1-1-3), (2-1-2-1) to (2-1-2-3), (2-1-3-1) to (2-1-3-3), (2-1-4-1) to (2-1-4-3) and (2-1-5-1) to (2-1-5-3) below are preferably used, and compounds represented by formulas (2-1-1-1), (2-1-1-2), (2-1-2-1), (2-1-2-2), (2-1-3-1), (2-1-3-2), (2-1-4-2), (2-1-4-3) and (2-1-5-3) below are further preferably used.
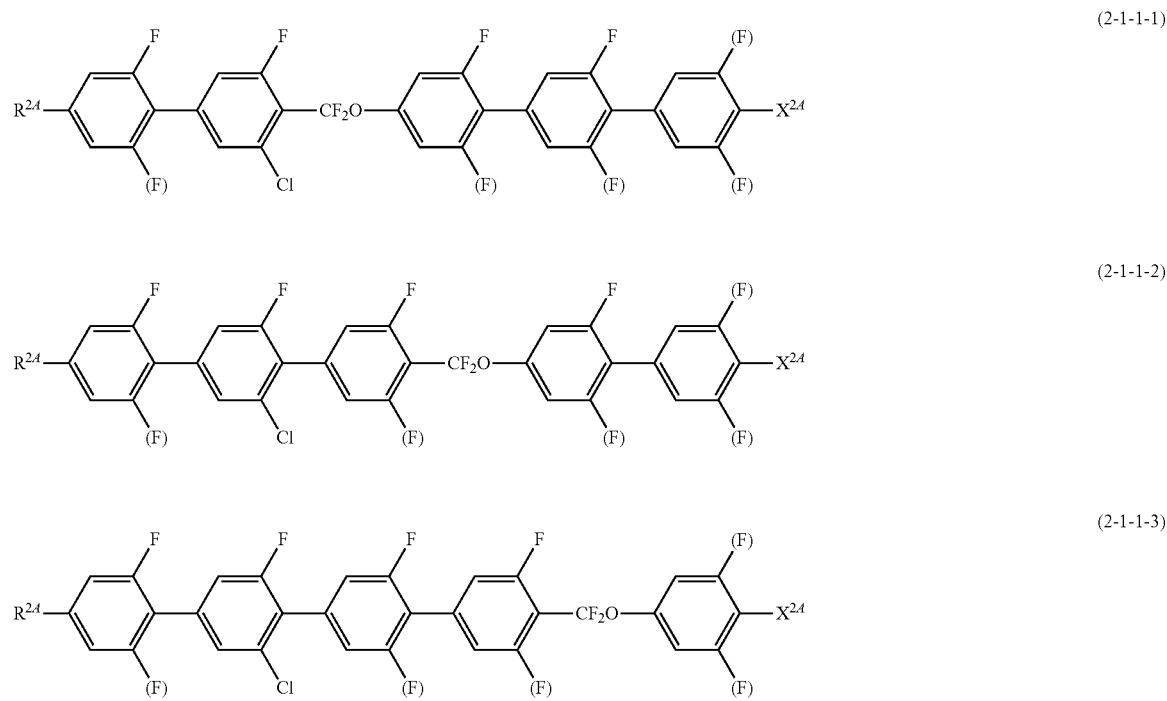

-continued
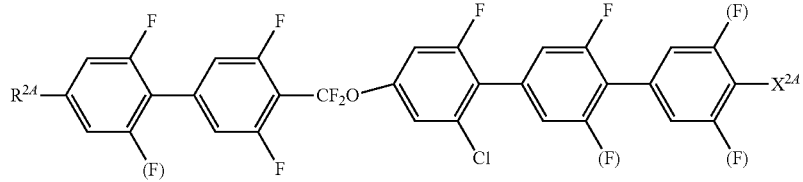 (2-1-2-1)
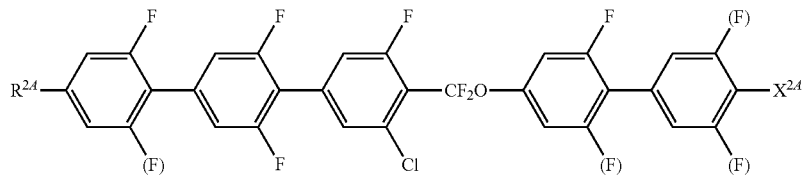 (2-1-2-2)
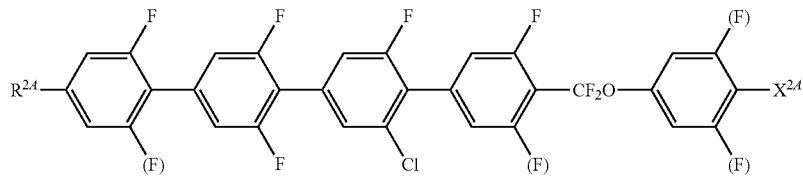 (2-1-2-3)
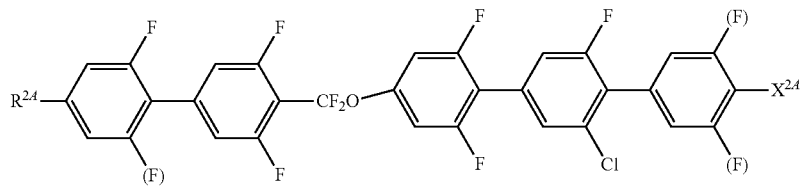 (2-1-3-1)
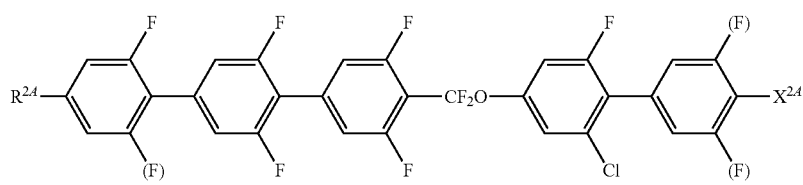 (2-1-3-2)
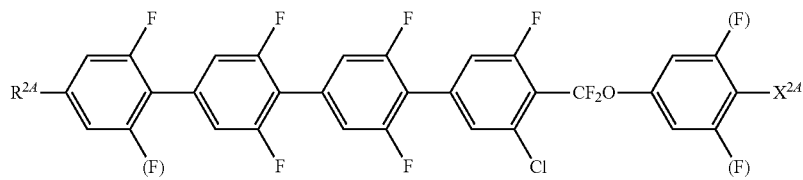 (2-1-3-3)
(2-1-4-1)
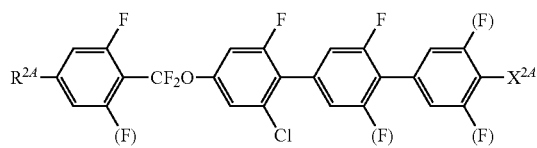
(2-1-4-2)
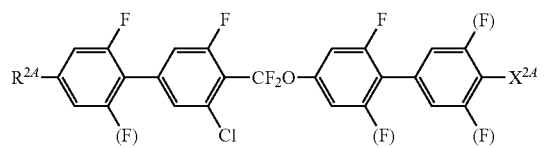
(2-1-4-3)
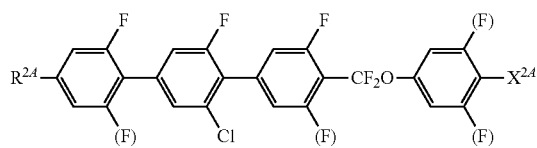
(2-1-5-1)
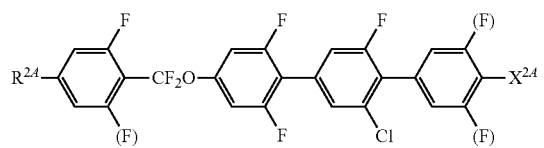

(2-1-5-2)

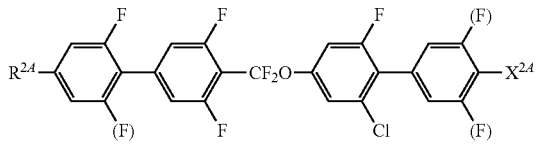

(2-1-5-3)

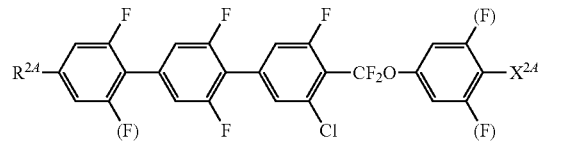

wherein, in the formula, $R^{2A}$, (F) and $X^{2A}$ are defined in a manner identical with the definitions in formula (2-1).

The invention includes, in achiral component T, a case where a component is composed of one kind of compound as compound 2, and also a case where a component contains two or more kinds of compounds represented by formula (2) as compound 2.

Compound 2 has a good compatibility, a large dielectric anisotropy, and a large refractive index anisotropy.

Compound 2 is contained in a total amount of, preferably, 0.5 wt % to 70 wt %, further preferably, 5 wt % to 60 wt %, and particularly preferably, 10 wt % to 50 wt %, based on the total weight of achiral component T.

2-2. Properties of Compound 2

Compound 2 has a chlorobenzene ring. Compound 2 is significantly physically and chemically stable under conditions in which the device is ordinarily used, and has a good compatibility with other liquid crystal compounds. Furthermore, the compound is hard to develop the smectic phase. A composition containing the compound is stable under the conditions in which the device is ordinarily used. Accordingly, a temperature range of a cholesteric phase can be extended in the composition, and the composition can be used in the form of a display device in a wide temperature range. Furthermore, the compound has a large dielectric anisotropy and refractive index anisotropy, and therefore is useful as a component for decreasing a driving voltage and increasing reflectance in the composition to be driven in the cholesteric phase.

Physical properties such as a clearing point, the refractive index anisotropy and the dielectric anisotropy can be arbitrarily adjusted by suitably selecting a combination of n22 to n25, left-terminal group $R^{2A}$ and a group on a rightmost benzene ring and a replacement position thereof ((F) and $X^{2A}$), or bonding groups $Z^{22}$ to $Z^{26}$ in formula (2). An effect of the combination of n22, n23, n24 and n25, kinds of left-terminal group $R^{2A}$, right-terminal group $X^{2A}$, bonding groups $Z^{21}$ to $Z^{26}$ and (F) on the physical properties of compound 2 will be described below.

In general, in formula (2), a compound satisfying an expression: n22+n23+n24+n25=2 has a high clearing point, and a compound satisfying an expression: n22+n23+n24+n25=1 has a low melting point.

When $R^{2A}$ in formula (2) is alkenyl, a preferred configuration depends on a position of a double bond. A trans configuration is preferred in alkenyl having the double bond in an odd-numbered position, such as —CH=CHCH₃, —CH=CHC₂H₅, —CH=CHC₃H₇, —CH=CHC₄H₉, —C₂H₄CH=CHCH₃ and —C₂H₄CH=CHC₂H₅. A cis configuration is preferred in alkenyl having the double bond in an even-numbered position, such as —CH₂CH=CHCH₃, —CH₂CH=CHC₂H₅ and —CH₂CH=CHC₃H₇. An alkenyl compound having the preferred configuration has a high maximum temperature or a wide temperature range of the liquid crystal phase. A detailed description is found in Mol. Cryst. Liq. Cryst., 1985, 131, 109 and Mol. Cryst. Liq. Cryst., 1985, 131, 327.

Bonding groups $Z^{21}$ to $Z^{26}$ in formula (2) are a single bond or —CF₂O—. Therefore, compound (2) is comparatively chemically stable and is comparatively hard to cause degradation. Furthermore, when a bonding group is a single bond, viscosity is small. Moreover, when a bonding group is —CF₂O—, the dielectric anisotropy is large.

When right terminal group $X^2$ in formula (2) is fluorine, chlorine or —OCF₃, low temperature compatibility with other liquid crystal compounds is excellent, and when $X^2$ is —CF₃, an effect of a decrease in the driving voltage is large.

When (F) in formula (2) is hydrogen, a melting point is low, and when (F) is fluorine, the dielectric anisotropy is large.

A compound having objective physical properties can be obtained by suitably selecting kinds of ring structures, terminal groups, bonding groups or the like in formula (2).

3-1. Compound 3

The liquid crystal composition of the invention may also include at least one kind of compound 3 represented by formula (3) in addition to compound 1. For example, the liquid crystal composition of the invention may also include at least one compound selected from the group consisting of compounds 2 and 3 in addition to compound 1.

A preferred configuration of —CH=CH— in alkenyl included in formula (3) depends on a position of a double bond. A trans configuration is preferred in alkenyl having the double bond in an odd-numbered position, such as —CH=CHCH₃, —CH=CHC₂H₅, —CH=CHC₃H₇, —CH=CHC₄H₉, —C₂H₄CH=CHCH₃ and —C₂H₄CH=CHC₂H₅. A cis configuration is preferred in alkenyl having the double bond in an even-numbered position, such as —CH₂CH=CHCH₃, —CH₂CH=CHC₂H₅ and —CH₂CH=CHC₃H₇. An alkenyl compound having the preferred configuration has a high maximum temperature or a wide temperature range of the liquid crystal phase. A detailed description is found in Mol. Cryst. Liq. Cryst., 1985, 131, 109 and Mol. Cryst. Liq. Cryst., 1985, 131, 327.

In formula (3), $Z^{31}$, $Z^{32}$ and $Z^{33}$ are independently a single bond, —COO— or —CF₂O—, but at least one of $Z^{31}$, $Z^{32}$ and $Z^{33}$ is —CF₂O—. Preferred examples of $Z^{31}$, $Z^{32}$ and $Z^{33}$ include a single bond and —CF₂O—.

In formula (3), $L^{31}$, $L^{32}$, $L^{33}$, $L^{34}$ and $L^{35}$ are independently hydrogen or fluorine. When $Z^{32}$ is —COO— or —CF₂O—, $L^{32}$, $L^{34}$ and $L^{35}$ are preferably fluorine, and when $Z^{33}$ is —COO— or —CF₂O—, $L^{33}$, $L^{34}$ and $L^{35}$ are preferably fluorine.

In formula (3), $X^3$ is hydrogen, halogen, —SF₅ or alkyl having 1 to 10 carbons, and at least one of —CH₂— in the alkyl may be replaced by —O—, —S—, —CH=CH— or —C≡C—, and at least one of hydrogen in the alkyl or in a group in which at least one of —CH₂— in the alkyl is replaced by —O—, —S—, —COO—, —OCO—, —CH=CH—, —CF=CF— or —C≡C— may be replaced by fluorine.

Specific examples of alkyl in which at least one of hydrogen is replaced by halogen include —CH₂F, —CHF₂, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, —CHFCF$_2$CF$_3$, —(CH$_2$)$_4$—F, —(CF$_2$)$_4$—F, —(CH$_2$)$_5$—F and —(CF$_2$)$_5$—F.

Specific examples of alkoxy in which at least one of hydrogen is replaced by halogen include —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F and —O—(CF$_2$)$_5$—F.

Specific examples of alkenyl in which at least one of hydrogen is replaced by halogen include —CH=CHF, —CH=CF$_2$, —CF=CHF, —CH=CHCH$_2$F, —CH=CHCF$_3$, —(OH$_2$)$_2$—CH=CF$_2$, —CH$_2$CH=CHCF$_3$, —CH=CHCF$_3$ and —CH=CHCF$_2$CF$_3$.

In formula (3), X$^3$ is preferably fluorine, chlorine, —CF$_3$, —CHF$_2$, —OCF$_3$ and —OCHF$_2$, and further preferably, fluorine, chlorine, —CF$_3$ and —OCF$_3$.

In compound 3, compounds represented by formulas (3-1) to (3-3) are preferably used, compounds represented by formulas (3-2) and (3-3) are further preferably used, compounds represented by formulas (3-2A) to (3-2H) and (3-3A) to (3-3D) are still further preferably used, compounds represented by formulas (3-2A) to (3-2D), (3-3A) and (3-3B) are particularly preferably used, and compounds represented by formulas (3-2A), (3-2C) and (3-3A) are most preferably used.

wherein, in the formula, R$^{3A}$ is each independently alkyl having 1 to 12 carbons, alkoxy having 1 to 12 carbons, alkenyl having 2 to 12 carbons, or alkenyl having 2 to 12 carbons in which at least one of hydrogen may be replaced by fluorine;

L$^{31}$ to L$^{35}$ are each independently hydrogen or fluorine; and

X$^{3A}$ is fluorine, chlorine, —CF$_3$, or —OCF$_3$.

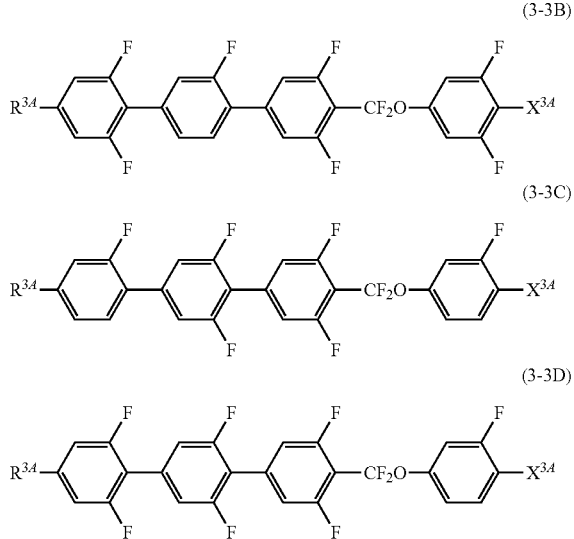

wherein, in the formula, $R^{34}$ is independently alkyl having 1 to 12 carbons, alkoxy having 1 to 12 carbons, alkenyl having 2 to 12 carbons, or alkenyl having 2 to 12 carbons in which at least one of hydrogen is replaced by fluorine; and $X^{34}$ is fluorine, chlorine, —$CF_3$ or —$OCF_3$.

The invention includes, in achiral component T, a case where a component is composed of one kind of compound as compound 3, and also a case where a component contains two or more kinds of compounds represented by formula (3) as compound (3).

Compound 3 has a comparatively high clearing point, and has a large dielectric anisotropy and a large refractive index anisotropy. Compound 3 is contained in a total amount of, preferably, 0.5 wt % to 70 wt %, further preferably, 5 wt % to 60 wt %, and particularly preferably, 10 wt % to 50 wt %, based on the total weight of achiral component T.

3-2. Properties of Compound 3

Compound 3 has four benzene rings and at least one —$CF_2O$— connecting group. Compound 3 is significantly physically and chemically stable under conditions in which the device is ordinarily used, and has a good compatibility with other liquid crystal compounds. A composition containing the compound is stable under the conditions in which the device is ordinarily used. Accordingly, the temperature range of the cholesteric phase can be extended in the composition, and the composition can be used in the form of a display device in a wide temperature range. Furthermore, the compound has a large dielectric anisotropy and refractive index anisotropy, and therefore is useful as a component for decreasing the driving voltage and increasing the reflectance in the composition to be driven in the cholesteric phase.

Physical properties such as the clearing point, the refractive index anisotropy and the dielectric anisotropy can be arbitrarily adjusted by suitably selecting left-terminal group $R^3$, groups on benzene rings ($L^{31}$ to $L^{35}$, and $X^3$), or bonding groups $Z^{31}$ to $Z^{33}$ in formula (3). An effect of kinds of left-terminal group $R^3$, groups on the benzene rings ($L^{31}$ to $L^{35}$, and $X^3$), or bonding groups $Z^{31}$ to $Z^{33}$ on the physical properties of compound (3) will be described below.

When $R^3$ in formula (3) is alkenyl, a preferred configuration of —CH=CH— in the alkenyl depends on a position of a double bond. A trans configuration is preferred in alkenyl having the double bond in an odd-numbered position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$ and —C$_2$H$_4$CH=CHC$_2$H$_5$. A cis configuration is preferred in alkenyl having the double bond in an even-numbered position, such as —CH$_2$CH=CHCH$_3$, —CH$_2$CH=CHC$_2$H$_5$ and —CH$_2$CH=CHC$_3$H$_7$. An alkenyl compound having the preferred configuration has a high maximum temperature or a wide temperature range of the liquid crystal phase. A detailed description is found in Mol. Cryst. Liq. Cryst., 1985, 131, 109 and Mol. Cryst. Liq. Cryst., 1985, 131, 327.

When bonding groups $Z^{31}$, $Z^{32}$ and $Z^{33}$ are a single bond or —$CF_2O$—, compound (3) has a small viscosity. When bonding groups $Z^{31}$, $Z^{32}$ and $Z^{33}$ are —$CF_2O$—, compound (3) has a large dielectric anisotropy. When $Z^{31}$, $Z^{32}$ and $Z^{33}$ are a single bond or —$CF_2O$—, compound (3) is comparatively chemically stable and comparatively hard to cause degradation.

When right-terminal group $X^3$ in formula (3) is fluorine, chlorine, —$SF_5$, —$CF_3$, —$CHF_2$, —$CH_2F$, —$OCF_3$, —$OCHF_2$ or —$OCH_2F$, compound (3) has a large dielectric anisotropy. When $X^3$ is fluorine, —$OCF_3$ or —$CF_3$, compound (3) is chemically stable.

When the number of fluorine in $L^{31}$ to $L^{35}$ is large in formula (3), the dielectric anisotropy is large. When $L^{31}$ is hydrogen, compound (3) has an excellent compatibility with other liquid crystals. The dielectric anisotropy is particularly large when both $L^{34}$ and $L^{35}$ are fluorine.

As described above, a compound having objective physical properties can be obtained by suitably selecting kinds of terminal groups, bonding groups or the like.

4. Compound 4

The liquid crystal composition of the invention may also contain at least one kind of compound 4 represented by formula (4) in addition to compound 1. For example, the liquid crystal composition of the invention may also contain at least one selected from the group consisting of compounds 2 to 4 in addition to compound 1.

Compound 4 is suitable for preparation of a composition having a large dielectric anisotropy or compatibility at a low temperature. Compound 4 is contained in a total amount of, preferably, 5 wt % to 40 wt %, further preferably, 5 wt % to 30 wt %, and particularly preferably, 5 wt % to 20 wt %, based on the total weight of achiral component T.

$R^4$ in formula (4) is alkyl having 1 to 12 carbons, alkoxy having 1 to 12 carbons, alkenyl having 2 to 12 carbons, or alkenyl having 2 to 12 carbons in which at least one of hydrogen is replaced by fluorine. Preferred $R^4$ in formula (4) is alkyl having 1 to 12 carbons for increasing stability to ultraviolet light or stability to heat. $R^4$ in formula (4) is preferably alkenyl having 2 to 12 carbons in view of decreasing the viscosity, and preferably, alkyl having 1 to 12 carbons in view of increasing the stability to heat or the stability to ultraviolet light.

In $R^4$ in formula (4), preferred alkyl is methyl, ethyl, propyl, butyl, pentyl, hexyl, heptyl or octyl, and further preferred alkyl is ethyl, propyl, butyl, pentyl or heptyl for decreasing the viscosity.

In $R^4$ in formula (4), preferred alkoxy is methoxy, ethoxy, propoxy, butoxy, pentyloxy, hexyloxy or heptyloxy, and further preferred alkoxy is methoxy or ethoxy for decreasing the viscosity.

In $R^4$ in formula (4), preferred alkenyl is vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl or 5-hexenyl, and further preferred alkenyl is vinyl, 1-propenyl, 3-butenyl or 3-pentenyl for decreasing the viscosity.

In $R^4$ in formula (4), a preferred configuration of —CH=CH— in the alkenyl depends on a position of a double bond. In order to decrease the viscosity, trans is preferred in alkenyl such as 1-propenyl, 1-butenyl, 1-pentenyl, 1-hexenyl, 3-pentenyl and 3-hexenyl. Cis is preferred in alkenyl such as 2-butenyl, 2-pentenyl and 2-hexenyl. In the alkenyl, straight-chain alkenyl is preferred to branched-chain alkenyl.

In $R^4$ in formula (4), specific preferred examples of alkenyl in which at least one of hydrogen is replaced by fluorine include 2,2-difluorovinyl, 3,3-difluoro-2-propenyl, 4,4-difluoro-3-butenyl, 5,5-difluoro-4-pentenyl and 6,6-difluoro-5-hexenyl, and in order to decrease the viscosity of the liquid crystal composition, 2,2-difluorovinyl and 4,4-difluoro-3-butenyl are preferred.

Alkyl in $R^4$ in formula (4) includes no cyclic alkyl. Alkoxy includes no cyclic alkoxy. Alkenyl includes no cyclic alkenyl. Alkenyl in which at least one of hydrogen is replaced by fluorine includes no cyclic alkenyl in which at least one of hydrogen is replaced by fluorine.

Ring B in formula (4) is independently 1,4-cyclohexylene, 1,4-phenylene, 2-fluoro-1,4-phenylene, 3-fluoro-1,4-phenylene, 3,5-difluoro-1,4-phenylene, 3,5-dichloro-1,4-phenylene or pyrimidine-2-5-diyl. At least two of ring B thereof when n41 is two or more may be identical or different. Ring B in formula (4) is preferably 1,4-phenylene or 3-fluoro-1,4-phenylene for increasing optical anisotropy, and 1,4-cyclohexylene for decreasing the viscosity.

$Z^{41}$ in formula (4) is independently a single bond, ethylene, —COO—, —OCO—, —CF$_2$O— or —OCF$_2$—, however, one of $Z^{12}$ when n41 is 3 or 4 is —CF$_2$O—. At least two of $Z^{12}$ when n41 is 2 or more may be identical or different. $Z^{41}$ in formula (4) is preferably a single bond for decreasing the viscosity. $Z^{41}$ in formula (4) is preferably —CF$_2$O— for increasing the dielectric anisotropy and achieving good compatibility.

$L^{48}$ and $L^{49}$ in formula (4) are independently hydrogen or fluorine, both of $L^{48}$ and $L^{49}$ are preferably fluorine for increasing the dielectric anisotropy, and both of $L^{48}$ and $L^{49}$ are preferably hydrogen for increasing the clearing point.

$X^4$ in formula (4) is fluorine, chlorine, —CF$_3$ or —OCF$_3$. $X^4$ is preferably —CF$_3$ for increasing the dielectric anisotropy, fluorine or —OCF$_3$ for achieving good compatibility, and chlorine for increasing the refractive index anisotropy.

In compound 4, compounds represented by formulas (4-1) to (4-9) are preferably used. In $L^{40}$ to $L^{49}$ in the above formulas, as the number of fluorine is larger, the dielectric anisotropy is larger.

In the compounds, compounds represented by formulas (4-1) to (4-3) have a high clearing point and excellent compatibility as a pentacyclic compound. Compounds represented by formulas (4-4) to (4-6) have a high clearing point and large Δn. Compounds represented by formulas (4-7) to (4-9) have excellent compatibility.

5-1. Compound 5

The liquid crystal composition of the invention may further contain at least one kind of compound 5 represented by formula (5) in addition to compound 1. For example, the liquid crystal composition of the invention may also contain at least one selected from the group consisting of compounds 2 to 4 in addition to compound 1.

In $R^{5A}$ in formula (5), a preferred configuration of —CH=CH— in alkenyl depends on a position of a double bond. Specifically, a trans configuration is preferred in alkenyl having the double bond in an odd-numbered position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$ and —C$_2$H$_4$CH=CHC$_2$H$_5$, and a cis configuration is preferred in alkenyl having the double bond in an even-numbered position, such as —CH$_2$CH=CHCH$_3$, —CH$_2$CH=CHC$_2$H$_5$ and —CH$_2$CH=CHC$_3$H$_7$. In formula (5), an alkenyl compound having the preferred configuration has a high maximum temperature or a wide temperature range of the liquid crystal phase. A detailed description is found in Mol. Cryst. Liq. Cryst., 1985, 131, 109 and Mol. Cryst. Liq. Cryst., 1985, 131, 327.

$X^5$ in formula (5) is hydrogen, halogen, —SF$_5$ or alkyl having 1 to 10 carbons, and at least one of —CH$_2$— in the alkyl may be replaced by —O—, —S—, —COO— or —OCO—, at least one of —CH$_2$—CH$_2$— in the alkyl may be replaced by —CH=CH—, —CF=CF— or —C≡C—, and in the alkyl, at least one of hydrogen in a group in which at least one of —CH$_2$— in the alkyl is replaced by —O—, —S—, —COO— or —OCO—, or in a group in which at least one of —CH$_2$—CH$_2$— in the alkyl is replaced by —CH=CH—, —CF=CF— or —C≡C— may be replaced by fluorine or chlorine, however, a case where —O— and —CH=CH—, and —CO— and —CH=CH— are adjacent in $X^5$ is excluded.

In $R^{5A}$ and $X^5$ in formula (5), specific examples of alkyl in which at least one of hydrogen is replaced by fluorine or chlorine include —CHF$_2$, —CF$_3$, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$ and —CHFCF$_2$CF$_3$.

In $R^{5A}$ and $X^5$ in formula (5), specific examples of alkoxy in which at least one of hydrogen is replaced by fluorine or chlorine include —OCHF$_2$, —OCF$_3$, —OCF$_2$CH$_2$F, —OCF$_2$CHF$_2$—OCH$_2$CF$_3$, —O—(CF$_2$)$_3$—F, —OCF$_2$CHFCF$_3$ and —OCHFCF$_2$CF$_3$.

In $R^{5A}$ and $X^5$ in formula (5), specific examples of alkenyl in which at least one of hydrogen is replaced by fluorine or chlorine include —CH=CF$_2$, —CF=CHF, —CH=CHCH$_2$F, —CH=CHCF$_3$, —(CH$_2$)$_2$—CH=CF$_2$, —CH$_2$CH=CHCF$_3$ and —CH=CHCF$_2$CF$_3$.

Specific examples of $X^5$ in formula (5) include fluorine, chlorine, —CF$_3$, —CHF$_2$, —OCF$_3$ and —OCHF$_2$, and fluorine, chlorine, —CF$_3$ and —OCF$_3$ are preferred. When $X^5$ in formula (5) is chlorine or fluorine, a melting point of compound 5 is comparatively low, and compatibility with other liquid crystal compounds is particularly excellent. When $X^5$ in formula (5) is —CF$_3$, —CHF$_2$, —OCF$_3$ and —OCHF$_2$, compound 5 exhibits a comparatively large dielectric anisotropy.

When $X^5$ in formula (5) is fluorine, chlorine, —SF$_5$, —CF$_3$, —OCF$_3$ or —CH=CH—CF$_3$, the dielectric anisotropy of compound 5 is comparatively large, and when $X^5$ is fluorine, —CF$_3$ or —OCF$_3$, compound 5 is comparatively chemically stabilized.

In compound 5, compounds represented by formulas (5-1) to (5-4) are preferably used, compounds represented by (5-1) to (5-3) are further preferred, and among the compounds, compounds represented by formulas (5-1-1), (5-1-2), (5-2-1) to (5-2-4), (5-3-1) and (5-3-2) are particularly preferred, and compounds represented by formulas (5-2-1), (5-2-2) and (5-3-2) are most preferred.

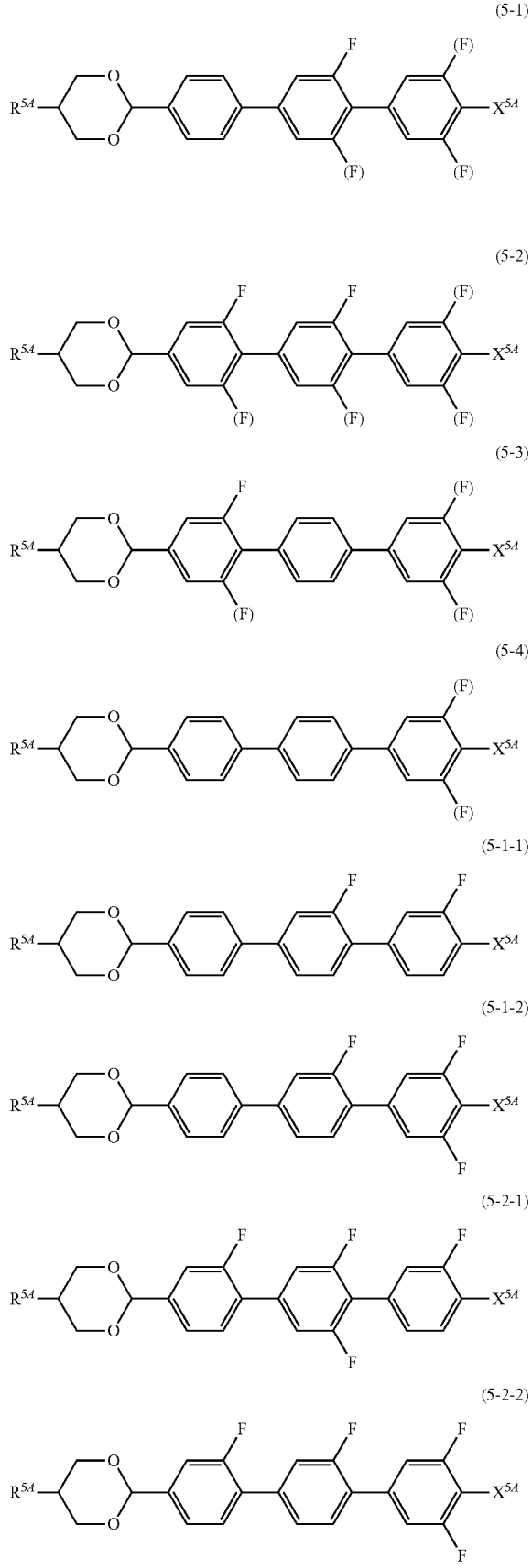
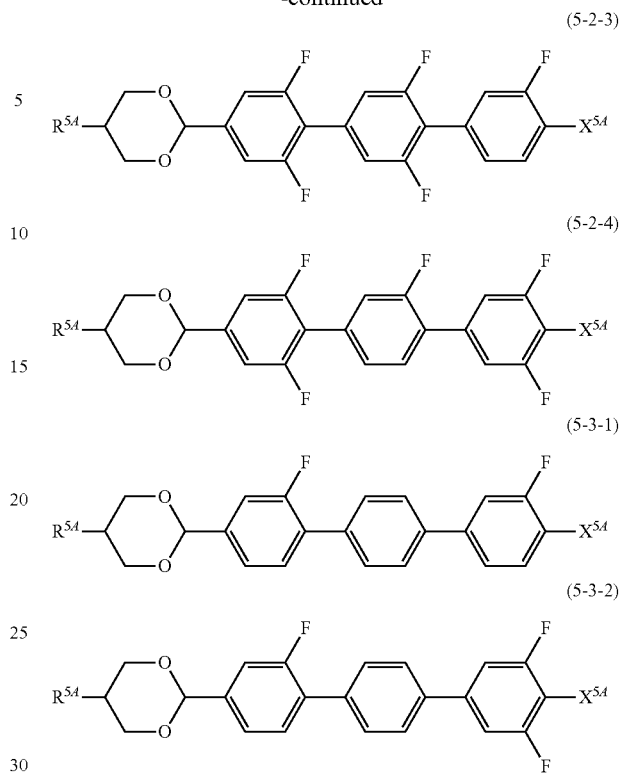

wherein, in the formula, $R^{5A}$ is alkyl having 1 to 12 carbons, alkoxy having 1 to 12 carbons, alkenyl having 2 to 12 carbons, or alkenyl having 2 to 12 carbons in which at least one of hydrogen is replaced by fluorine;

(F) is each independently hydrogen or fluorine; and $X^{5A}$ is fluorine, chlorine, —$CF_3$ or —$OCF_3$.

The invention includes, in achiral component T, a case where a component is composed of one kind of compound as compound 5, and also a case where a component contains two or more kinds of compounds represented by formula (5) as compound 5.

Compound 5 is suitable for preparation of a composition having a large dielectric anisotropy.

In order to increase the clearing point, compound 5 is contained in a total amount of, preferably, 1.0 wt % or more based on the total weight of achiral component T. Moreover, for decreasing a minimum temperature of the liquid crystal phase, compound 5 is contained in a total amount of, preferably, 1 wt % to 50 wt % based on the total weight of achiral component T. Furthermore, compound 5 is contained in a total amount of, preferably, 1 wt % to 25 wt %, and further preferably, 1 wt % to 15 wt %, based on the total weight of achiral component T.

5-2. Properties of Compound 5

Compound 5 has a dioxane ring and three benzene rings. Compound 5 is significantly physically and chemically stable under conditions in which the device is ordinarily used, and has a comparatively good compatibility with other liquid crystal compounds even though the clearing point is high. A composition containing compound 5 is stable under the conditions in which the device is ordinarily used. Accordingly, the temperature range of the optically isotropic liquid crystal phase can be extended in the composition containing compound 5, and the composition can be used in the form of a display device in a wide temperature range.

Furthermore, compound 5 is useful as a component for decreasing the driving voltage of the composition to be driven in the optically isotropic liquid crystal phase. When a blue phase is allowed to develop in a composition in a preferred embodiment in which the chiral agent and compound 5 are contained, a uniform blue phase without coexistence with an N* phase and an isotropic phase is formed. Thus, the composition in the preferred embodiment in which compound 5 is contained easily exhibits the uniform blue phase.

5-3. Synthesis of Compound 5

Next, a synthesis of compound 5 will be described. Compound 5 can be prepared by suitably combining techniques in synthetic organic chemistry. Methods for introducing an objective terminal group, ring and bonding group into a starting material are described in Organic Syntheses (John Wiley & Sons, Inc.), Organic Reactions (John Wiley & Sons, Inc.), Comprehensive Organic Synthesis (Pergamon Press), New Experimental Chemistry Course (Shin Jikken Kagaku Koza in Japanese) (Maruzen Co., Ltd.), or the like.

For example, a compound represented by formula (5) according to the invention can be prepared also by correspondingly applying the method described in Patent JP 2959526 B.

A fifth component of achiral component T easily exhibits the blue phase and is effective in increasing the clearing point.

6. Compound 6

The liquid crystal composition of the invention may further contain at least one kind of compound 6 represented by formula (6) in addition to compound 1.

For example, the liquid crystal composition of the invention may also contain at least one compound selected from the group consisting of compounds 2 to 6 in addition to compound 1.

Compound 6 has a small absolute value of dielectric anisotropy, and is close to neutrality. A compound in which r is 1 in formula (6) is effective mainly in adjusting the viscosity or a value of refractive index anisotropy. Moreover, a compound in which r is 2 or 3 in formula (6) is effective in extending the temperature range of the optically isotropic liquid crystal phase, such as increasing the clearing point, or in adjusting the value of refractive index anisotropy.

When a content of the compound represented by formula (6) is increased, the driving voltage of the liquid crystal composition is increased and the viscosity is decreased. Therefore, as long as a desired value of viscosity of the liquid crystal composition is satisfied, the content thereof is desirably as small as possible. The content of the sixth component in achiral component T is preferably 0 wt % to 40 wt %, further preferably, 1 wt % to 40 wt %, and particularly preferably, 1 wt % to 20 wt %, based on the total weight of achiral component T.

$R^{6A}$ and $R^{6B}$ in formula (6) are each independently alkyl having 1 to 12 carbons, alkoxy having 1 to 12 carbons, alkenyl having 2 to 12 carbons, or alkenyl having 2 to 12 carbons in which at least one of hydrogen is replaced by fluorine. In order to decrease the viscosity of compound 6, $R^{6A}$ and $R^{6B}$ in formula (6) are preferably alkenyl having 2 to 12 carbons. In order to increase the stability to ultraviolet light or increasing the stability to heat, $R^{6A}$ and $R^{6B}$ in formula (6) are preferably alkyl having 1 to 12 carbons.

In $R^{6A}$ and $R^{6B}$ in formula (6), alkyl is preferably methyl, ethyl, propyl, butyl, pentyl, hexyl, heptyl or octyl, and in order to decrease the viscosity, preferably, ethyl, propyl, butyl, pentyl or heptyl.

In $R^{6A}$ and $R^{6B}$ in formula (6), alkoxy is preferably methoxy, ethoxy, propoxy, butoxy, pentyloxy, hexyloxy or heptyloxy, and in order to decrease the viscosity, preferably, methoxy or ethoxy.

In $R^{6A}$ and $R^{6B}$ in formula (6), a preferred configuration of —CH=CH— in alkenyl depends on a position of a double bond. A trans configuration is preferred in alkenyl having the double bond in an odd-numbered position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$ and —C$_2$H$_4$CH=CHC$_2$H$_5$. A cis configuration is preferred in alkenyl having the double bond in an even-numbered position, such as —CH$_2$CH=CHCH$_3$, —CH$_2$CH=CHC$_2$H$_5$ and —CH$_2$CH=CHC$_3$H$_7$. An alkenyl compound having the preferred configuration has a high maximum temperature or a wide temperature range of the liquid crystal phase. A detailed description is found in Mol. Cryst. Liq. Cryst., 1985, 131, 109 and Mol. Cryst. Liq. Cryst., 1985, 131, 327.

In $R^{6A}$ and $R^{6B}$ in formula (6), alkenyl in which at least one of hydrogen is replaced by fluorine is preferably 2,2-difluorovinyl, 3,3-difluoro-2-propenyl, 4,4-difluoro-3-butenyl, 5,5-difluoro-4-pentenyl and 6,6-difluoro-5-hexenyl. In order to decrease the viscosity of a composition containing compound 6, $R^{6A}$ and $R^{6B}$ are preferably 2,2-difluorovinyl and 4,4-difluoro-3-butenyl.

Ring C and ring D in formula (6) are independently 1,4-cyclohexylene, 1,4-phenylene, 2-fluoro-1,4-phenylene, 3-fluoro-1,4-phenylene or 2,5-difluoro-1,4-phenylene, and at least two of ring C when r is two or more may be identical or different. In order to increase the optical anisotropy of compound 6, ring C and ring D are preferably 1,4-phenylene or 3-fluoro-1,4-phenylene. In order to decrease the viscosity of compound 6, ring C and ring D are 1,4-cyclohexylene.

$Z^{61}$ in formula (6) is each independently a single bond, ethylene, —COO— or —OCO, and at least two of $Z^{61}$ when r is two or more may be identical or different. Preferred $Z^{61}$ is a single bond for decreasing the viscosity.

In compound 6, compounds represented by formulas (6-1) to (6-13) are preferably used.

In the compounds, compounds represented by formulas (6-1) to (6-3) have a comparatively low viscosity, compounds represented by formulas (6-4) to (6-8) have a comparatively high clearing point, and compounds represented by formulas (6-9) to (6-13) have a comparatively high clearing point.

7-1. Compound 7

The liquid crystal composition of the invention may further contain at least one kind of compound 7 represented by formula (7) in addition to compound 1.

For example, the liquid crystal composition of the invention may also contain at least one selected from the group consisting of compounds 2 to 7 in addition to compound 1.

In $R^7$ and $X^7$ in formula (7), a preferred configuration of —CH=CH— in the alkenyl depends on a position of a double bond. A trans configuration is preferred in alkenyl having the double bond in an odd-numbered position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$ and —C$_2$H$_4$CH=CHC$_2$H$_5$. A cis configuration is preferred in alkenyl having the double bond in an even-numbered position, such as —CH$_2$CH=CHCH$_3$, —CH$_2$CH=CHC$_2$H$_5$ and —CH$_2$CH=CHC$_3$H$_7$. An alkenyl compound having the preferred configuration has a high maximum temperature or a wide temperature range of the liquid crystal phase. Detailed explanation is found in Mol. Cryst. Liq. Cryst., 1985, 131, 109, and Mol. Cryst. Liq. Cryst., 1985, 131, 327.

In $X^7$ in formula (7), specific examples of alkyl in which at least one of hydrogen is replaced by fluorine include —CHF$_2$, —CF$_3$, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$ and —CHFCF$_2$CF$_3$.

In $X^7$ in formula (7), specific examples of alkoxy in which at least one of hydrogen is replaced by fluorine include —OCHF$_2$, —OCF$_3$, —OCF$_2$CH$_2$F, —OCF$_2$CHF$_2$, —OCH$_2$CF$_3$, —O—(CF$_2$)$_3$—F, —OCF$_2$CHFCF$_3$ and —OCHFCF$_2$CF$_3$.

In $X^7$ in formula (7), specific examples of alkenyl in which at least one of hydrogen is replaced by fluorine include —CH=CF$_2$, —CF=CHF, —CH=CHCH$_2$F, —CH=CHCF$_3$, —(CH$_2$)$_2$—CH=CF$_2$, —CH$_2$CH=CHCF$_3$ and —CH=CHCF$_2$CF$_3$.

In formula (7), specific examples of preferred $X^7$ include fluorine, chlorine, —CF$_3$, —CHF$_2$, —OCF$_3$ and —OCHF$_2$, and fluorine, chlorine, —CF$_3$ and —OCF$_3$ are further preferred.

When $X^7$ in formula (7) is chlorine or fluorine, a melting point of compound 7 is comparatively low, and compatibility with other liquid crystal compounds is particularly excellent. When $X^7$ in formula (7) is —CF$_3$, —SF$_5$, —CHF$_2$, —OCF$_3$ and —OCHF$_2$, compound 7 exhibits a particularly large dielectric anisotropy.

When $X^7$ is fluorine, —CF$_3$ or —OCF$_3$, compound 7 is chemically stable.

In compound 7, compounds represented by formulas (7-1) to (7-8) are further preferably used, compounds represented by formulas (7-1-1), (7-1-2), (7-2-1) to (7-2-5), (7-3-1), (7-3-2), (7-4-1), (7-5-1) and (7-5-2) are still further preferably used, compounds represented by formulas (7-2-1) to (7-2-5) are particularly preferably used, and compounds represented by (7-2-2-E), (7-2-5-E), (7-2-2-F) and (7-2-5-F) are still further preferred.

The invention includes, in achiral component T, a case where a component is composed of one kind of compound as compound 7 and also a case where a component contains two or more kinds of compounds represented by formula (2) as compound 7.

Compound 7 is suitable for preparation of a composition having a large dielectric anisotropy, and can decrease the driving voltage in the device according to the invention. Compound 7 is contained in a total amount of, preferably, 5 wt % to 80 wt %, further preferably, 20 wt % to 75 wt %, and particularly preferably, 30 wt % to 75 wt %, based on the total weight of achiral component T.

7-2. Properties of Compound (7)

Compound 7 has a dioxane ring and three benzene rings, and has at least one —CF$_2$O— connecting group. Compound 7 is significantly physically and chemically stable under conditions in which the device is ordinarily used, and has a comparatively good compatibility with other liquid crystal compounds even though the clearing point is high. A composition containing compound 7 is comparatively stable under the conditions in which the device is ordinarily used. Accordingly, the temperature range of the optically isotropic liquid crystal phase can be extended in a composition containing compound 7, and the composition can be used in the form of a display device in a wide temperature range. Furthermore, compound 7 is useful as a component for decreasing the driving voltage of the composition to be driven in the optically isotropic liquid crystal phase. Moreover, if the blue phase is developed in the composition containing compound 7 and the chiral agent, a uniform blue phase without coexistence with an N* phase or an isotropic phase is easily formed. More specifically, compound 7 easily exhibits the uniform blue phase. Moreover, a significantly large dielectric anisotropy is developed.

7-3. Synthesis of Compound 7

Compound 7 can be prepared by suitably combining techniques in synthetic organic chemistry. Methods for introducing an objective terminal group, ring and bonding group into a starting material are described in Organic Syntheses (John Wiley & Sons, Inc.), Organic Reactions (John Wiley & Sons, Inc.), Comprehensive Organic Synthesis (Pergamon Press), New Experimental Chemistry Course (Shin Jikken Kagaku Koza in Japanese) (Maruzen Co., Ltd.), or the like.

2. Chiral Agent

The chiral agent contained in the optically isotropic liquid crystal composition is an optically active compound, and is preferably composed of a compound selected from compounds having no radically polymerizable group.

As the chiral agent used for the composition of the invention, a compound having a large helical twisting power is preferred. In the compound having the large helical twisting power, an amount of addition required for obtaining a desired pitch can be reduced. Therefore a rise in the driving voltage can be suppressed, and the compound is advantageous in practical use. Specifically, compounds represented by formulas (K1) to (K5) are preferred. Among the compounds, as the chiral agent to be added to the liquid crystal composition, compounds represented by formula (K2-1) to formula (K2-8) included in formula (K2), formula (K4-1) to formula (K4-6) included in formula (K4), and formula (K5-1) to formula (K5-3) included in formula (K5) are preferred, and compounds represented by formula (K4-1) to formula (K4-6) and formula (K5-1) to formula (K5-3) are further preferred.

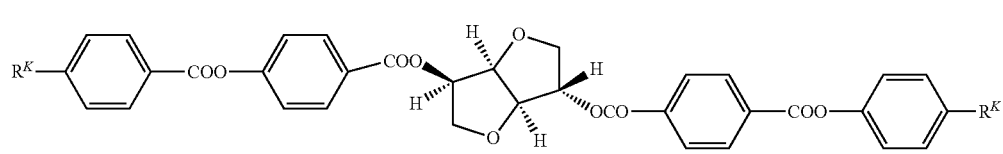
(K2-1)

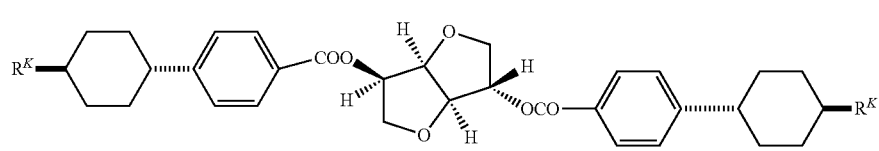
(K2-2)

-continued
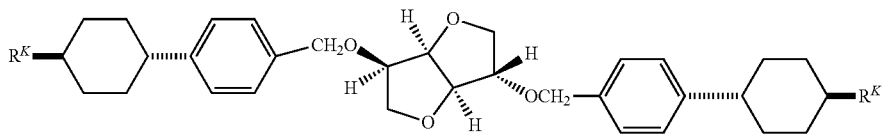
(K2-3)
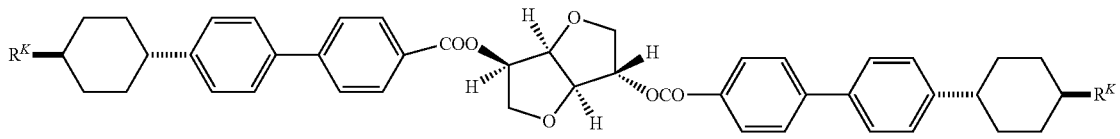
(K2-4)
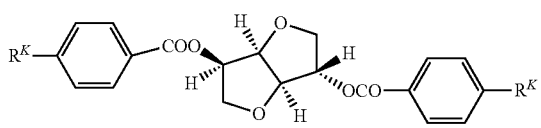
(K2-5)
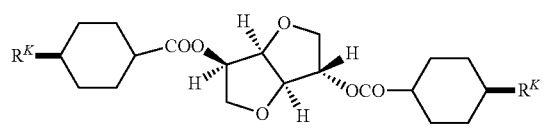
(K2-6)
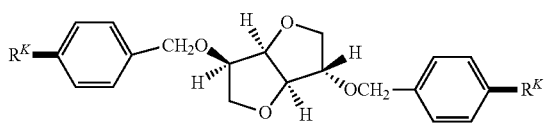
(K2-7)
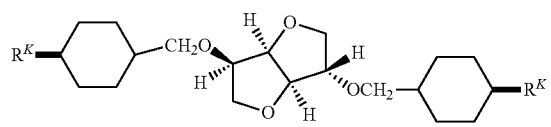
(K2-8)
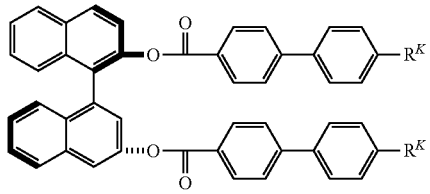
(K4-1)
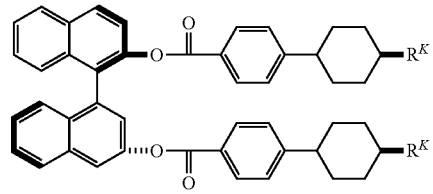
(K4-2)
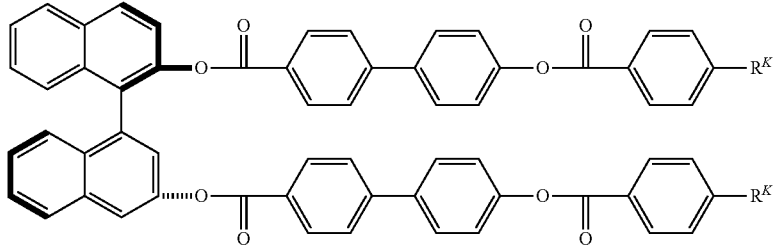
(K4-3)
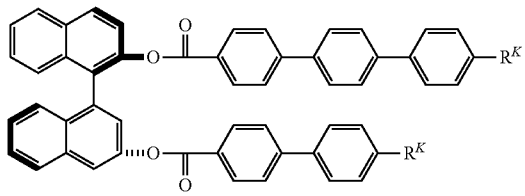
(K4-4)
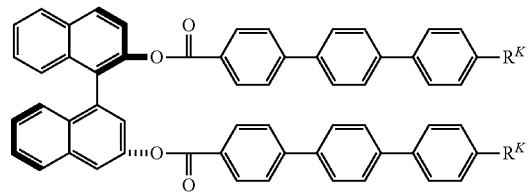
(K4-5)
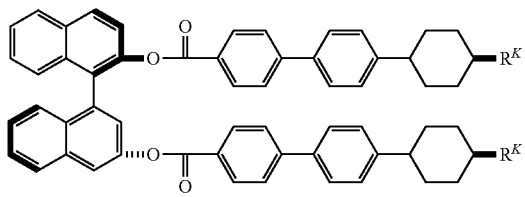
(K4-6)
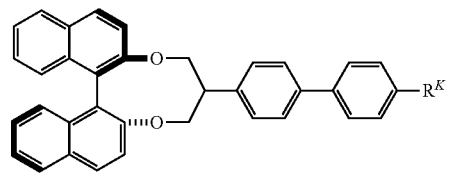
(K-5-1)

(K-5-2)

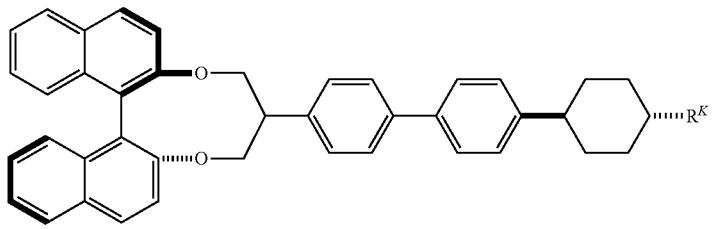

(K-5-3)

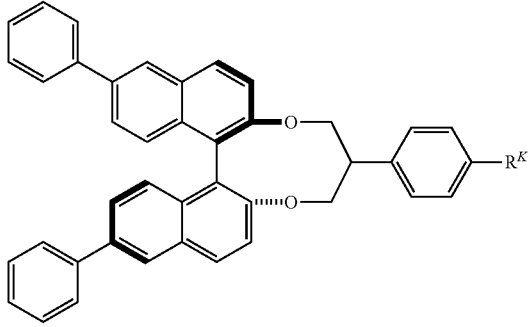

wherein, in the formula, $R^K$ is independently alkyl having 3 to 10 carbons or alkoxy having 3 to 10 carbons, and at least one of —$CH_2$—$CH_2$— in the alkyl or the alkoxy may be replaced by —CH=CH—.

Depending on properties required for the liquid crystal composition, a chiral agent having a comparatively modest twisting power is preferably used. Specific examples of the chiral agent having comparatively modest twisting power include compounds represented by formulas (Op-1) to (Op-13).

(Op-1)

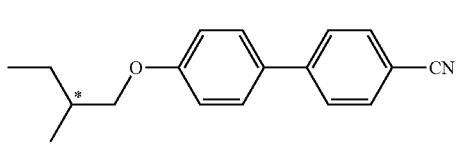

(Op-2)

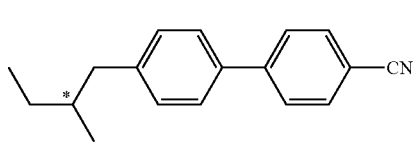

(Op-3)

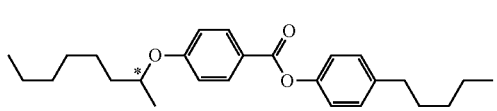

(Op-4)

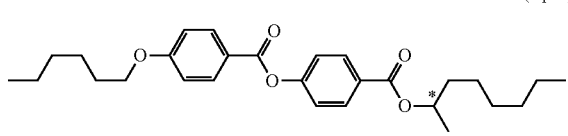

(Op-5)

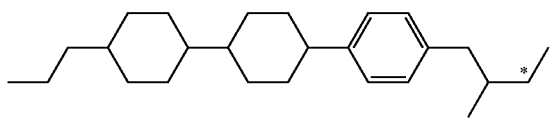

(Op-6)

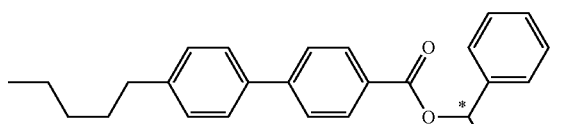

(Op-7)

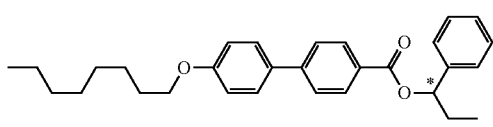

(Op-8)

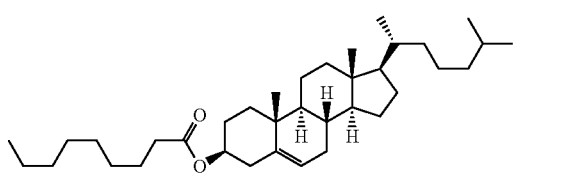

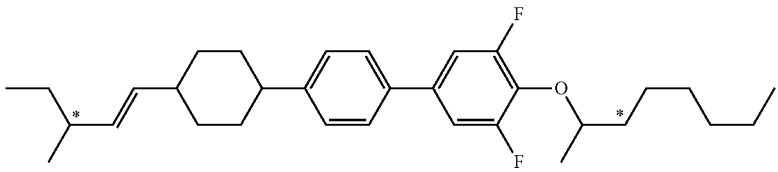

(Op-9)

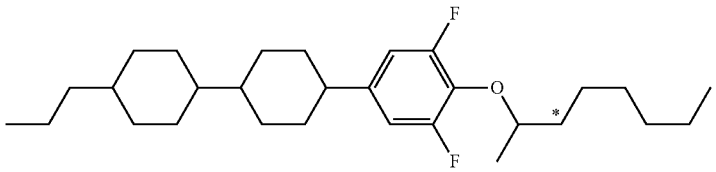

(Op-10)

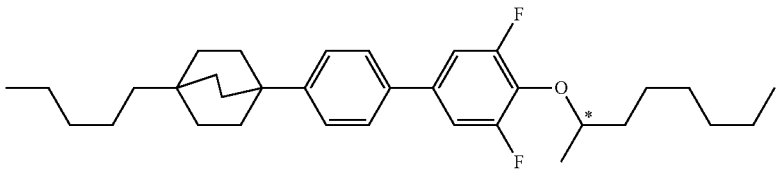

(Op-11)

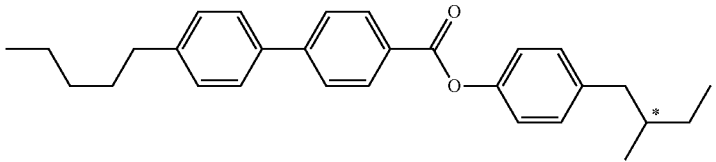

(Op-12)

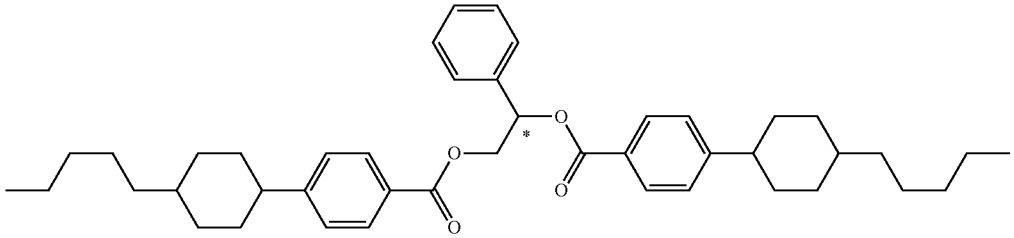

(Op-13)

As the chiral agent contained in the liquid crystal composition, one kind of compound or two or more kinds of compounds may be used.

In order to facilitate development of the optically isotropic liquid crystal phase, the chiral agent is contained in an amount of, preferably, 1 to 40 wt %, further preferably, 3 to 25 wt %, and particularly preferably, 5 to 15 wt %, based on the total weight of the liquid crystal composition of the invention.

3. Optically Isotropic Liquid Crystal Phase

An expression "liquid crystal composition has optical isotropy" means that the liquid crystal composition shows the optical isotropy macroscopically because alignment of liquid crystal molecules is isotropic, in which liquid crystal order is present microscopically. "Pitch based on the liquid crystal order that the liquid crystal composition microscopically has (hereinafter, occasionally referred to as a pitch)" is preferably 700 nm or less, further preferably, 500 nm or less, most preferably, 350 nm or less.

Here, "non-liquid crystal isotropic phase" means a generally defined isotropic phase, more specifically, a disordered phase, and an isotropic phase in which, even if an area in which a local order parameter is not zero is produced, the area is caused by a fluctuation. For example, the isotropic phase developed on a side of a higher temperature of the nematic phase corresponds to the non-liquid crystal isotropic phase herein. A similar definition is applied to chiral liquid crystals herein.

Then, "optically isotropic liquid crystal phase" herein represents a phase that exhibits the optically isotropic liquid crystal phase, and not by the fluctuation. One example includes a phase that exhibits a platelet texture (blue phase in a narrow sense).

In the optically isotropic liquid crystal composition of the invention, the platelet texture typical to the blue phase is occasionally not observed under observation by a polarizing microscope, although the liquid crystal composition has the optically isotropic phase. Then, the phase that exhibits the platelet texture is herein referred to as the blue phase, and the optically isotropic liquid crystal phase including the blue phase is referred to as the optically isotropic liquid crystal phase. More specifically, the blue phase is included in the optically isotropic liquid crystal phase.

In general, the blue phases are classified into three kinds, blue phase I, blue phase II and blue phase III, all of the three kinds of blue phases are optically active, and isotropic. In the blue phase of blue phase I or blue phase II, two or more kinds of diffracted light resulting from Bragg reflection from different lattice planes are observed. The blue phase is generally observed between the non-liquid crystal isotropic phase and a chiral nematic phase.

"State in which the optically isotropic liquid crystal phase does not show diffracted light having two or more colors" means that the optically isotropic liquid crystal phase has almost monochrome in everywhere in which the platelet texture to be observed in blue phase I and blue phase II is not observed. In the optically isotropic liquid crystal phase that shows no diffracted light having two or more colors, uniformity of contrast in the plane is unnecessary.

The optically isotropic liquid crystal phase that shows no diffracted light having two or more colors has advantages that intensity of reflected light by Bragg reflection is suppressed, or reflection is shifted to a side of a lower wavelength.

Moreover, in a liquid crystal material that reflects visible light, color may occasionally become a problem when the liquid crystal material is utilized in the form of the display device. However, in the liquid crystals that show no diffracted light having two or more colors, a reflection wavelength is shifted to a side of a lower wavelength. Therefore, reflection of visible light can be caused to disappear by a pitch longer than a pitch of the blue phase in a narrow sense (phase that exhibits the platelet texture).

The liquid crystal composition of the invention contains achiral component T and the chiral agent. On the occasion, the chiral agent is preferably added in the concentration in which the pitch becomes 700 nm or less. In addition, the composition having the nematic phase contains compound 1, and as required, any other component.

The optically isotropic liquid crystal composition of the invention also has the chiral nematic phase, and can also be obtained by adding the chiral agent to the composition having no optically isotropic liquid crystal phase. In addition, the composition having the chiral nematic phase and no optically isotropic liquid crystal phase contains compound 1, the optically active compound, and as required, any other component. On the occasion, the chiral agent is added in a concentration in which the pitch becomes 700 nm or more in order to avoid development of the optically isotropic liquid crystal phase. Here, as the compound to be added, compounds represented by formulas (K1) to (K5) as the compound having a large helical twisting power can be used, further preferably, compounds represented by formulas (K2-1) to (K2-8), formulas (K4-1) to (K4-6) or formulas (K5-1) to (K5-3) can be used.

Moreover, the chiral agent to be added may have helical twisting power being not so large. Specific examples of such a compound include a compound to be added to the liquid crystal composition for use in a device to be driven in the nematic phase (a TN mode, an STN mode and so forth). Specific examples include compounds represented by formulas (Op-1) to (Op-13).

A temperature range in which the liquid crystal composition of a preferred embodiment of the invention exhibits the optically isotropic liquid crystal phase can be extended by adding the chiral agent to the liquid crystal composition having a wide temperature range in which the nematic phase or the chiral nematic phase and the isotropic phase coexist, and exhibiting the optically isotropic liquid crystal phase. For example, the composition that exhibits the optically isotropic liquid crystal phase in the wide temperature range can be prepared by mixing a liquid crystal compound having a high clearing point and a liquid crystal compound having a low clearing point to prepare a liquid crystal composition having a wide temperature range in which the nematic phase and the isotropic phase coexist, and adding the chiral agent thereto.

As the liquid crystal composition having the wide temperature range in which the nematic phase or the chiral nematic phase and the isotropic phase coexist, a liquid crystal composition having a difference between a maximum temperature and a minimum temperature in which the chiral nematic phase and the non-liquid crystal isotropic phase coexist of 3 to 150° C. is preferred, and a liquid crystal composition having a difference in the range of 5 to 150° C. is further preferred. Moreover, a compound having a difference between a maximum temperature and a minimum temperature in which the nematic phase and the non-liquid crystal isotropic phase coexist is 3 to 150° C. is preferred.

If an electric field is applied to a liquid crystal medium of the invention in the optically isotropic liquid crystal phase, electric birefringence is caused, but the birefringence does not necessarily result from a Kerr effect.

The electric birefringence in the optically isotropic liquid crystal phase becomes larger as the pitch becomes longer. Therefore, the electric birefringence can be increased by setting a long pitch by adjusting a kind and a content of the chiral agent, as long as a demand for other optical characteristics (transmittance, a diffraction wavelength or the like) is satisfied.

4. Any Other Component

The optically isotropic liquid crystal composition of the invention may further contain a solvent, a polymer material, a dichroic dye, a photochromic compound and so forth within the range in which the characteristics of the composition are not adversely affected.

Specific examples of the dichroic dye to be used in the liquid crystal composition of the invention include a merocyanine type, a styryl type, an azo type, an azomethine type, an azoxy type, a quinophthalone type, an anthraquinone type and a tetrazine type.

5. Optically Isotropic Polymer/Liquid Crystal Composite Material

1. Polymer/Liquid Crystal Composite Material

The polymer/liquid crystal composite material of the invention is a composite material containing the liquid crystal composition and a polymer, shows optical isotropy, and can be used for an optical device driven in the optically isotropic liquid crystal phase. The liquid crystal composition contained in the polymer/liquid crystal composite material of the invention is the liquid crystal composition of the invention.

"Polymer/liquid crystal composite material" herein is not particularly limited, if the composite material contains both the liquid crystal material and the polymer compound, but may be in a state in which the polymer and the liquid crystal material cause phase separation in a state in which the polymer is not partially or wholly dissolved into the liquid crystal material. In addition, unless otherwise noted, the nematic phase herein means the nematic phase in a narrow sense without including the chiral nematic phase.

The optically isotropic polymer/liquid crystal composite material according to a preferred embodiment of the invention can develop the optically isotropic liquid crystal phase in a wide temperature range. Moreover, the polymer/liquid crystal composite material according to a preferred embodiment of the invention has a significantly high response speed. Moreover, the polymer/liquid crystal composite material according to a preferred embodiment of the invention can be suitably used for the optical device such as the display device, based on the effects.

2. Polymer

The composite material of the invention can be manufactured by mixing the optically isotropic liquid crystal composition and the polymer obtained by allowing polymerization in advance, but is preferably manufactured by mixing a low molecular weight monomer, macro monomer, oligomer or the like (hereinafter, collectively referred to as "monomer or the like") to be the polymer material, and the liquid crystal composition CLC, and then performing a polymerization reaction in the mixture. The mixture containing the monomer or the like and the liquid crystal composition is referred to as "polymerizable monomer/liquid crystal mixture" herein. "Polymerizable monomer/liquid crystal mixture" may contain, as required, a polymerization initiator, a curing agent, a catalyst, a stabilizer, a dichroic dye or a photochromic compound as described later in the range in which advantageous effects of the invention are not adversely affected. For example, the polymerizable monomer/liquid crystal mixture of the invention may contain, as required, 0.1 to 20 parts by weight of the polymerization initiator based on 100 parts by weight of the polymerizable monomer. When "polymerizable monomer/liquid crystal mixture" is polymerized in the blue phase, the mixture essentially becomes the liquid crystal medium, but when the polymerization is performed in the isotropic phase, the mixture does not necessarily be the liquid crystal medium.

A polymerization temperature preferably includes temperature at which the polymer/liquid crystal composite material shows a high transparency and isotropy. The polymerization temperature further preferably includes temperature at which the mixture of the monomer and the liquid crystal material exhibits the isotropic phase or the blue phase, and polymerization is terminated in the isotropic phase or the optically isotropic liquid crystal phase. More specifically, the polymerization temperature preferably includes temperature at which, after polymerization, the polymer/liquid crystal composite material does not substantially scatter light on a side of a wavelength longer than a wavelength of visible light, and exhibits an optically isotropic state.

As a raw material of the polymer that composes the composite material of the invention, a low molecular weight monomer, macro monomer or oligomer can be used, for example. A raw material monomer of the polymer herein is used in the meaning including the low molecular weight monomer, the macro monomer or the oligomer. Moreover, the polymer obtained preferably has a three-dimensional crosslinking structure, and therefor a polyfunctional monomer having two or more polymerizable functional groups is preferably used as the raw material monomer of the polymer. The polymerizable functional group is not particularly limited. Specific examples include an acrylic group, a methacrylic group, a glycidyl group, an epoxy group, an oxetanyl group and a vinyl group, preferably, an acrylic group and a methacrylic group from a viewpoint of a rate of polymerization. Among the raw material monomers of the polymer, a content of a monomer having two or more polymerizable functional groups in the range of 10 wt % or more in the monomer is preferred because a high transparency and isotropy are easily developed in the composite material of the invention. In order to obtain a suitable composite material, the polymer preferably has a mesogen moiety, and a raw material monomer having the mesogen moiety can be partially or wholly used as the raw material monomer of the polymer.

2-1. Monofunctional or Bifunctional Monomer Having Mesogen Moiety

A monofunctional or bifunctional monomer having the mesogen moiety is not particularly limited structurally, but specific examples include a compound represented by formula (M1) or formula (M2) as described below.

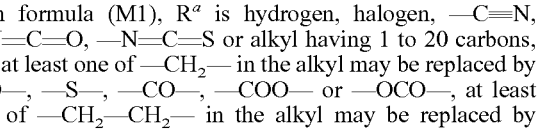

In formula (M1), $R^a$ is hydrogen, halogen, —C≡N, —N=C=O, —N=C=S or alkyl having 1 to 20 carbons, and at least one of —CH$_2$— in the alkyl may be replaced by —O—, —S—, —CO—, —COO— or —OCO—, at least one of —CH$_2$—CH$_2$— in the alkyl may be replaced by —CH=CH—, —CF=CF— or —C≡C—, and in the alkyl, at least one of hydrogen in a group in which at least one of —CH$_2$— in the alkyl is replaced by —O—, —S—, —CO—, —COO— or —OCO—, or in a group in which at least one of —CH$_2$—CH$_2$— in the alkyl is replaced by —CH=CH—, —CF=CF— or +C≡C— may be replaced by halogen or —C≡N. $R^b$ is each independently a polymerizable group represented by formula (M3-1) to formula (M3-7).

Preferred $R^a$ is hydrogen, halogen, —C≡N, —CF$_3$, —CF$_2$H, —CFH$_2$, —OCF$_3$, —OCF$_2$H, alkyl having 1 to 20 carbons, alkoxy having 1 to 19 carbons, alkenyl having 2 to 21 carbons and alkynyl having 2 to 21 carbons. Particularly preferred $R^a$ is —C≡N, alkyl having 1 to 20 carbons and alkoxy having 1 to 19 carbons.

In formula (M2), $R^b$ is each independently a polymerizable group represented by formula (M3-1) to formula (M3-7).

Here, $R^d$ in formulas (M3-1) to (M3-7) is each independently hydrogen, halogen or alkyl having 1 to 5 carbons, and at least one of hydrogen in the alkyl may be replaced by halogen. Preferred $R^d$ is hydrogen, halogen and methyl. Particularly preferred $R^d$ is hydrogen, fluorine and methyl.

A monomer represented by formula (M3-2), formula (M3-3), formula (M3-4) or formula (M3-7) is suitably polymerized according to radical polymerization. A monomer represented by formula (M3-1), formula (M3-5) or formula (M3-6) is suitably polymerized according to cationic polymerization. Any polymerization progresses in the form of living polymerization, and therefore polymerization starts if a small amount of radicals or cation active species is generated in a reaction system. A polymerization initiator can be used in order to accelerate generation of active species. For example, light or heat can be used for generation of the active species.

In formulas (M1) and (M2), $A^M$ is each independently an aromatic or non-aromatic five-membered ring or six-membered ring, or a condensed ring having 9 or more carbons, and —$CH_2$— in the ring may be replaced by —O—, —S—, —NH— or —$NCH_3$—, —CH= in the ring may be replaced by —N=, and a hydrogen atom on the ring may be replaced by halogen, and alkyl or alkyl halide each having 1 to 5 carbons. Specific examples of preferred $A^M$ include 1,4-cyclohexylene, 1,4-cyclohexenylene, 1,4-phenylene, naphthalene-2,6-diyl, tetrahydronaphthalene-2,6-diyl, fluorene-2,7-diyl or bicyclo[2.2.2]octane-1,4-diyl, and in the rings, at least one of —$CH_2$— may be replaced by —O—, at least one of —CH= may be replaced by —N=, and in the rings, at least one of hydrogen may be replaced by halogen, alkyl having 1 to 5 carbons or alkyl halide having 1 to 5 carbons.

In consideration of stability of the compound, —$CH_2$—O—$CH_2$—O— in which oxygen and oxygen are not adjacent is preferred to —$CH_2$—O—O—$CH_2$— in which oxygen and oxygen are adjacent. A similar explanation is applied also to sulfur.

Among types of $A^M$, particularly preferred $A^M$ is 1,4-cyclohexylene, 1,4-cyclohexenylene, 1,4-phenylene, 2-fluoro-1,4-phenylene, 2,3-difluoro-1,4-phenylene, 2,5-difluoro-1,4-phenylene, 2,6-difluoro-1,4-phenylene, 2-methyl-1,4-phenylene, 2-trifluoromethyl-1,4-phenylene, 2,3-bis(trifluoromethyl)-1,4-phenylene, naphthalene-2,6-diyl, tetrahydronaphthalene-2,6-diyl, fluorene-2,7-diyl, 9-methylfluorene-2,7-diyl, 1,3-dioxane-2,5-diyl, pyridine-2,5-diyl and pyrimidine-2,5-diyl. In addition, with regard to a configuration of 1,4-cyclohexylene and 1,3-dioxane-2,5-diyl described above, trans is preferred to cis.

Then, 2-fluoro-1,4-phenylene is structurally identical with 3-fluoro-1,4-phenylene, and specific examples are not shown for the latter. A same rule is also applied to a relationship between 2,5-difluoro-1,4-phenylene and 3,6-difluoro-1,4-phenylene, or the like.

In formulas (M1) and (M2), Y is each independently a single bond or alkylene having 1 to 20 carbons, and in the alkylene, at least one of —$CH_2$— may be replaced by —O— or —S—, and at least one of —$CH_2$—$CH_2$— in the alkyl may be replaced by —CH=CH—, —C≡C—, —COO— or —COO—. Preferred Y is a single bond, —$(CH_2)_{m2}$—, —$O(CH_2)_{m2}$— and —$(CH_2)_{m2}O$—(in the formulas, m2 is an integer from 1 to 20.). Particularly preferred Y is a single bond, —$(CH_2)_{m2}$—, —$O(CH_2)_{m2}$— and —$(CH_2)_{m2}O$—(in the formulas, m2 is an integer from 1 to 10.) In consideration of stability of the compound, —Y—$R^a$ and —Y—$R^b$ preferably have no —O—O—, no —O—S—, no —S—O— or no —S—S— in the groups.

In formulas (M1) and (M2), $Z^M$ is each independently a single bond, —$(CH_2)_{m3}$—, —$O(CH_2)_{m3}$—, —$(CH_2)_{m3}O$—, —$O(CH_2)_{m3}O$—, —CH=CH—, —C≡C—, —COO—, —OCO—, —$(CF_2)_2$—, —$(CH_2)_2$—COO—, —OCO—$(CH_2)_2$—, —CH=CH—COO—, —OCO—CH=CH—, —C≡C—COO—, —OCO—C≡C—, —CH=CH—$(CH_2)_2$—, —$(CH_2)_2$—CH=CH—, —CF=CF—, —C≡C—CH=CH—, —CH=CH—C≡C—, —$OCF_2$—$(CH_2)_2$—, —$(CH_2)_2$—$CF_2O$—, —$OCF_2$— or —$CF_2O$— (in the formulas, m3 is an integer from 1 to 20.).

Preferred $Z^M$ is a single bond, —$(CH_2)_{m3}$—, —$O(CH_2)_{m3}$—, —$(CH_2)_{m3}O$—, —CH=CH—, —C≡C—, —COO—, —OCO—, —$(CH_2)_2$—COO—, —OCO—$(CH_2)_2$—, —CH=CH—COO—, —OCO—CH=CH—, —$OCF_2$— and —$CF_2O$—.

In formulas (M1) and (M2), m1 is an integer from 1 to 6. Preferred m1 is an integer from 1 to 3. When m1 is 1, the compound represented by formulas (M1) and (M2) is a bicyclic compound having two rings such as a six-membered ring. When m1 is 2 and 3, the compounds are a tricyclic compound and a tetracyclic compound, respectively. For example, two of $A^M$ when m1 is 1 may be identical or different. For example, three of $A^M$ (or two of $Z^M$) when m1 is 2 may be identical or different. A same rule is applied to a case when m1 is 3 to 6. A same rule is also applied to $R^a$, $R^b$, $R^d$, $Z^M$, $A^M$ and Y.

If compound (M1) represented by formula (M1) and compound (M2) represented by formula (M2) contain an isotope such as $^2H$ (deuterium) and $^{13}C$ in an amount higher than an amount of natural abundance, such compound (M1) and compound (M2) have similar characteristics, and therefore can be preferably used.

Further preferred examples of compound (M1) and compound (M2) include compounds (M1-1) to (M1-41) and compounds (M2-1) to (M2-27) as represented by formulas (M1-1) to (M1-41) and (M2-1) to (M2-27), respectively. In the compounds, meanings of $R^a$, $R^b$, $R^d$, $Z^M$, $A^M$, Y and p are identical with the meanings in formulas (M1) and (M2) as described in the embodiment of the invention.

A partial structure as described below in compounds (M1-1) to (M1-41) and (M2-1) to (M2-27) will be described. Partial structure (a1) represents 1,4-phenylene in which at least one of hydrogen is replaced by fluorine. Partial structure (a2) represents 1,4-phenylene in which at least one of hydrogen may be replaced by fluorine. Partial structure (a3) represents 1,4-phenylene in which at least one of hydrogen may be replaced by either fluorine or methyl. Partial structure (a4) represents fluorine in which hydrogen in 9-position may be replaced by methyl.

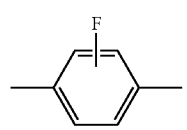

(a1)

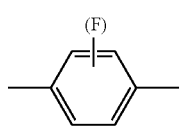

(a2)

-continued
(a3)
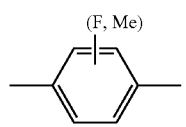
(a4)
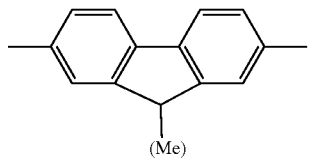
(M1-1)
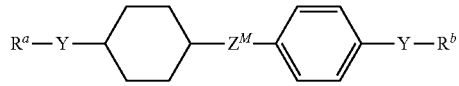
(M1-2)
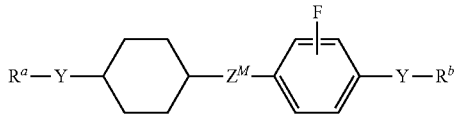
(M1-3)
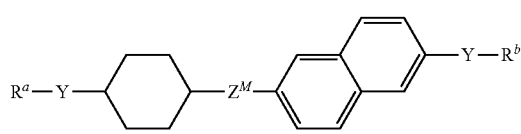
(M1-4)
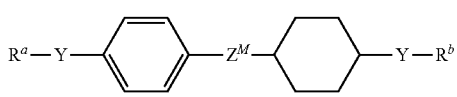
(M1-5)
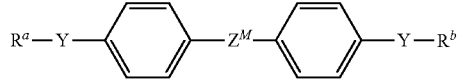
(M1-6)
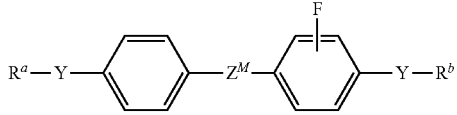
(M1-7)
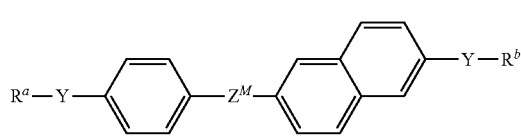
(M1-8)
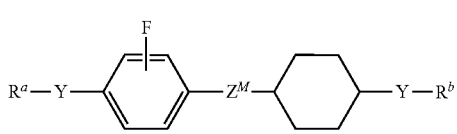
(M1-9)
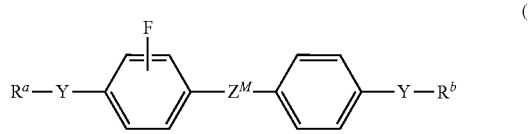
(M1-10)
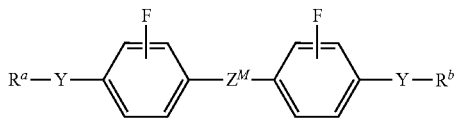
(M1-11)
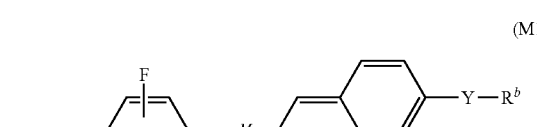
(M1-12)
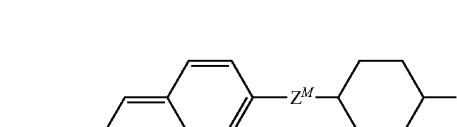
(M1-13)
(M1-14)
(M1-15)
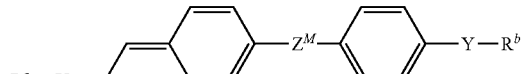
(M1-16)
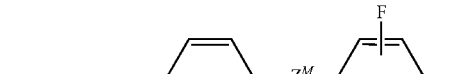
(M1-17)
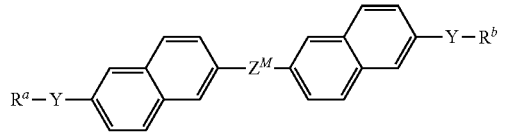
(M1-18)
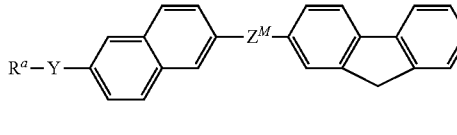

-continued
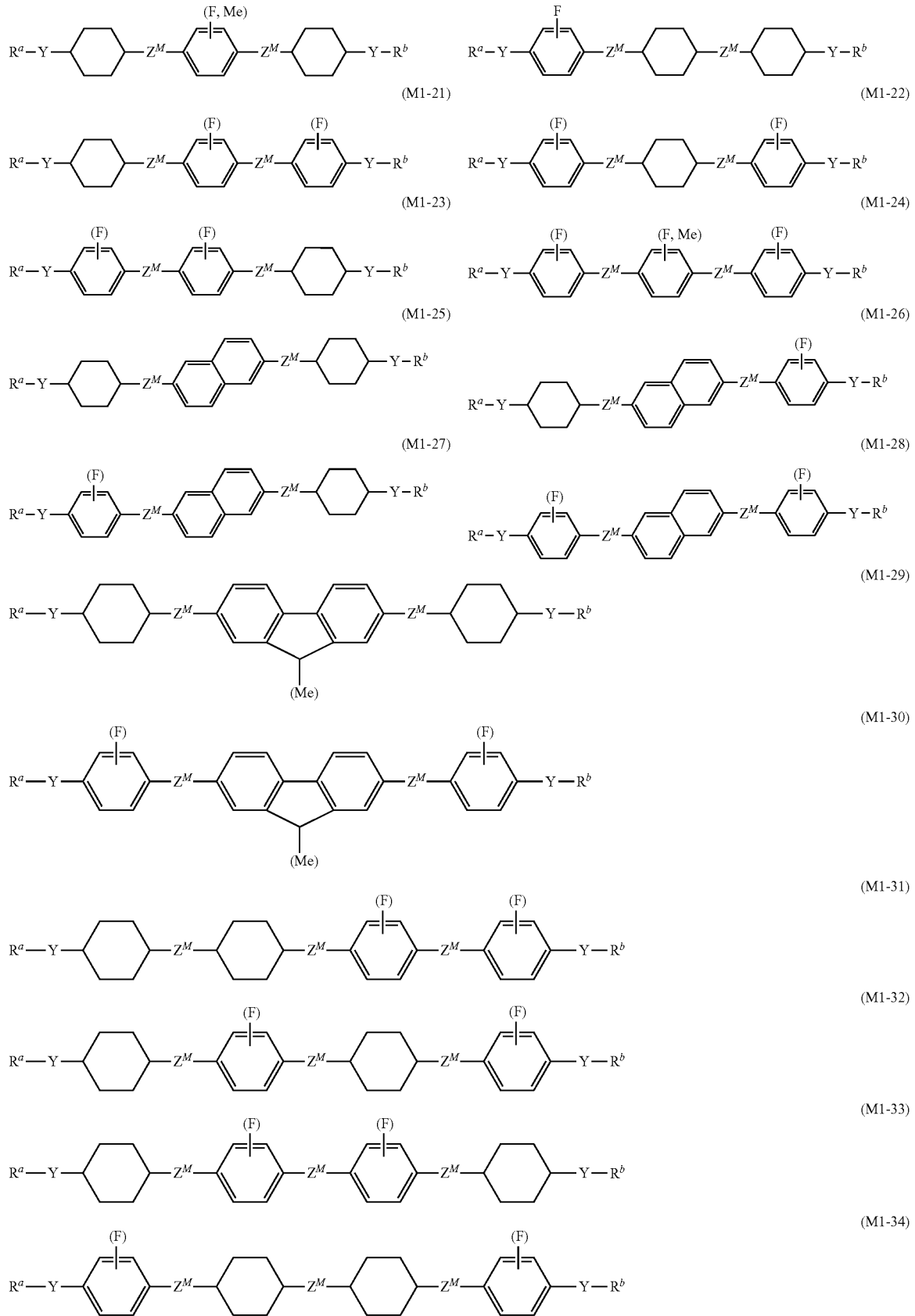

-continued
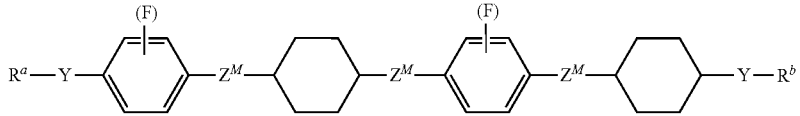
(M1-35)
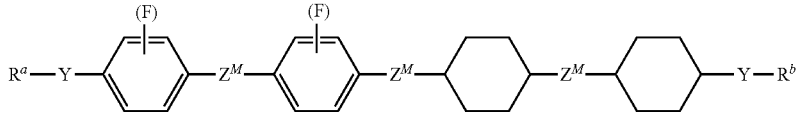
(M1-36)
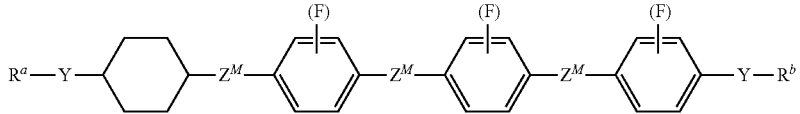
(M1-37)
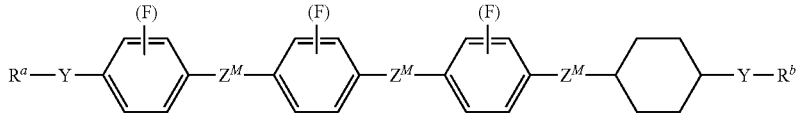
(M1-38)
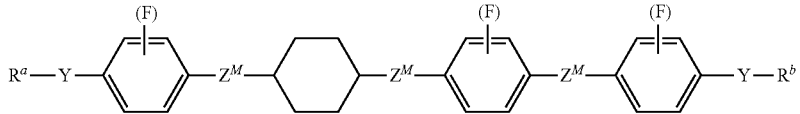
(M1-39)
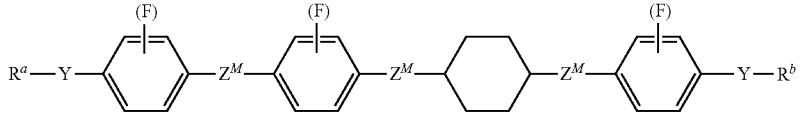
(M1-40)
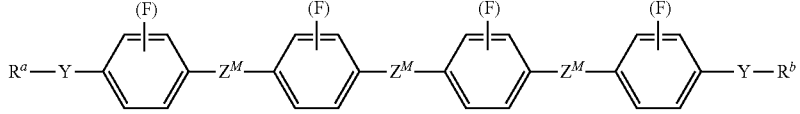
(M1-41)
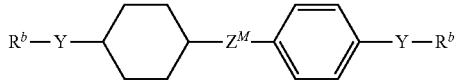
(M2-1)
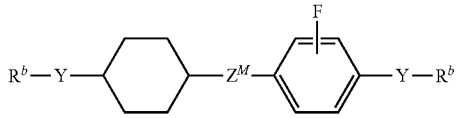
(M2-2)
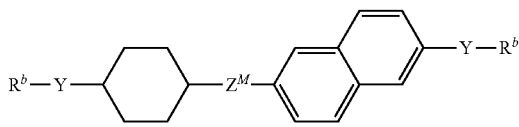
(M2-3)
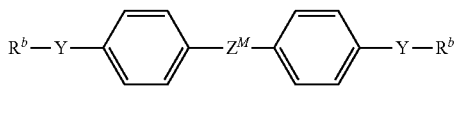
(M2-4)
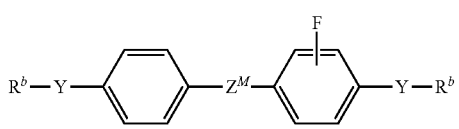
(M2-5)
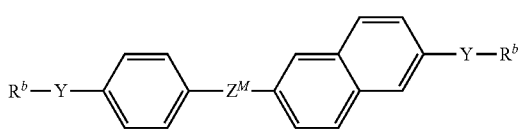
(M2-6)
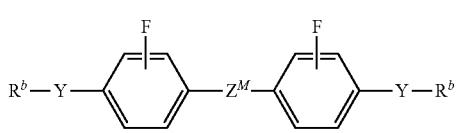
(M2-7)
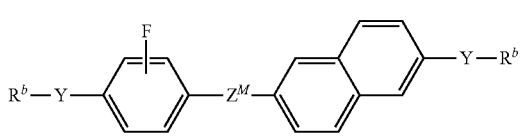
(M2-8)

(M2-9)
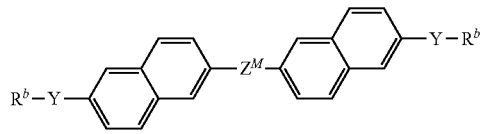
(M2-10)
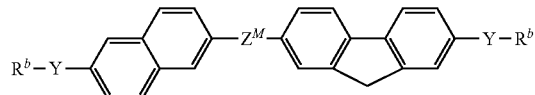
(M2-11)
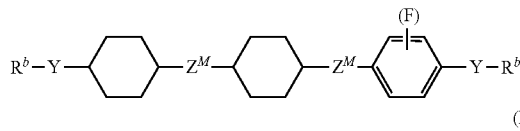
(M2-12)
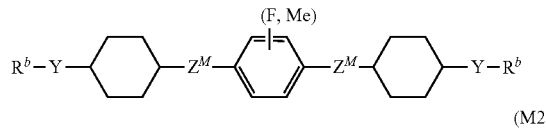
(M2-13)
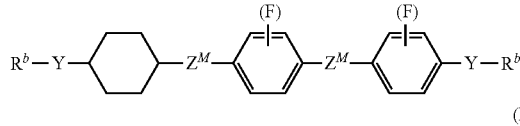
(M2-14)
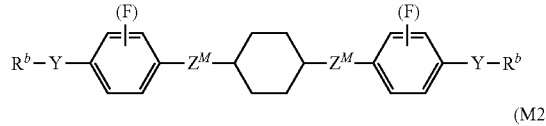
(M2-15)
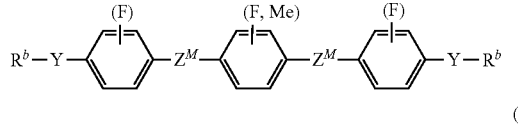
(M2-16)
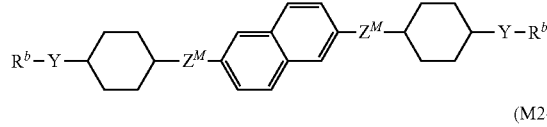
(M2-17)
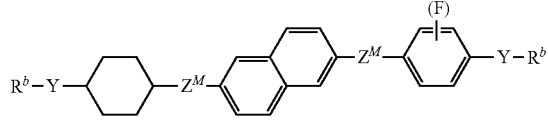
(M2-18)
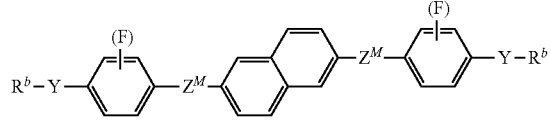
(M2-19)
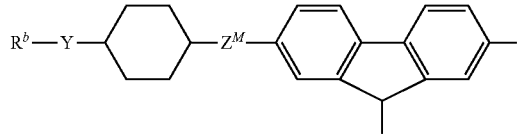
(M2-20)
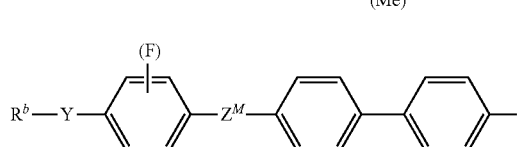
(M2-21)
(M2-22)
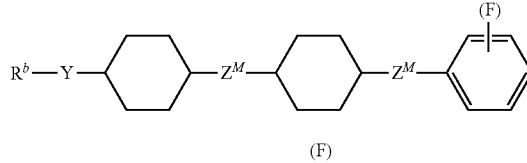
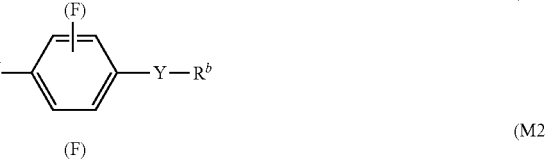
(M2-23)
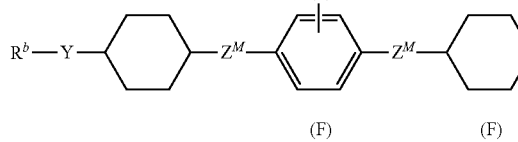
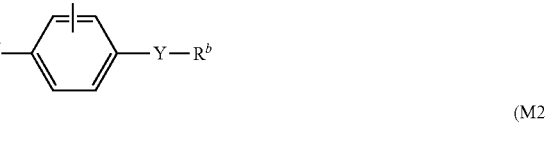
(M2-24)
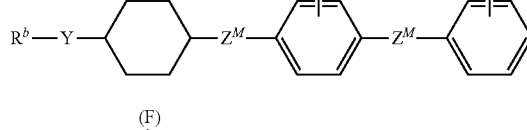
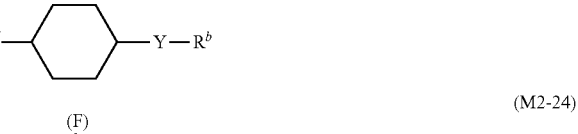
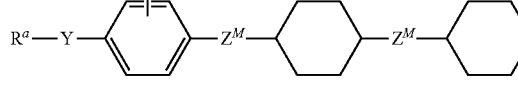

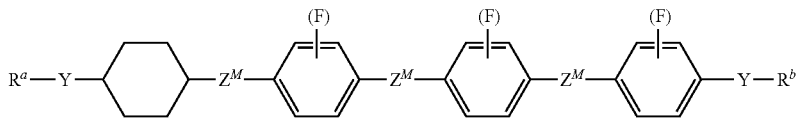
(M2-25)

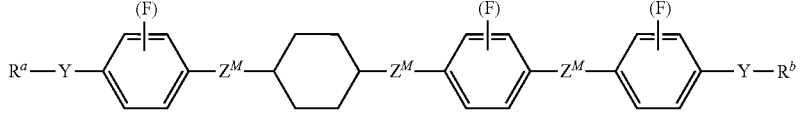
(M2-26)

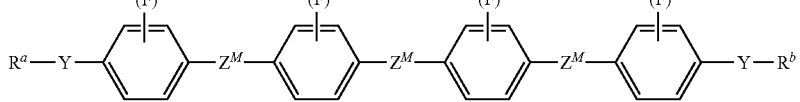
(M2-27)

A polymerizable compound other than the monomer having no mesogen moiety, and monomers (M1) and (M2) both having the mesogen moiety as described above can be used as required.

For the purpose of optimizing the optical isotropy of the polymer/liquid crystal composite material of the invention, a monomer having a mesogen moiety and three or more polymerizable functional groups can also be used. As the monomer having the mesogen moiety and three or more polymerizable functional groups, a publicly known compound can be suitably used. Specific examples include compounds represented by formulas (M4-1) to (M4-3), and further specific examples include compounds described in JP 2000-327632 A, JP 2004-182949 A or JP 2004-59772 A. However, in formulas (M4-1) to (M4-3), $R^b$, Za, Y and (F) indicate meanings identical with the meanings as described above.

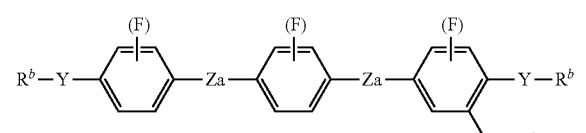
(M4-1)

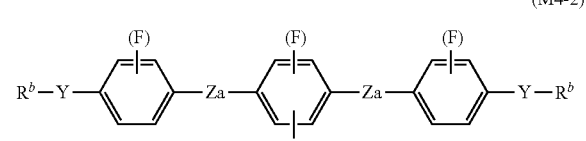
(M4-2)

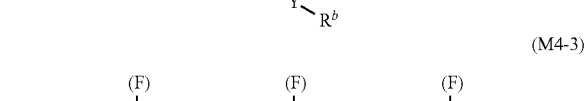
(M4-3)

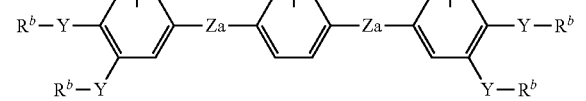

2-2. Monomer Having Polymerizable Functional Group and No Mesogen Moiety

Specific examples of a monomer having a polymerizable functional group and no mesogen moiety include straight-chain or branched-chain acrylate having 1 to 30 carbons and straight-chain or branched-chain diacrylate having 1 to 30 carbons, and a monomer having three or more polymerizable functional groups such as glycerol propoxylate (1PO/OH) triacrylate, pentaerythritol propoxylate triacrylate, pentaerythritol triacrylate, trimethylolpropane ethoxylate triacrylate, trimethylolpropane propoxylate triacrylate, trimethylolpropane triacrylate, di(trimethylolpropane)tetraacrylate, pentaerythritol tetraacrylate, di(pentaerythritol)pentaacrylate, di(pentaerythritol)hexacrylate and trimethylolpropane triacrylate, but are not limited thereto.

2-3. Polymerization Initiator

The polymerization reaction in manufacturing the polymer constituting the composite material according to the invention is not particularly limited. For example, photoradical polymerization, thermal radical polymerization, photocationic polymerization or the like is performed.

Specific examples of a photoradical polymerization initiator that can be used in the photoradical polymerization include Darocur 1173 and 4265 (both being trade names, BASF Japan Ltd.) and Irgacure 184, 369, 500, 651, 784, 819, 907, 1300, 1700, 1800, 1850 and 2959 (all being trade names, BASF Japan Ltd.).

Specific examples of a preferred initiator for radical polymerization by heat that can be used in the thermal radical polymerization include benzoyl peroxide, diisopropyl peroxydicarbonate, t-butyl peroxy-2-ethylhexanoate, t-butyl peroxypivalate, t-butyl peroxydiisobutyrate, lauroyl peroxide, dimethyl-2,2'-azobisisobutyrate (MAIB), di-t-butyl peroxide (DTBPO), azobisisobutyronitrile (AIBN) and azobiscyclohexanecarbonitrile (ACN).

Specific examples of a photocationic polymerization initiator that can be used in the photocationic polymerization include diaryliodonium salt (hereinafter, referred to as "DAS") and a triarylsulfonium salt (hereinafter, referred to as "TAS").

Specific examples of DAS include diphenyliodonium tetrafluoroborate, diphenyliodonium hexafluorophosphonate, diphenyliodonium hexafluoroarsenate, diphenyliodonium trifluoromethanesulfonate, diphenyliodonium trifluoroacetate, diphenyliodonium p-toluenesulfonate, diphenyliodonium tetra(pentafluorophenyl)borate, 4-methoxyphenyphenyliodonium tetrafluoroborate, 4-methoxyphenyphenyliodonium hexafluorophosphonate, 4-methoxyphenyphenyliodonium hexafluoroarsenate, 4-methoxyphenyphenyliodonium trifluoromethanesulfonate, 4-methoxyphenylphenyliodonium trifluoroacetate and 4-methoxyphenyphenyliodonium p-toluenesulfonate.

An improvement in sensitivity can be achieved by adding a photosensitizer such as thioxanthone, phenothiazine, chlorothioxanthone, xanthone, anthracene, diphenylanthracene and rubrene to DAS.

Specific examples of TAS include triphenylsulfonium tetrafluoroborate, triphenylsulfonium hexafluorophosphonate, triphenylsulfonium hexafluoroarsenate, triphenylsulfonium trifluoromethanesulfonate, triphenylsulfonium trifluoroacetate, triphenylsulfonium p-toluenesulfonate, triphenylsulfonium tetra(pentafluorophenyl)borate, 4-methoxyphenydiphenylsulfonium tetrafluoroborate, 4-methoxyphenydiphenylsulfonium hexafluorophosphonate, 4-methoxyphenydiphenylsulfonium hexafluoroarsenate, 4-methoxyphenyldiphenylsulfonium trifluoromethanesulfonate, 4-methoxyphenyldiphenylsulfonium trifluoroacetate, and 4-methoxyphenydiphenylsulfonium p-toluenesulfonate.

Specific examples of trade names of the photocationic polymerization initiator include Cyracure UVI-6990, Cyracure UVI-6974 and Cyracure UVI-6992 (each being a trade name, UCC), Adekaoptomer SP-150, SP-152, SP-170 and SP-172 (each being a trade name, ADEKA Corporation) and Rhodorsil Photoinitiator 2074 (trade name, Rhodia Japan, Ltd.), Irgacure 250 (a trade name, BASF Japan Ltd.) and UV-9380C (a trade name, GE Toshiba Silicones Co., Ltd.).

2-4. Curing Agent or the Like

In manufacturing the polymer constituting the composite material according to the invention, one kind or two or more kinds of other suitable components, for example, the curing agent, the catalyst and the stabilizer, may be added in addition to the monomer or the like and the polymerization initiator.

As the curing agent, a publicly known latent curing agent that has been used as a curing agent for an epoxy resin so far can be ordinarily used. Specific examples of the latent curing agent for the epoxy resin include an amine curing agent, a novolak resin curing agent, an imidazole curing agent and an acid anhydride curing agent. Specific examples of the amine curing agent include aliphatic polyamine such as diethylenetriamine, triethylenetetramine, tetraethylenepentamine, m-xylenediamine, trimethylhexamethylenediamine, 2-methylpentamethylenediamine and diethylaminopropylamine, alicyclic polyamine such as isophoronediamine, 1,3-bisaminomethylcyclohexane, bis(4-aminocyclohexyl)methane, norbornenediamine, 1,2-diaminocyclohexane and laromin, and aromatic polyamine such as diaminodiphenylmethane, diaminodiphenylethane and metaphenylenediamine.

Specific examples of the novolak resin curing agent include a phenol novolak resin and a bisphenol novolak resin. Specific examples of the imidazole curing agent include 2-methylimidazole, 2-ethylhexylimidazole, 2-phenylimidazole and 1-cyanoethyl-2-phenylimidazolium-trimellitate.

Specific examples of the acid anhydride curing agent include tetrahydrophthalic anhydride, hexahydrophthalic anhydride, methyltetrahydrophthalic anhydride, methylhexahydrophthalic anhydride, methylcyclohexenetetracarboxylic dianhydride, phthalic anhydride, trimellitic anhydride, pyromellitic anhydride and benzophenonetetracarboxylic dianhydride.

Moreover, a curing accelerator for accelerating a curing reaction between a polymerizable compound having a glycidyl group, an epoxy group or an oxetanyl group and the curing agent may be further used. Specific examples of the curing accelerator include tertiary amines such as benzyldimethyl amine, tris(dimethylaminomethyl)phenol and dimethylcyclohexylamine, imidazoles such as 1-cyanoethyl-2-ethyl-4-methylimidazole and 2-ethyl-4-methylimidazole, an organic phosphorus compound such as triphenyl phosphine, quaternary phosphonium salts such as tetraphenylphosphonium bromide, diazabicycloalkenes such as 1,8-diazabicyclo[5.4.0]undecene-7 and an organic acid salt thereof, a quaternary ammonium salt such as tetraethylammonium bromide and tetrabutylammonium bromide, and a boron compound such as boron trifluoride and triphenyl borate. The curing accelerators can be used alone or by mixing two or more kinds.

In order to prevent unwanted polymerization during storage, for example, the stabilizer is preferably added. As the stabilizer, all the compounds known by those skilled in the art can be used. Representative examples of the stabilizer include 4-ethoxyphenol, hydroquinone and butylated hydroxytoluene (BHT).

3. Composition of Polymer/Liquid Crystal Composite Material

The content of the liquid crystal composition in the polymer/liquid crystal composite material according to the invention is preferably as high as possible, as long as the composite material can develop the optically isotropic liquid crystal phase. The reason is that a value of electric birefringence of the composite material of the invention becomes larger as the content of the liquid crystal composition is higher.

In the polymer/liquid crystal composite material of the invention, the content of the liquid crystal composition is preferably in the range of 60 wt % to 99 wt %, further preferably, in the range of 60 wt % to 98 wt %, and particularly preferably, in the range of 80 wt % to 97 wt %, based on the composite material. In the polymer/liquid crystal composite material of the invention, the content of the polymer is preferably in the range of 1 wt % to 40 wt %, further preferably, in the range of 2 wt % to 40 wt %, and particularly preferably, in the range of 3 wt % to 20 wt %, based on the composite material.

6. Optical Device

The optical device of the invention includes an optical device including the liquid crystal composition or the polymer/liquid crystal composite material (hereinafter, the liquid crystal composition and the polymer/liquid crystal composite material according to the invention may be occasionally referred to generically as the liquid crystal medium) and to be driven in the optically isotropic liquid crystal phase.

The liquid crystal medium is optically isotropic during no application of electric field, but when the electric field is applied, the optical anisotropy is caused in the liquid crystal medium to allow optical modulation by the electric field.

Specific examples of a structure of the liquid crystal display device include, as shown in FIG. 1, a structure in which electrode 1 extended from a left side and electrode 2 extended from a right side are alternately arranged in electrodes of a comb-shaped electrode substrate. When a potential difference exists between electrode 1 and electrode 2, a state in which electric fields of two directions, namely, an upward direction and a downward direction on a diagram, can be provided on the comb-shaped electrode substrate as shown in FIG. 1, if attention is paid to one electrode.

Thus, the liquid crystal composition of the invention can be used for the optical device. The liquid crystal composition of the invention exhibits a low driving voltage and a short response time, and therefore the optical device in the preferred embodiment of the invention can be driven at a low voltage to allow a high-speed response.

EXAMPLES

The invention will be described below in greater detail byway of Examples, but the invention is not limited by the Examples. In addition, unless otherwise noted, "%" is expressed in terms of "wt %."

Because a compound obtained was identified on the basis of a nuclear magnetic resonance spectrum obtained by $^1$H-NMR analysis, a gas chromatogram obtained by gas chromatography (GC) analysis and so forth, analytical methods will be described first.

$^1$H-NMR Analysis:

As a measuring apparatus, DRX-500 (made by Bruker BioSpin Corporation) was used. A sample prepared in Examples and so forth was dissolved into a deuterated solvent such as $CDCl_3$ in which the sample was soluble, and measurement was carried out under the conditions of room temperature, 500 MHz and 24 times of accumulation. In the explanation of the nuclear magnetic resonance spectrum obtained, s, d, t, q and m stand for a singlet, a doublet, a triplet, a quartet and a multiplet, respectively. Tetramethylsilane (TMS) was used for a reference material for a zero point of chemical shifts (δ values).

GC Analysis:

As a measuring apparatus, GC-14B Gas Chromatograph made by Shimadzu Corporation was used. A capillary column CBP1-M25-025 (length 25 m, bore 0.22 mm, film thickness 0.25 µm; dimethylpolysiloxane as a stationary liquid phase; non-polar) made by Shimadzu Corporation was used. Helium was used as a carrier gas, and a flow rate was adjusted at 1 milliliter per minute. Temperature in a sample injector was set at 300° C. and temperature of a detector (FID) part was set at 300° C.

A sample was dissolved into toluene to prepare a 1% solution, and then 1 microliter of the solution obtained was injected into the sample injector.

As a recorder, C-R6A Chromatopac made by Shimadzu Corporation or an equivalent thereof was used. The resulting gas chromatogram showed a retention time of a peak and a value of a peak area corresponding to each of component compounds.

As a solvent for diluting the sample, chloroform or hexane, for example, may also be used. Moreover, as the column, capillary column DB-1 (length 30 m, bore 0.32 mm, film thickness 0.25 µm) made by Agilent Technologies Inc., HP-1 (length 30 m, bore 0.32 mm, film thickness 0.25 µm) made by Agilent Technologies Inc., Rtx-1 (length 30 m, bore 0.32 mm, film thickness 0.25 µm) made by Restek Corporation, BP-1 (length 30 m, bore 0.32 mm, film thickness 0.25 µm) made by SGE International Pty. Ltd. and so forth may be used.

A ratio of the peak areas in the gas chromatogram corresponds to a ratio of the component compounds. In general, weight percent of each of the component compounds in an analytical sample is not completely identical with a percentage of each of the peak areas in the analytical sample. However, when the column described above was used in the invention, the weight percent of each of the component compounds in the analytical sample substantially corresponds to the percentage of each of the peak areas in the analytical sample because a correction coefficient is essentially 1 (one). The reason is that no significant difference exists among the correction coefficients of the component compounds. In order to more accurately determine a composition ratio of the liquid crystal compounds in the liquid crystal composition by the chromatogram, an internal standard method by the chromatogram is applied. Each component (test-component) of the liquid crystal compounds and a liquid crystal compound as a standard (standard reference material) as weighed accurately in a fixed amount are simultaneously measured by gas chromatography, and relative intensity is calculated in advance relative to a ratio of a peak area of the test-component to a peak area of the standard reference material. When correction is performed using the relative intensity of the peak area of each component to the peak area of the standard reference material, the composition ratio of the liquid crystal compounds in the liquid crystal composition can be more accurately determined from the gas chromatographic analysis.

Sample for determining physical properties of liquid crystal compound or the like:

As a sample for determining values of physical properties of the liquid crystal compound, two cases exist: a case where a compound itself is used as the sample, and a case where the compound is mixed with a base liquid crystal, and the resulting mixture was used as the sample.

In the latter case where the sample prepared by mixing the compound with the base liquid crystal is used, measurement is carried out according to the method described below. First, a sample is prepared by mixing 15% of the liquid crystal compound obtained and 85% of the base liquid crystal. Then, according to an extrapolation method based on an equation as described below, extrapolated values are calculated from measured values of the sample obtained. The extrapolated values are described as the values of physical properties of the compound.

(Extrapolated value)={100×(measured value of a sample)−(% of base liquid crystal)×(measured value of the base liquid crystal)}/(% of the compound).

When a smectic phase or crystals precipitated even at the ratio of the compound to the base liquid crystal at 25° C., a ratio of the liquid crystal compound to the base liquid crystal was changed in the order of (10 wt %:90 wt %), (5 wt %:95 wt %) and (1 wt %:99 wt %). The values of physical properties of the sample were determined at the ratio in which neither smectic phase nor crystals precipitated at 25° C. Extrapolated values were determined according to the above equation, and regarded as the values of physical properties of the liquid crystal compound.

As the base liquid crystal used for measurement, various kinds exist. For example, a composition (%) of base liquid crystal A is as described below.

Base Liquid Crystal A:

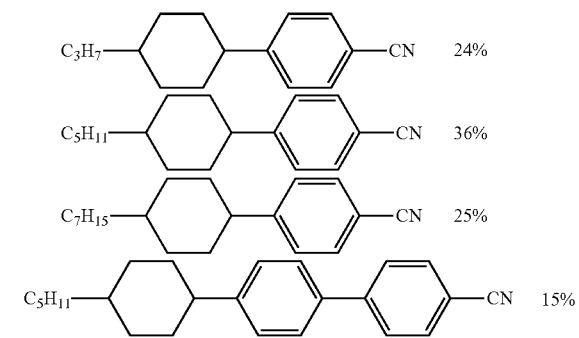

Methods for determining values of physical properties of a liquid crystal compound or the like:

The values of physical properties were determined according to the methods described below. Most of the measuring methods are described in EIAJ ED-2521A of the Standard of Electronic Industries Association of Japan, or modified thereon. Moreover, no TFT was attached to a TN device used for measurement.

Among measured values, in the case where the liquid crystal compound itself was used as the sample, values obtained were described as experimental data. In the case where a mixture of the liquid crystal compound with the base liquid crystal was used as the sample, values obtained according to the extrapolation method were described as experimental data.

Phase Structure and Phase Transition Temperature (° C.):

Measurement was carried out according to the methods 1) and 2) described below.

1) A compound was placed on a hot plate of a melting point apparatus (FP52 Hot Stage, made by Mettler-Toledo International Inc.) equipped with a polarizing microscope, and a state of phase and a change thereof were observed with the polarizing microscope while the compound was heated at a rate of 3° C. per minute, and a kind of the liquid crystal phase was specified.

2) A sample was heated and then cooled at a rate of 3° C. per minute using a differential scanning calorimeter, DSC-7 System or Diamond DSC System, made by PerkinElmer, Inc. A starting point (on set) of an endothermic peak or an exothermic peak caused by a phase change of the sample was obtained by extrapolation, and thus a phase transition temperature was determined.

The crystals were expressed below as K, and when the crystals were further distinguishable, each of the crystals was expressed as $K_1$ or $K_2$. Moreover, a smectic phase was expressed as Sm, a nematic phase as N and a chiral nematic phase as N*. A liquid (isotropic) was expressed as I. When smectic B phase or smectic A phase was distinguishable among the smectic phases, the phases were expressed as SmB or SmA, respectively. "BP" stands for a blue phase or an optically isotropic phase. Coexistence state of the two phases may be occasionally expressed in the form of (N*+I) or (N*+BP). Specifically, (N*+I) stands for a phase in which a non-liquid crystal isotropic phase and a chiral nematic phase coexist, and (N*+BP) stands for a phase in which the BP phase or the optically isotropic liquid crystal phase and the chiral nematic phase coexist. "Un" stands for an unidentified phase that is not optically anisotropic. As an expression of the phase transition temperature, for example, "K 50.0 N 100.0 I" indicates that a phase transition temperature (KN) from the crystals to the nematic phase is 50.0° C., and a phase transition temperature (NI) from the nematic phase to the liquid is 100.0° C. A same rule applied to other expressions.

Maximum Temperature of a Nematic Phase ($T_{NI}$; ° C.):

A sample (a mixture of a liquid crystal compound and a base liquid crystal) was placed on a hot plate of a melting point apparatus (FP52 Hot Stage, made by Mettler-Toledo International Inc.) equipped with a polarizing microscope, and was observed with the polarizing microscope while heating the sample at a rate of 1° C. per minute. Temperature when part of the sample changed from the nematic phase to the isotropic liquid was described as a maximum temperature of the nematic phase. A higher limit of a temperature range of the nematic phase may be occasionally abbreviated simply as "maximum temperature" below.

Compatibility at a Low Temperature:

Samples prepared by mixing a liquid crystal compound with a base liquid crystal to be 20%, 15%, 10%, 5%, 3% and 1% in an amount of the liquid crystal compound were put in glass vials. After the glass vials were kept in freezers at −10° C. or −20° C. for a predetermined period of time, whether or not the crystals or the smectic phase precipitated was observed.

Viscosity (in; 20° C. Measurement; mPa·s):

Viscosity of a mixture of s liquid crystal compound and a base liquid crystal was measured using a cone-plate (E type) viscometer.

Refractive index anisotropy (Δn):

Measurement was carried out by Abbe refractometer with a polarizing plate mounted on an ocular by using light at a wavelength of 589 nm at a temperature of 25° C. A surface of a main prism was rubbed in one direction, and then a sample (a mixture of a liquid crystal compound and a base liquid crystal) was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of refractive index anisotropy (Δn) was calculated from an equation: Δn=n∥−n⊥.

Dielectric Anisotropy (Δ∈; Measured at 25° C.):

A sample (a mixture of a liquid crystal compound and a base liquid crystal) was put in a liquid crystal cell in which a distance (gap) between two glass substrates was approximately 9 micrometers and a twist angle was 80 degrees. A voltage of 20 V was applied to the cell, and a dielectric constant (∈∥) in the major axis direction of liquid crystal molecules was measured. A voltage of 0.5 V was applied to the cell, and a dielectric constant (∈⊥) in the minor axis direction of the liquid crystal molecules was measured. A value of dielectric anisotropy was calculated from an equation: Δ∈=∈∥−∈⊥.

Pitch (P; Measured at 25° C.; Nm):

A pitch length was measured using selective reflection (Handbook of Liquid Crystals (Ekisho Binran in Japanese), page 196, issued in 2000, Maruzen Co., Ltd.). A relational expression: <n>p/λ=1 applies for selective reflection wavelength λ. Here, <n> represents an average refractive index and is provided by the following expression: $<n>=\{(n_\parallel^2+n_{195}^2)/2\}^{1/2}$. The selective reflection wavelength was measured using a microspectrophotometer (trade name: MSV-350, JEOL Co., Ltd.). The pitch was determined by dividing the thus obtained reflection wavelength by the average refractive index. A pitch of cholesteric liquid crystals having a reflection wavelength in a region of wavelength longer than a wavelength of visible light is proportional to the reciprocal number of concentration of an optically active compound in a region in which a concentration of the optically active compound is low. Thus, the pitch length of liquid crystals having a selective reflection wavelength in a visible light region was measured in several points, and the pitch was determined according to a linear extrapolation method. "Optically active compound" corresponds to a chiral agent in the invention.

In the invention, values of characteristics of the liquid crystal composition can be determined according to the methods described below. Most of the measuring methods are described in EIAJ ED-2521A of the Standard of Electronic Industries Association of Japan, or modified thereon. No TFT was attached to a TN device used for measurement.

Maximum Temperature of a Nematic Phase (NI; ° C.):

A sample was placed on a hot plate in a melting point apparatus equipped with a polarizing microscope and was heated at a rate of 1° C. per minute. Temperature when part of the sample changed from the nematic phase to the isotropic liquid was measured. An upper limit of a temperature range of the nematic phase may be occasionally abbreviated as "maximum temperature."

Minimum Temperature of a Nematic Phase ($T_c$; ° C.):

Samples each having a nematic phase were kept in freezers at 0° C., −10° C., −20° C., −30° C. and −40° C. for 10 days, and then liquid crystal phases were observed. For example, when a sample maintained the nematic phase at −20° C. and changed to crystals (or a smectic phase) at −30° C., $T_c$ was expressed as $T_c \leq -20°$ C. A lower limit of the temperature range of the nematic phase may be occasionally abbreviated as "minimum temperature."

Transition Temperature of an Optically Isotropic Liquid Crystal Phase:

A sample was placed on a hot plate of a melting point apparatus equipped with a polarizing microscope, and in a state of a crossed nicol, first heated until the sample reached temperature at which the sample became a non-liquid crystal isotropic phase, and cooled at a rate of 1° C. per minute to completely develop a chiral nematic phase or an optically isotropic liquid crystal phase. Temperature at which a phase transition was caused in a cooling process was measured, and then temperature was increased at a rate of 1° C. per minute, and temperature at which a phase transition was caused in a heating process was measured. In the invention, unless otherwise noted, the temperature at which the phase transition was caused in the heating process was described as a phase transition temperature. When judgment of the phase transition temperature was difficult in a dark field under the crossed nicol in the optically isotropic liquid crystal phase, the phase transition temperature was measured by shifting a polarizing plate by 1 to 10° from the state of the crossed nicol.

Viscosity (η; Measured at 20° C.; mPa·s):

A cone-plate (E type) viscometer was used for measurement.

Rotational viscosity (γ1; measured at 25° C.; mPas):

1) Sample having the value of a positive dielectric anisotropy: Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. A voltage was stepwise applied to the device in the range of 16 V to 19.5 V at an increment of 0.5 V. After a period of 0.2 second with no voltage application, a voltage was applied repeatedly under the conditions of only one of rectangular waves (rectangular pulse; 0.2 second) and no voltage application (2 seconds). A peak current and a peak time of a transient current generated by the applied voltage were measured. A value of rotational viscosity was obtained from the measured values and a calculation equation (8) on page 40 of the paper presented by M. Imai et al. A value of dielectric anisotropy necessary for the calculation was determined according to a method as described below by using the device used for measuring the rotational viscosity.

2) Sample having the value of a negative dielectric anisotropy: Measurement was carried out according to the method described in M. Imai et al., Molecular Crystals and Liquid Crystals, Vol. 259, p. 37 (1995). A sample was put in a VA device in which a distance (cell gap) between two glass substrates was 20 micrometers. A voltage was applied stepwise to the device in the range of 30 V to 50 V at an increment of 1 V. After a period of 0.2 second with no voltage application, a voltage was applied repeatedly under the conditions of only one of rectangular waves (rectangular pulse; 0.2 second) and no voltage application (2 seconds). A peak current and a peak time of a transient current generated by the applied voltage were measured. A value of rotational viscosity was obtained from the measured values and a calculation equation (8) on page 40 of the paper presented by M. Imai et al. As for dielectric anisotropy necessary for the calculation, a value of dielectric anisotropy measured as described below was used.

Refractive Index Anisotropy (Δn; Measured at 25° C.)

Measurement was carried out by an Abbe refractometer with a polarizing plate mounted on an ocular, using light at a wavelength of 589 nm. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of refractive index anisotropy was calculated from an equation: Δn=n∥−n⊥. When the sample was a composition, the refractive index anisotropy was measured according to the above method.

Dielectric Anisotropy (Δ∈; Measured at 25° C.):

1) Composition having a positive dielectric anisotropy: A sample was put in a liquid crystal cell in which a distance (gap) between two glass substrates was about 9 micrometers and a twist angle was 80 degrees. A voltage of 20 V was applied to the cell, and a dielectric constant (∈∥) in the major axis direction of liquid crystal molecules was measured. A voltage of 0.5 V was applied to the cell, and a dielectric constant (∈⊥) in the minor axis direction of the liquid crystal molecules was measured. A value of dielectric anisotropy was calculated from an equation: Δ∈=∈∥−∈⊥.

2) Composition having a negative dielectric anisotropy: A sample was put in a liquid crystal cell subjected to treatment in homeotropic alignment, a voltage of 0.5 V was applied to the cell, and a dielectric constant (∈∥) was measured. A sample was put in a liquid crystal cell subjected to treatment in homogeneous alignment, a voltage of 0.5 V was applied to the cell, and a dielectric constant (∈⊥) was measured. A value of dielectric anisotropy was calculated from an equation: $\Delta\varepsilon=\varepsilon_\parallel-\varepsilon_\perp$.

Threshold Voltage (Vth; Measured at 25° C.; V):

(1) Composition having a positive dielectric anisotropy: A sample was put in a normally white mode liquid crystal display device in which a distance (gap) between two glass substrates (cell gap) was $(0.5/\Delta n)$ μm and a twist angle was 80 degrees. Here, $\Delta n$ is a value of refractive index anisotropy measured according to the method described above. Rectangular waves having a frequency of 32 Hz were applied to the device. A voltage of rectangular waves was increased, and a value of voltage at 90% transmittance of light passing through the device was measured.

(2) Composition having a negative dielectric anisotropy: A sample was put in a normally black mode liquid crystal display device subjected to treatment in homeotropic alignment in which a distance (gap) between two glass substrates (cell gap) was about 9 micrometers. Rectangular waves having a frequency of 32 Hz were applied to the device. A voltage of rectangular waves was increased, and a value of voltage at 10% transmittance of light passing through the device was measured.

Voltage Holding Ratio (VHR; Measured at 25° C.; %):

A TN device used for measurement had a polyimide alignment film and a distance (cell gap) between two glass plates was 6 micrometers. A sample was put in the device, and then the device was sealed with an ultraviolet-polymerizable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was determined. Area B is an area without decay. A voltage holding ratio is a percentage of area A to area B.

Helical Pitch (Measured at 20° C.; μm):

For measuring a helical pitch, a Cano's wedge cell method was applied. A sample was injected into a Cano's wedge cell, and a gap between disclination lines (a; unit: μm) as observed from the cell was measured. The helical pitch (P) was calculated according to an equation: $P=2\times a\times \tan\theta$, in which $\theta$ is an angle between two glass plates in the wedge cell.

Alternatively, a pitch length was measured using selective reflection (Handbook of Liquid Crystals (Ekisho Binran in Japanese), page 196, issued in 2000, Maruzen Co., Ltd.). A relational expression: $\langle n\rangle p/\lambda=1$ applies for selective reflection wavelength $\lambda$. Here, $\langle n\rangle$ represents an average refractive index and is provided by the following expression: $\langle n\rangle=\{(n_\parallel^2+n_\perp^2)/2\}^{1/2}$. The selective reflection wavelength was measured using a microspectrophotometer (trade name: MSV-350, JEOL Co., Ltd.). The pitch was determined by dividing the thus obtained reflection wavelength by the average refractive index.

A pitch of cholesteric liquid crystals having a reflection wavelength in a region of wavelength longer than a wavelength of visible light is proportional to the reciprocal number of concentration of chiral gent in a region in which a concentration of the chiral agent is low. Thus, the pitch length of liquid crystals having a selective reflection wavelength in a visible light region was measured in several points, and the pitch was determined according to a linear extrapolation method.

A ratio (percentage) of components or liquid crystal compounds is expressed in terms of weight percent (wt %) based on the total weight of the liquid crystal compound. A composition is prepared by measuring weight of the components such as the liquid crystal compounds, and then mixing the components. Accordingly, calculation of weight percent of the components is easy.

Preparation of Liquid Crystal Composition NLC-A (Comparative Example 1A)

Liquid crystal composition NLC-A was prepared by mixing a plurality of liquid crystal compounds at a ratio as described below.

Liquid crystal composition NLC-A

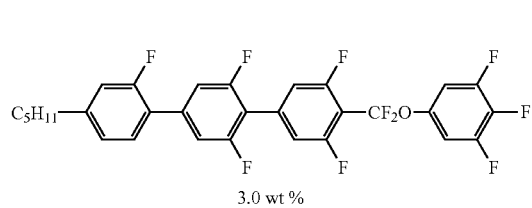

(3-3)

3.0 wt %

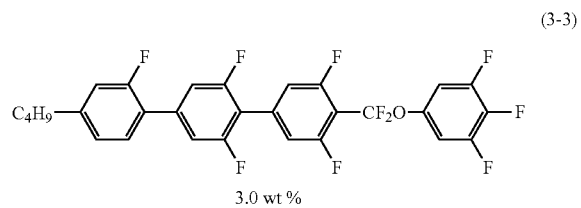

(3-3)

3.0 wt %

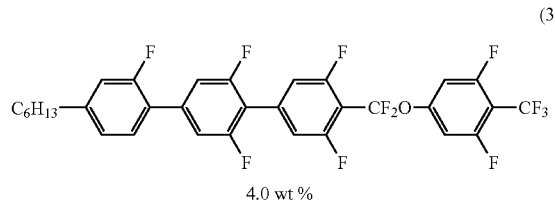

(3-3)

4.0 wt %

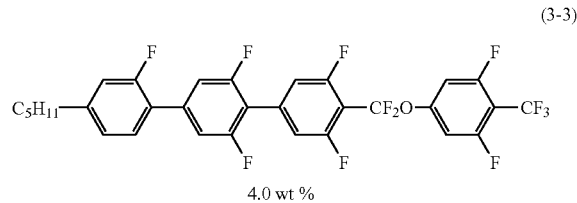

(3-3)

4.0 wt %

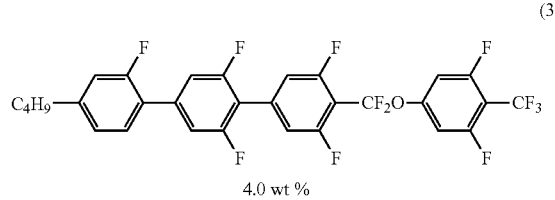

(3-3)

4.0 wt %

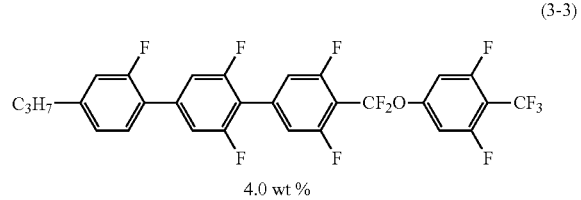

(3-3)

4.0 wt %

-continued

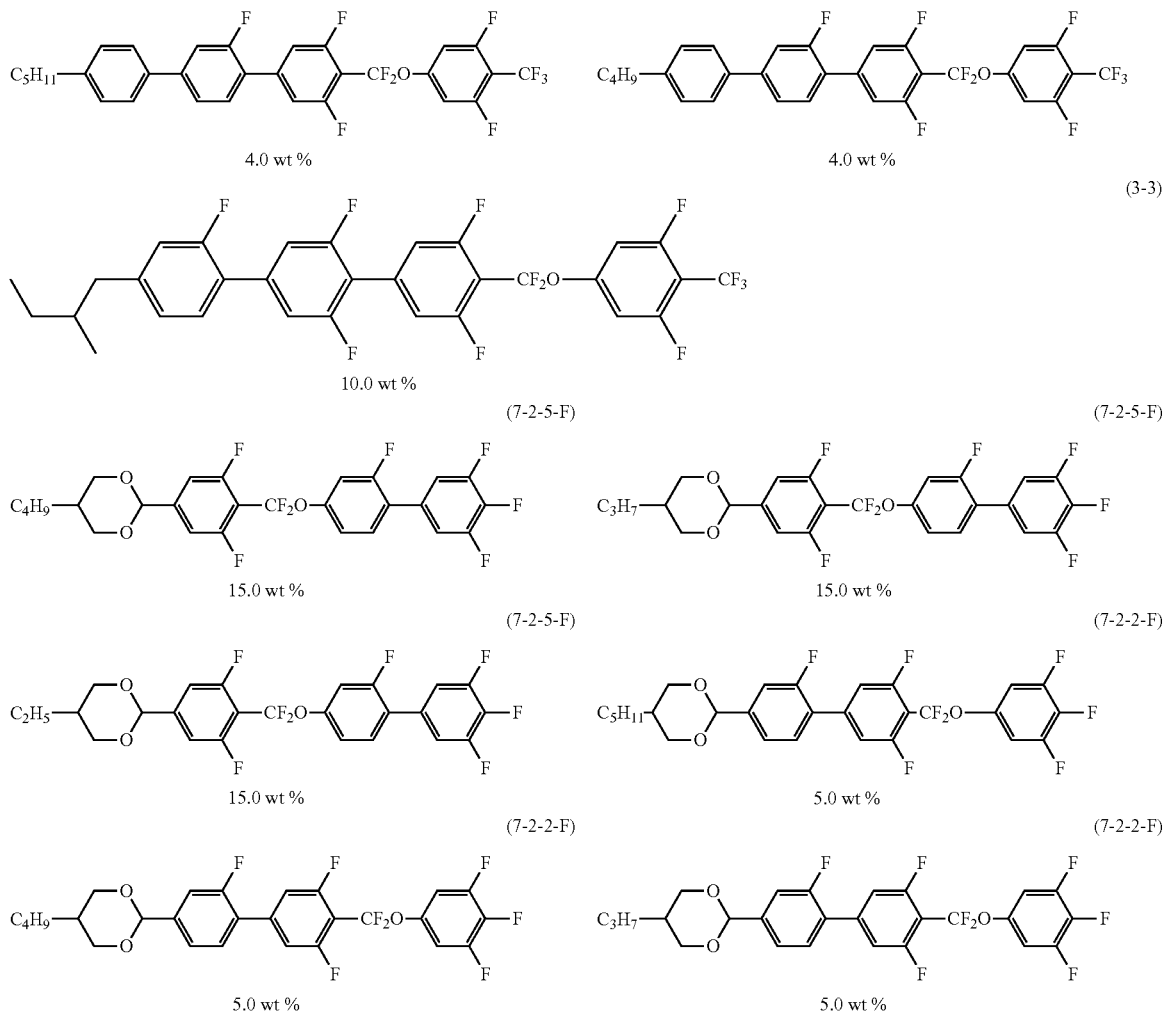

A phase transition temperature (° C.) of liquid crystal composition NLC-A was N 77.6 I.

Next, liquid crystal composition CLC-A including liquid crystal composition NLC-A (94.8 wt %) and chiral agents BN-H4 (2.6 wt %) and BN-H5 (2.6 wt %) represented by formulas as described below was obtained. A phase transition temperature (° C.) of liquid crystal composition CLC-A was N* 69.8 BP 71.6 I.

BN-H4

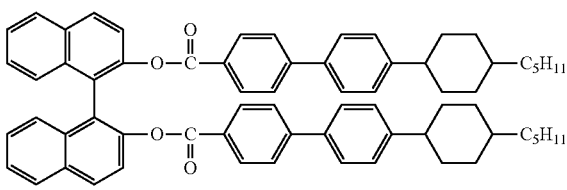

BN-H5

Preparation of Mixture of Monomer and Liquid Crystal Composition (Comparative Example 1B)

Liquid crystal composition MLC-A was prepared in which 88.8 wt % of liquid crystal composition CLC-A obtained in Comparative Example 1A, 6.0 wt % of n-dodecylacrylate, 4.8 wt % of 1,4-di-(4-(6-(acryloyloxy)hexyloxy)benzoyloxy)-2-methylbenzene (LCA-6) and 0.4 wt % of 2,2'-dimethoxyphenylacetophenone to serve as a photo-polymerization initiator were mixed. A phase transition temperature (° C.) of liquid crystal composition MLC-A was N* 40.1 BP 44.6 BP+I 45.2 I, I 44.2 BP 37.6 N*.

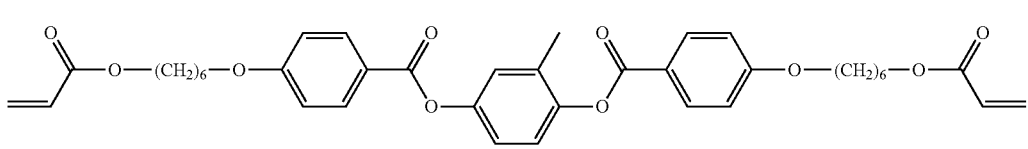
LCA-6

Preparation of Polymer/Liquid Crystal Composite Material (Comparative Example 1C)

Liquid crystal composition MLC-A obtained in Comparative Example 1B was interposed between a comb-shaped electrode substrate not subjected to alignment treatment, and an opposite glass substrate (not provided with an electrode) (cell thickness 8 μm), and a cell obtained was heated to a blue phase at 40.5° C. In the state, a polymerization reaction was performed by irradiating the composition with ultraviolet light (intensity of ultraviolet light: 23 mWcm$^{-2}$ (365 nm)) for 1 minute.

The thus obtained polymer/liquid crystal composite material (PSBP-A) maintained an optically isotropic liquid crystal phase, even when cooled to room temperature.

Optical System (Comparative Example 1D)

Figure 2:
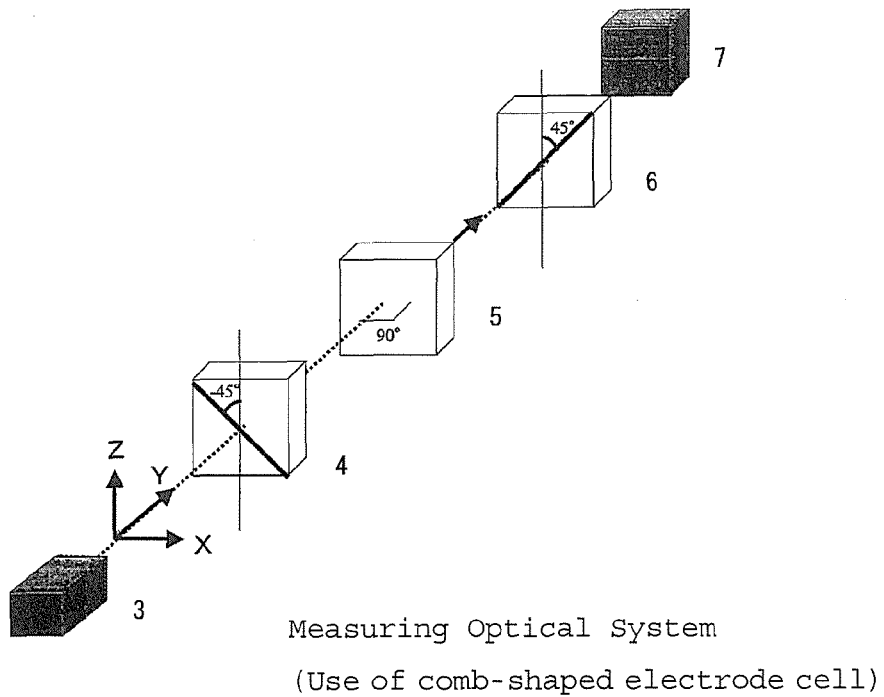
FIG. 2 shows an optical system used in Examples.

As a light source, a white light source of a polarizing microscope (ECLIPSE LV100POL, made by Nikon Corporation) was used, and an angle of incidence to a cell was adjusted to be perpendicular to a cell plane, a cell in which the polymer/liquid crystal composite material PSBP-A obtained in Comparative Example 1C was interposed was arranged in the optical system shown in FIG. 2 such that a line direction of a comb-shaped electrode was 45 degrees relative to a polarizer and an analyzer polarizing plate, and a relationship between applied voltage and transmittance was examined at room temperature. When rectangular waves having a voltage of 43 V were applied, transmittance became 85% and intensity of transmitted light saturated. Contrast was 1,100.

Preparation of Liquid Crystal Composition NLC-A3 (Comparative Example 2A)

Liquid crystal composition NLC-A3 was prepared by mixing a plurality of liquid crystal compounds at a ratio as described below.
Liquid Crystal Composition NLC-A3

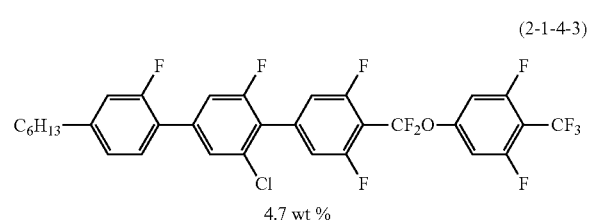
(2-1-4-3)
4.7 wt %

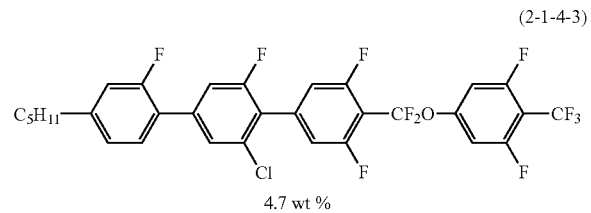
(2-1-4-3)
4.7 wt %

-continued

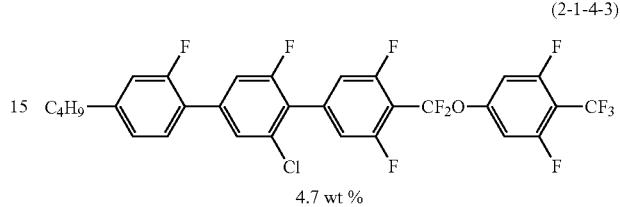
(2-1-4-3)
4.7 wt %

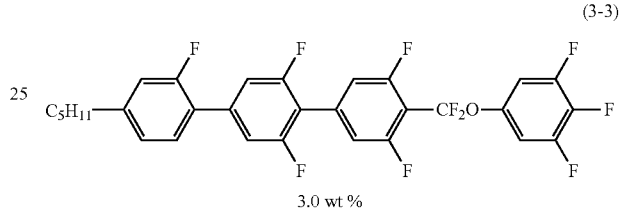
(3-3)
3.0 wt %

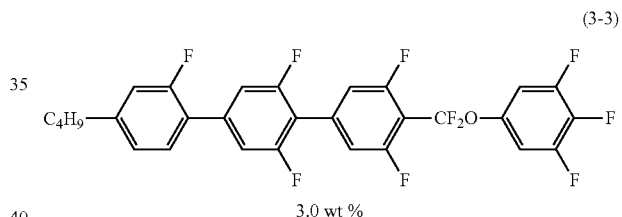
(3-3)
3.0 wt %

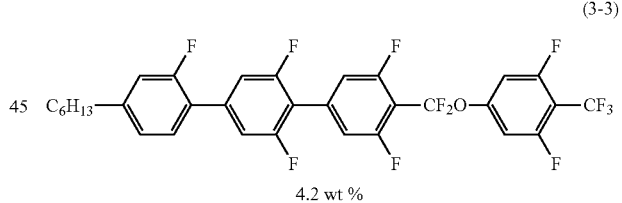
(3-3)
4.2 wt %

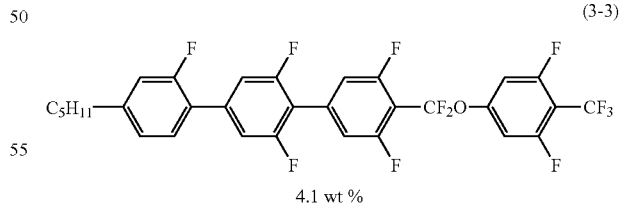
(3-3)
4.1 wt %

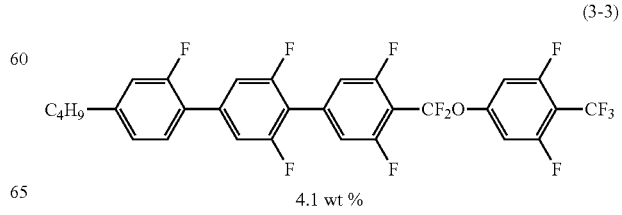
(3-3)
4.1 wt %

-continued
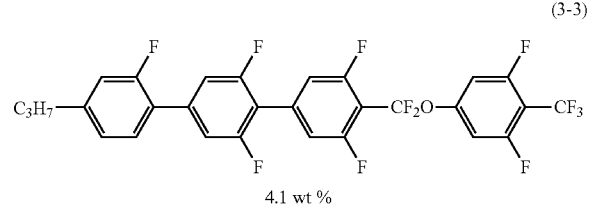
(3-3)
4.1 wt %
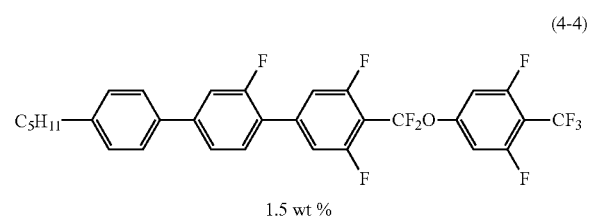
(4-4)
1.5 wt %
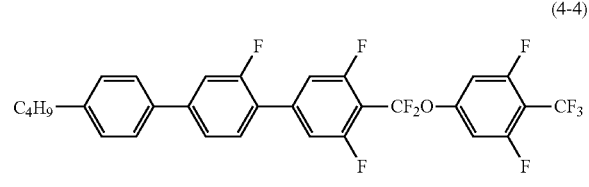
(4-4)
1.5 wt %
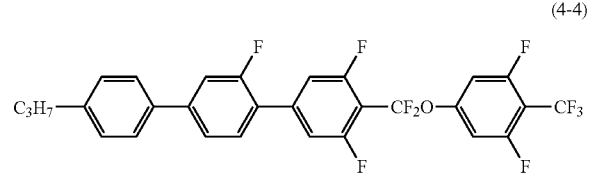
(4-4)
1.5 wt %
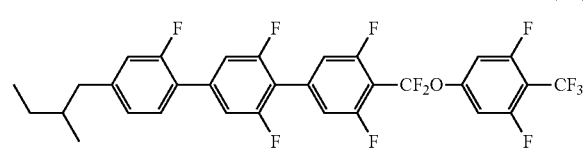
(3-3)
10.0 wt %
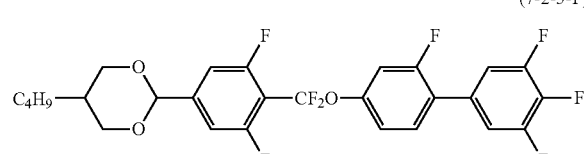
(7-2-5-F)
10.0 wt %
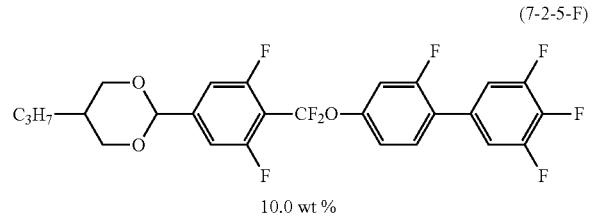
(7-2-5-F)
10.0 wt %
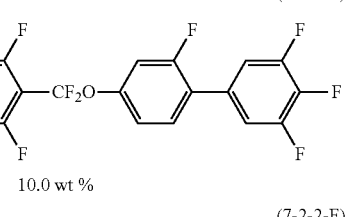
(7-2-5-F)
10.0 wt %
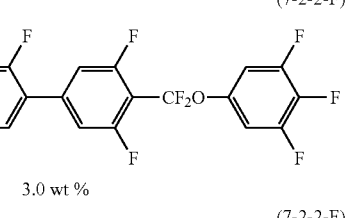
(7-2-2-F)
3.0 wt %
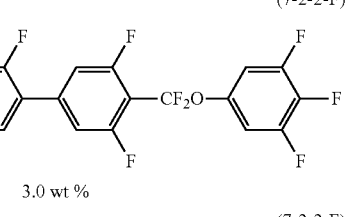
(7-2-2-F)
3.0 wt %
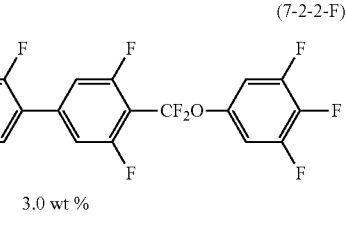
(7-2-2-F)
3.0 wt %
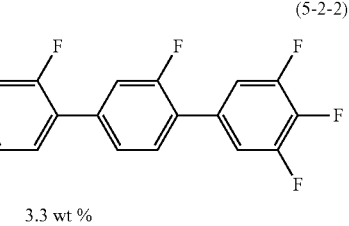
(5-2-2)
3.3 wt %
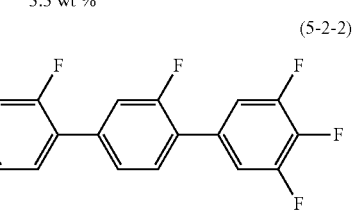
(5-2-2)
3.3 wt %
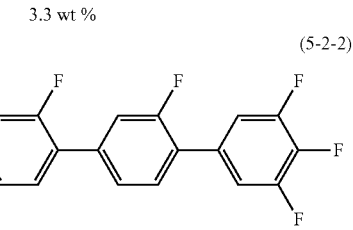
(5-2-2)
3.3 wt %
A phase transition temperature (° C.) of liquid crystal composition NLC-A3 was N 79.1 I.
Next, liquid crystal composition CLC-A3 including liquid crystal composition NLC-A3 (94.8 wt % and chiral agents BN-H4 (2.6 wt %) and BN-H5 (2.6 wt %) represented by formulas as described above was obtained. A phase transition temperature (° C.) of liquid crystal composition CLC-A3 was N* 70.1 BP 71.7 BP+I 72.4 I.

Preparation of Mixture of Monomer and Liquid Crystal Composition (Comparative Example 2B)

Liquid crystal composition MLC-A3 was prepared by mixing 88.8 wt % of liquid crystal composition CLC-A3 obtained in Comparative Example 2A, 6.0 wt % of n-dodecylacrylate, 4.8 wt % of 1,4-di(4-(6-(acryloyloxy)hexyloxy)benzoyloxy)-2-methylbenzene (LCA-6) and 0.4 wt % of 2,2'-dimethoxyphenylacetophenone as a photopolymerization initiator. A phase transition temperature (° C.) of liquid crystal composition MLC-A3 was N* 39.8 BP 44.1 BP+I-I, I-BP 43.1 BP 37.8 N*.

Preparation of Polymer/Liquid Crystal Composite Material (Comparative Example 2C)

Liquid crystal composition MLC-A3 obtained in Comparative Example 2B was interposed between a comb-shaped electrode substrate not subjected to alignment treatment, and an opposite glass substrate (not provided with an electrode) (cell thickness: 9 µm), and a cell obtained was heated to a blue phase at 39.6° C. In the state, a polymerization reaction was performed by irradiating the composition with ultraviolet light (intensity of ultraviolet light: 23 mWcm$^{-2}$ (365 nm)) for 1 minute.

The thus obtained polymer/liquid crystal composite material (PSB-A3) maintained an optically isotropic liquid crystal phase, even when cooled to room temperature.

Optical System (Comparative Example 2D)

A cell was set to the optical system shown in FIG. 2, and a relationship between applied voltage and transmittance was examined at room temperature in a manner similar to the operations in Comparative Example 1D except that a cell in which polymer/liquid crystal composite material PSBP-A3 obtained in Comparative Example 2C was interposed was used. When rectangular waves having a voltage of 42.8 V were applied, transmittance became 84% and intensity of transmitted light saturated. Contrast was 1,160.

Preparation of Liquid Crystal Composition NLC-A2 (Comparative Example 3A)

Liquid crystal composition NLC-A2 was prepared by mixing a plurality of liquid crystal compounds at a ratio as described below.
Liquid Crystal Composition NLC-A2

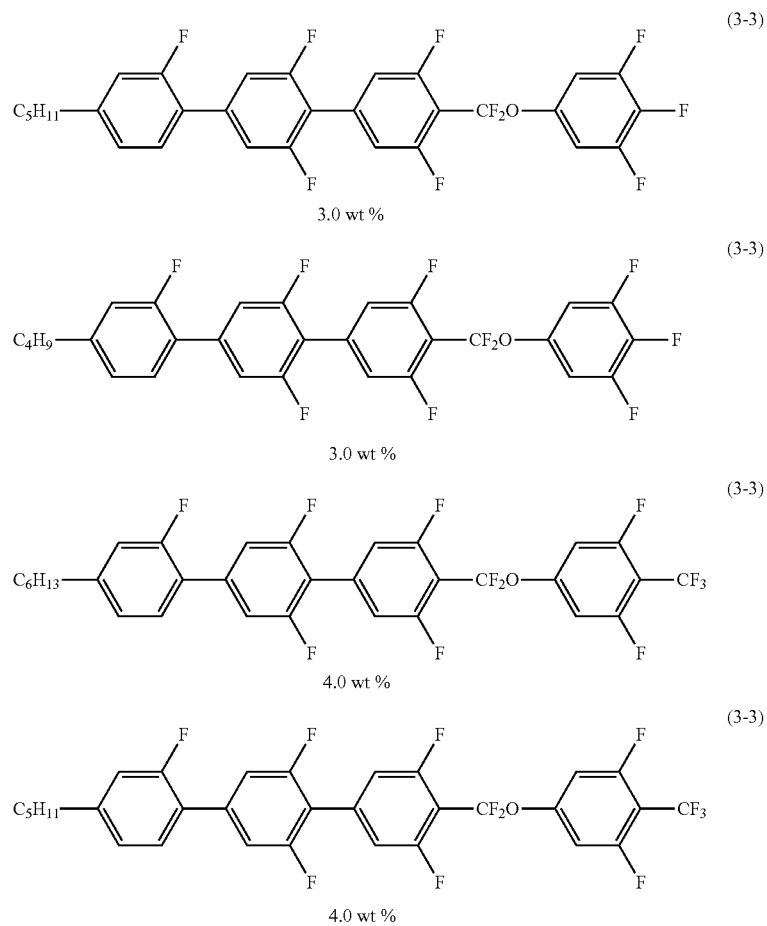

-continued
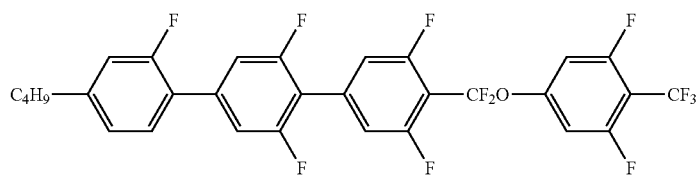
(3-3)
4.0 wt %
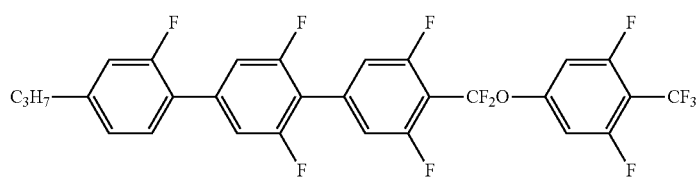
(3-3)
4.0 wt %
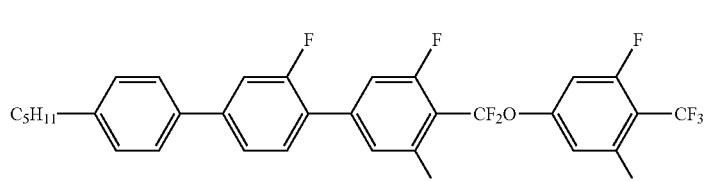
(4-4)
2.0 wt %
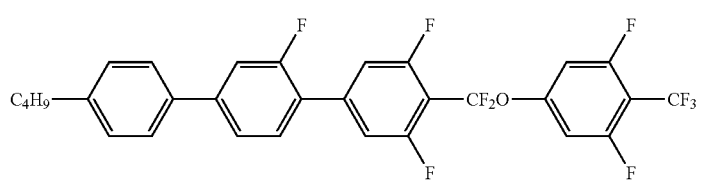
(4-4)
2.0 wt %
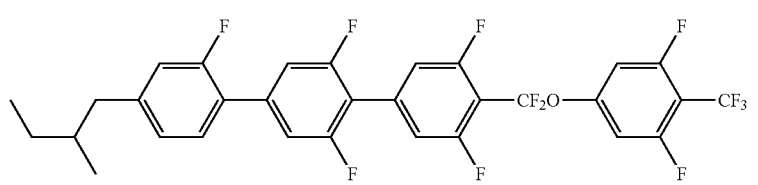
(3-3)
12.4 wt %
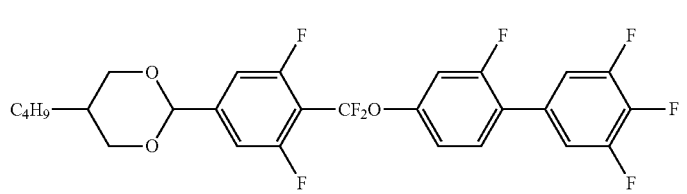
(7-2-5-F)
7.8 wt %

-continued

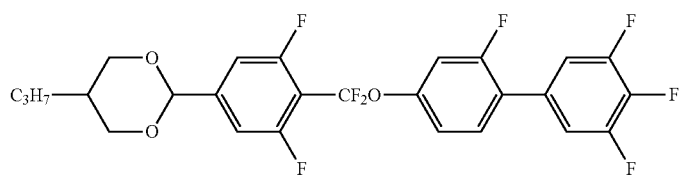
(7-2-5-F)

7.8 wt %

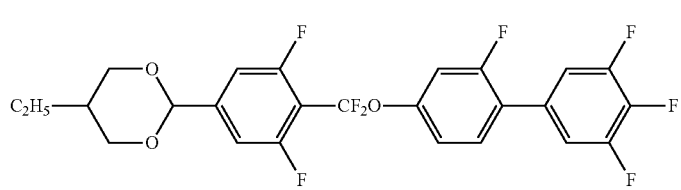
(7-2-5-F)

31.0 wt %

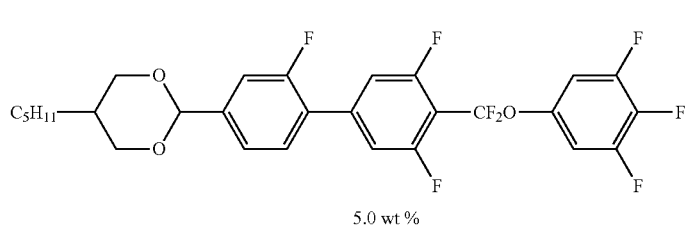
(7-2-2-F)

5.0 wt %

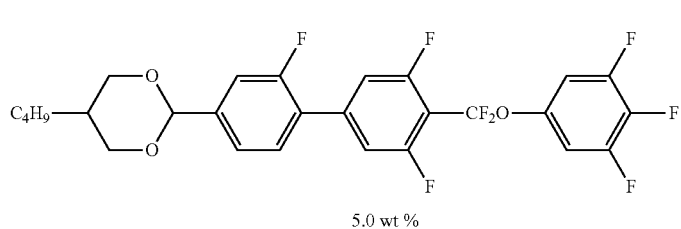
(7-2-2-F)

5.0 wt %

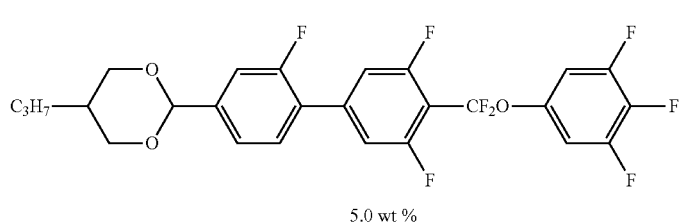
(7-2-2-F)

5.0 wt %

A phase transition temperature (° C.) of liquid crystal composition NLC-A2 was N 71.9 I.

Next, liquid crystal composition CLC-A2 including liquid crystal composition NLC-A2 (94.7 wt %) and chiral agents BN-H4 (2.6 wt %) and BN-H5 (2.7 wt %) represented by formulas as described above was obtained. A phase transition temperature (° C.) of liquid crystal composition CLC-A2 was N* 64.1 BP 65.1 BP+I 66.0 I.

Preparation of Mixture of Monomer and Liquid Crystal Composition (Comparative Example 3B)

Liquid crystal composition MLC-A2 was prepared by mixing 88.8 wt % of liquid crystal composition CLC-A2 obtained in Comparative Example 3A, 6.0 wt % of n-dodecylacrylate, 4.8 wt % of 1,4-di(4-(6-(acryloyloxy)hexyloxy)benzoyloxy)-2-methylbenzene (LCA-6) and 0.4 wt % of 2,2'-dimethoxyphenylacetophenone as a photopolymerization initiator. A phase transition temperature (° C.) of liquid crystal composition MLC-A2 was N* 35.1 BP 39.7 BP+I 40.8 I, I 39.6 BP 38.7 BP 33.2 N*.

Preparation of Polymer/Liquid Crystal Composite Material (Comparative Example 3C)

Liquid crystal composition MLC-A2 obtained in Comparative Example 3B was interposed between a comb-shaped electrode substrate not subjected to alignment treatment, and an opposite glass substrate (not provided with an electrode) (cell thickness: 8 μm), and a cell obtained was heated to a blue phase at 35.3° C. In the state, a polymerization reaction was performed by irradiating the composition with ultraviolet light (intensity of ultraviolet light: 23 mWcm$^{-2}$ (365 nm)) for 1 minute.

The thus obtained polymer/liquid crystal composite material (PSBP-A2) maintained an optically isotropic liquid crystal phase, even when cooled to room temperature.

Optical System (Comparative Example 3D)

A cell was set to the optical system shown in FIG. 2, and a relationship between applied voltage and transmittance was examined at room temperature in a manner similar to the operations in Comparative Example 1D except that a cell in which polymer/liquid crystal composite material PSBP-A2 obtained in Comparative Example 3C was interposed was used. When rectangular waves having a voltage of 40.4 V were applied, transmittance became 82% and intensity of transmitted light saturated. Contrast was 1,006.

Preparation of Liquid Crystal Composition NLC-B (Example 1A)

Liquid crystal composition NLC-B having a composition below was prepared by mixing 10.0 wt % of one kind of a compound represented by general formula (1-2-5) as described above, as compound 1, with 90 wt % of liquid crystal composition NLC-A in Comparative Example 1A.

Liquid Crystal Composition NLC-B (3-3)

$C_5H_{11}$—[structure with CF$_2$O linkage]

2.7 wt %

-continued (3-3)

$C_4H_9$—[structure with CF$_2$O linkage]

2.7 wt %

(3-3)

$C_6H_{13}$—[structure with CF$_2$O—CF$_3$ linkage]

3.6 wt %

(3-3)

$C_5H_{11}$—[structure with CF$_2$O—CF$_3$ linkage]

3.6 wt %

(3-3)

$C_4H_9$—[structure with CF$_2$O—CF$_3$ linkage]

3.6 wt %

(3-3)

$C_3H_7$—[structure with CF$_2$O—CF$_3$ linkage]

3.6 wt %

(4-4)

$C_5H_{11}$—[structure with CF$_2$O—CF$_3$ linkage]

3.6 wt %

-continued (4-4)
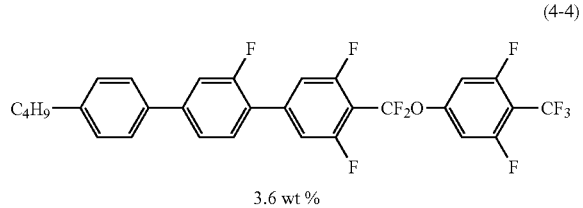
3.6 wt %

(3-3)
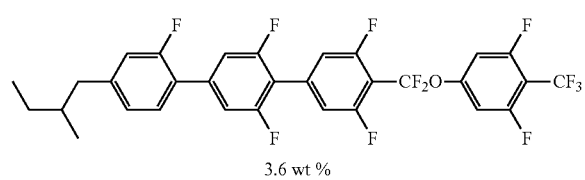
3.6 wt %

(7-2-5-F)
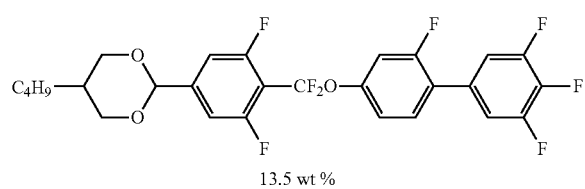
13.5 wt %

(7-2-5-F)

C3H7 ... 13.5 wt %

(7-2-5-F)

C2H5 ... 13.5 wt %

(7-2-2-F)

C5H11 ... 4.5 wt %

-continued (7-2-2-F)

C4H9 ... 4.5 wt %

(7-2-2-F)

C3H7 ... 4.5 wt %

(1-2-5-F)

... 10.0 wt %

A phase transition temperature (° C.) of liquid crystal composition NLC-B was N 66.4 I.

Next, liquid crystal composition CLC-B including liquid crystal composition NLC-B (94.6 wt %) and chiral agents BN-H4 (2.7 wt %) and BN-H5 (2.7 wt %) represented by formulas as described above was obtained. A phase transition temperature (° C.) of liquid crystal composition CLC-B was N* 56.8 BP-I.

Preparation of Mixture of Monomer and Liquid Crystal Composition (Example 1B)

Liquid crystal composition MLC-B was prepared by mixing 88.8 wt % of liquid crystal composition CLC-B obtained in Example 1A, 6.0 wt % of n-dodecylacrylate, 4.8 wt % of 1,4-di(4-(6-(acryloyloxy)dodecyloxy)benzoyloxy)-2-methylbenzene (LCA-12) and 0.4 wt % of 2,2'-dimethoxyphenylacetophenone as a photopolymerization initiator. A phase transition temperature (° C.) of liquid crystal composition MLC-B was N* 28.2 BP-I, I 30.2 BP 25.0 N*.

LCA-12

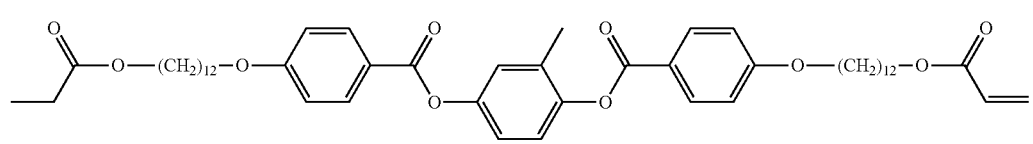

Preparation of Polymer/Liquid Crystal Composite Material (Example 1C)

Liquid crystal composition MLC-B obtained in Example 1B was interposed between a comb-shaped electrode substrate not subjected to alignment treatment, and an opposite glass substrate (not provided with an electrode) (cell thickness: 7 μm), and a cell obtained was heated to a blue phase at 28.4° C. In the state, a polymerization reaction was performed by irradiating the composition with ultraviolet light (intensity of ultraviolet light: 23 mWcm$^{-2}$ (365 nm)) for 1 minute.

The thus obtained polymer/liquid crystal composite material (PSBP-B) maintained an optically isotropic liquid crystal phase, even when cooled to room temperature.

Optical System (Example 1D)

A cell was set to the optical system shown in FIG. 2, and a relationship between applied voltage and transmittance was examined at room temperature in a manner similar to the operations in Comparative Example 1D except that a cell in which polymer/liquid crystal composite material PSBP-B obtained in Comparative Example 1C was interposed was used. When rectangular waves having a voltage of 35.2 V were applied, transmittance became 91% and intensity of transmitted light saturated. Contrast was 1,564. Thus, PSBP-B containing compound 1 was found to be driven at a low voltage.

Preparation of liquid crystal composition NLC-C (Example 2A)

Liquid crystal composition NLC-C having a composition below was prepared by mixing 15.0 wt % of one kind of compound represented by general formula (1-2-5) as described above, as compound 1, with 85 wt % of liquid crystal composition NLC-A in Comparative Example 1A.

Liquid Crystal Composition NLC-C

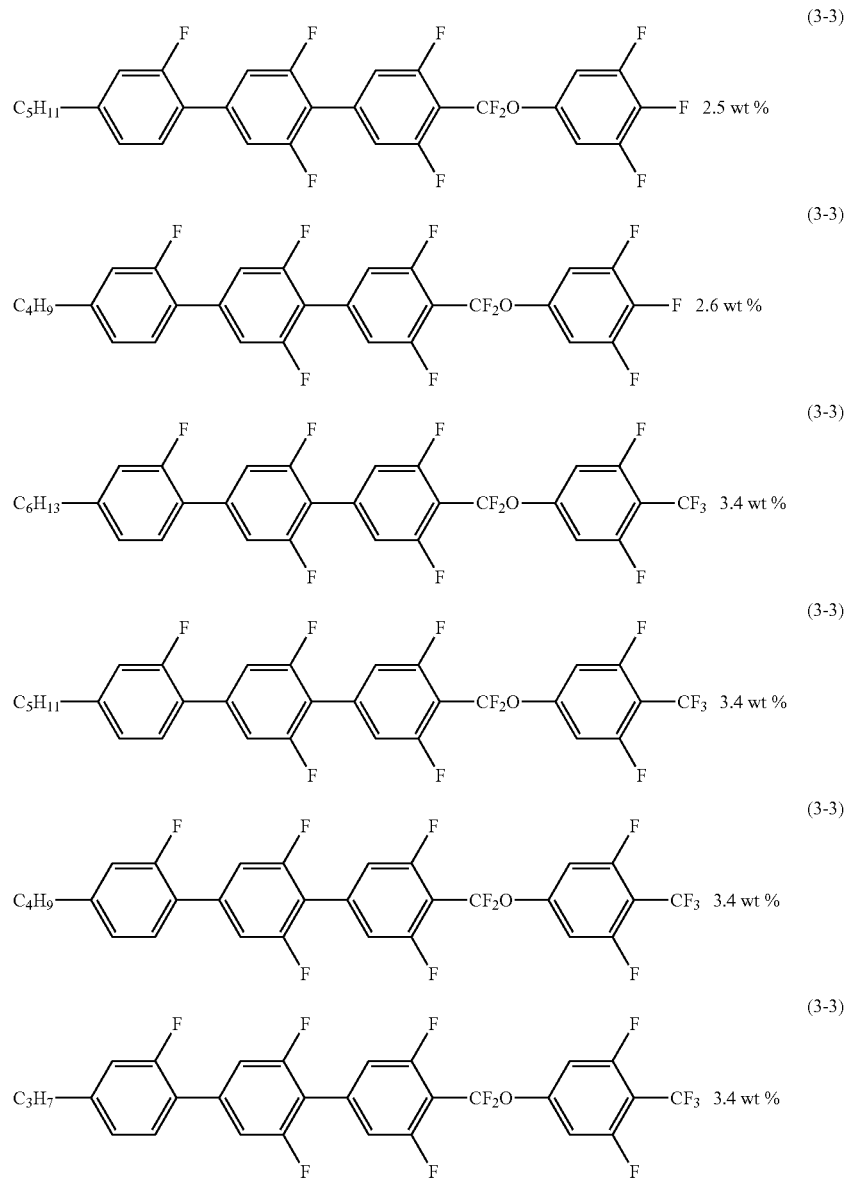

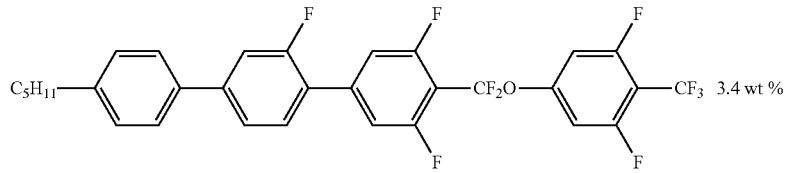 (4-4) 3.4 wt%
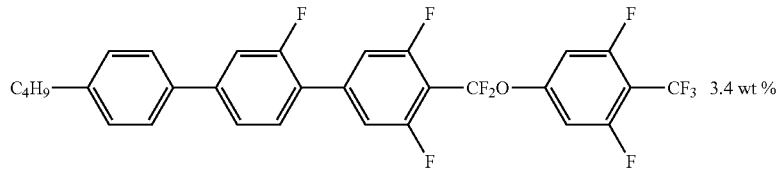 (4-4) 3.4 wt%
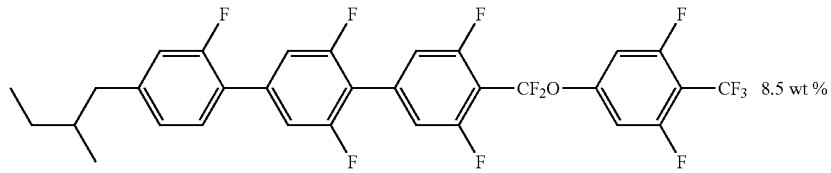 (3-3) 8.5 wt%
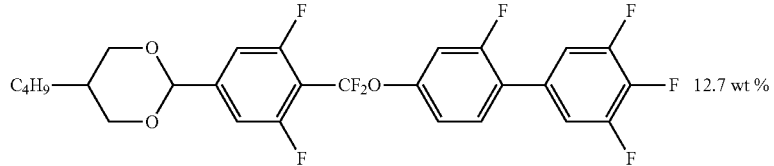 (7-2-5-F) 12.7 wt%
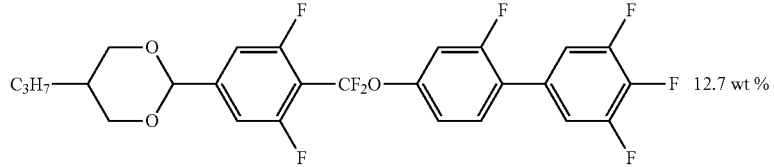 (7-2-5-F) 12.7 wt%
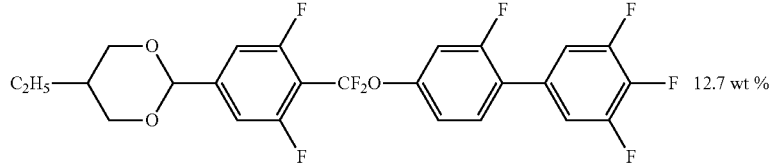 (7-2-5-F) 12.7 wt%
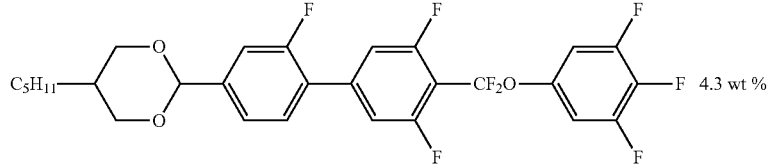 (7-2-2-F) 4.3 wt%
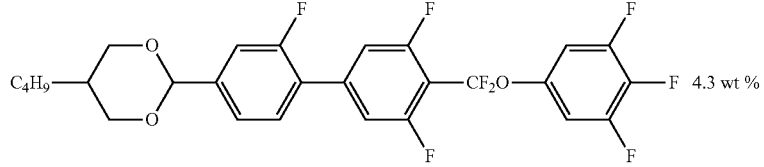 (7-2-2-F) 4.3 wt%
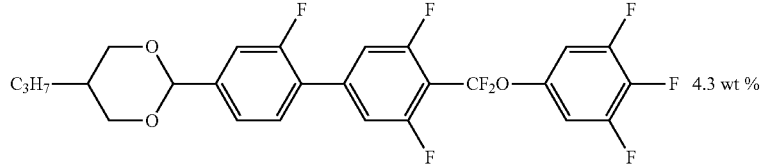 (7-2-2-F) 4.3 wt%

-continued (1-2-5-F)

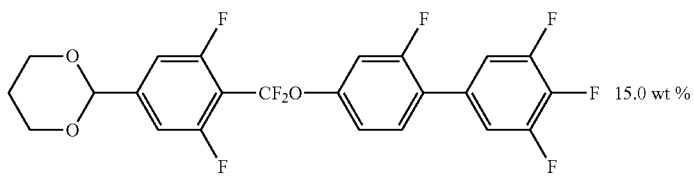
15.0 wt %

A phase transition temperature (° C.) of liquid crystal composition NLC-C was N 59.8 I.

Next, liquid crystal composition CLC-C including liquid crystal composition NLC-C (94.6 wt %) and chiral agents BN-H4 (2.7 wt %) and BN-H5 (2.7 wt %) represented by formulas as described above was obtained. A phase transition temperature (° C.) of liquid crystal composition CLC-C was N* 49.0 BP 52.2 I.

Preparation of Mixture of Monomer and Liquid Crystal Composition (Example 2B)

Preparation of Mixture of Monomer and Liquid Crystal Composition

Liquid crystal composition MLC-C was prepared by mixing 88.8 wt % of liquid crystal composition CLC-C obtained in Example 2A, 6.0 wt % of n-dodecylacrylate, 4.8 wt % of 1,4-di(4-(6-(acryloyloxy)dodecyloxy)benzoyloxy)-2-methylbenzene (LCA-12) and 0.4 wt % of 2,2'-dimethoxyphenylacetophenone as a photopolymerization initiator. A phase transition temperature (° C.) of liquid crystal composition MLC-C was N* 22.4 BP 25.4 BP+I 29.6 I, I 27.1 I+BP-BP 19.8 N*.

Preparation of Polymer/Liquid Crystal Composite Material (Example 2C)

Liquid crystal composition MLC-C obtained in Example 2B was interposed between a comb-shaped electrode substrate not subjected to alignment treatment, and an opposite glass substrate (not provided with an electrode) (cell thickness: 7 μm), and a cell obtained was heated to a blue phase at 22.6° C. In the state, a polymerization reaction was performed by irradiating the composition with ultraviolet light (intensity of ultraviolet light: 23 mWcm$^{-2}$ (365 nm)) for 1 minute.

The thus obtained polymer/liquid crystal composite material (PSBP-C) maintained an optically isotropic liquid crystal phase, even when cooled to room temperature.

Optical System (Example 2D)

A cell was set to the optical system shown in FIG. 2, and a relationship between applied voltage and transmittance was examined at room temperature in a manner similar to the operations in Comparative Example 1D except that a cell in which the polymer/liquid crystal composite material PSBP-C obtained in Example 2C was interposed was used. When rectangular waves having a voltage of 32.8 V were applied, transmittance became 89% and intensity of transmitted light saturated. Contrast was 1,825. Thus, PSBP-C containing compound 1 was found to be driven at a low voltage.

Preparation of Liquid Crystal Composition NLC-D (Example 3A)

Liquid crystal composition NLC-D having a composition below was prepared by mixing 20.0 wt % of one kind of a compound represented by general formula (1-2-5) described above, as compound 1, with 80 wt % of liquid crystal composition NLC-A in Comparative Example 1 A.

Liquid Crystal Composition NLC-D

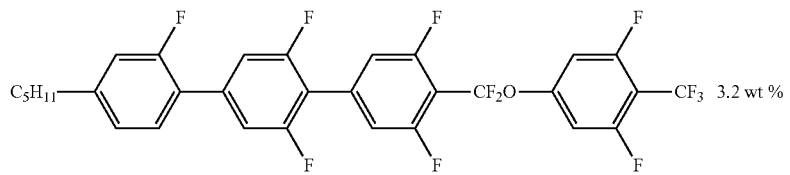 (3-3) 3.2 wt%
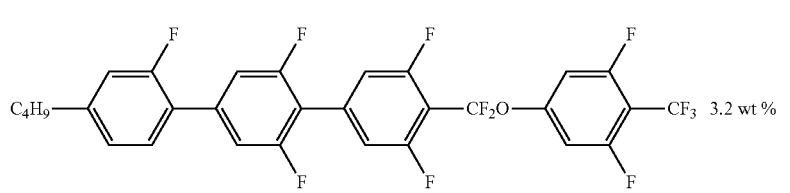 (3-3) 3.2 wt%
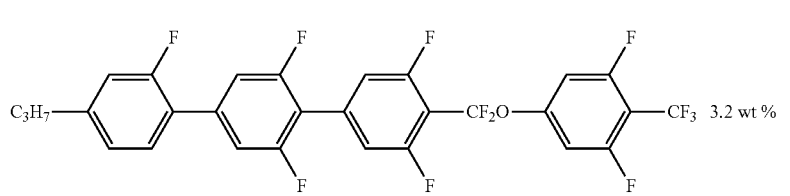 (3-3) 3.2 wt%
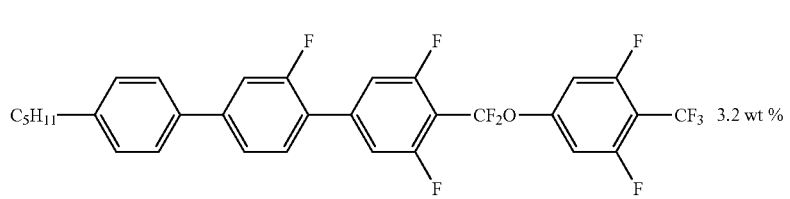 (4-4) 3.2 wt%
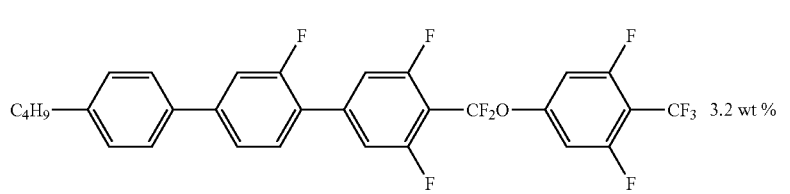 (4-4) 3.2 wt%
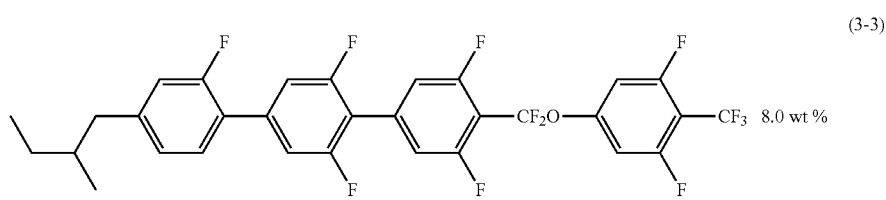 (3-3) 8.0 wt%
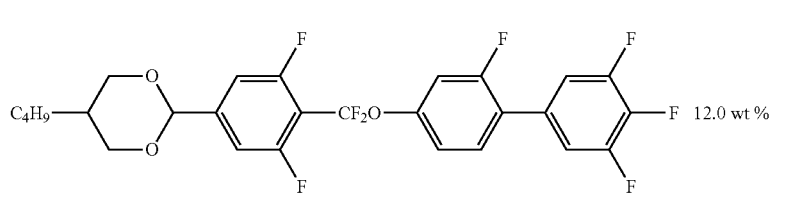 (7-2-5-F) 12.0 wt%

-continued

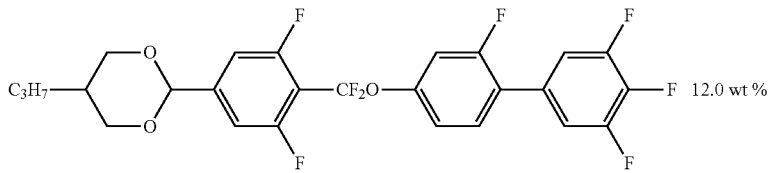
(7-2-5-F) 12.0 wt %

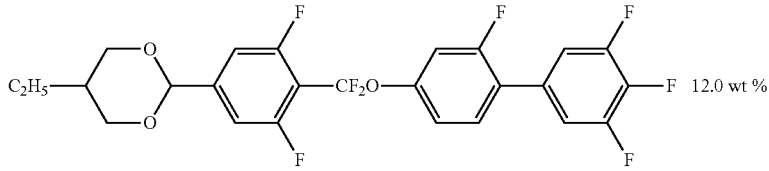
(7-2-5-F) 12.0 wt %

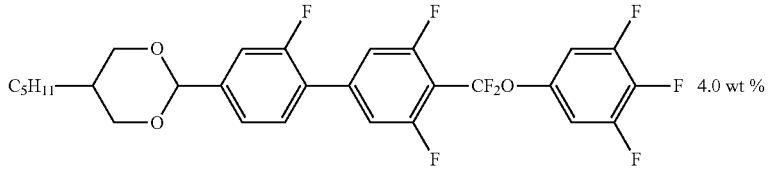
(7-2-2-F) 4.0 wt %

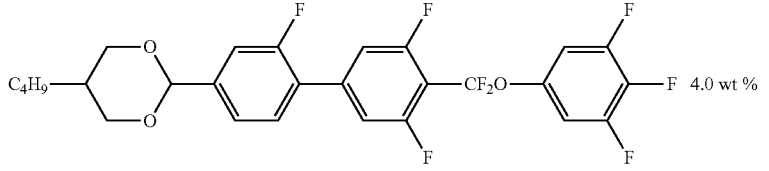
(7-2-2-F) 4.0 wt %

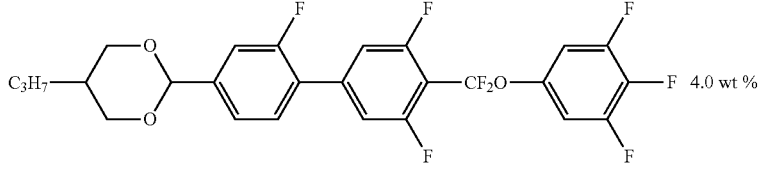
(7-2-2-F) 4.0 wt %

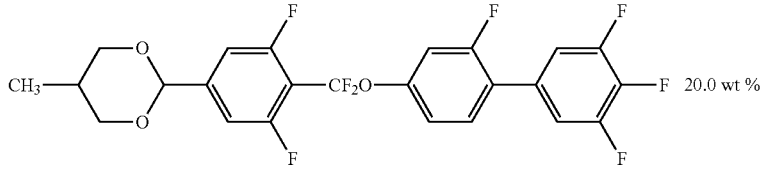
(1-2-5-F) 20.0 wt %

A phase transition temperature (° C.) of liquid crystal composition NLC-D was N 54.6 I.

Next, liquid crystal composition CLC-D including liquid crystal composition NLC-D (94.7 wt %) and chiral agents BN-H4 (2.6 wt %) and BN-H5 (2.7 wt %) represented by formulas as described above was obtained.

A phase transition temperature (° C.) of liquid crystal composition CLC-D was N* 40.3 BP 43.5 I.

Preparation of Mixture of Monomer and Liquid Crystal Composition (Example 3B)

Liquid crystal composition MLC-D was prepared by mixing 88.8 wt % of liquid crystal composition CLC-D obtained in Example 3A, 6.0 wt % of n-dodecylacrylate, 4.8 wt % of 1,4-di(4-(6-(acryloyloxy)hexyloxy)benzoyloxy)-2-methylbenzene (LCA-6) and 0.4 wt % of 2,2'-dimethoxyphenylacetophenone as a photopolymerization initiator. A phase transition temperature (° C.) of liquid crystal composition MLC-D was N* 31.2 BP 36.0 BP+I 37.1 I, I 36.1 I+BP-BP 29.4 N*.

Preparation of Polymer/Liquid Crystal Composite Material (Example 3C)

Liquid crystal composition MLC-D obtained in Example 3B was interposed between a comb-shaped electrode substrate not subjected to alignment treatment, and an opposite glass substrate (not provided with an electrode) (cell thickness: 9 μm), and a cell obtained was heated to a blue phase at 31.4° C. In the state, a polymerization reaction was performed by irradiating the composition with ultraviolet light (intensity of ultraviolet light: 23 mWcm$^{-2}$ (365 nm)) for 1 minute.

The thus obtained polymer/liquid crystal composite material (PSBP-D) maintained an optically isotropic liquid crystal phase, even when cooled to room temperature.

Optical System (Example 3D)

A cell was set to the optical system shown in FIG. 2, and a relationship between applied voltage and transmittance was examined at room temperature in a manner similar to the operations in Comparative Example 1D except that a cell in which the polymer/liquid crystal composite material PSBP-D obtained in Example 3C was interposed was used. When rectangular waves having a voltage of 32.6 V were applied, transmittance became 86% and intensity of transmitted light saturated. Contrast was 1,217.3.

Examples 3A to 3D demonstrate that CLC-D containing compound 1 has a high clearing point and PSBP-D is driven at a low voltage.

Preparation of Liquid Crystal Composition NLC-E
(Example 4A)

Liquid crystal composition NLC-E having a composition below was prepared by mixing 10.0 wt % of one kind of compound represented by general formula (1-2-5) described above, as compound, 1 with 90 wt % of liquid crystal composition NLC-A3 in Comparative Example 2A.

Liquid Crystal Composition NLC-E

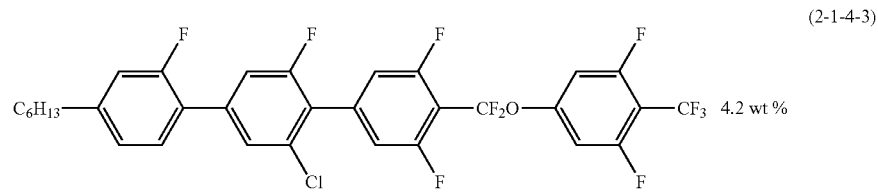
(2-1-4-3) 4.2 wt %

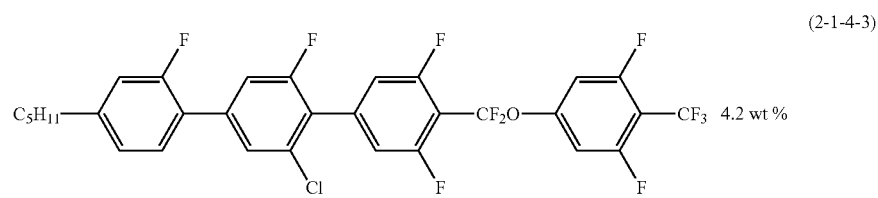
(2-1-4-3) 4.2 wt %

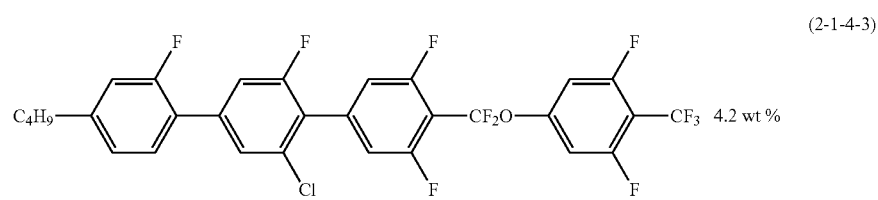
(2-1-4-3) 4.2 wt %

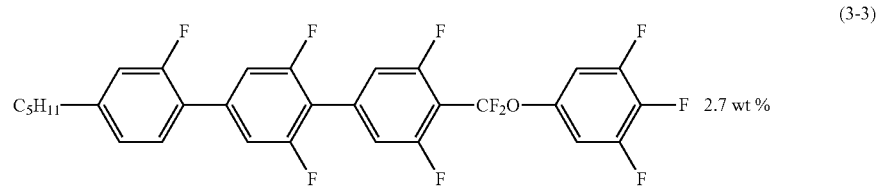
(3-3) 2.7 wt %

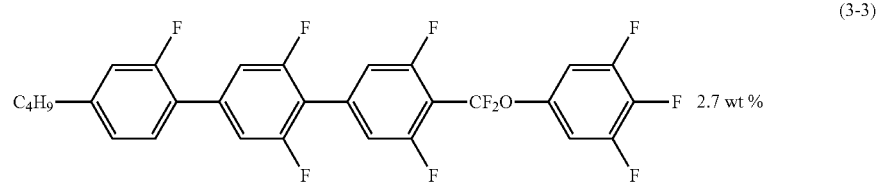
(3-3) 2.7 wt %

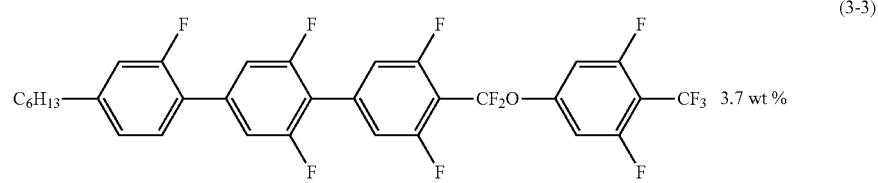
(3-3) 3.7 wt %

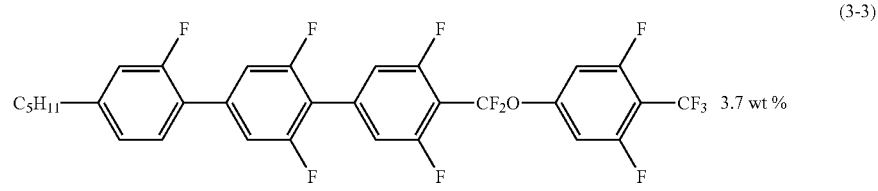
(3-3) 3.7 wt %

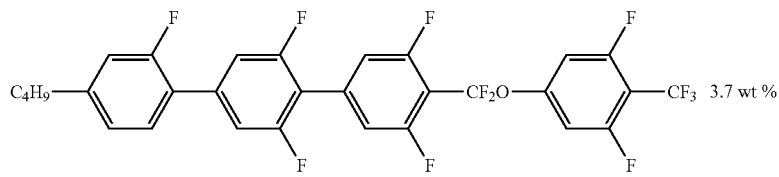
(3-3) 3.7 wt %
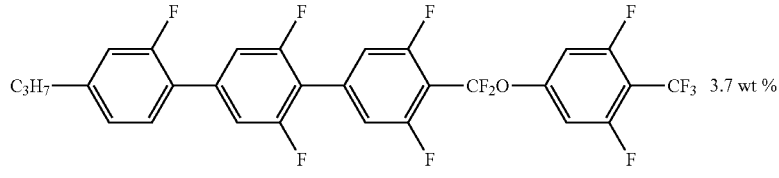
(3-3) 3.7 wt %
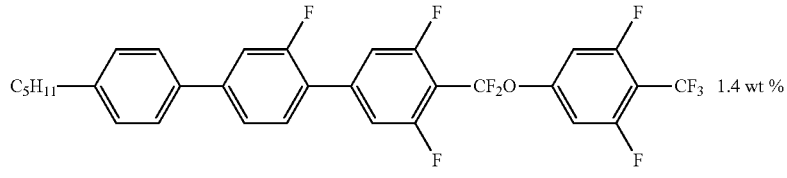
(4-4) 1.4 wt %
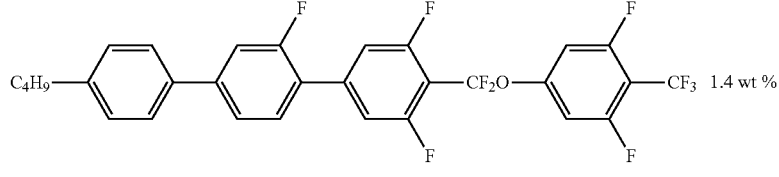
(4-4) 1.4 wt %
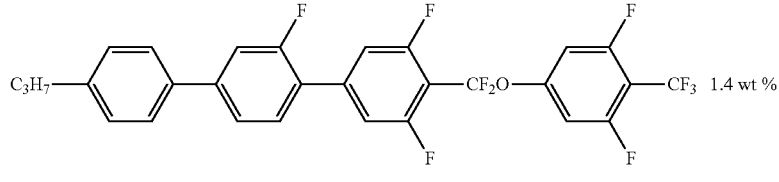
(4-4) 1.4 wt %
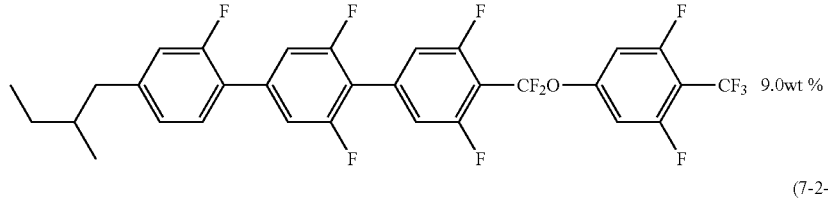
(3-3) 9.0 wt %
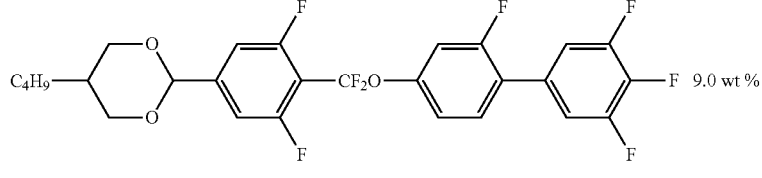
(7-2-5-F) 9.0 wt %
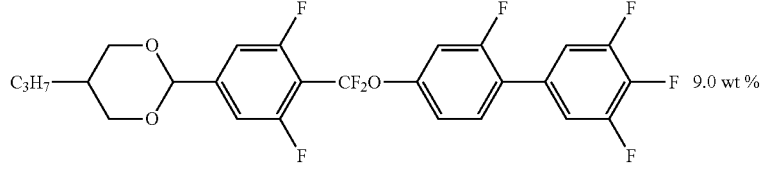
(7-2-5-F) 9.0 wt %
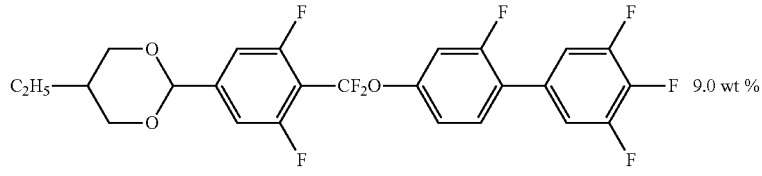
(7-2-5-F) 9.0 wt %

-continued

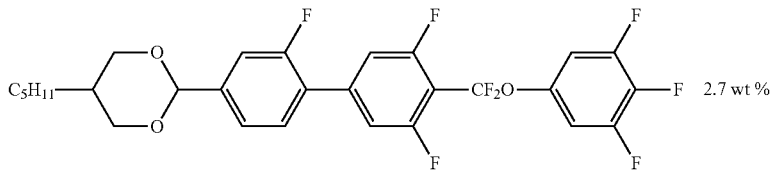 (7-2-2-F) 2.7 wt %

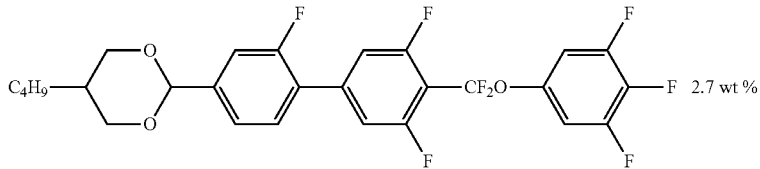 (7-2-2-F) 2.7 wt %

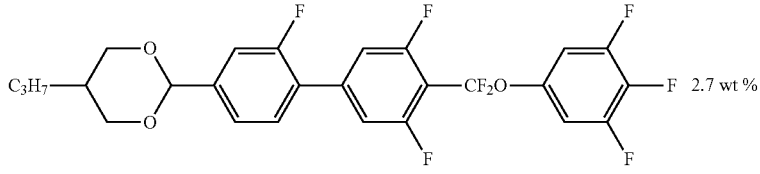 (7-2-2-F) 2.7 wt %

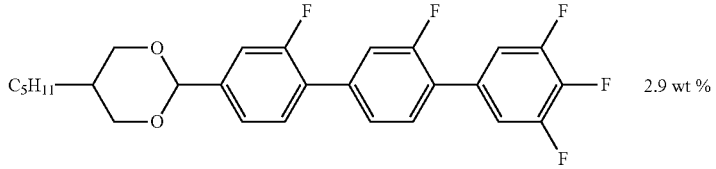 (5-2-2) 2.9 wt %

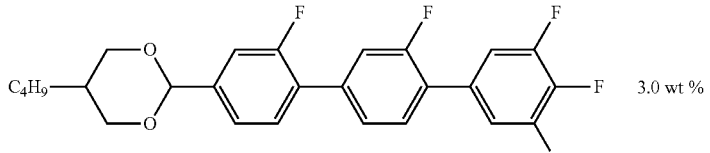 (5-2-2) 3.0 wt %

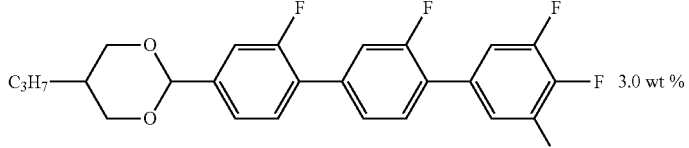 (5-2-2) 3.0 wt %

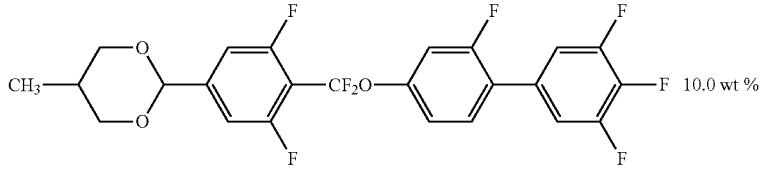 (1-2-5-F) 10.0 wt %

A phase transition temperature (° C.) of liquid crystal composition NLC-E was N 76.5 I.

Next, liquid crystal composition CLC-E including liquid crystal composition NLC-E (94.4 wt %) and chiral agents BN-H4 (2.6 wt %) and BN-H5 (2.7 wt %) represented by formulas as described above was obtained.

A phase transition temperature (° C.) of liquid crystal composition CLC-E was N* 66.5 BP 68.7 BP+I 69.5 I.

Preparation of Mixture of Monomer and Liquid Crystal Composition (Example 4B)

Liquid crystal composition MLC-E was prepared by mixing 88.8 wt % of liquid crystal composition CLC-E obtained in Example 4A, 6.0 wt % of n-dodecylacrylate, 4.8 wt % of 1,4-di(4-(6-(acryloyloxy)hexyloxy)benzoyloxy)-2-methylbenzene (LCA-6) and 0.4 wt % of 2,2'-dimethoxy-phenylacetophenone as a photopolymerization initiator. A phase transition temperature (° C.) of liquid crystal composition MLC-E was N* 34.5 BP 40.6 BP+I 41.9 I, I 38.6 BP 31.7 N*.

Preparation of Polymer/Liquid Crystal Composite Material (Example 4C)

Liquid crystal composition MLC-E obtained in Example 4B was interposed between a comb-shaped electrode substrate not subjected to alignment treatment, and an opposite glass substrate (not provided with an electrode) (cell thickness: 8 μm), and a cell obtained was heated to a blue phase at 34.7° C. In the state, a polymerization reaction was performed by irradiating the composition with ultraviolet light (intensity of ultraviolet light: 23 mWcm$^{-2}$ (365 nm)) for 1 minute.

The thus obtained polymer/liquid crystal composite material (PSBP-E) maintained an optically isotropic liquid crystal phase, even when cooled to room temperature.

Optical System (Example 4D)

A cell was set to the optical system shown in FIG. 2, and a relationship between applied voltage and transmittance was examined at room temperature in a manner similar to the operations in Comparative Example 1D except that a cell in which the polymer/liquid crystal composite material PSBP-E obtained in Example 4C was interposed was used. When rectangular waves having a voltage of 37.5 V were applied, transmittance became 90% and intensity of transmitted light saturated. Contrast was 1,245.

Examples 4A to 4D demonstrate that CLC-E containing compound 1 has a high clearing point, and PSBP-E is driven at a low voltage.

Preparation of Liquid Crystal Composition NLC-F
(Example 5A)

Liquid crystal composition NLC-F having a composition below was prepared by mixing 15.0 wt % of one kind of compound represented by general formula (1-2-5) described above, as compound 1, with 85 wt % of liquid crystal composition NLC-A3 in Comparative Example 2A.

Liquid Crystal Composition NLC-F

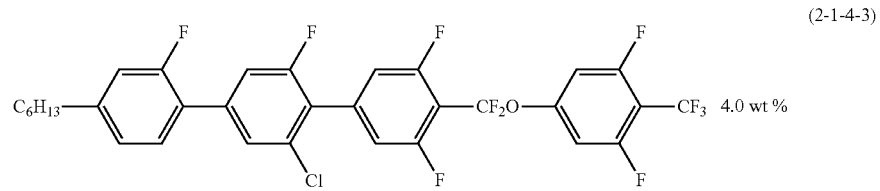

(2-1-4-3) 4.0 wt %

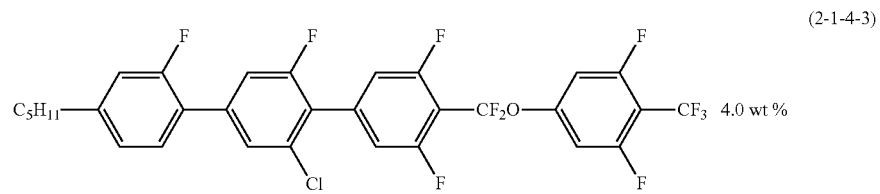

(2-1-4-3) 4.0 wt %

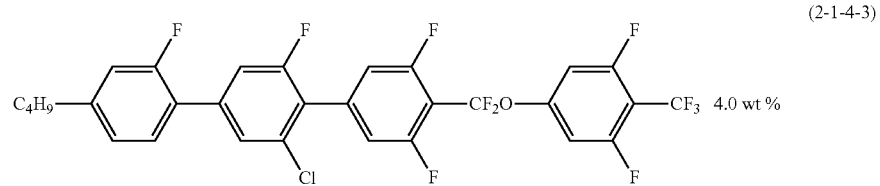

(2-1-4-3) 4.0 wt %

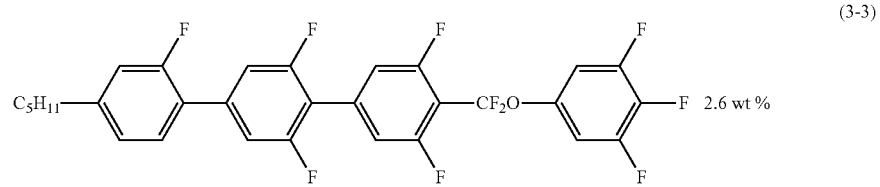

(3-3) 2.6 wt %

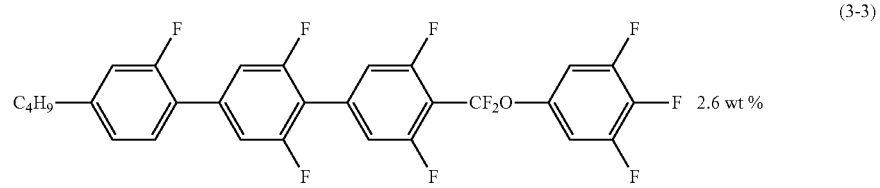

(3-3) 2.6 wt %

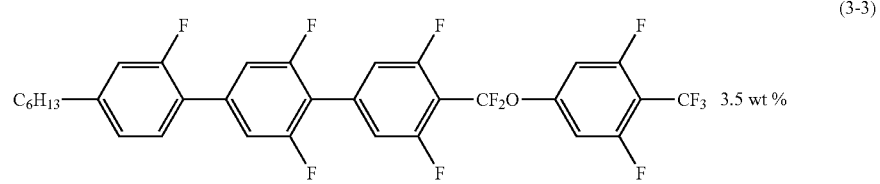

(3-3) 3.5 wt %

-continued
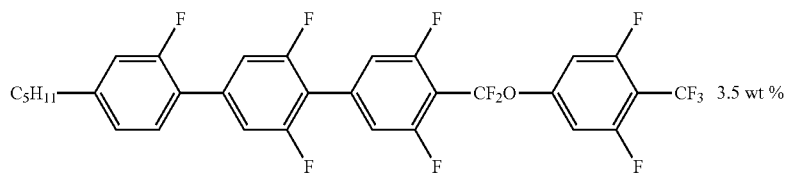 (3-3) 3.5 wt %
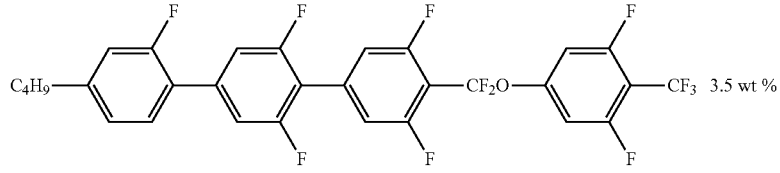 (3-3) 3.5 wt %
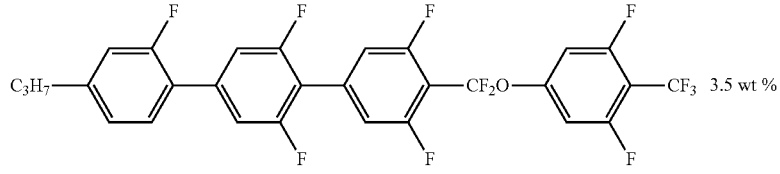 (3-3) 3.5 wt %
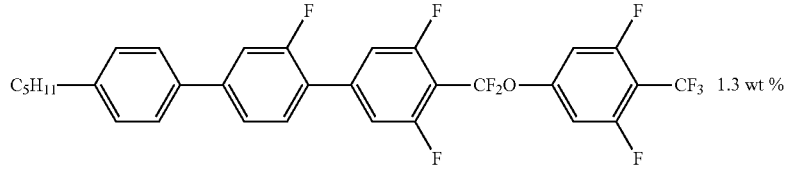 (4-4) 1.3 wt %
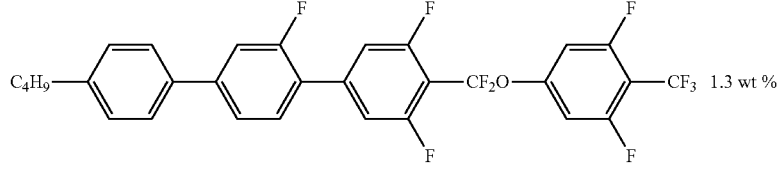 (4-4) 1.3 wt %
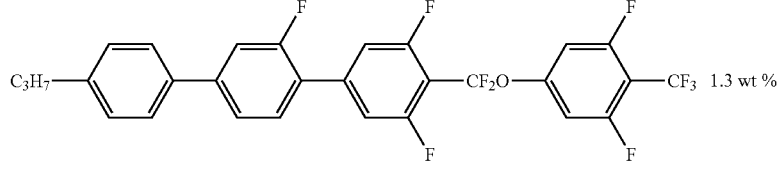 (4-4) 1.3 wt %
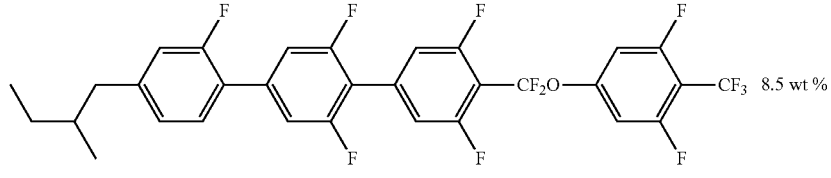 (3-3) 8.5 wt %
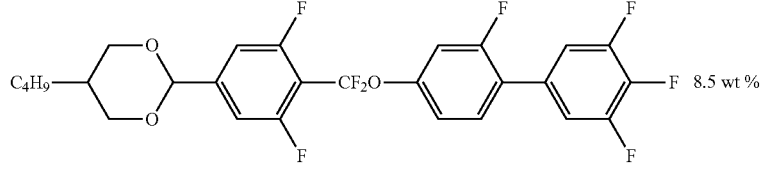 (7-2-5-F) 8.5 wt %
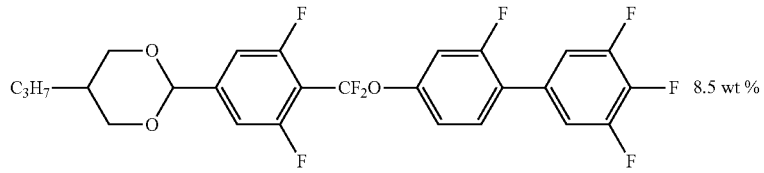 (7-2-5-F) 8.5 wt %

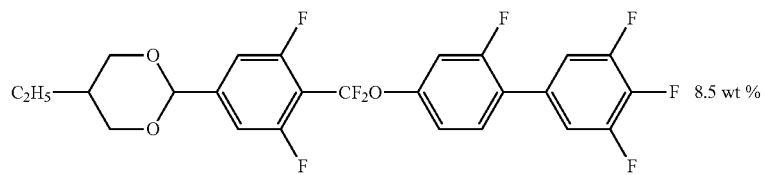
(7-2-5-F) 8.5 wt%
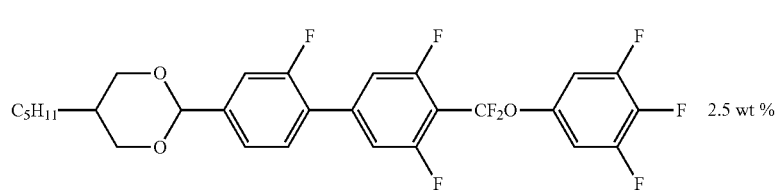
(7-2-2-F) 2.5 wt%
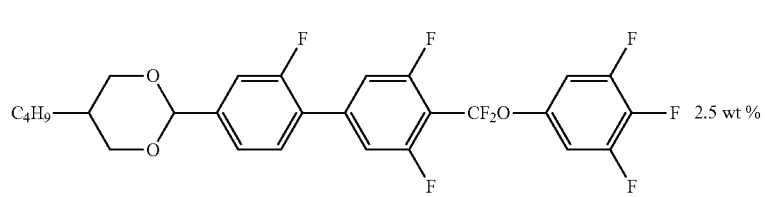
(7-2-2-F) 2.5 wt%
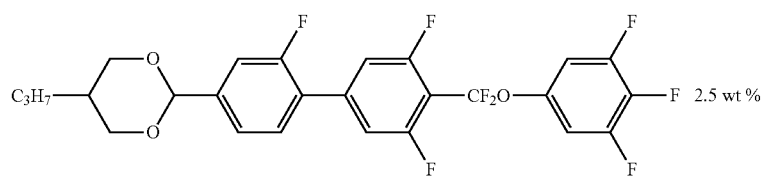
(7-2-2-F) 2.5 wt%
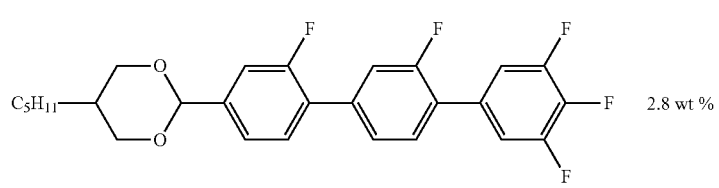
(5-2-2) 2.8 wt%
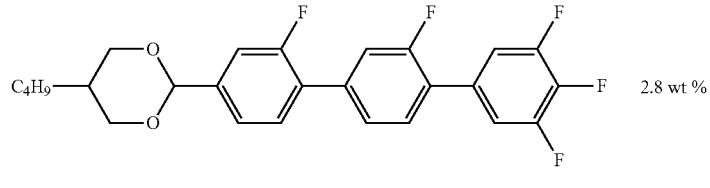
(5-2-2) 2.8 wt%
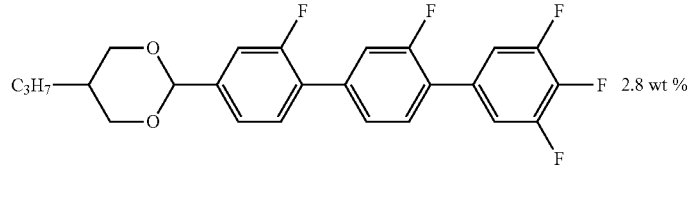
(5-2-2) 2.8 wt%
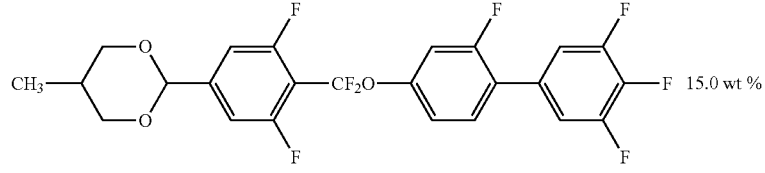
(1-2-5-F) 15.0 wt%

A phase transition temperature (° C.) of liquid crystal composition NLC-F was N 66.4 I.

Next, liquid crystal composition CLC-F including liquid crystal composition NLC-F (94.6 wt %), and chiral agents BN-H4 (2.7 wt %) and BN-H5 (2.7 wt %) represented by formulas described above was obtained.

A phase transition temperature (° C.) of liquid crystal composition CLC-F was N* 64.4 BP 66.5 BP+I 67.3 I.

Preparation of Mixture of Monomer and Liquid Crystal Composition (Example 5B)

Liquid crystal composition MLC-F was prepared by mixing 88.8 wt % of liquid crystal composition CLC-F obtained in Example 5A, 6.0 wt % of n-dodecylacrylate, 4.8 wt % of 1,4-di(4-(6-(acryloyloxy)hexyloxy)benzoyloxy)-2-methylbenzene (LCA-6) and 0.4 wt % of 2,2'-dimethoxyphenylacetophenone as a photopolymerization initiator. A phase transition temperature (° C.) of liquid crystal composition MLC-F was N* 33.8 BP 38.8 BP+I 40.6 I, I 36.4 BP 31.5 N*.

Preparation of Polymer/Liquid Crystal Composite Material (Example 5C)

Liquid crystal composition MLC-F obtained in Example 5B was interposed between a comb-shaped electrode substrate not subjected to alignment treatment, and an opposite glass substrate (not provided with an electrode) (cell thickness: 8 μm), and a cell obtained was heated to a blue phase at 34.4° C. In the state, a polymerization reaction was performed by irradiating the resulting composition with ultraviolet light (intensity of ultraviolet light: 23 mWcm$^{-2}$ (365 nm)) for 1 minute.

The thus obtained polymer/liquid crystal composite material (PSBP-F) maintained an optically isotropic liquid crystal phase, even when cooled to room temperature.

Optical System (Example 5D)

A cell was set to the optical system shown in FIG. 2, and a relationship between applied voltage and transmittance was examined at room temperature in a manner similar to the operations in Comparative Example 1D except that a cell in which the polymer/liquid crystal composite material PSBP-F obtained in Example 5C was interposed was used. When rectangular waves having a voltage of 32.6 V were applied, transmittance became 90% and intensity of transmitted light saturated. Contrast was 1,270.

Examples 5A to 5D demonstrate that CLC-F containing compound 1 has a high clearing point, and PSBP-F is driven at a low voltage.

Preparation of Liquid Crystal Composition NLC-G (Example 6A)

Liquid crystal composition NLC-G having a composition below was prepared by mixing 10.0 wt % of one kind of compound represented by general formula (1-2-5-F) described above, as compound 1, with 90 wt % of liquid crystal composition NLC-A in Comparative Example 1A.

Liquid Crystal Composition NLC-G

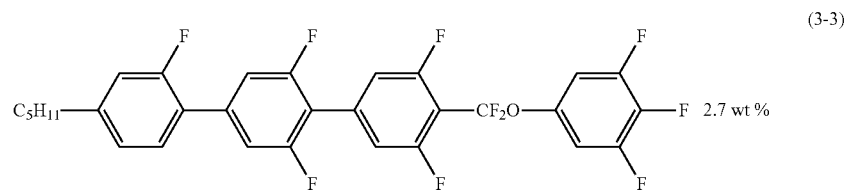

(3-3) 2.7 wt %

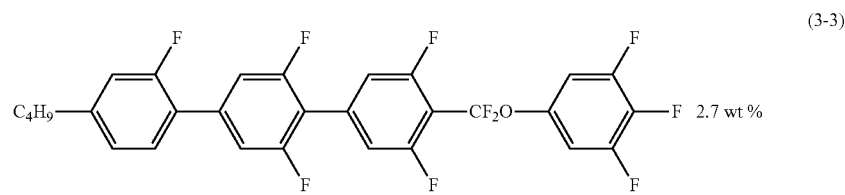

(3-3) 2.7 wt %

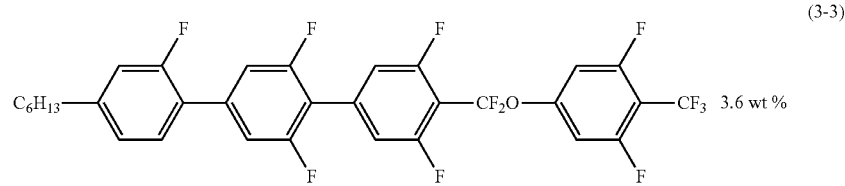

(3-3) 3.6 wt %

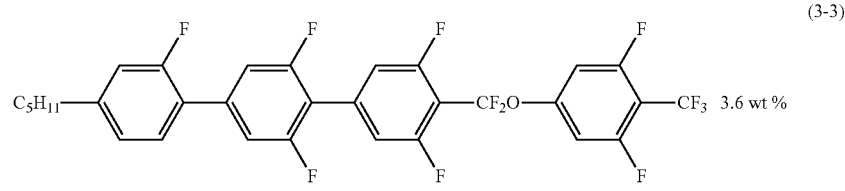

(3-3) 3.6 wt %

-continued
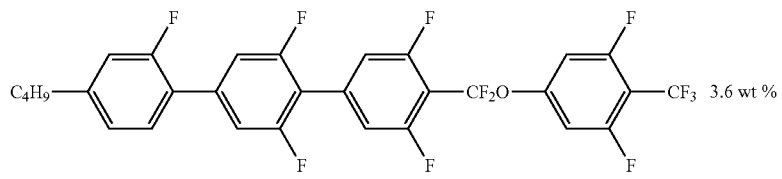 (3-3) 3.6 wt %
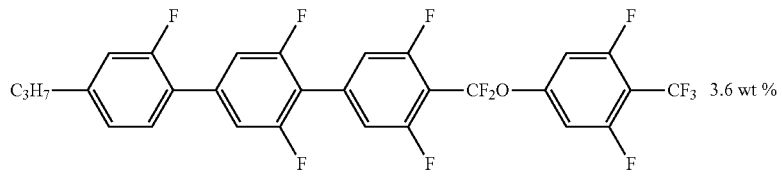 (3-3) 3.6 wt %
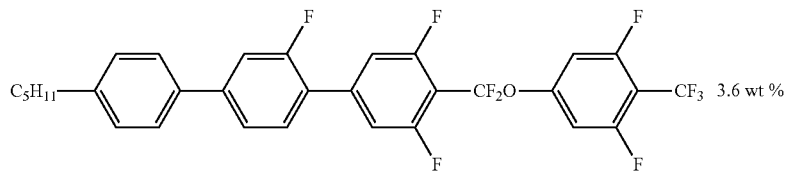 (4-4) 3.6 wt %
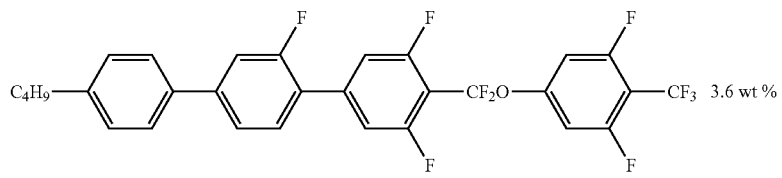 (4-4) 3.6 wt %
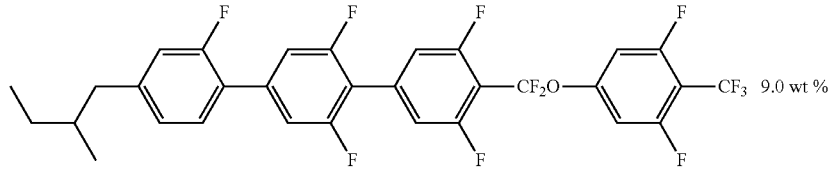 (3-3) 9.0 wt %
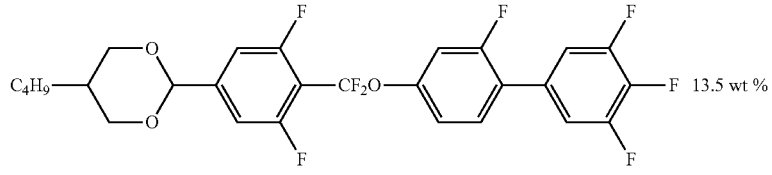 (7-2-5-F) 13.5 wt %
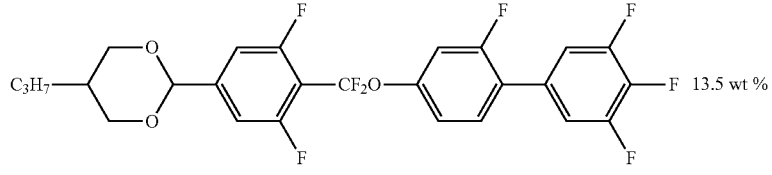 (7-2-5-F) 13.5 wt %
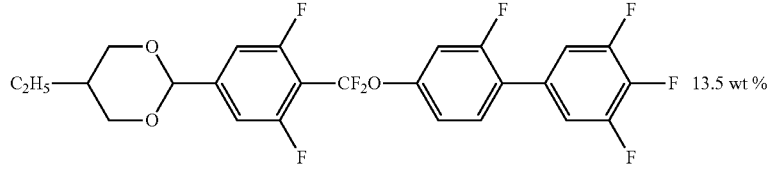 (7-2-5-F) 13.5 wt %
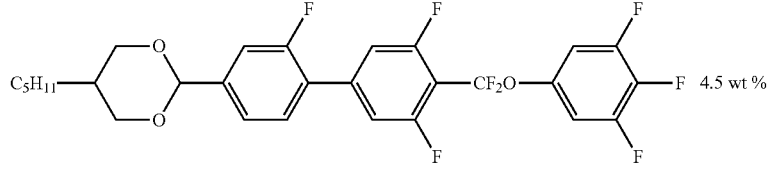 (7-2-2-F) 4.5 wt %

-continued

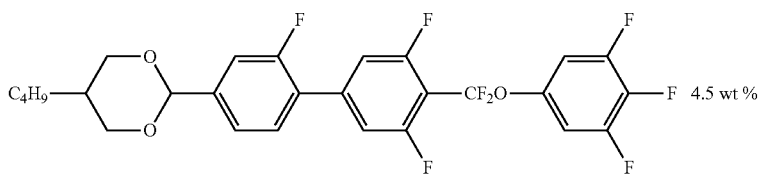

(7-2-2-F)

4.5 wt %

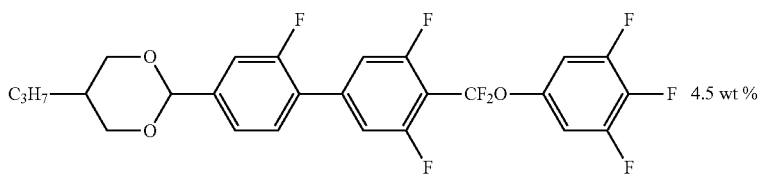

(7-2-2-F)

4.5 wt %

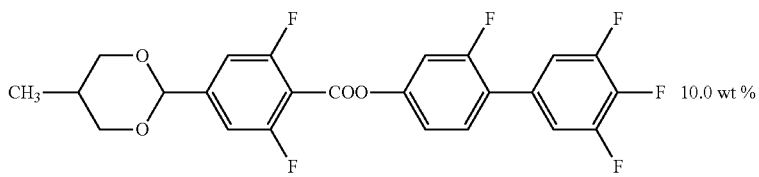

(1-2-5-E)

10.0 wt %

A phase transition temperature (° C.) of liquid crystal composition NLC-G was N 83.6 I.

Next, liquid crystal composition CLC-G including liquid crystal composition NLC-G (94.8 wt %) and chiral agents BN-H4 (2.6 wt %) and BN-H5 (2.6 wt %) represented by formulas as described above was obtained.

A phase transition temperature (° C.) of liquid crystal composition CLC-G was N* 74.5 BP 75.9 BP+I 76.7 I.

Preparation of Mixture of Monomer and Liquid Crystal Composition (Example 6B)

Liquid crystal composition MLC-G was prepared by mixing 88.8 wt % of liquid crystal composition CLC-G obtained in Example 6A, 6.0 wt % of n-dodecylacrylate, 4.8 wt % of 1,4-di(4-(6-(acryloyloxy)dodecyloxy)benzoyloxy)-2-methylbenzene (LCA-12) and 0.4 wt % of 2,2'-dimethoxyphenylacetophenone as a photopolymerization initiator. A phase transition temperature (° C.) of liquid crystal composition MLC-G was N* 31.2 BP 36.0 BP+I 37.1 I, I 36.1 I+BP-BP 29.4 N*.

Preparation of Polymer/Liquid Crystal Composite Material (Example 6C)

Liquid crystal composition MLC-G obtained in Example 6B was interposed between a comb-shaped electrode substrate not subjected to alignment treatment, and an opposite glass substrate (not provided with an electrode) (cell thickness: 7 μm), and a cell obtained was heated to a blue phase at 42.7° C. In the state, a polymerization reaction was performed by irradiating the composition with ultraviolet light (intensity of ultraviolet light: 23 mWcm$^{-2}$ (365 nm)) for 1 minute.

The thus obtained polymer/liquid crystal composite material (PSBP-G) maintained an optically isotropic liquid crystal phase, even when cooled to room temperature.

Optical System (Example 6D)

A cell was set to the optical system shown in FIG. 2, and a relationship between applied voltage and transmittance was examined at room temperature in a manner similar to the operations in Comparative Example 1D except that a cell in which the polymer/liquid crystal composite material PSBP-G obtained in Example 6C was interposed was used. When rectangular waves having a voltage of 27.6 V were applied, transmittance became 82% and intensity of transmitted light saturated. Contrast was 1,165.

Examples 6A to 6C demonstrate that CLC-G containing compound 1 has a high clearing point, and PSBP-G is driven at a low voltage.

Preparation of Liquid Crystal Composition NLC-H (Example 7A)

Liquid crystal composition NLC-H was prepared by mixing a plurality of compounds such that a compound represented by general formula (1-2-5) described above was contained in an amount of 16.0 wt % as compound 1.
Liquid Crystal Composition NLC-H

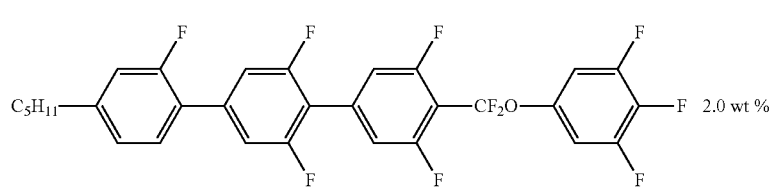

(3-3)

2.0 wt %

-continued
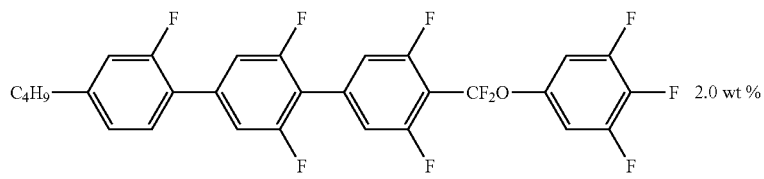 (3-3) 2.0 wt%
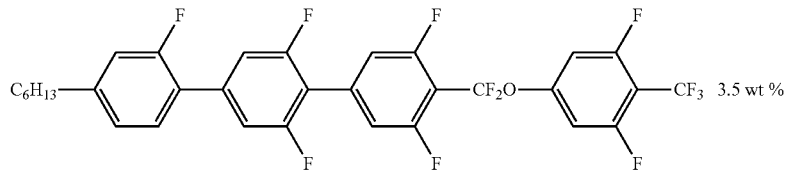 (3-3) 3.5 wt%
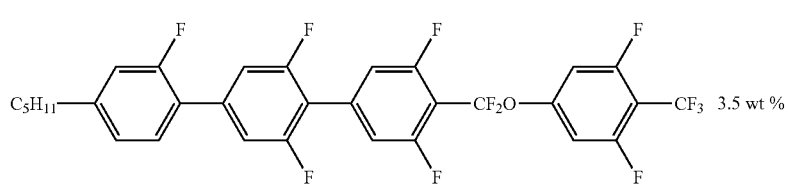 (3-3) 3.5 wt%
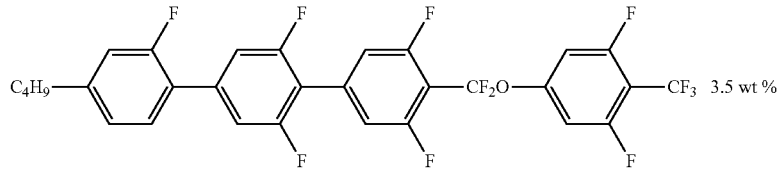 (3-3) 3.5 wt%
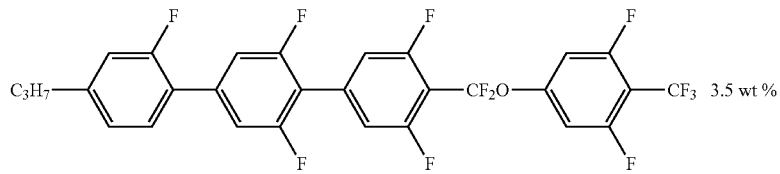 (3-3) 3.5 wt%
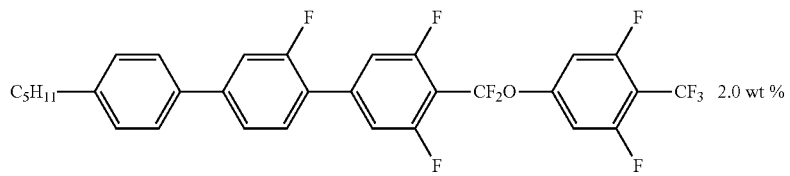 (4-4) 2.0 wt%
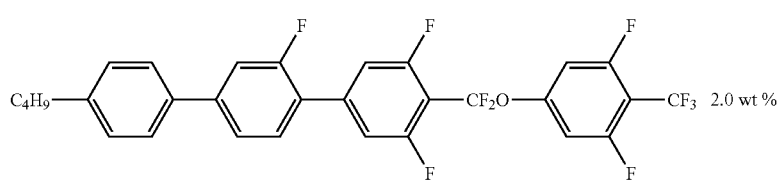 (4-4) 2.0 wt%
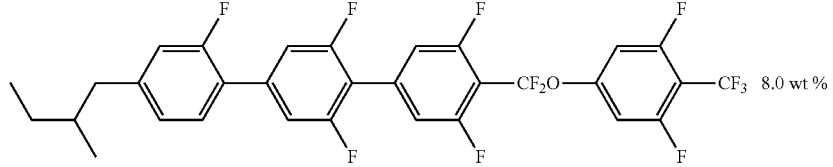 (3-3) 8.0 wt%
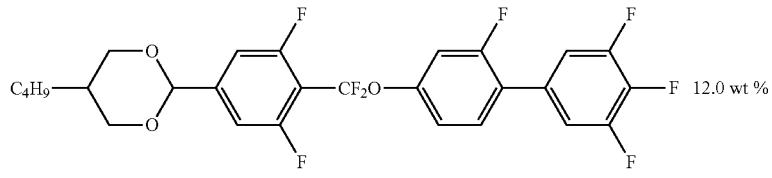 (7-2-5-F) 12.0 wt%

-continued

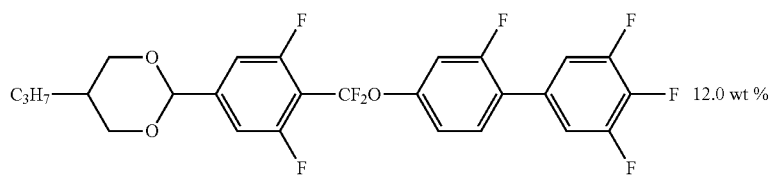
(7-2-5-F)
12.0 wt %

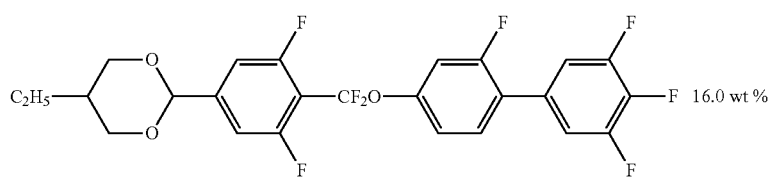
(7-2-5-F)
16.0 wt %

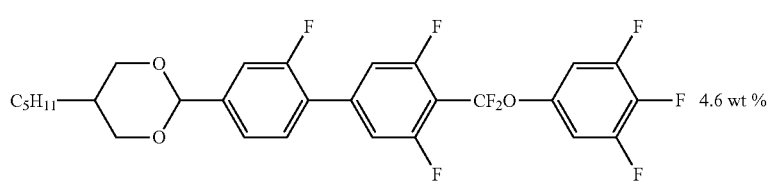
(7-2-2-F)
4.6 wt %

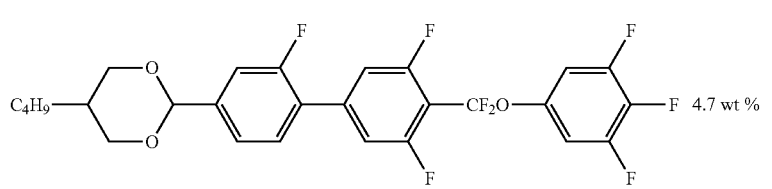
(7-2-2-F)
4.7 wt %

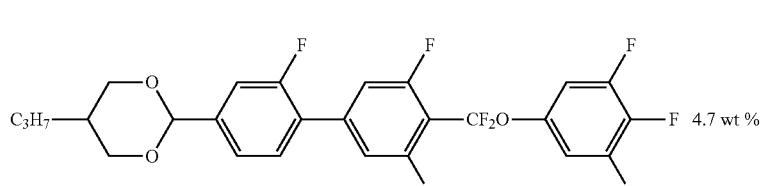
(7-2-2-F)
4.7 wt %

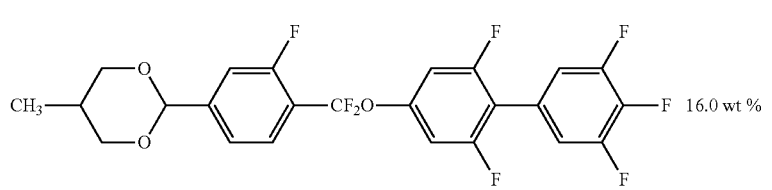
(1-2-5-F)
16.0 wt %

A phase transition temperature (° C.) of liquid crystal composition NLC-H was N 70.5 I.

Next, liquid crystal composition CLC-H including liquid crystal composition NLC-H (94.7 wt %), and chiral agents BN-H4 (2.7 wt %) and BN-H5 (2.6 wt %) represented by formulas described above was obtained.

A phase transition temperature (° C.) of liquid crystal composition CLC-H was N* 62.4 BP-I.

Preparation of Mixture of Monomer and Liquid Crystal Composition (Example 7B)

Liquid crystal composition MLC-H was prepared by mixing 88.8 wt % of liquid crystal composition CLC-H obtained in Example 7A, 6.0 wt % of n-dodecylacrylate, 4.8 wt % of 1,4-di(4-(6-(acryloyloxy)dodecyloxy)benzoyloxy)-2-methylbenzene (LCA-12) and 0.4 wt % of 2,2'-dimethoxyphenylacetophenone as a photopolymerization initiator. A phase transition temperature (° C.) of liquid crystal composition MLC-H was N* 36.5 BP 41.3 BP+I 42.0 I, I-I+BP 40.5 BP 34.9 N*.

Preparation of Polymer/Liquid Crystal Composite Material (Example 7C)

Liquid crystal composition MLC-H obtained in Example 7B was interposed between a comb-shaped electrode substrate not subjected to alignment treatment, and an opposite glass substrate (not provided with an electrode) (cell thickness: 7 μm), and a cell obtained was heated to a blue phase at 37.9° C. In the state, a polymerization reaction was performed by irradiating the composition with ultraviolet light (intensity of ultraviolet light: 23 mWcm$^{-2}$ (365 nm)) for 1 minute.

The thus obtained polymer/liquid crystal composite material (PSBP-H) maintained an optically isotropic liquid crystal phase, even when cooled to room temperature.

Optical System (Example 7D)

A cell was set to the optical system shown in FIG. 2, and a relationship between applied voltage and transmittance was examined at room temperature in a manner similar to the operations in Comparative Example 1D except that a cell in which the polymer/liquid crystal composite material PSBP-H obtained in Example 7C was interposed was used.

When rectangular waves having a voltage of 35.2 V were applied, transmittance became 91% and intensity of transmitted light saturated. Contrast was 1,534. Thus, PSBP-H containing compound 1 of the invention was found to be driven at a low voltage.

Preparation of Liquid Crystal Composition NLC-I
(Example 8A)

Liquid crystal composition NLC-I was prepared by mixing a plurality of compounds at a ratio described below such that four kinds of compounds represented by general formula (1-2-5) described above were contained in a total amount of 24.0 wt % as compound 1.

Liquid crystal composition NLC-I

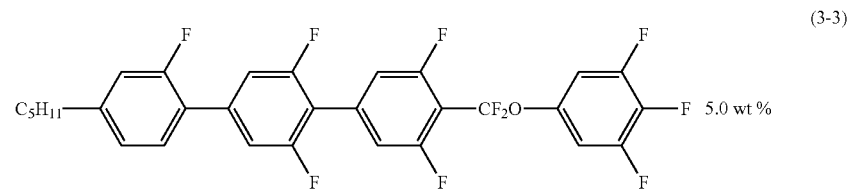
(3-3) 5.0 wt %

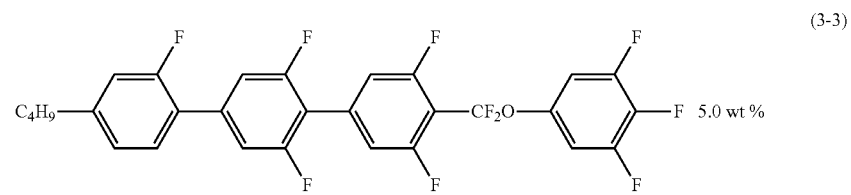
(3-3) 5.0 wt %

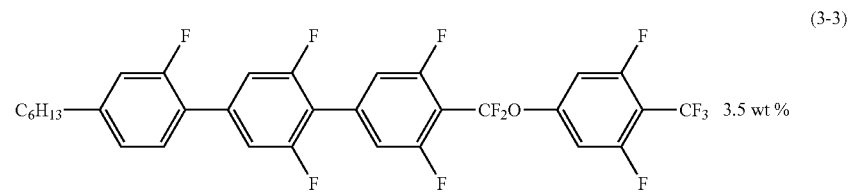
(3-3) 3.5 wt %

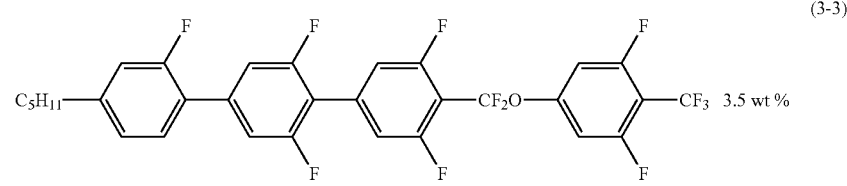
(3-3) 3.5 wt %

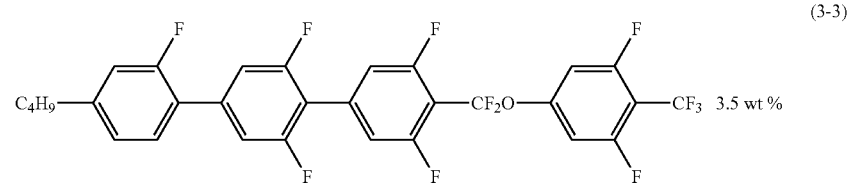
(3-3) 3.5 wt %

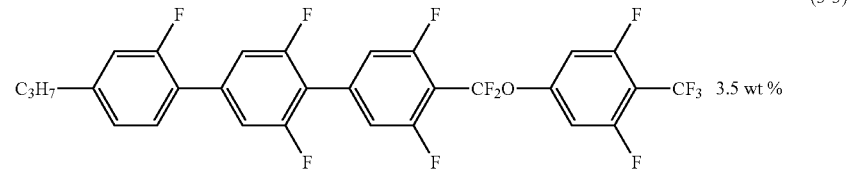
(3-3) 3.5 wt %

-continued
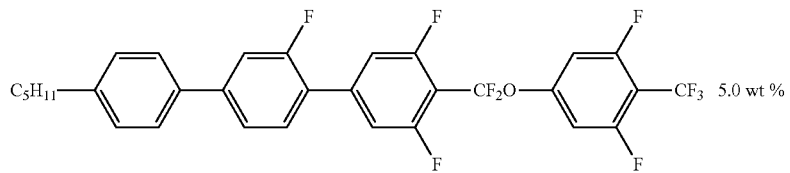 (4-4) 5.0 wt%
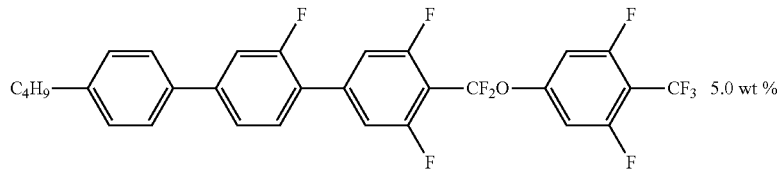 (4-4) 5.0 wt%
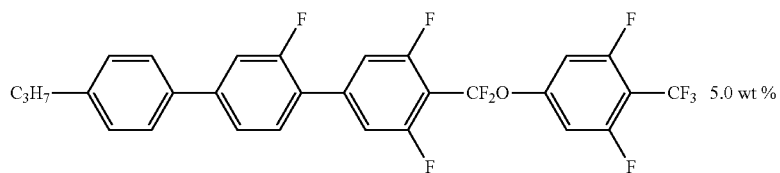 (4-4) 5.0 wt%
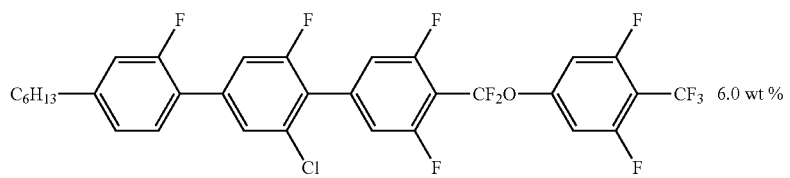 (2-1-4-3) 6.0 wt%
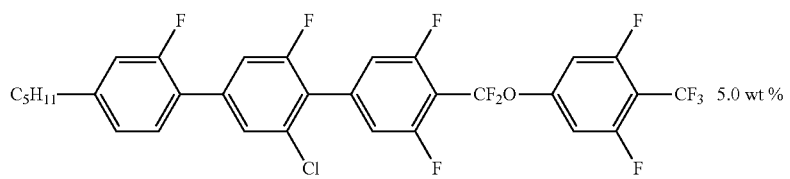 (2-1-4-3) 5.0 wt%
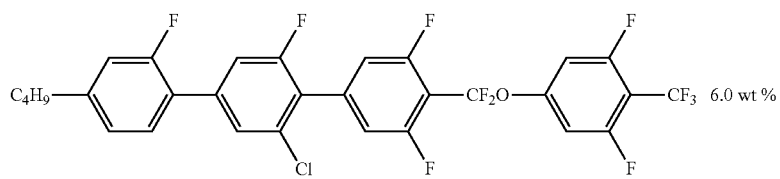 (2-1-4-3) 6.0 wt%
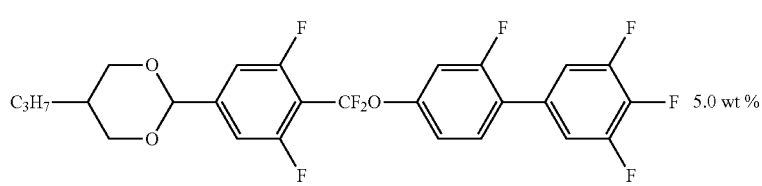 (7-2-5-F) 5.0 wt%
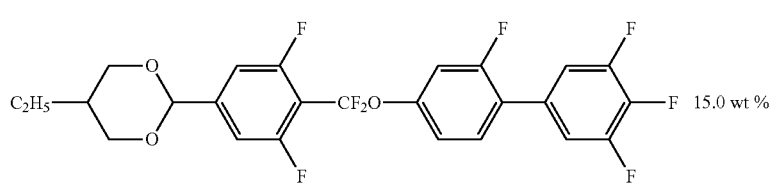 (7-2-5-F) 15.0 wt%
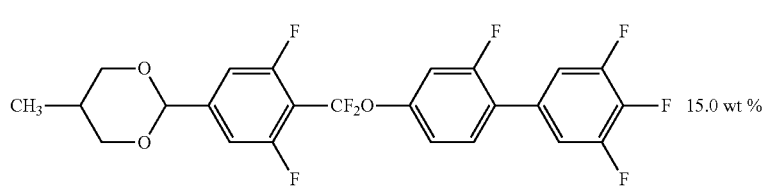 (1-2-5-F) 15.0 wt%

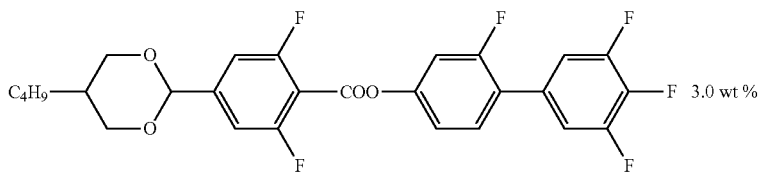

(1-2-5-E) 3.0 wt %

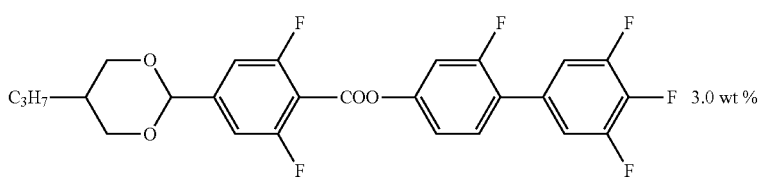

(1-2-5-E) 3.0 wt %

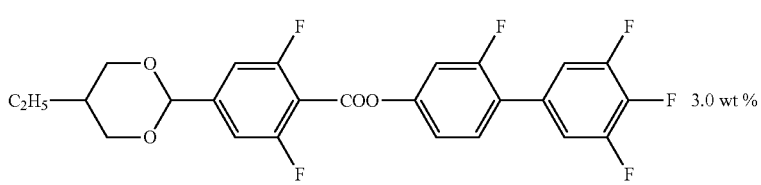

(1-2-5-E) 3.0 wt %

A phase transition temperature (° C.) of liquid crystal composition NLC-I was N 73.0 I.

Next, liquid crystal composition CLC-I including liquid crystal composition NLC-I (94.7 wt %) and chiral agents BN-H4 (2.7 wt %) and BN-H5 (2.6 wt %) represented by formulas described above was obtained. A phase transition temperature (° C.) of liquid crystal composition CLC-I was N* 62.6 BP 65.0 BP+I 65.5 I.

Preparation of Mixture of Monomer and Liquid Crystal Composition (Example 8B)

Liquid crystal composition MLC-I was prepared by mixing 88.8 wt % of liquid crystal composition CLC-I obtained in Example 8A, 6.0 wt % of n-hexadecyl acrylate, 4.8 wt % of 1,4-di(4-(6-(acryloyloxy)dodecyloxy)benzoyloxy)-2-methylbenzene (LCA-12) and 0.5 wt % of 2,2'-dimethoxyphenylacetophenone as a photopolymerization initiator. A phase transition temperature (° C.) of liquid crystal composition MLC-I was N* 35.6 BP 40.8 BP+I 42.1 I, I 40.4 BP 33.6 N*.

Preparation of Polymer/Liquid Crystal Composite Material (Example 7C)

Liquid crystal composition MLC-I obtained in Example 8B was interposed between a comb-shaped electrode substrate not subjected to alignment treatment, and an opposite glass substrate (not provided with an electrode) (cell thickness: 8 μm), and a cell obtained was heated to a blue phase at 36.0° C. In the state, a polymerization reaction was performed by irradiating the composition with ultraviolet light (intensity of ultraviolet light: 23 mWcm$^{-2}$ (365 nm)) for 1 minute.

The thus obtained polymer/liquid crystal composite material (PSBP-I) maintained an optically isotropic liquid crystal phase, even when cooled to room temperature.

Optical System (Example 8D)

A cell was set to the optical system shown in FIG. 2, and a relationship between applied voltage and transmittance was examined at room temperature in a manner similar to the operations in Comparative Example 1D except that a cell in which the polymer/liquid crystal composite material PSBP-I obtained in Example 8C was interposed was used. When rectangular waves having a voltage of 25.2 V were applied, transmittance became 82% and intensity of transmitted light saturated. Contrast was 701. Thus, PSBP-I containing compound 1 of the application was found to be driven at a low voltage.

Preparation of Liquid Crystal Composition NLC-J (Example 9A)

Liquid crystal composition NLC-J was prepared by mixing a plurality of compounds at a ratio described below such that four kinds of compounds represented by general formula (1-2-5) described above were contained in a total amount of 24.0 wt % as compound 1.

Liquid crystal composition NLC-J

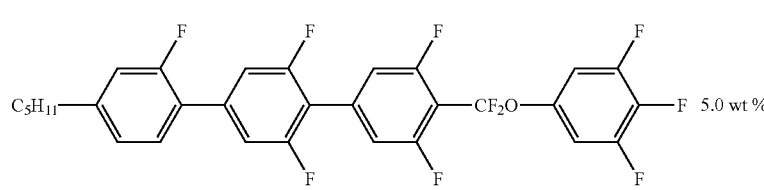

(3-3) 5.0 wt %

-continued
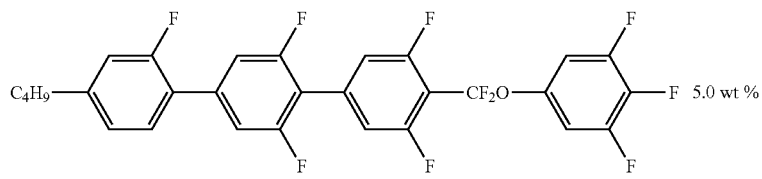 (3-3) 5.0 wt %
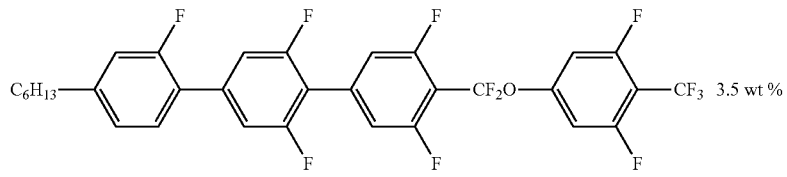 (3-3) 3.5 wt %
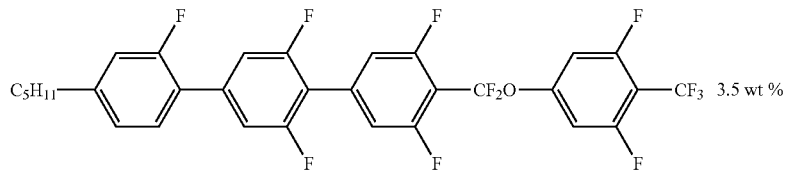 (3-3) 3.5 wt %
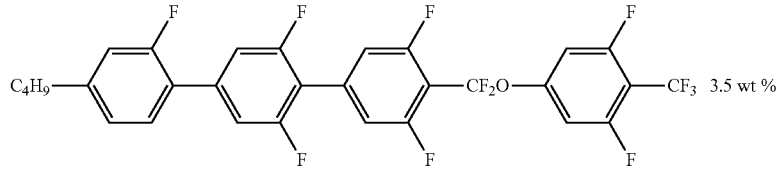 (3-3) 3.5 wt %
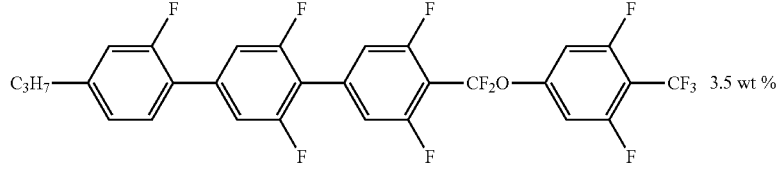 (3-3) 3.5 wt %
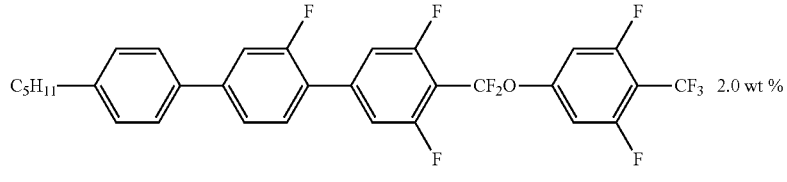 (4-4) 2.0 wt %
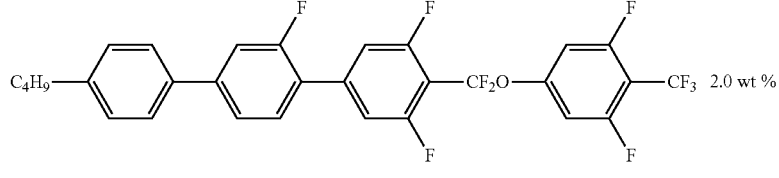 (4-4) 2.0 wt %
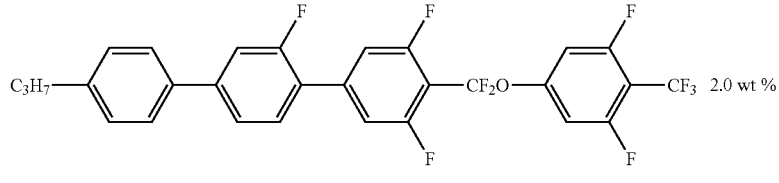 (4-4) 2.0 wt %
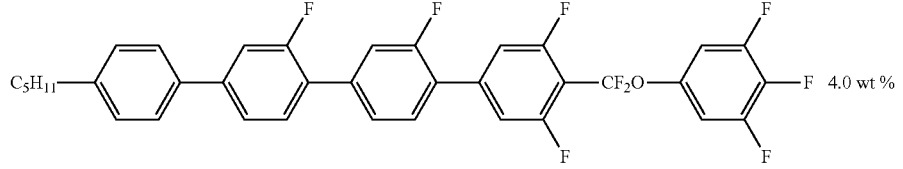 (4) 4.0 wt %

-continued
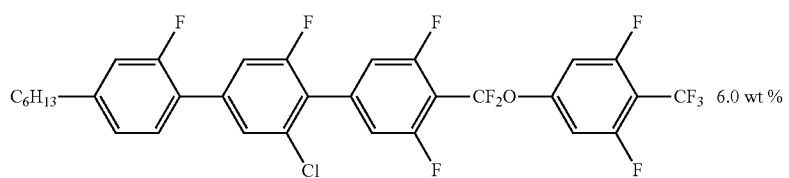 (2-1-4-3) 6.0 wt %
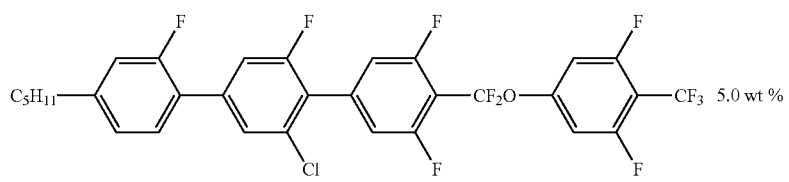 (2-1-4-3) 5.0 wt %
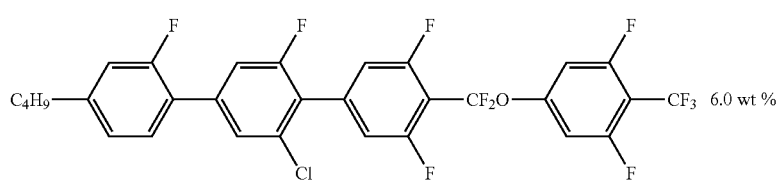 (2-1-4-3) 6.0 wt %
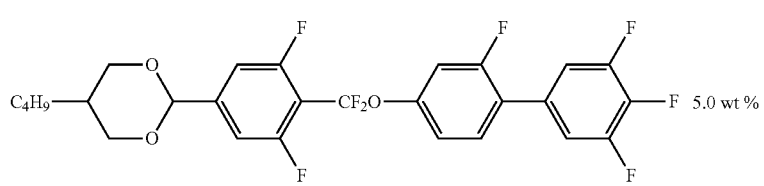 (7-2-5-F) 5.0 wt %
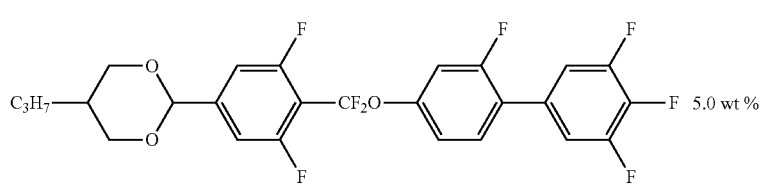 (7-2-5-F) 5.0 wt %
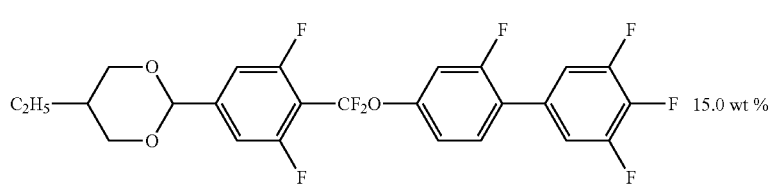 (7-2-5-F) 15.0 wt %
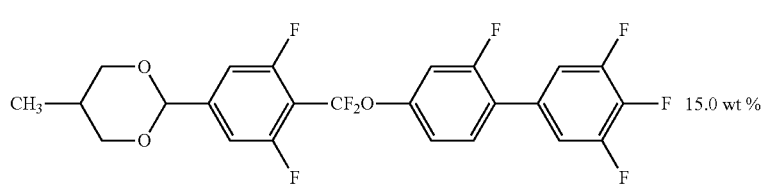 (1-2-5-F) 15.0 wt %
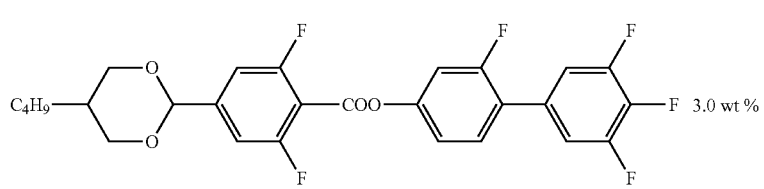 (1-2-5-E) 3.0 wt %
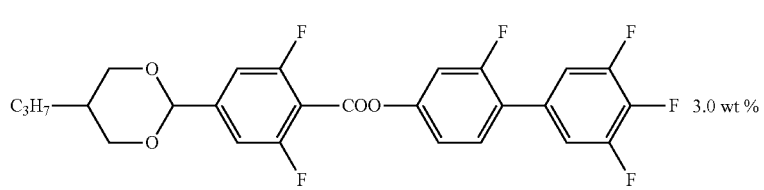 (1-2-5-E) 3.0 wt %

-continued

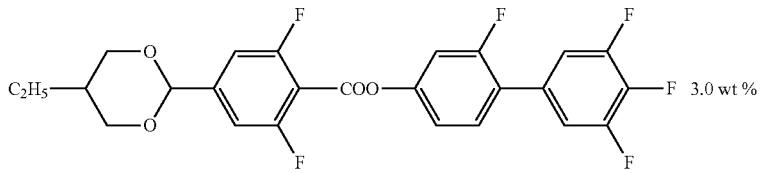

(1-2-5-E) 3.0 wt %

A phase transition temperature (° C.) of liquid crystal composition NLC-J was N 79.0 I.

Next, liquid crystal composition CLC-J including liquid crystal composition NLC-J (94.2 wt %), and chiral agents BN-H4 (2.9 wt %) and BN-J5 (2.9 wt %) represented by a formula described above was obtained. A phase transition temperature (° C.) of liquid crystal composition CLC-J was N* 66.3 BP 68.8 BP+I 70.2 I.

Preparation of Mixture of Monomer and Liquid Crystal Composition (Example 9B)

Liquid crystal composition MLC-J was prepared by mixing 89.4 wt % of liquid crystal composition CLC-J obtained in Example 7A, 5.7 wt % of n-hexadecyl acrylate, 4.6 wt % of 1,4-di(4-(6-(acryloyloxy)dodecyloxy)benzoyloxy)-2-methylbenzene (LCA-12) and 0.3 wt % of 2,2'-dimethoxyphenylacetophenone as a photopolymerization initiator. A phase transition temperature (° C.) of liquid crystal composition MLC-J was N* 39.4 BP 45.3 BP+I 46.8 I, I 44.8 BP 36.3 N*.

Preparation of Polymer/Liquid Crystal Composite Material (Example 9C)

Liquid crystal composition MLC-H obtained in Example 9B was interposed between a comb-shaped electrode substrate not subjected to alignment treatment, and an opposite glass substrate (not provided with an electrode) (cell thickness: 8 μm), and a cell obtained was heated to an isotropic phase, and then cooled to a supercooled blue phase at 38.7° C. In the state, a polymerization reaction was performed by irradiating the composition with ultraviolet light (intensity of ultraviolet light: 23 mWcm$^{-2}$ (365 nm)) for 1 minute.

The thus obtained polymer/liquid crystal composite material PSBP-J maintained an optically isotropic liquid crystal phase, even when cooled to room temperature.

Optical System (Example 9D)

A cell was set to an optical system shown in FIG. 2, and a relationship between applied voltage and transmittance was examined at room temperature in a manner similar to the operations in Comparative Example 1D except that a cell in which the polymer/liquid crystal composite material PSBP-J obtained in Example 9C was interposed was used. When rectangular waves having a voltage of 25.2 V were applied, transmittance became 79% and intensity of transmitted light saturated. Contrast was 818. Thus, PSBP-J containing compound 1 of the application was found to be driven at a low voltage.

Preparation of liquid crystal composition NLC-K (Example 10A)

Liquid crystal composition NLC-K was prepared by mixing a plurality of compounds at a ratio described below such that four kinds of compounds represented by general formula (1-2-5) described above were contained in a total amount of 17.4 wt % as compound 1.

Liquid crystal composition NLC-K

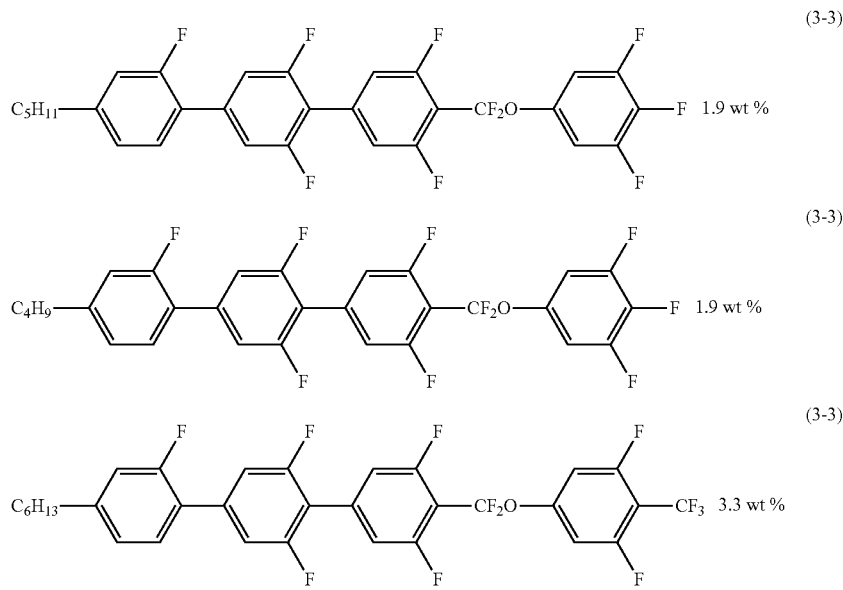

-continued
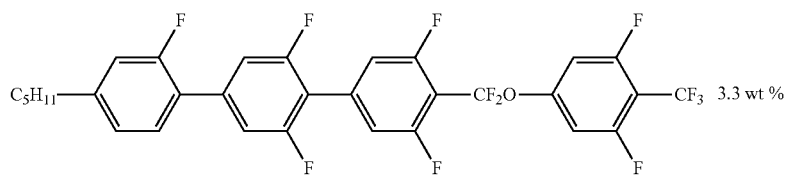 (3-3) 3.3 wt %
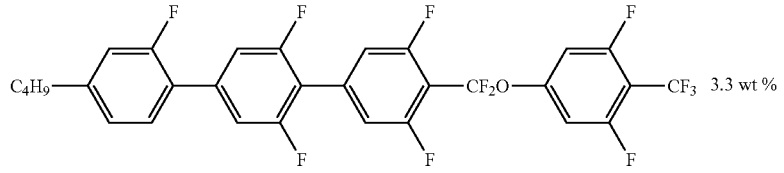 (3-3) 3.3 wt %
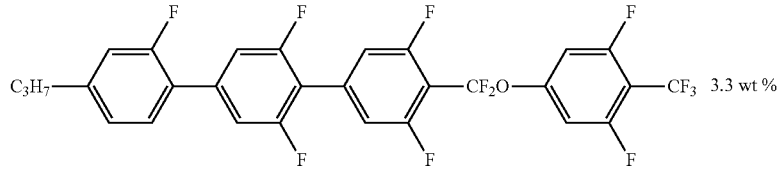 (3-3) 3.3 wt %
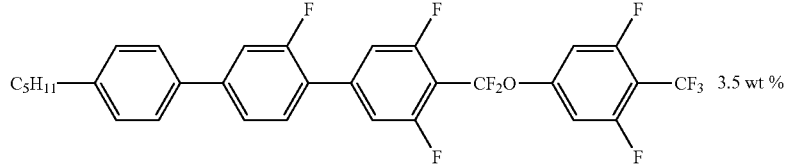 (4-4) 3.5 wt %
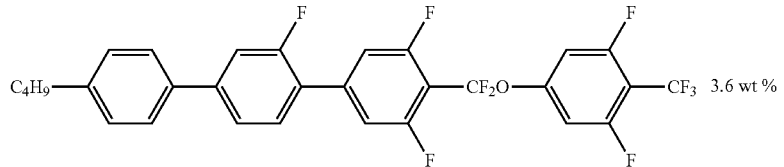 (4-4) 3.6 wt %
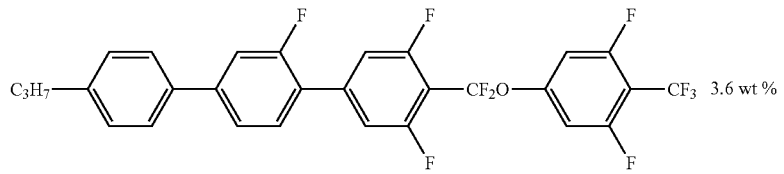 (4-4) 3.6 wt %
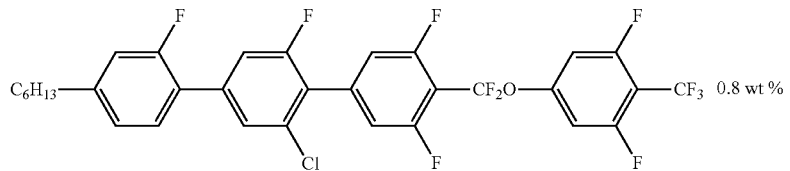 (2-1-4-3) 0.8 wt %
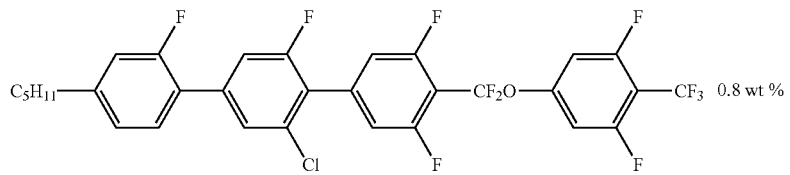 (2-1-4-3) 0.8 wt %
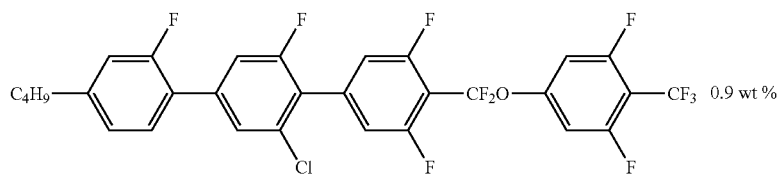 (2-1-4-3) 0.9 wt %

-continued
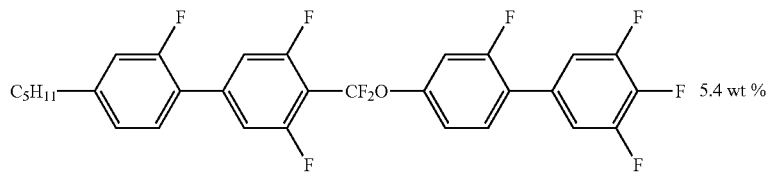 (3-3) 5.4 wt %
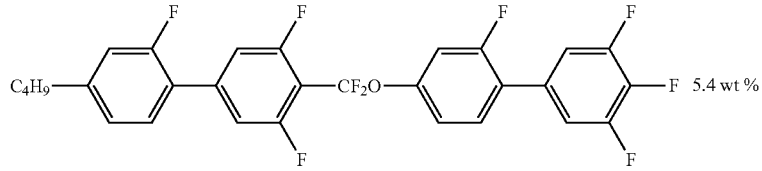 (3-3) 5.4 wt %
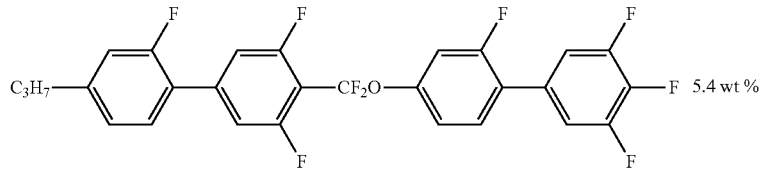 (3-3) 5.4 wt %
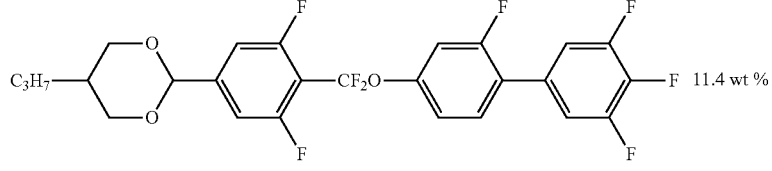 (7-2-5-F) 11.4 wt %
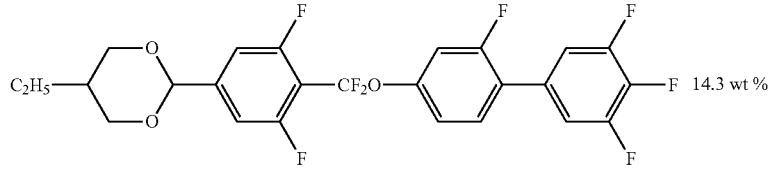 (7-2-5-F) 14.3 wt %
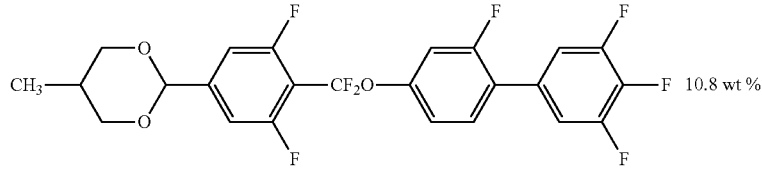 (1-2-5-F) 10.8 wt %
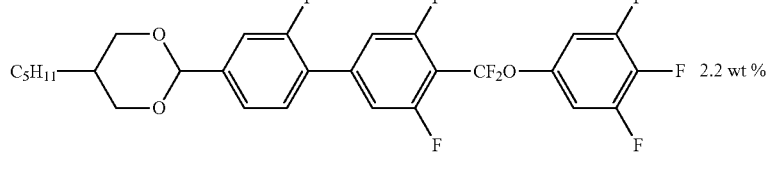 (7-2-2-F) 2.2 wt %
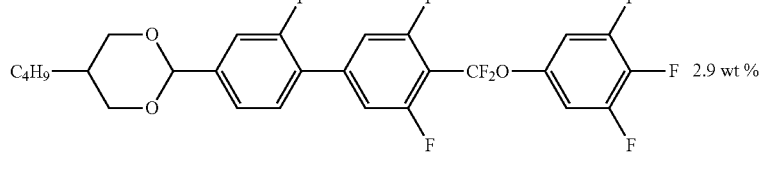 (7-2-2-F) 2.9 wt %
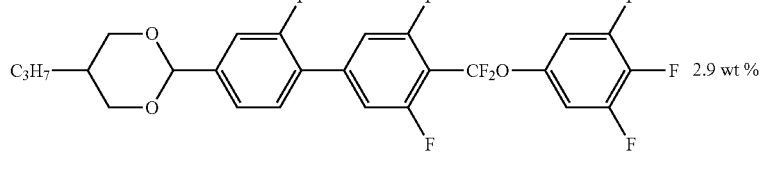 (7-2-2-F) 2.9 wt %

-continued

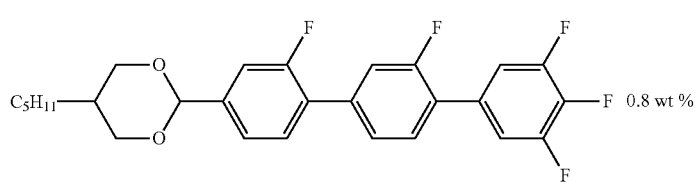 (5-2-2) 0.8 wt%

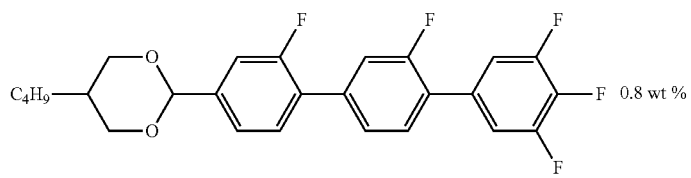 (5-2-2) 0.8 wt%

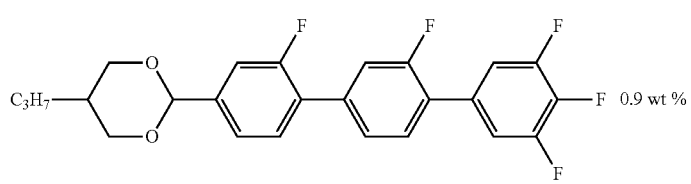 (5-2-2) 0.9 wt%

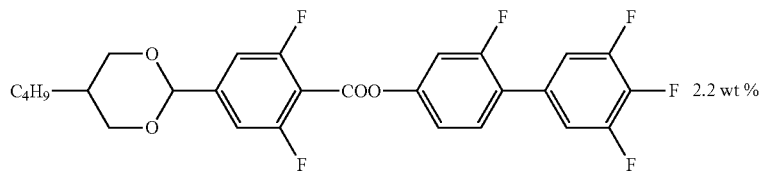 (1-2-5-E) 2.2 wt%

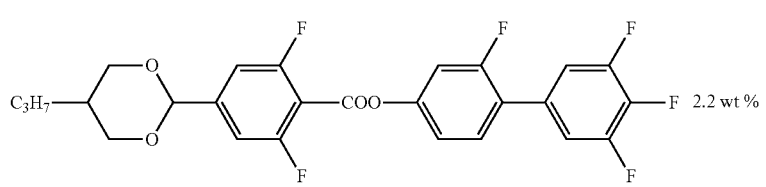 (1-2-5-E) 2.2 wt%

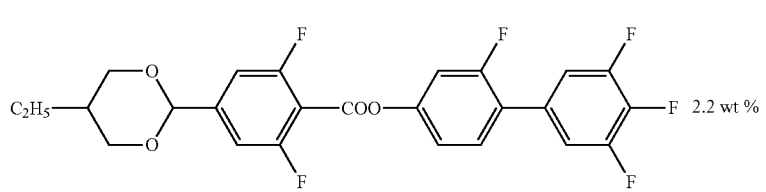 (1-2-5-E) 2.2 wt%

A phase transition temperature (° C.) of liquid crystal composition NLC-K was N 83.7 I.

Next, liquid crystal composition CLC-K including liquid crystal composition NLC-K (94.7 wt %), and chiral agents BN-K4 (2.7 wt %) and BN-K5 (2.6 wt %) represented by formulas described above was obtained.

A phase transition temperature (° C.) of liquid crystal composition CLC-K was N* 74.6 BP 76.2 BP+I 77.2 I.

Preparation of Mixture of Monomer and Liquid Crystal Composition (Example 10B)

Liquid crystal composition MLC-K was prepared by mixing 88.8 wt % of liquid crystal composition CLC-K obtained in Example 10A, 6.0 wt % of n-hexadecyl acrylate, 4.8 wt % of 1,4-di(4-(6-(acryloyloxy)dodecyloxy)benzoyloxy)-2-methylbenzene (LCA-12) and 0.4 wt % of 2,2'-dimethoxyphenylacetophenone as a photopolymerization initiator. A phase transition temperature (° C.) of liquid crystal composition MLC-K was N* 47.6 BP 53.3 BP+I 53.3 I, I 51.4 BP 45.3 N*.

Preparation of Polymer/Liquid Crystal Composite Material (Example 10C)

Liquid crystal composition MLC-K obtained in Example 10B was interposed between a comb-shaped electrode substrate not subjected to alignment treatment, and an opposite glass substrate (not provided with an electrode) (cell thickness: 8 μm), and a cell obtained was heated to a blue phase at 38.9° C. In the state, a polymerization reaction was performed by irradiating the resulting composition with ultraviolet light (intensity of ultraviolet light: 23 mWcm$^{-2}$ (365 nm)) for 1 minute.

The thus obtained polymer/liquid crystal composite material PSBP-K maintained an optically isotropic liquid crystal phase, even when cooled to room temperature.

Optical System (Example 10D)

A cell was set to an optical system shown in FIG. 2, and a relationship between applied voltage and transmittance was examined at room temperature in a manner similar to the operations in Comparative Example 1D except that a cell in which the polymer/liquid crystal composite material PSBP-K obtained in Example 7C was interposed was used.

When rectangular waves having a voltage of 27.6 V were applied, transmittance became 82% and intensity of transmitted light saturated. Contrast was 703. Thus, PSBP-K containing compound 1 of the invention was found to be driven at a low voltage.

Preparation of Liquid Crystal Composition NLC-L
(Example 11A)

Liquid crystal composition NLC-L was prepared by mixing a plurality of compounds at a ratio described below such that four kinds of compounds represented by general formula (1-2-5) described above were contained in a total amount of 23.4 wt % as compound 1.
Liquid crystal composition NLC-L

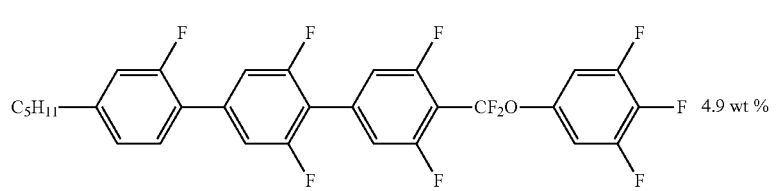
(3-3) 4.9 wt %

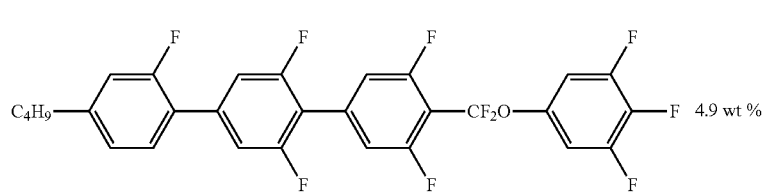
(3-3) 4.9 wt %

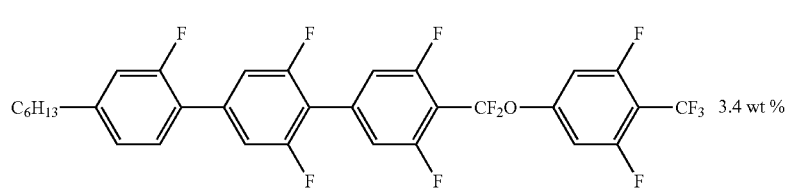
(3-3) 3.4 wt %

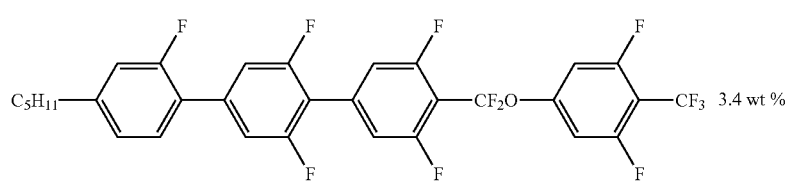
(3-3) 3.4 wt %

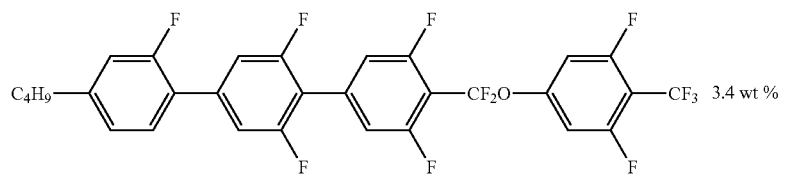
(3-3) 3.4 wt %

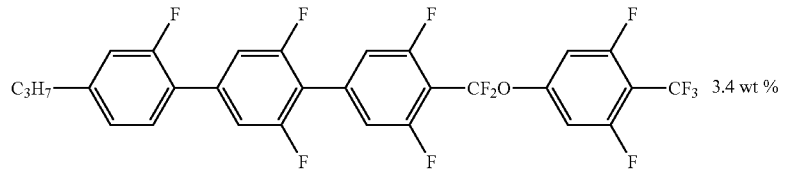
(3-3) 3.4 wt %

-continued
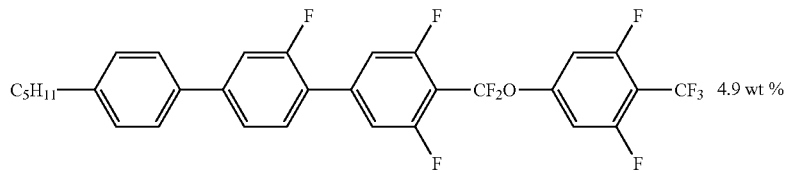 (4-4)
4.9 wt %
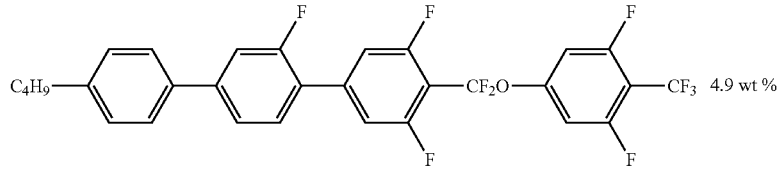 (4-4)
4.9 wt %
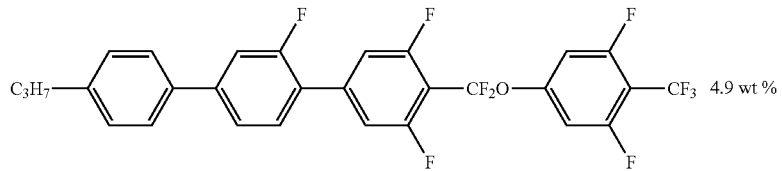 (4-4)
4.9 wt %
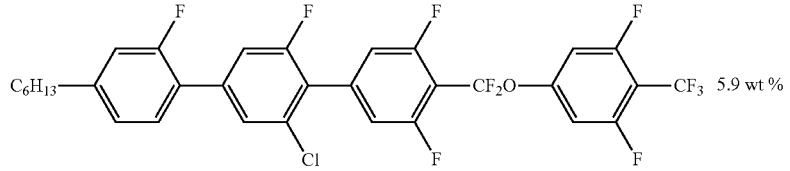 (2-1-4-3)
5.9 wt %
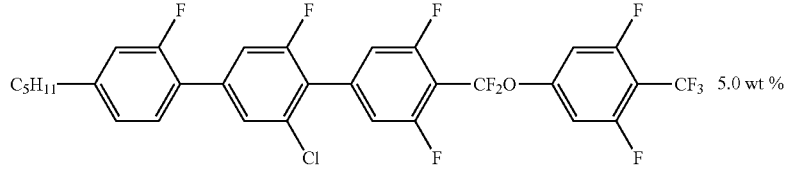 (2-1-4-3)
5.0 wt %
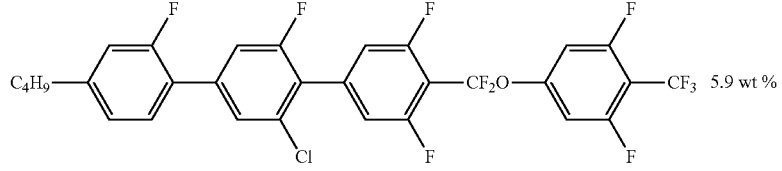 (2-1-4-3)
5.9 wt %
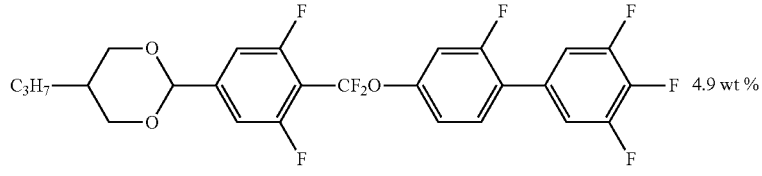 (7-2-5-F)
4.9 wt %
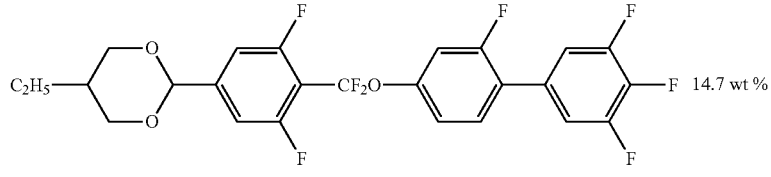 (7-2-5-F)
14.7 wt %
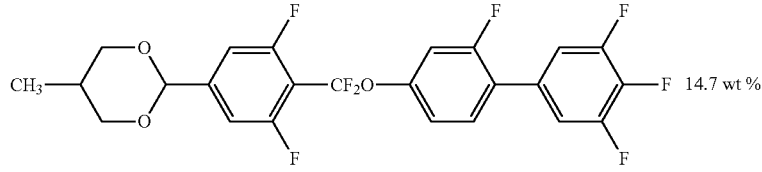 (1-2-5-F)
14.7 wt %

-continued

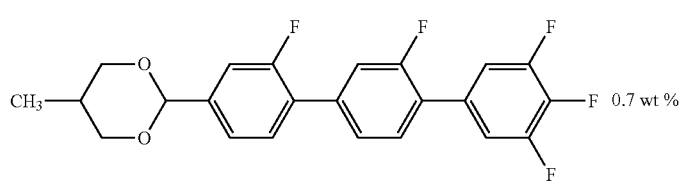 0.7 wt % (5-2-2)

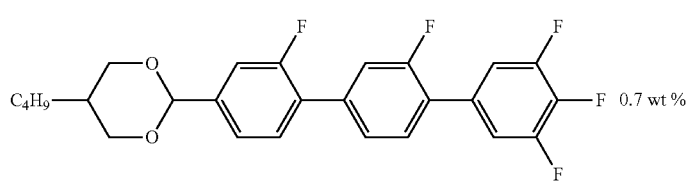 0.7 wt % (5-2-2)

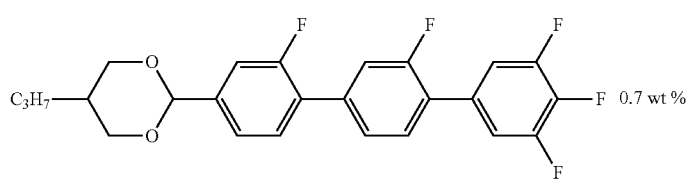 0.7 wt % (5-2-2)

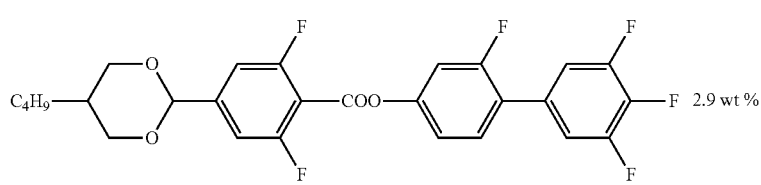 2.9 wt % (1-2-5-E)

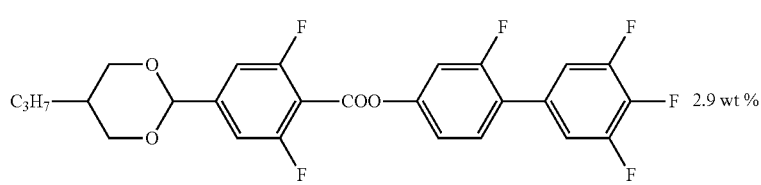 2.9 wt % (1-2-5-E)

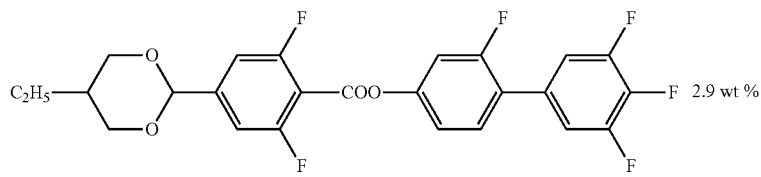 2.9 wt % (1-2-5-E)

A phase transition temperature (° C.) of liquid crystal composition NLC-L was N 73.9-75.1 I.

Next, liquid crystal composition CLC-L including liquid crystal composition NLC-L (94.7 wt %), and chiral agents BN-H4 (2.7 wt %) and BN-L5 (2.6 wt %) represented by formulas described above was obtained.

A phase transition temperature (° C.) of liquid crystal composition CLC-L was N* 63.4 BP 66.5 BP+I 68.0 I.

Preparation of Mixture of Monomer and Liquid Crystal Composition (Example 11B)

Liquid crystal composition MLC-L was prepared by mixing 88.8 wt % of liquid crystal composition CLC-L obtained in Example 11A, 6.0 wt % of n-hexadecyl acrylate, 4.8 wt % of 1,4-di(4-(6-(acryloyloxy)dodecyloxy)benzoyloxy)-2-methylbenzene (LCA-12) and 0.4 wt % of 2,2'-dimethoxyphenylacetophenone as a photopolymerization initiator. A phase transition temperature (° C.) of liquid crystal composition MLC-L was N* 33.5 BP 37.9 BP+I 40.1 I, I 38.6 BP 29.6 N*.

Preparation of Polymer/Liquid Crystal Composite Material (Example 11C)

Liquid crystal composition MLC-L obtained in Example 11B was interposed between a comb-shaped electrode substrate not subjected to alignment treatment, and an opposite glass substrate (not provided with an electrode) (cell thickness: 7 μm), and a cell obtained was heated to a blue phase at 33.6° C. In the state, a polymerization reaction was performed by irradiating the composition with ultraviolet light (intensity of ultraviolet light: 23 mWcm$^{-2}$ (365 nm)) for 1 minute.

The thus obtained polymer/liquid crystal composite material PSBP-L maintained an optically isotropic liquid crystal phase, even when cooled to room temperature.

Optical System (Example 11D)

A cell was set to the optical system shown in FIG. 2, and a relationship between applied voltage and transmittance was examined at room temperature in a manner similar to the operations in Comparative Example 1D except that a cell in which the polymer/liquid crystal composite material PSBP-L obtained in Example 7C was interposed was used. When rectangular waves having a voltage of 30.0 V were applied, transmittance became 86% and intensity of transmitted light saturated. Contrast was 1,143. Thus, PSBP-L containing compound 1 of the application was found to be driven at a low voltage.

As is clear from Examples and Comparative Examples described above, the optical device of the invention has a high maximum temperature of a liquid crystal phase and a high contrast, can be driven at a low voltage and is high in the contrast, and is superior in comparison with a conventional technology.

INDUSTRIAL APPLICABILITY

Specific examples of a method of utilization of the invention include an optical device such as a display device using a polymer/liquid crystal composite.

LIST OF SYMBOLS

1 Electrode
2 Electrode
3 Light source
4 Polarizer (polarizing plate)
5 Comb-shaped electrode cell
6 Analyzer (analyzing plate)
7 Photodetector

The invention claimed is:

1. A liquid crystal composition that exhibits an optically isotropic liquid crystal phase and contains a chiral agent and an achiral component T containing at least one compound 1 represented by formula (1):

(1)

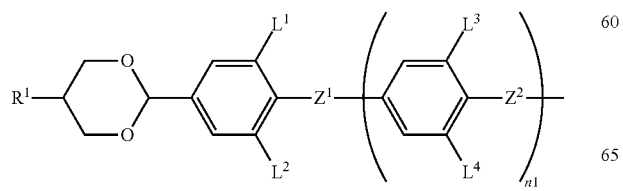

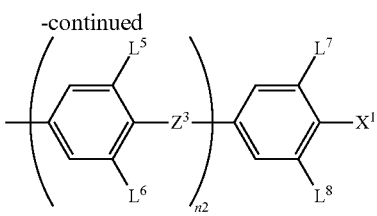

wherein in formula (1), R' is hydrogen or methyl;
$L^1, L^2, L^3, L^4, L^5, L^6, L^7$ and $L^8$ are each independently hydrogen or fluorine;
$Z^1$, and $Z^3$ are each independently a single bond, —COO— or —CF$_2$O—, and at least one of $Z^1$, $Z^2$ and $Z^3$ is —COO— or —CF$_2$O—;
n1 and n2 are each independently 0 or 1; and
$X^1$ is hydrogen, halogen, —SF$_5$ or alkyl having 1 to 10 carbons, and at least one of —CH$_2$— in the alkyl may be replaced by —O—, —S—, —COO— or —OCO—, at least one of —CH$_2$—CH$_2$— in the alkyl may be replaced by —CH═CH—, —CF═CF— or —C≡C—, and at least one of hydrogen in the alkyl may be replaced by fluorine or chlorine, however, a case where —O— and —CH═CH—, and —CO— and —CH═CH— are adjacent in $X^1$ is excluded.

2. The liquid crystal composition of claim 1, wherein compound 1 is represented by formula (1-1-1), (1-1-2), (1-2-1) to (1-2-5), (1-3-1), (1-3-2), (1-4-1), (1-5-1) or (1-5-2):

(1-1-1)

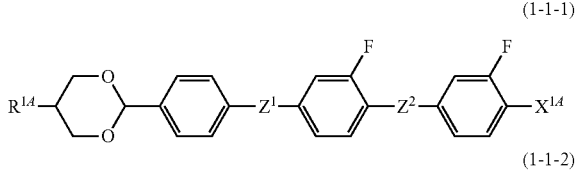

(1-1-2)

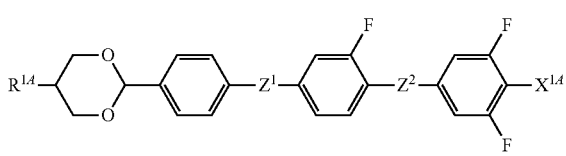

(1-2-1)

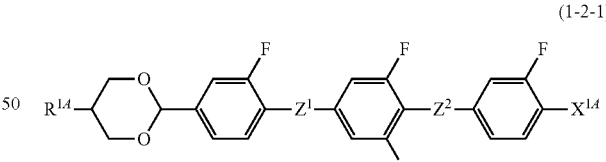

(1-2-2)

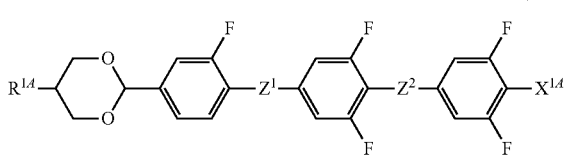

(1-2-3)

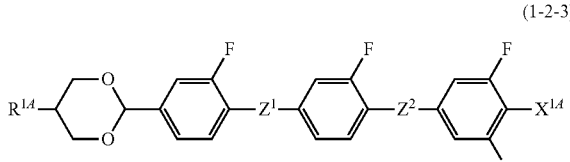

-continued

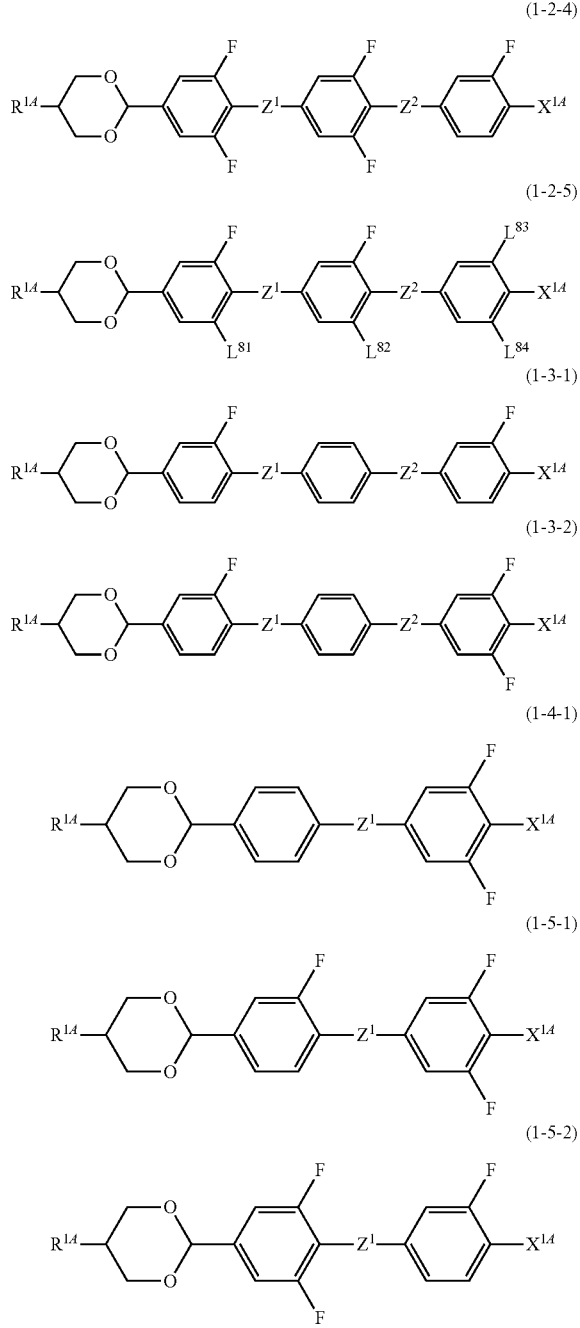

wherein in the formulas, $R^{1A}$ is hydrogen or methyl;
in formulas (1-1-1), (1-1-2), (1-2-1) to (1-2-5) and (1-3-1) to (1-3-2), $Z^1$ and $Z^2$ are each independently a single bond, —COO— or —CF$_2$O—, however, at least one of $Z^1$ and $Z^2$ is —COO— or —CF$_2$O—;

in formulas (1-4-1), (1-5-1) and (1-5-2), $Z^1$ is —COO— or —CF$_2$O—, and $L^{81}$, $L^{82}$, $L^{83}$ and $L^{84}$ are each independently hydrogen or fluorine; and in the formulas, $X^{1A}$ is fluorine, chlorine, —CF$_3$ or —OCF$_3$.

3. The liquid crystal composition of claim 1, wherein the compound 1 is represented by formula (1-2-2-E), (1-2-5-E), (1-2-2-F) or (1-2-5-F):

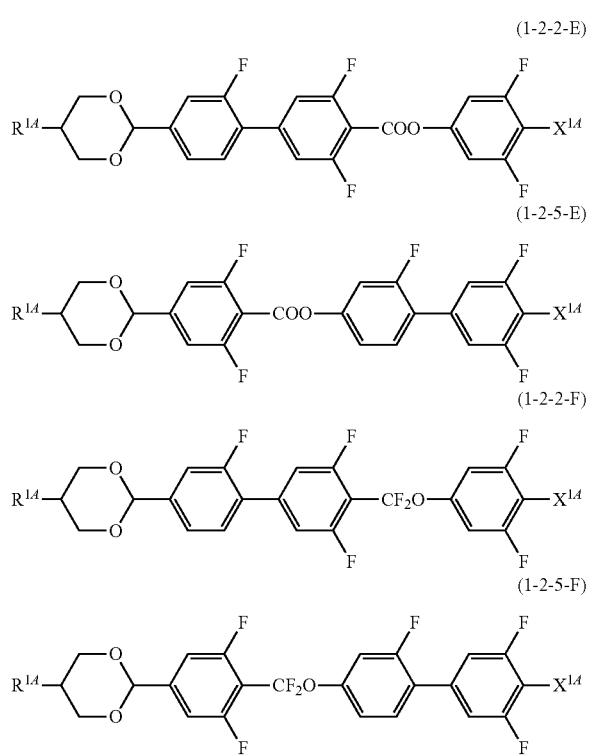

wherein in the formulas, $R^{1A}$ is hydrogen or methyl; and $X^{1A}$ is fluorine, chlorine, —CF$_3$ or —OCF$_3$.

4. The liquid crystal composition of claim 2, wherein $R^{1A}$ is methyl.

5. The liquid crystal composition of claim 1, containing the compound 1 in an amount of 1 wt % to 90 wt % based on a total weight of the achiral component T.

6. The liquid crystal composition of claim 1, wherein the achiral component T further contains at least one compound selected from the group consisting of at least one compound 2 represented by formula (2), at least one compound 3 represented by formula (3), at least one compound 4 represented by formula (4), at least one compound 5 represented by formula (5), at least one compound 6 represented by formula (6), and at least one compound 7 represented by formula (7):

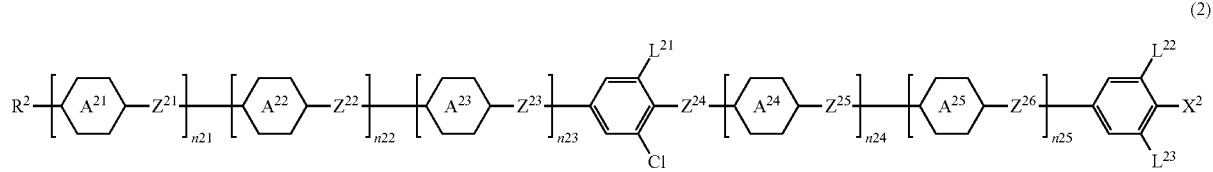

wherein in formula (2), $R^2$ is hydrogen or alkyl having 1 to 20 carbons, and at least one of —$CH_2$— in the alkyl may be replaced by —O—, —S—, —COO— or —OCO—, at least one of —$CH_2$—$CH_2$— in the alkyl may be replaced by —CH=CH—, —CF=CF— or —C≡C—, and at least one of hydrogen in the alkyl may be replaced by fluorine or chlorine, however, a case where —O— and —CH=CH—, and —CO— and —CH=CH— are adjacent in $R^2$ is excluded;

ring $A^{21}$, ring $A^{22}$, ring $A^{23}$, ring $A^{24}$ and ring $A^{25}$ are each independently 1,4-cyclohexylene, 1,3-dioxane-2,5-diyl, 1,4-phenylene, 1,4-phenylene in which one or two of hydrogen are replaced by fluorine, or 1,4-phenylene in which two of hydrogen are each replaced by fluorine and chlorine, pyridine-2,5-diyl or pyrimidine-2,5-diyl;

$Z^{21}$, $Z^{22}$, $Z^{23}$, $Z^{24}$, $Z^{25}$ and $Z^{26}$ are each independently a single bond or alkylene having 1 to 4 carbons, and at least one of —$CH_2$— in the alkylene may be replaced by —O—, —OCO— or —$CF_2$O—;

$L^{21}$, $L^{22}$ and $L^{23}$ are each independently hydrogen or fluorine;

$X^2$ is fluorine, chlorine, —$CF_3$ or —$OCF_3$;

n21, n22, n23, n24 and n25 are each independently 0 or 1, and satisfy an expression: 2≤n21+n22+n23+n24+n25≤3;

(3)

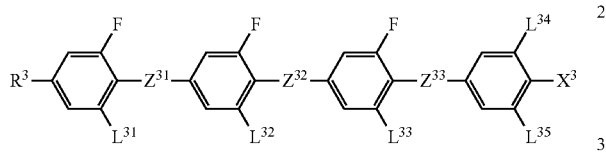

wherein in formula (3), $R^3$ is hydrogen or alkyl having 1 to 20 carbons, and at least one of —$CH_2$— in the alkyl may be replaced by —O—, —S—, —COO— or —OCO—, at least one of —$CH_2$—$CH_2$— in the alkyl may be replaced by —CH=CH—, —CF=CF— or —C≡C—, and at least one of hydrogen in the alkyl may be replaced by fluorine or chlorine, however, a case where —O— and —CH=CH—, and —CO— and —CH=CH— are adjacent in $R^3$ is excluded;

$Z^{31}$, $Z^{32}$ and $Z^{33}$ are each independently a single bond or alkylene having 1 to 4 carbons, and at least one of —$CH_2$— in the alkylene may be replaced by —O—, —COO— or —$CF_2$O—;

$L^{31}$, $L^{32}$, $L^{33}$, $L^{34}$ and $L^{35}$ are each independently hydrogen or fluorine;

$X^3$ is hydrogen, halogen, —$SF_5$, or alkyl having 1 to 10 carbons, and at least one of —$CH_2$— in the alkyl may be replaced by —O—, —S—, —COO— or —OCO—, at least one of —$CH_2$—$CH_2$— in the alkyl may be replaced by —CH=CH—, —CF=CF— or —C≡C—, and in the alkyl, at least one of hydrogen in a group in which at least one of —$CH_2$— in the alkyl is replaced by —O—, —S—, —COO— or —OCO—, or in a group in which at least one of —$CH_2$—$CH_2$— in the alkyl is replaced by —CH=CH—, —CF=CF— or —C≡C— may be replaced by fluorine or chlorine, however, a case where —O— and —CH=CH—, and —CO— and —CH=CH— are adjacent in $X^3$ is excluded;

(4)

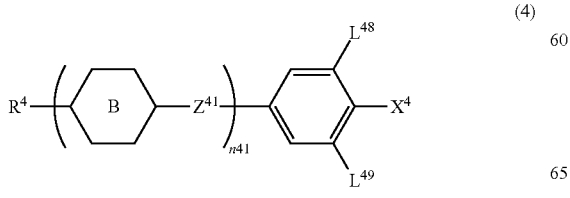

wherein in formula (4), $R^4$ is alkyl having 1 to 12 carbons, alkoxy having 1 to 12 carbons, alkenyl having 2 to 12 carbons, or alkenyl having 2 to 12 carbons in which at least one of hydrogen is replaced by fluorine;

ring B is each independently 1,4-cyclohexylene, 1,4-phenylene, 2-fluoro-1,4-phenylene, 3-fluoro-1,4-phenylene, 3,5-difluoro-1,4-phenylene, 3,5-dichloro-1,4-phenylene or pyrimidine-2,5-diyl;

$Z^{41}$ is each independently a single bond, ethylene, —COO—, —OCO—, —$CF_2$O— or —$OCF_2$—;

$L^{48}$ and $L^{49}$ are each independently hydrogen or fluorine;

$X^4$ is fluorine, chlorine, —$CF_3$ or —$OCF_3$; and n41 is 1, 2, 3 or 4, however, when n41 is 3 or 4, one of $Z^{41}$ is —$CF_2$O— or —$OCF_2$—, and when n41 is 3, a case where all of rings B are 1,4-phenylene replaced by fluorine is excluded;

(5)

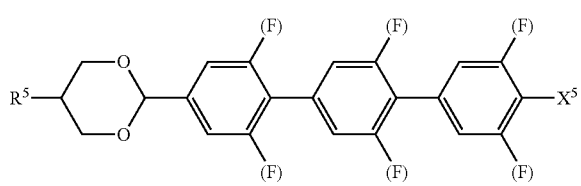

wherein in formula (5), $R^5$ is hydrogen, or alkyl having 1 to 20 carbons, and at least one of —$CH_2$— in the alkyl may be replaced by —O—, —S—, —COO— or —OCO—, at least one of —$CH_2$—$CH_2$— in the alkyl may be replaced by —CH=CH—, —CF=CF— or —C≡C—, and at least one of hydrogen in the alkyl may be replaced by fluorine or chlorine, however, a case where, —O— and —CH=CH—, and —CO— and —CH=CH— are adjacent in $X^1$ is excluded;

(F) is each independently hydrogen or fluorine; and $X^5$ is hydrogen, halogen, —$SF_5$ or alkyl having 1 to 10 carbons, and at least one of —$CH_2$— in the alkyl may be replaced by —O—, —S—, —COO— or —OCO, at least one of —$CH_2$—$CH_2$— in the alkyl may be replaced by —CH=CH—, —CF=CF— or —C≡C—, and in the alkyl, at least one of hydrogen in a group in which at least one of —$CH_2$— in the alkyl is replaced by —O—, —S—, —COO— or —OCO—, or in a group in which at least one of —$CH_2$—$CH_2$— in the alkyl is replaced by —CH=CH—, —CF=CF— or —C≡C— may be replaced by fluorine or chlorine, however, a case where —O— and —CH=CH—, and —CO— and —CH=CH— are adjacent in $X^5$ is excluded;

(6)

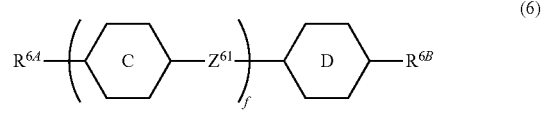

wherein in formula (6), $R^{6A}$ and $R^{6B}$ are each independently alkyl having 1 to 12 carbons, alkoxy having 1 to 12 carbons, alkenyl having 2 to 12 carbons, or alkenyl having 2 to 12 carbons in which at least one of hydrogen is replaced by fluorine;

ring C and ring D are each independently 1,4-cyclohexylene, 1,4-phenylene, 2-fluoro-1,4-phenylene, 3-fluoro-1,4-phenylene or 2,5-difluoro-1,4-phenylene;

$Z^{6'}$ is each independently a single bond, ethylene, —COO— or —OCO—; and r is 1, 2 or 3;

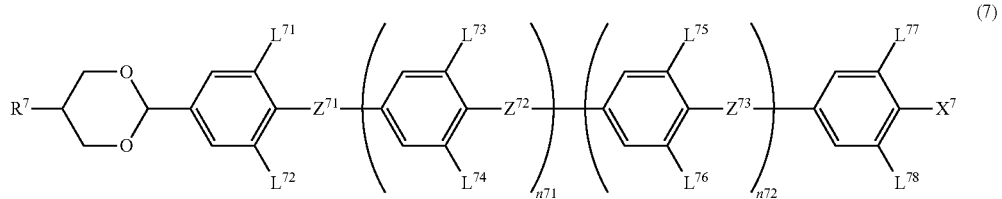

wherein in formula (7), $R^7$ is alkyl having 2 to 20 carbons, and at least one of —$CH_2$— in the alkyl may be replaced by —O—, —S—, —COO— or —OCO—, at least one of —$CH_2$—$CH_2$— in the alkyl may be replaced by —CH=CH—, —CF=CF— or —C≡C—, and at least one of hydrogen in the alkyl may be replaced by fluorine or chlorine, however, a case where —O— and —CH=CH—, and —CO— and —CH=CH— are adjacent in $X^1$ is excluded; $L^{71}$, $L^{72}$, $L^{73}$, $L^{74}$, $L^{75}$, $L^{76}$, $L^{77}$ and $L^{78}$ are each independently hydrogen or fluorine; $Z^{71}$, $Z^{72}$ and $Z^{73}$ are each independently a single bond or —COO—, —$CF_2O$—, and at least one is —COO— or —$CF_2O$—;

n71 and n72 are each independently 0 or 1; and $X^7$ is hydrogen, halogen, —$SF_5$ or alkyl having 1 to 10 carbons, and at least one of —$CH_2$— in the alkyl may be replaced by —O—, —S—, —COO— or —OCO—, at least one of —$CH_2$—$CH_2$— in the alkyl may be replaced by —CH=CH—, —CF=CF— or —C≡C—, and in the alkyl, at least one of hydrogen in a group in which at least one of —$CH_2$— in the alkyl is replaced by —O—, —S—, —COO— or —OCO—, or in a group in which at least one of —$CH_2$—$CH_2$— in the alkyl is replaced by —CH=CH—, —CF=CF— or —C≡C— may be replaced by fluorine or chlorine, however, a case where —O— and —CH=CH—, and —CO— and —CH=CH— are adjacent in $X^7$ is excluded.

7. The liquid crystal composition of claim 6, wherein the compound 2 is represented by formula (2-1-1-2), (2-1-2-1), (2-1-3-1), (2-1-3-2), (2-1-4-2) or (2-1-4-3):

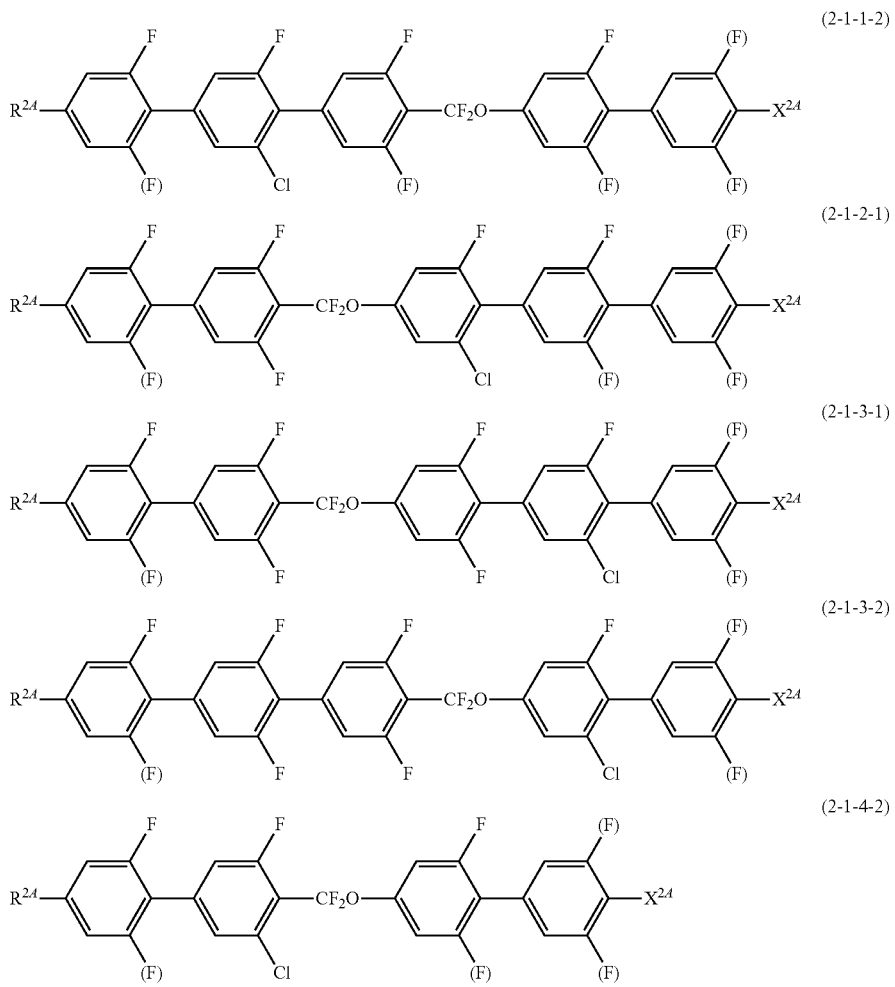

-continued

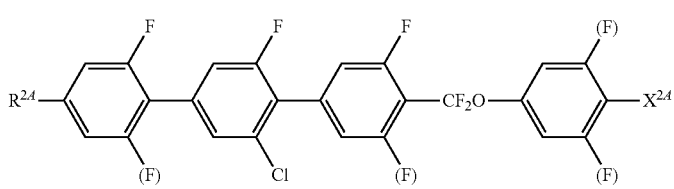

wherein in the formulas, $R^{2A}$ is alkyl having 1 to 12 carbons, alkoxy having 1 to 12 carbons, alkenyl having 2 to 12 carbons, or alkenyl having 2 to 12 carbons in which at least one of hydrogen is replaced by fluorine; (F) is each independently hydrogen or fluorine; and $X^{2A}$ is fluorine, chlorine, —CF₃ or —OCF₃.

8. The liquid crystal composition of claim 6, wherein the compound 3 is represented by formula (3-2) or (3-3):

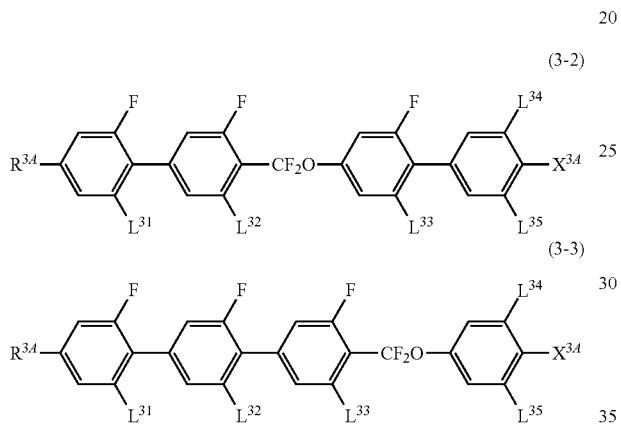

wherein, in the formula, $R^{3A}$ is each independently alkyl having 1 to 12 carbons, alkoxy having 1 to 12 carbons, alkenyl having 2 to 12 carbons, or alkenyl having 2 to 12 carbons in which at least one of hydrogen may be replaced by fluorine;
$L^{31}$ to $L^{35}$ are each independently hydrogen or fluorine; and
$X^{3A}$ is fluorine, chlorine, —CF₃ or —OCF₃.

9. The liquid crystal composition of claim 8, containing the compound 3 in a total amount of 0.5 wt % to 70 wt % based on a total weight of the achiral component T.

10. The liquid crystal composition of claim 6, wherein the compound 4 is at least one compound selected from the group consisting of compounds represented by formula (4-1) to (4-9):

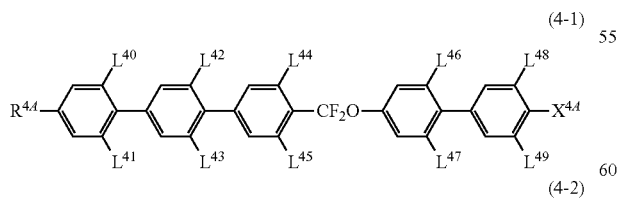

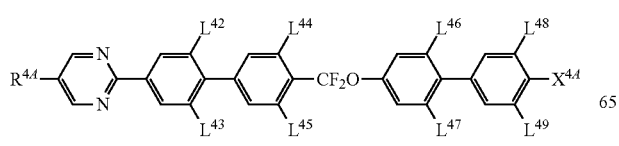

(2-1-4-3)

-continued

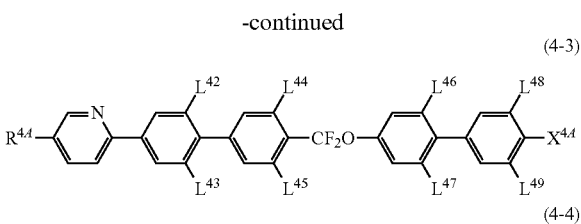

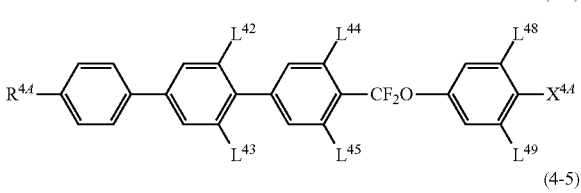

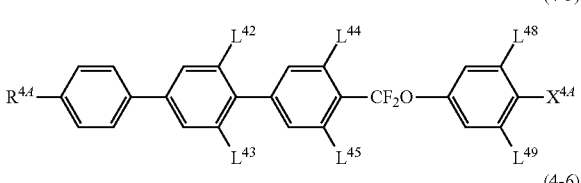

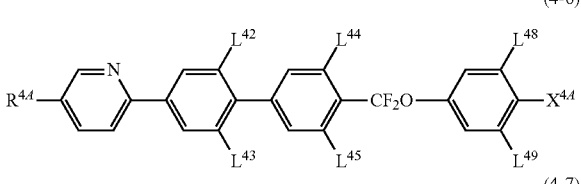

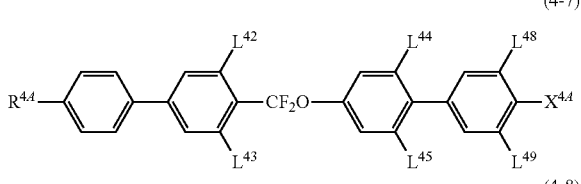

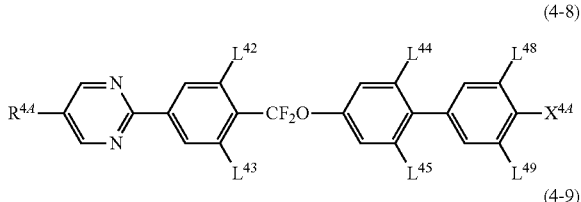

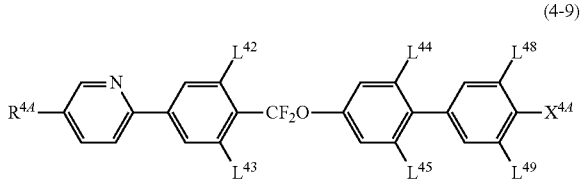

wherein in the formulas, $R^{4A}$ is each independently alkyl having 1 to 12 carbons, alkoxy having 1 to 12 carbons, alkenyl having 2 to 12 carbons, or alkenyl having 2 to 12 carbons in which at least one of hydrogen is replaced by fluorine;

X$^{4A}$ is fluorine, chlorine, —CF$_3$ or —OCF$_3$; and
L$^{40}$ to L$^{49}$ are each independently hydrogen or fluorine.

11. The liquid crystal composition of claim 6, wherein the compound 6 is at least one compound selected from the group consisting of compounds represented by formulas (6-1) to (6-13):

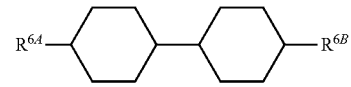
(6-1)

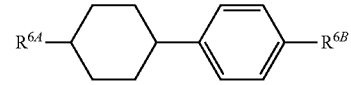
(6-2)

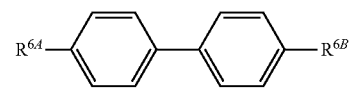
(6-3)

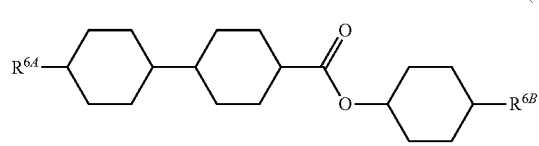
(6-4)

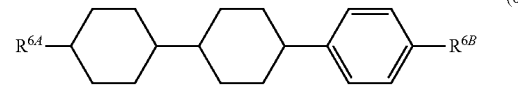
(6-5)

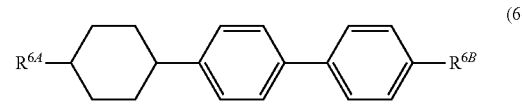
(6-6)

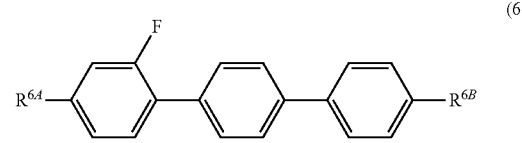
(6-7)

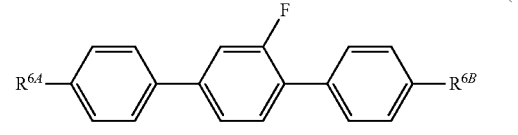
(6-8)

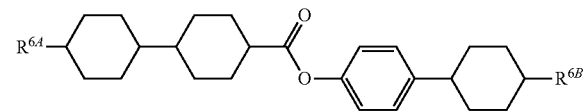
(6-9)

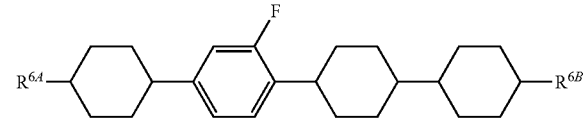
(6-10)

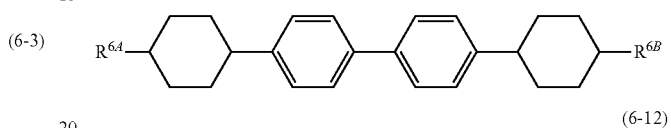
(6-11)

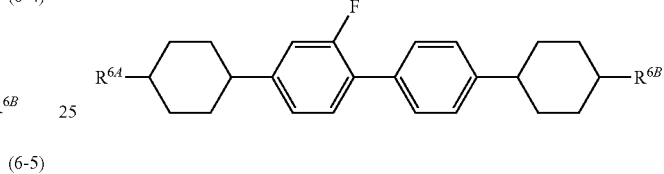
(6-12)

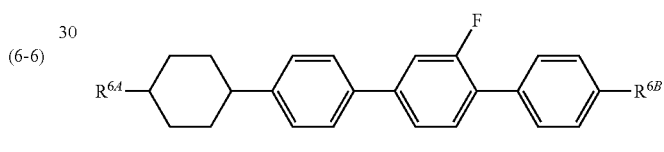
(6-13)

wherein R$^{6A}$ and R$^{6B}$ are each independently alkyl having 1 to 12 carbons, alkoxy having 1 to 12 carbons, alkenyl having 2 to 12 carbons, or alkenyl having 2 to 12 carbons in which at least one of hydrogen is replaced by fluorine.

12. The liquid crystal composition of claim 6, wherein the compound 7 is at least one compound selected from the group consisting of compounds represented by formulas (7-1) to (7-8):

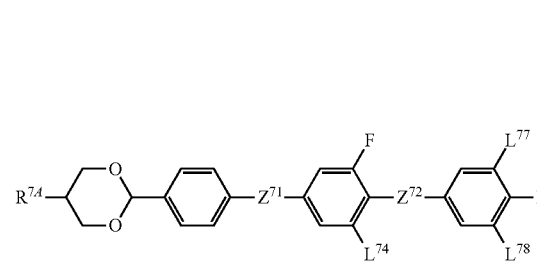
(7-1)
(7-3)

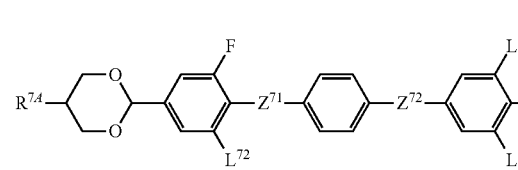
(7-2)
(7-4)

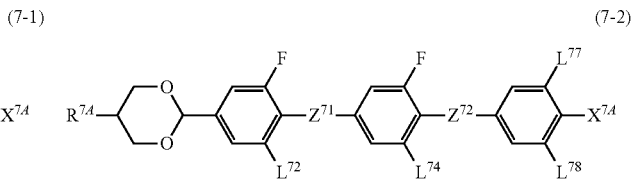

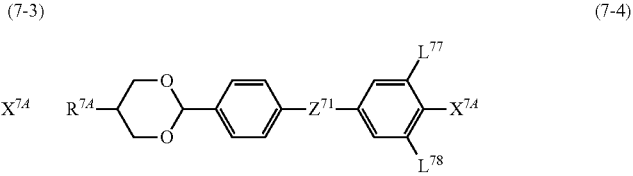

-continued (7-5)
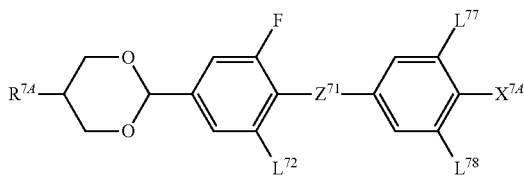

(7-6)
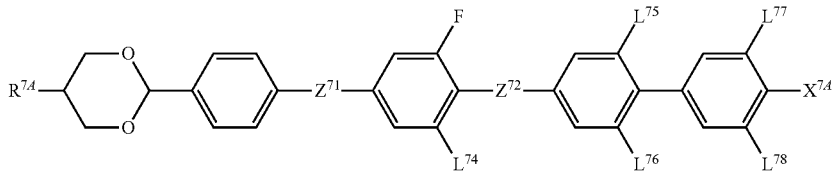

(7-7)
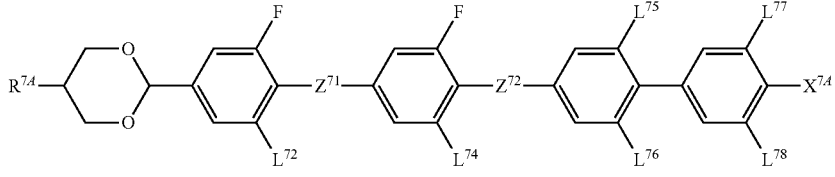

(7-8)
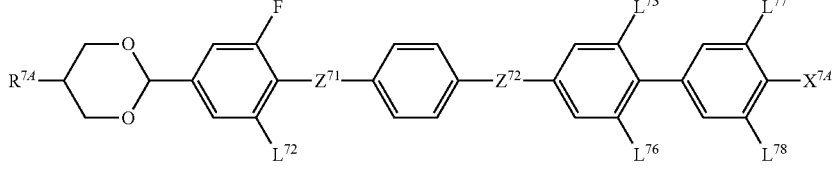

wherein in the formulas, $R^{74}$ is alkyl having 2 to 12 carbons, alkoxy having 1 to 11 carbons, alkenyl having 2 to 12 carbons, or alkenyl having 2 to 12 carbons in which at least one of hydrogen is replaced by fluorine; $L^{72}$, $L^{74}$, $L^{75}$, $L^{76}$, $L^{77}$ and $L^{78}$ are each independently hydrogen or fluorine;

in formulas (7-1) to (7-3) and (7-6) to (7-8), $Z^{7'}$ and $Z^{72}$ are each independently a single bond, —COO— or —CF$_2$O—, however, at least one of $Z^{7'}$ and $Z^{72}$ is —COO— or —CF$_2$O—, and in formulas (7-4) and (7-5), $Z^{71}$ is each independently —COO— or —CF$_2$O—, and $X^{74}$ is fluorine, chlorine, —CF$_3$ or —OCF$_3$.

13. The liquid crystal composition of claim 12, wherein the compound 7 is at least one compound selected from the group consisting of compounds represented by formulas (7-1-1), (7-1-2), (7-2-1) to (7-2-5), (7-3-1), (7-3-2), (7-4-1), (7-5-1) and (7-5-2):

(7-1-1)
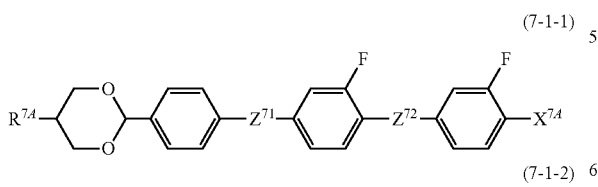

(7-1-2)
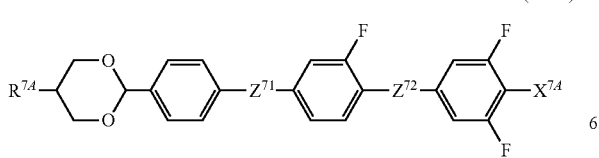

-continued (7-2-1)
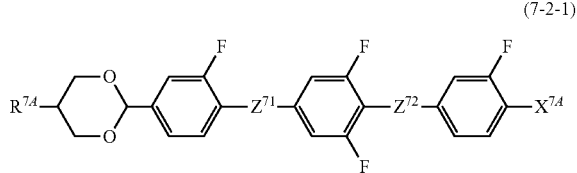

(7-2-2)
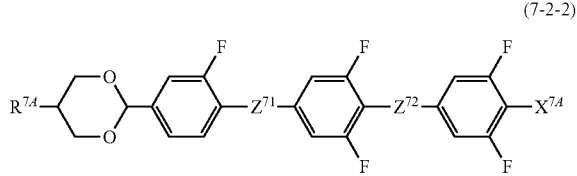

(7-2-3)
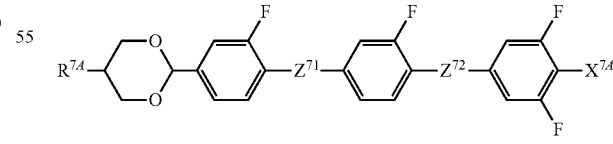

(7-2-4)
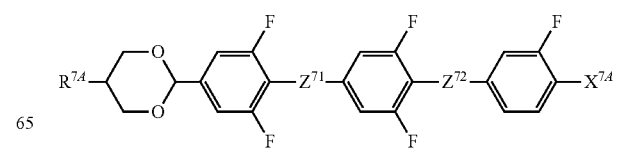

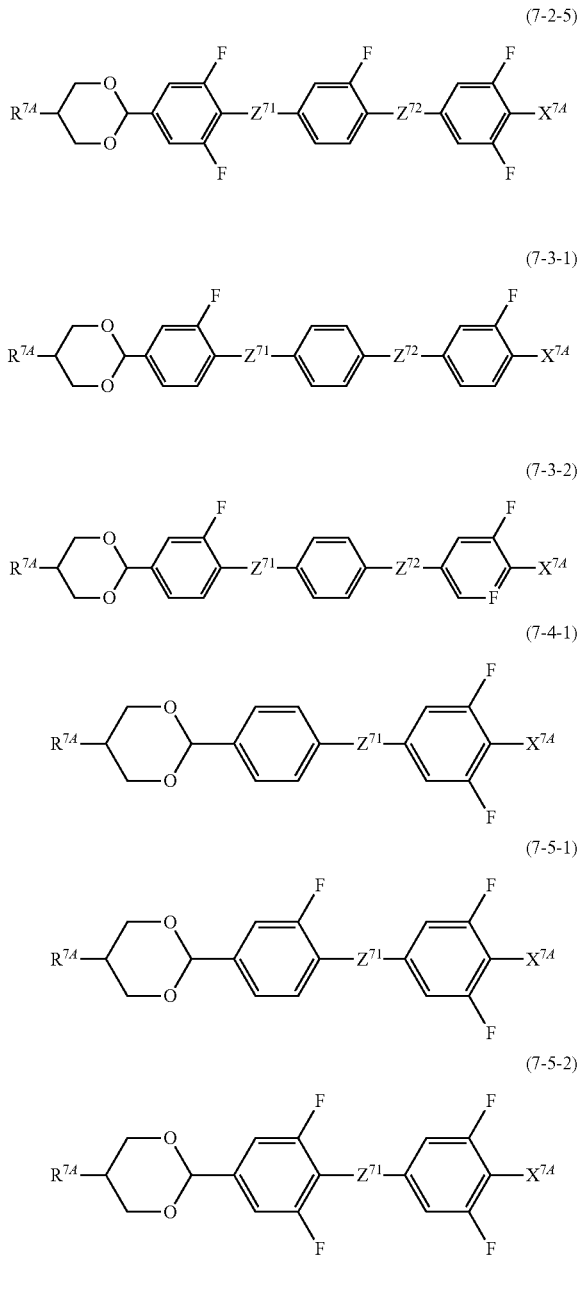

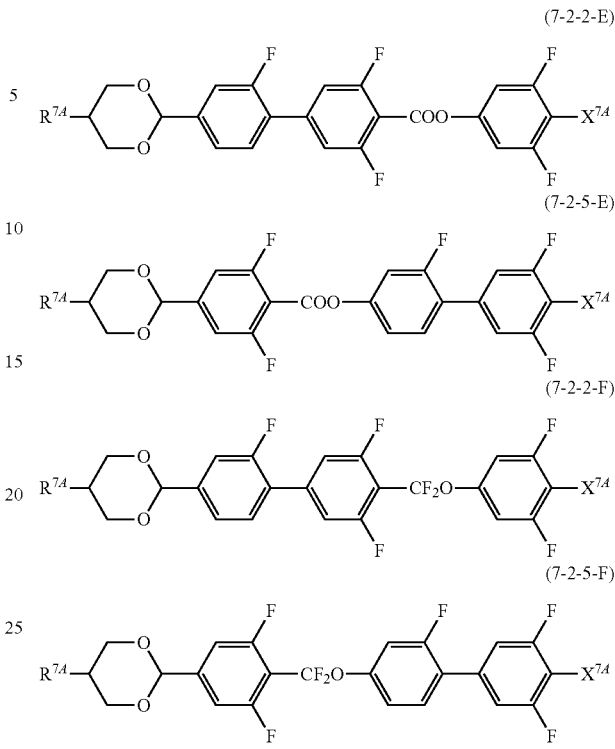

wherein in the formulas, $R^{7A}$ is alkyl having 2 to 12 carbons, alkoxy having 1 to 11 carbons, alkenyl having 2 to 12 carbons, or alkenyl having 2 to 12 carbons in which at least one of hydrogen is replaced by fluorine; and $X^{7A}$ is fluorine, chlorine, —$CF_3$ or —$OCF_3$.

15. The liquid crystal composition of claim 12, containing the compound 1 in a total amount of 5 wt % to 30 wt %, and the compound 7 in a total amount of 30 wt % to 70 wt %, based on a total weight of the achiral component T.

16. The liquid crystal composition of claim 1, wherein the chiral agent is at least one compound selected from the group consisting of compounds represented by formulas (K1) to (K5):

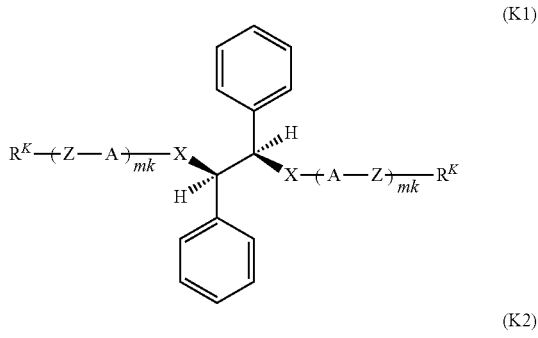

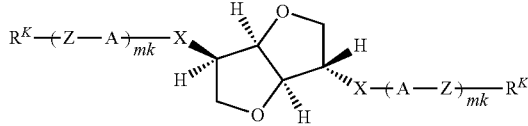

wherein in the formulas, $R^{7A}$ is alkyl having 2 to 12 carbons, alkoxy having 1 to 11 carbons, alkenyl having 2 to 12 carbons, or alkenyl having 2 to 12 carbons in which at least one of hydrogen is replaced by fluorine; in formulas (7-1-1), (7-1-2), (7-2-1) to (7-2-5), (7-3-1) and (7-3-2), $Z^{71}$ and $Z^{72}$ are each independently a single bond, —COO— or —$CF_2O$—, however, at least one of $Z^{71}$ and $Z^{72}$ is —COO— or —$CF_2O$—, and in formulas (7-4-1), (7-5-1) and (7-5-2), $Z^{71}$ is —COO— or —$CF_2O$—; and $X^{7A}$ is fluorine, chlorine, —$CF_3$ or —$OCF_3$.

14. The liquid crystal composition of claim 12, wherein the compound 7 is at least one compound selected from the group consisting of compounds represented by formulas (7-2-2-E), (7-2-5-E), (7-2-2-F) and (7-2-5-F):

-continued (K3)

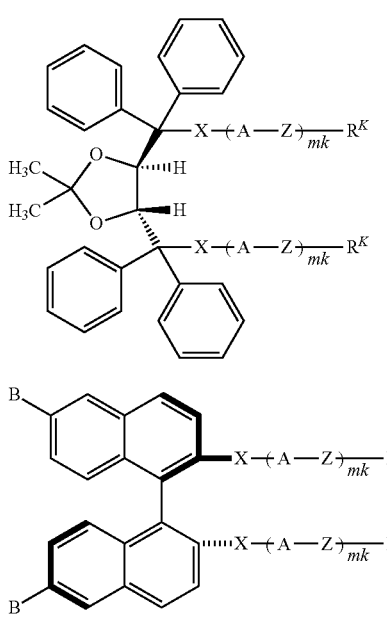

(K4)

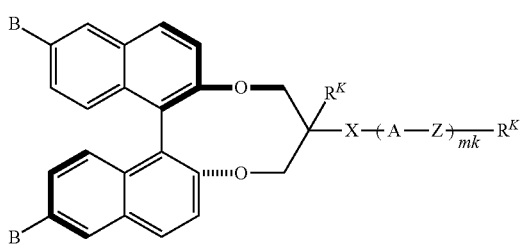

(K5)

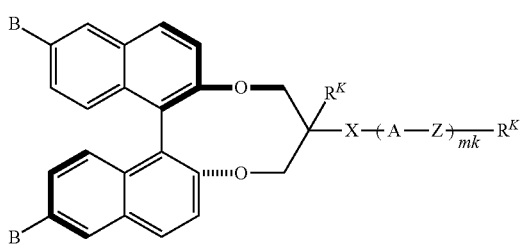

wherein in the formulas, $R^K$ is each independently hydrogen, halogen, —C≡N, —N=C=O, —N=C=S or alkyl having 1 to 20 carbons, and arbitrary —CH$_2$— in the alkyl may be replaced by —O—, —S—, —COO— or —OCO—, at least one of —CH$_2$— in the alkyl may be replaced by —O—, —S—, —COO— or —OCO—, at least one of —CH$_2$—CH$_2$— in the alkyl may be replaced by —CH=CH—, —CF=CF— or —C≡C—, and in the alkyl, at least one of hydrogen in a group in which at least one of —CH$_2$— in the alkyl is replaced by —O—, —S—, —COO— or —OCO—, or in a group in which at least one of —CH$_2$—CH$_2$— in the alkyl is replaced by —CH=CH—, —CF=CF— or —C≡C— may be replaced by fluorine or chlorine;

A is each independently an aromatic 6-membered to 8-membered ring, a non-aromatic 3-membered to 8-membered ring, or a condensed ring having 9 or more carbons, and at least one of hydrogen on the rings may be replaced by halogen, alkyl or haloalkyl having 1 to 3 carbons, —CH$_2$— of the ring may be replaced by —O—, —S— or —NH—, and —CH= may be replaced by —N=;

B is each independently hydrogen, halogen, alkyl having 1 to 3 carbons, haloalkyl having 1 to 3 carbons, a 6- to 8-membered aromatic ring, a 3-membered to 8-membered non-aromatic ring or a condensed ring having 9 or more carbons, arbitrary hydrogen on the rings may be replaced by halogen, alkyl or haloalkyl having 1 to 3 carbons, —CH$_2$— may be replaced by —O—, —S— or —NH—, and —CH= may be replaced by —N—;

Z is each independently a single bond or alkylene having 1 to 8 carbons, and arbitrary —CH$_2$— in the alkylene may be replaced by —O—, —S—, —COO—, —OCO—, —CSO—, —OCS—, —N=N—, —CH=N— or —N=CH—, at least one of —CH$_2$—CH$_2$— in the alkylene may be replaced by —CH=CH—, —CF=CF— or —C≡C—, and in the alkyl, at least one of hydrogen in a group in which at least one of —CH$_2$— in the alkylene is replaced by —O—, —S—, —COO— or —OCO—, or in a group in which at least one of —CH$_2$—CH$_2$— in the alkyl is replaced by —CH=CH—, —CF=CF— or —C≡C— may be replaced by halogen;

X is each independently a single bond, —COO—, —OCO—, —CH$_2$O—, —OCH$_2$—, —CF$_2$O—, —OCF$_2$— or —CH$_2$CH$_2$—; and mK is each independently an integer from 1 to 4.

17. The liquid crystal composition of claim 16, wherein the chiral agent is at least one compound selected from the group consisting of compounds represented by formulas (K4-1) to (K4-6) and (K5-1) to (K5-3):

(K4-1)
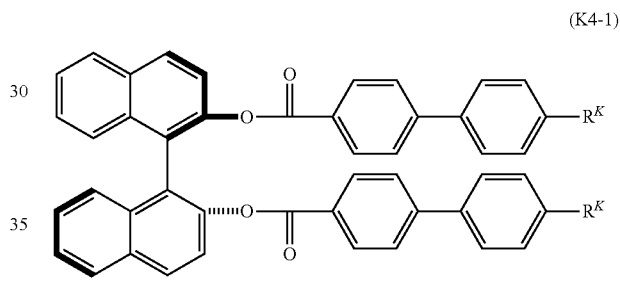

(K4-2)
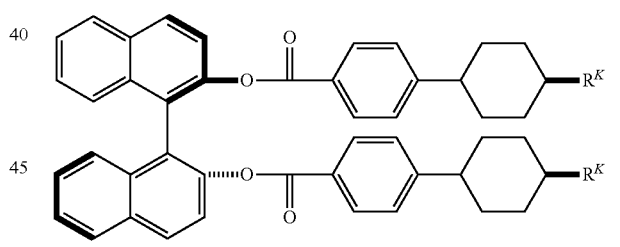

(K4-3)
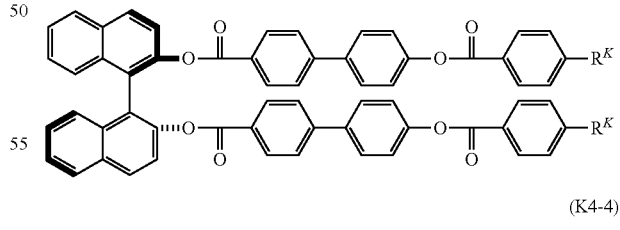

(K4-4)
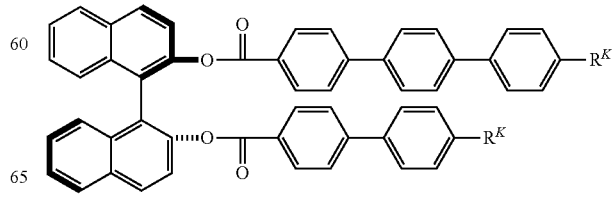

-continued (K4-5)
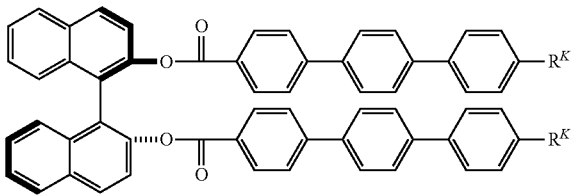

(K4-6)
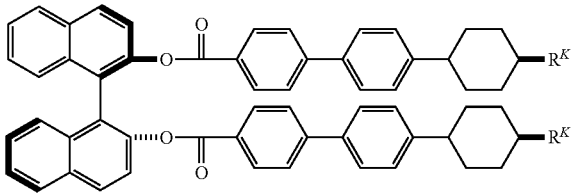

(K5-1)
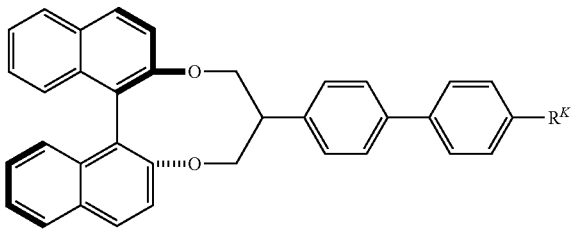

(K5-2)
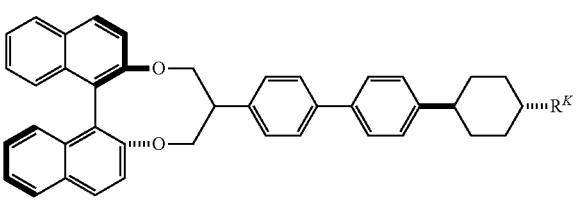

(K5-3)
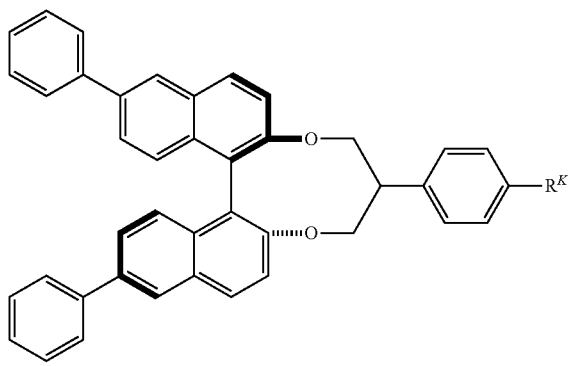

wherein in the formulas, $R^K$ is each independently alkyl having 3 to 10 carbons or alkoxy having 3 to 10 carbons, and at least one of —$CH_2$— in the alkyl or the alkoxy may be replaced by —CH=CH—, however, a case where —O— and —C≡C— are adjacent is excluded.

18. The liquid crystal composition of claim 1, wherein a chiral nematic phase is exhibited at any temperature in a temperature range of from −20° C. to 70° C., and a helical pitch is 700 nm or less at least in a part of the temperature range.

19. The liquid crystal composition of claim 1, containing at least one selected from the group consisting of an antioxidant and an ultraviolet light absorbent.

20. A mixture, containing the liquid crystal composition claim 1, and a polymerizable monomer.

21. A polymer/liquid crystal composite material, obtained by polymerizing the mixture of claim 20, and used in a device to be driven in an optically isotropic liquid crystal phase.

22. The polymer/liquid crystal composite material of claim 21, wherein the mixture is polymerized in a non-liquid crystal isotropic phase or an optically isotropic liquid crystal phase.

23. An optical device comprising a liquid crystal medium arranged between substrates in which an electrode is arranged on one face or on both faces of the substrate, and an electric field applying means for applying an electric field to the liquid crystal medium through the electrode, wherein the liquid crystal medium is the liquid crystal composition of claim 1.

24. An optical device comprising one set of substrates in which an electrode is arranged on one face or on both faces thereof, and at least one thereof is transparent, a liquid crystal medium arranged between the substrates, a polarizing plate arranged outside the substrate, and an electric field applying means for applying an electric field to the liquid crystal medium through the electrode, wherein the liquid crystal medium is the liquid crystal composition of claim 1.

25. A compound represented by formula (1-2-5):

(1-2-5)
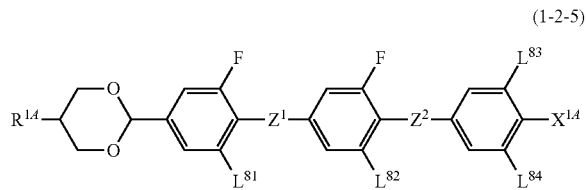

wherein in the formula, $R^{14}$ is hydrogen or methyl;

$L^{81}$, $L^{82}$, $L^{83}$ and $L^{84}$ are each independently hydrogen or fluorine;

$Z^1$ and $Z^2$ are each independently a single bond, —COO— or —$CF_2O$—, however, at least one of $Z^1$ and $Z^2$ is —COO— or —$CF_2O$—; and $X^{14}$ is fluorine, chlorine, —$CF_3$ or —$OCF_3$.

26. The compound of claim 25, wherein in formula (1-2-5), $Z^1$ is —COO— or —$CF_2O$—; and $Z^2$ is a single bond.

27. The compound of claim 25, wherein in formula (1-2-5), $R^{14}$ is hydrogen;

$Z^1$ is —COO— or —$CF_2O$—; and $Z^2$ is a single bond.

28. An optical device comprising a liquid crystal medium arranged between substrates in which an electrode is arranged on one face or on both faces of the substrate, and an electric field applying means for applying an electric field to the liquid crystal medium through the electrode, wherein the liquid crystal medium is the polymer/liquid crystal composite material of claim 21.

29. An optical device comprising one set of substrates in which an electrode is arranged on one face or on both faces thereof, and at least one thereof is transparent, a liquid crystal medium arranged between the substrates, a polarizing plate arranged outside the substrate, and an electric field applying means for applying an electric field to the liquid crystal medium through the electrode, wherein the liquid crystal medium is the polymer/liquid crystal composite material of claim 21.

\* \* \* \* \*